(12) United States Patent
Iamberger et al.

(10) Patent No.: US 12,156,644 B2
(45) Date of Patent: Dec. 3, 2024

(54) SUTURE CLOSURE DEVICES

(71) Applicant: THE GLOBAL HEART VALVE INNOVATION CENTER LTD, Or Yehuda (IL)

(72) Inventors: Meni Iamberger, Kfar Saba (IL); Nir Lilach, Kfar Yehoshua (IL); Amit Segal, Afula (IL); Eliahu Eliachar, Haifa (IL); Ohad Yehoshua Henn, Ramat Gan (IL); Oded Aldaag, Motza Ilit (IL)

(73) Assignee: THE GLOBAL HEART VALVE INNOVATION CENTER (ISRAEL) LTD., Or Yehuda (IL)

( * ) Notice: Subject to any disclaimer, the term of this patent is extended or adjusted under 35 U.S.C. 154(b) by 0 days.

(21) Appl. No.: 18/517,764

(22) Filed: Nov. 22, 2023

(65) Prior Publication Data
US 2024/0081800 A1    Mar. 14, 2024

Related U.S. Application Data

(63) Continuation of application No. PCT/IL2023/050966, filed on Sep. 7, 2023.
(Continued)

(51) Int. Cl.
*A61B 17/00* (2006.01)
*A61B 17/04* (2006.01)

(52) U.S. Cl.
CPC ...... *A61B 17/0057* (2013.01); *A61B 17/0469* (2013.01); *A61B 2017/00663* (2013.01); *A61B 2017/0472* (2013.01)

(58) Field of Classification Search
CPC ...... A61B 17/0469; A61B 2017/00663; A61B 2017/0472
See application file for complete search history.

(56) References Cited

U.S. PATENT DOCUMENTS 5,417,699 A * 5/1995 Klein ................. A61B 17/0625
                                              112/80.03
5,613,974 A   3/1997 Andreas et al.
(Continued)

FOREIGN PATENT DOCUMENTS

WO    03/099134 A2   12/2003
WO   2004/098415 A2  11/2004
(Continued)

OTHER PUBLICATIONS

Invitation to Pay Additional Fees issued Nov. 14, 2023 in International Application No. PCT/IL2023/050966.
(Continued)

*Primary Examiner* — Alexander J Orkin
(74) *Attorney, Agent, or Firm* — Sughrue Mion, PLLC

(57) ABSTRACT

A closure device (320) is provided for suturing a puncture. The closure device (320) includes a suture (322, 822), an elongate support (328), a suture-positioning support (330), and an elongate dilator (344). The suture-positioning support (330) is coupled to a distal end portion (332) of the elongate support (328), laterally extendable with respect to the distal end portion (332) of the elongate support (328), and configured to removably receive the suture (322, 822). The dilator (344) is configured to be inserted through the puncture, and has a proximal end (348) that is coupled to the distal end portion (332) of the elongate support (328). The closure device (320) is configured to allow movement of the distal end portion (332) of the elongate support (328) with respect to the proximal end (348) of the dilator (344) with at least two degrees of freedom. Other embodiments are also described.

30 Claims, 92 Drawing Sheets

Related U.S. Application Data

(60) Provisional application No. 63/526,765, filed on Jul. 14, 2023, provisional application No. 63/404,630, filed on Sep. 8, 2022.

(56) References Cited

U.S. PATENT DOCUMENTS

| | | | |
|---|---|---|---|
| 5,700,273 A * | 12/1997 | Buelna | A61B 17/0483 606/144 |
| 5,921,994 A | 7/1999 | Andreas et al. | |
| 6,036,699 A * | 3/2000 | Andreas | A61B 17/11 606/139 |
| 6,136,010 A * | 10/2000 | Modesitt | A61B 17/0482 606/139 |
| 6,171,317 B1 | 1/2001 | Jackson et al. | |
| 6,245,079 B1 | 6/2001 | Nobles et al. | |
| 6,641,592 B1 | 11/2003 | Sauer et al. | |
| 6,663,577 B2 | 12/2003 | Jen et al. | |
| 6,733,509 B2 | 5/2004 | Nobles et al. | |
| 6,743,241 B2 | 6/2004 | Kerr | |
| 7,285,097 B2 | 10/2007 | Tenerz et al. | |
| 7,341,595 B2 | 3/2008 | Hinchliffe et al. | |
| 7,449,024 B2 | 11/2008 | Stafford | |
| 7,842,051 B2 | 11/2010 | Dana et al. | |
| 7,918,868 B2 | 4/2011 | Marshall et al. | |
| 7,992,571 B2 | 8/2011 | Gross et al. | |
| 8,105,355 B2 | 1/2012 | Page et al. | |
| 8,137,364 B2 | 3/2012 | Zung et al. | |
| 8,211,122 B2 | 7/2012 | Mcintosh | |
| 8,211,123 B2 | 7/2012 | Gross et al. | |
| 8,267,947 B2 | 9/2012 | Pantages et al. | |
| 8,282,659 B2 | 10/2012 | Oren et al. | |
| 8,562,630 B2 | 10/2013 | Campbell | |
| 8,574,244 B2 | 11/2013 | Reynolds | |
| 8,663,252 B2 | 3/2014 | Fortson | |
| 8,915,933 B2 | 12/2014 | Argentine | |
| 9,138,214 B2 | 9/2015 | Voss et al. | |
| 9,241,706 B2 | 1/2016 | Paraschac et al. | |
| 9,241,707 B2 * | 1/2016 | Roorda | A61B 17/06061 |
| 9,271,721 B2 | 3/2016 | Jimenez et al. | |
| 9,332,980 B2 | 5/2016 | George et al. | |
| 9,358,077 B2 | 6/2016 | Tegels | |
| 9,393,011 B2 | 7/2016 | Heneveld | |
| 9,533,076 B2 | 1/2017 | Roorda et al. | |
| 9,801,720 B2 | 10/2017 | Gilmore et al. | |
| 9,861,356 B2 | 1/2018 | Sherwinter | |
| 9,888,915 B2 | 2/2018 | Torrie | |
| 9,993,237 B2 | 6/2018 | Ma | |
| 10,143,463 B2 | 12/2018 | Dana et al. | |
| 10,271,837 B1 * | 4/2019 | Rajebi | A61B 17/3415 |
| 10,322,020 B2 | 6/2019 | Lam et al. | |
| 10,426,449 B2 | 10/2019 | Fortson | |
| 10,537,312 B2 | 1/2020 | Voss | |
| 10,675,018 B2 | 6/2020 | Jast et al. | |
| 10,772,621 B2 | 9/2020 | Fortson et al. | |
| 10,952,850 B2 | 3/2021 | Hariton et al. | |
| 11,129,610 B2 | 9/2021 | Voss et al. | |
| 11,154,285 B2 | 10/2021 | Bennett, III | |
| 11,154,293 B2 | 10/2021 | Fortson et al. | |
| 11,202,624 B2 | 12/2021 | Nobles | |
| 11,213,288 B2 | 1/2022 | Kumar | |
| 11,375,994 B2 | 7/2022 | Fortson | |
| 11,389,192 B2 | 7/2022 | Shelton, IV et al. | |
| 11,439,383 B2 | 9/2022 | Fortson | |
| 11,666,315 B2 | 6/2023 | Fortson | |
| 11,839,351 B2 | 12/2023 | Roorda et al. | |
| 11,844,515 B2 | 12/2023 | Voss et al. | |
| 2003/0120287 A1 | 6/2003 | Gross et al. | |
| 2004/0087975 A1 * | 5/2004 | Lucatero | A61B 17/0469 606/139 |
| 2004/0225301 A1 | 11/2004 | Roop et al. | |
| 2005/0121042 A1 | 6/2005 | Belhe et al. | |
| 2005/0228405 A1 * | 10/2005 | Maruyama | A61B 17/0057 606/144 |
| 2006/0069397 A1 | 3/2006 | Nobles et al. | |
| 2007/0173865 A1 | 7/2007 | Oren et al. | |
| 2007/0198035 A1 | 8/2007 | Threlkeld | |
| 2007/0276413 A1 | 11/2007 | Nobles | |
| 2008/0045979 A1 | 2/2008 | Ma | |
| 2008/0269786 A1 | 10/2008 | Nobles et al. | |
| 2009/0082802 A1 * | 3/2009 | Benjamin | A61B 17/0057 606/213 |
| 2010/0145364 A1 | 6/2010 | Keren et al. | |
| 2011/0082475 A1 | 4/2011 | Smith | |
| 2011/0112557 A1 | 5/2011 | Beeley | |
| 2011/0118758 A1 | 5/2011 | Sauer | |
| 2013/0245646 A1 | 9/2013 | Lane et al. | |
| 2013/0274870 A1 | 10/2013 | Lombardi et al. | |
| 2013/0310856 A1 | 11/2013 | Sherts et al. | |
| 2014/0067050 A1 | 3/2014 | Costello et al. | |
| 2014/0128887 A1 * | 5/2014 | Argentine | A61B 17/0469 606/144 |
| 2014/0236188 A1 | 8/2014 | Mehl et al. | |
| 2017/0238914 A1 | 8/2017 | Sherwinter | |
| 2018/0228478 A1 | 8/2018 | Fortson | |
| 2018/0235604 A1 | 8/2018 | Comee et al. | |
| 2018/0325504 A1 * | 11/2018 | Phillips | A61B 17/0057 |
| 2019/0142402 A1 | 5/2019 | Larzon et al. | |
| 2020/0289108 A1 | 9/2020 | Nobles | |
| 2021/0145421 A1 | 5/2021 | Hauck et al. | |
| 2022/0183674 A1 | 6/2022 | Wiebe et al. | |
| 2022/0183677 A1 | 6/2022 | Shattuck et al. | |
| 2022/0354485 A1 | 11/2022 | Rotem et al. | |
| 2022/0395288 A1 | 12/2022 | Shelton, IV et al. | |

FOREIGN PATENT DOCUMENTS

| | | |
|---|---|---|
| WO | 2009091509 A1 | 7/2009 |
| WO | 2010/045297 A2 | 4/2010 |
| WO | 2018/035453 A1 | 2/2018 |
| WO | 2021/111429 A1 | 6/2021 |
| WO | 2021/221907 A1 | 11/2021 |
| WO | 2022/125808 A1 | 6/2022 |
| WO | 2022/125812 A1 | 6/2022 |
| WO | 2024/013700 A1 | 1/2024 |

OTHER PUBLICATIONS

International Search Report and Written Opinion issued Jan. 10, 2024 in International Application No. PCT/IL2023/050966.
Eric K. Hoffer, et al., "Percutaneous Arterial Closure Devices", J Vasc Interv Radiol, 2003, vol. 14, pp. 865-885 (21 pages total).
Shaphan R. Jernigan, et al., "A laparoscopic knot-tying device for minimally invasive cardiac surgery", European Journal of Cardiothoracic Surgery, 2010, vol. 37, pp. 626-630 (5 pages total).
Lapro-Shark IFU_VERSION2_Rev_H-P10136, Sep. 2016, LB-001 Rev.01 (1 page total).
Laproshark™ DemeTECH® Brochure, Jun. 2022 (4 pages total).
International Search Report and Written Opinion in International Application PCT/IL2023/050966, dated Feb. 28, 2024.

* cited by examiner

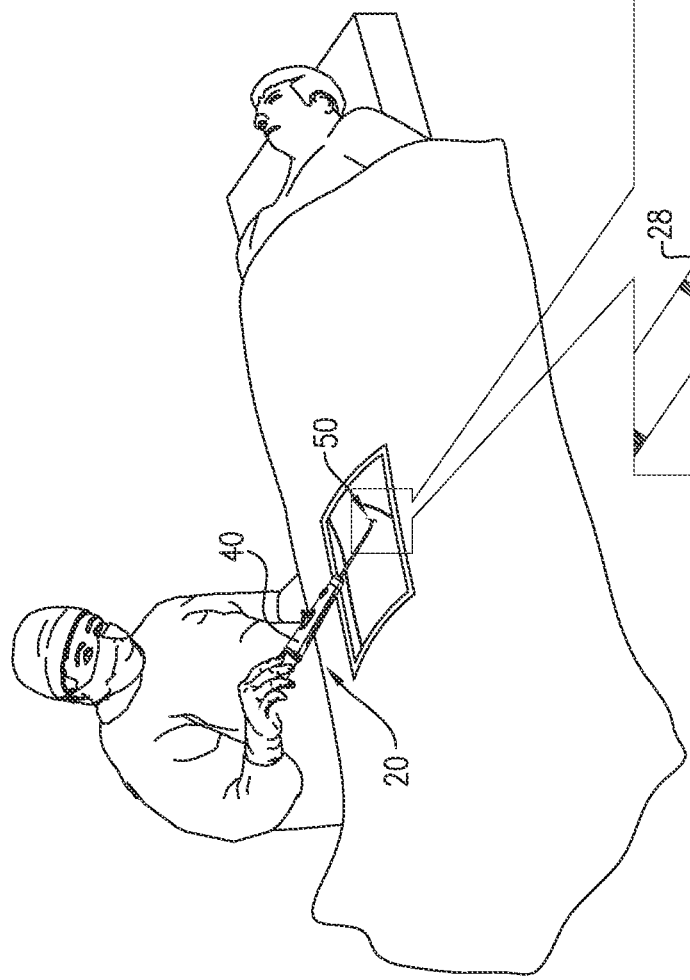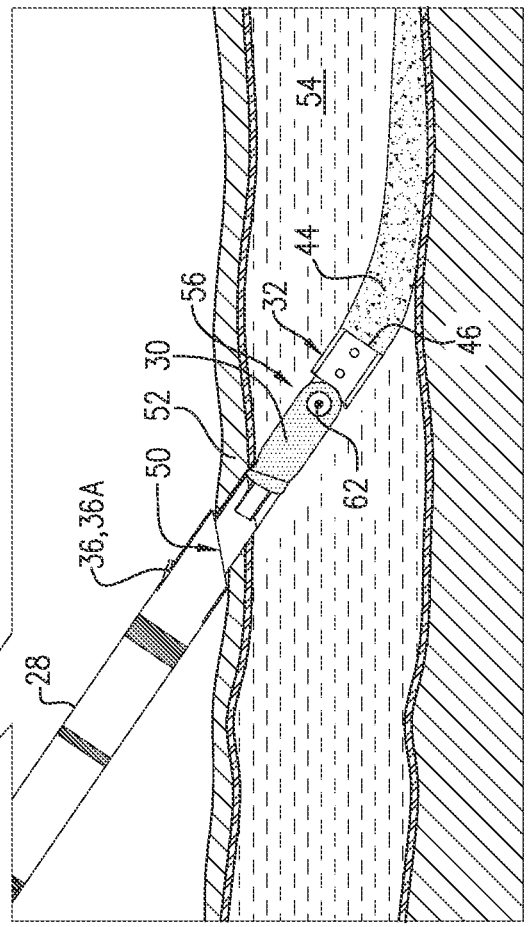
FIG. 5A

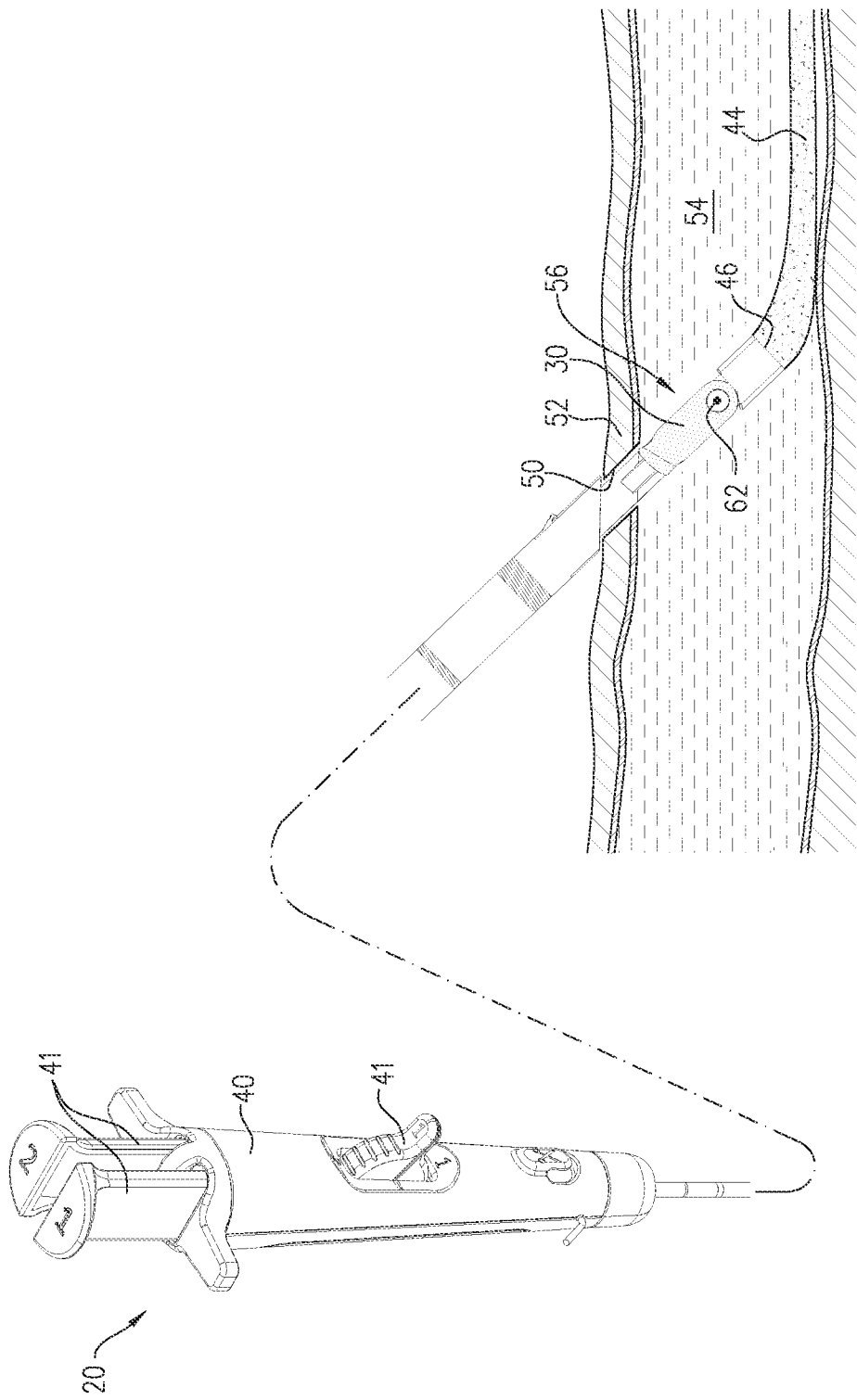

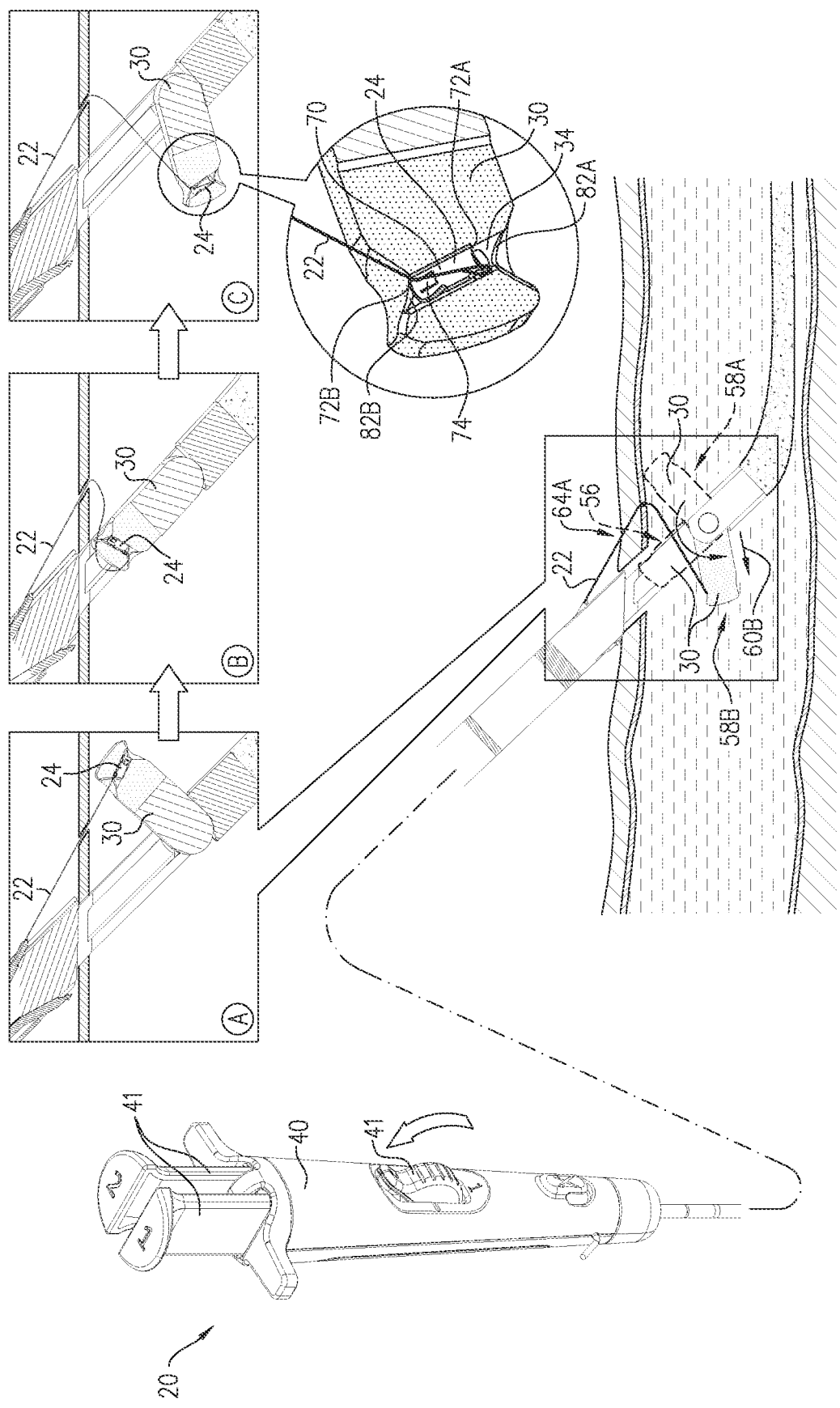

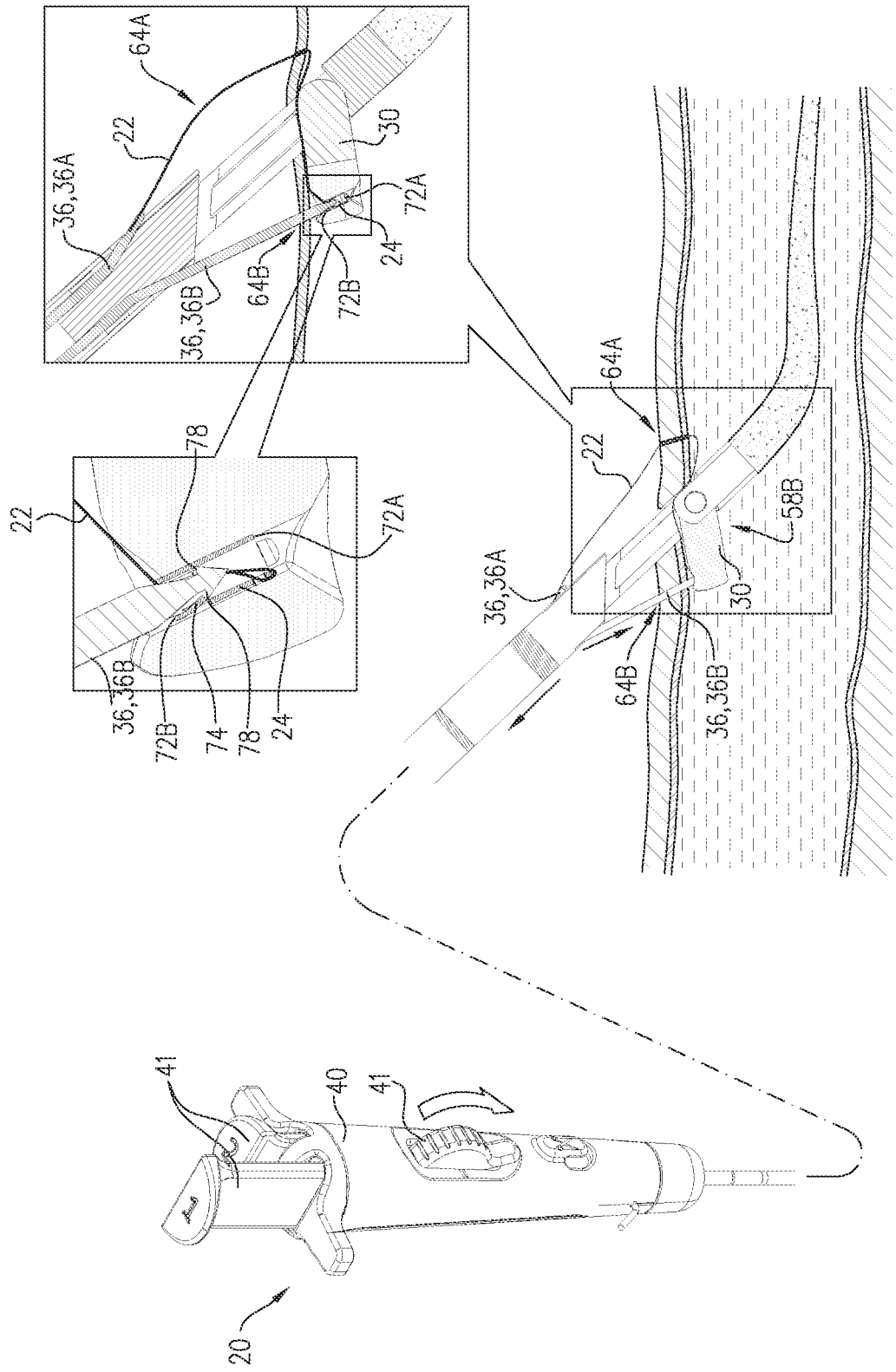

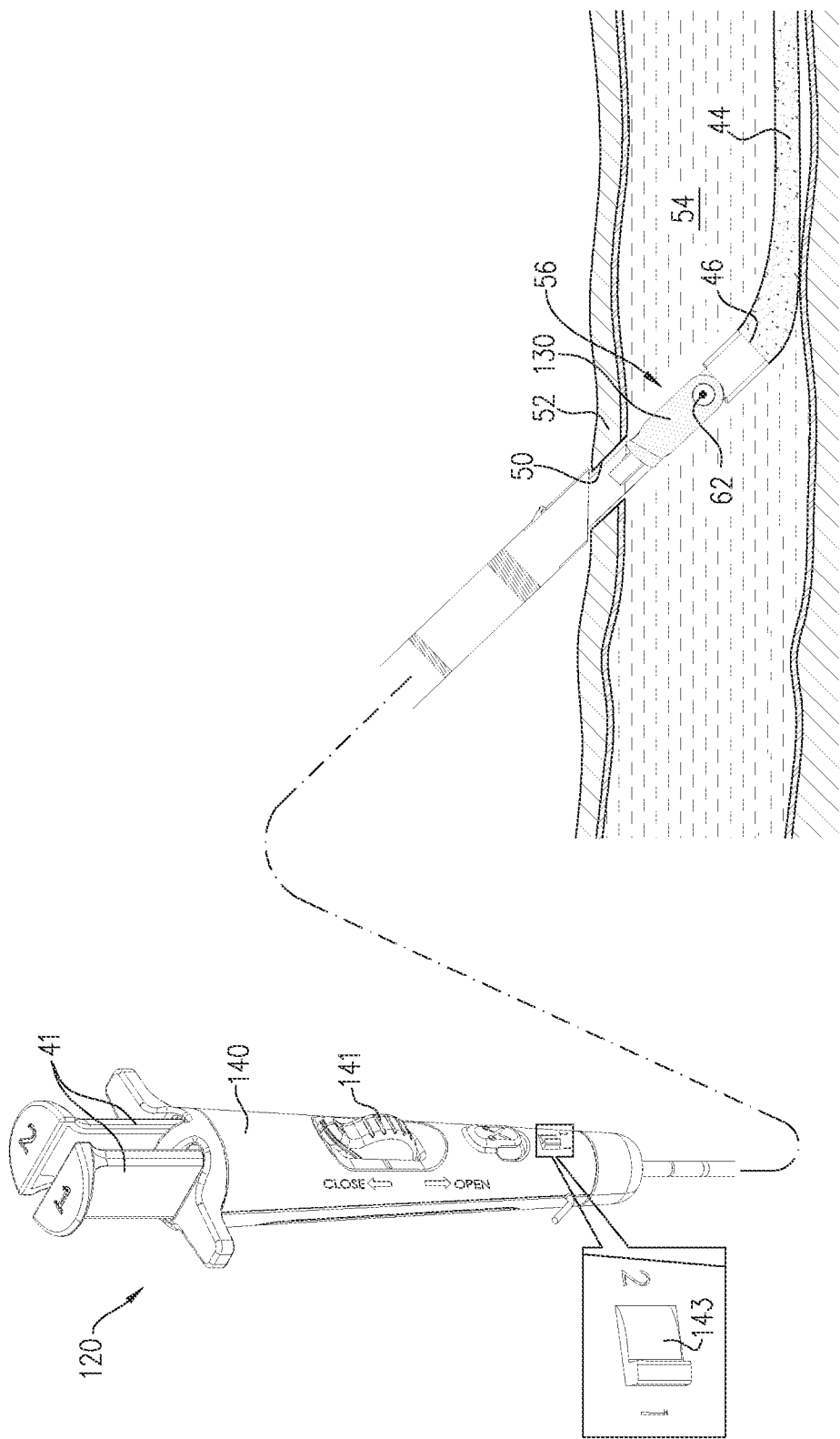

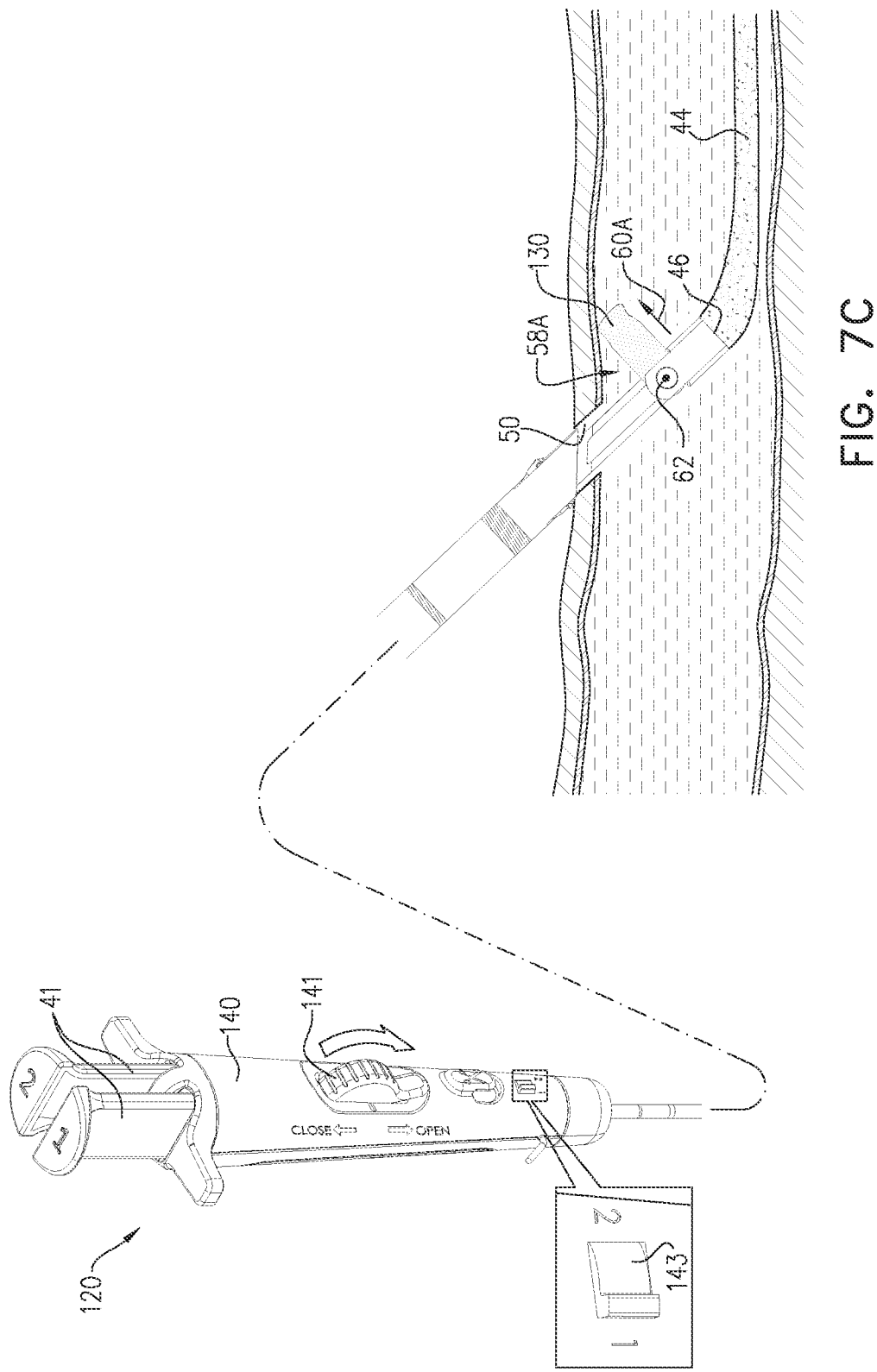

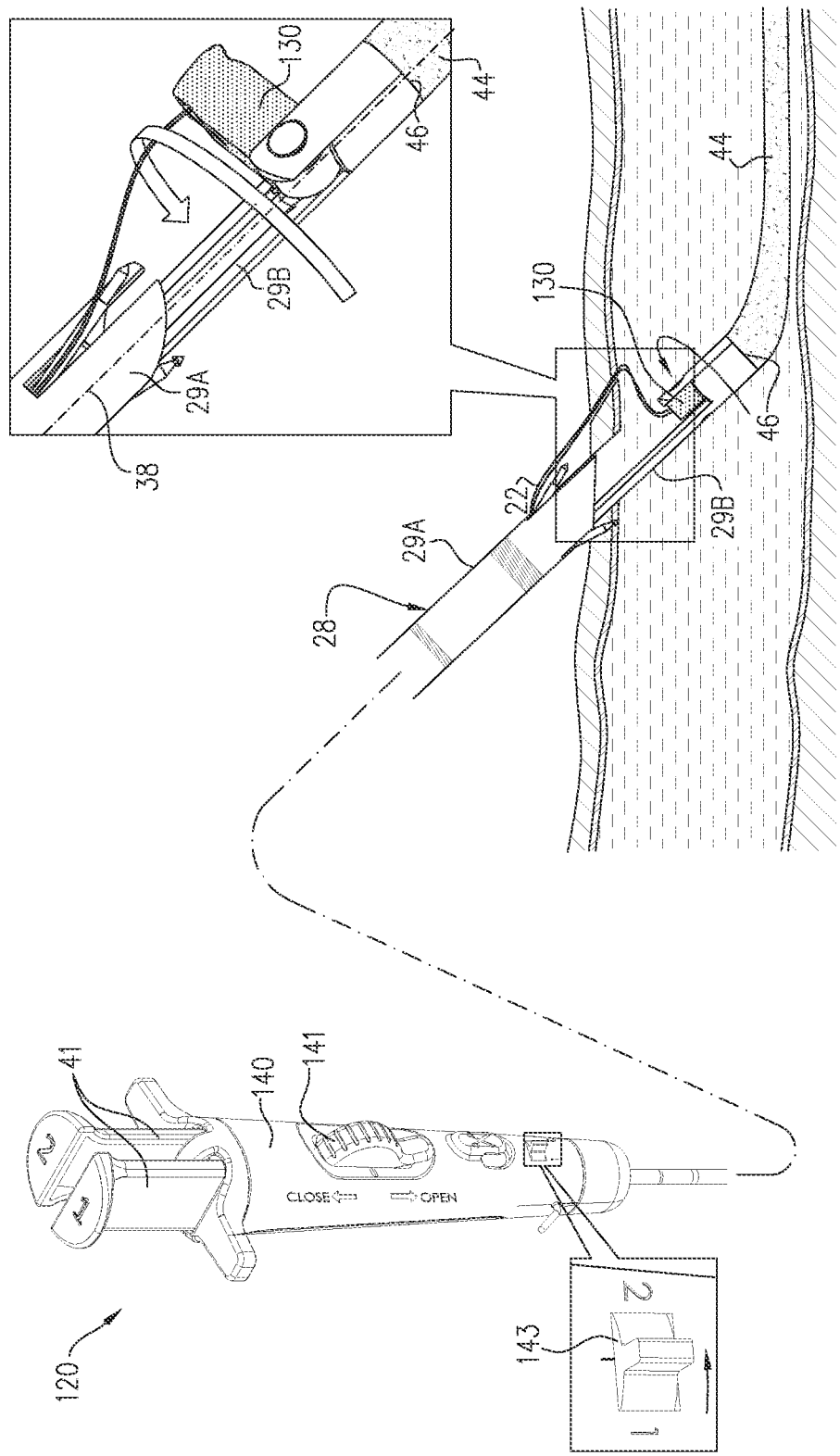

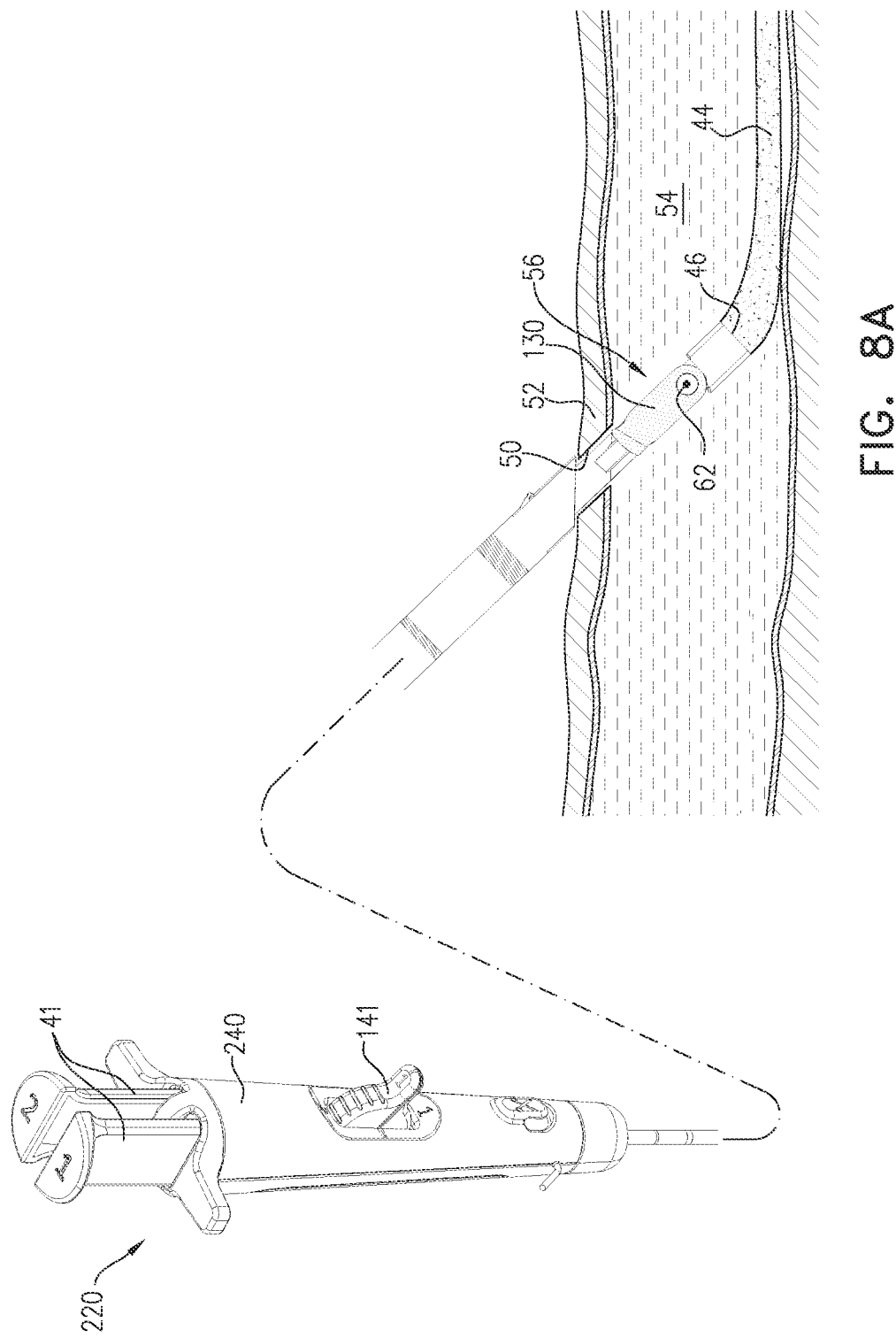

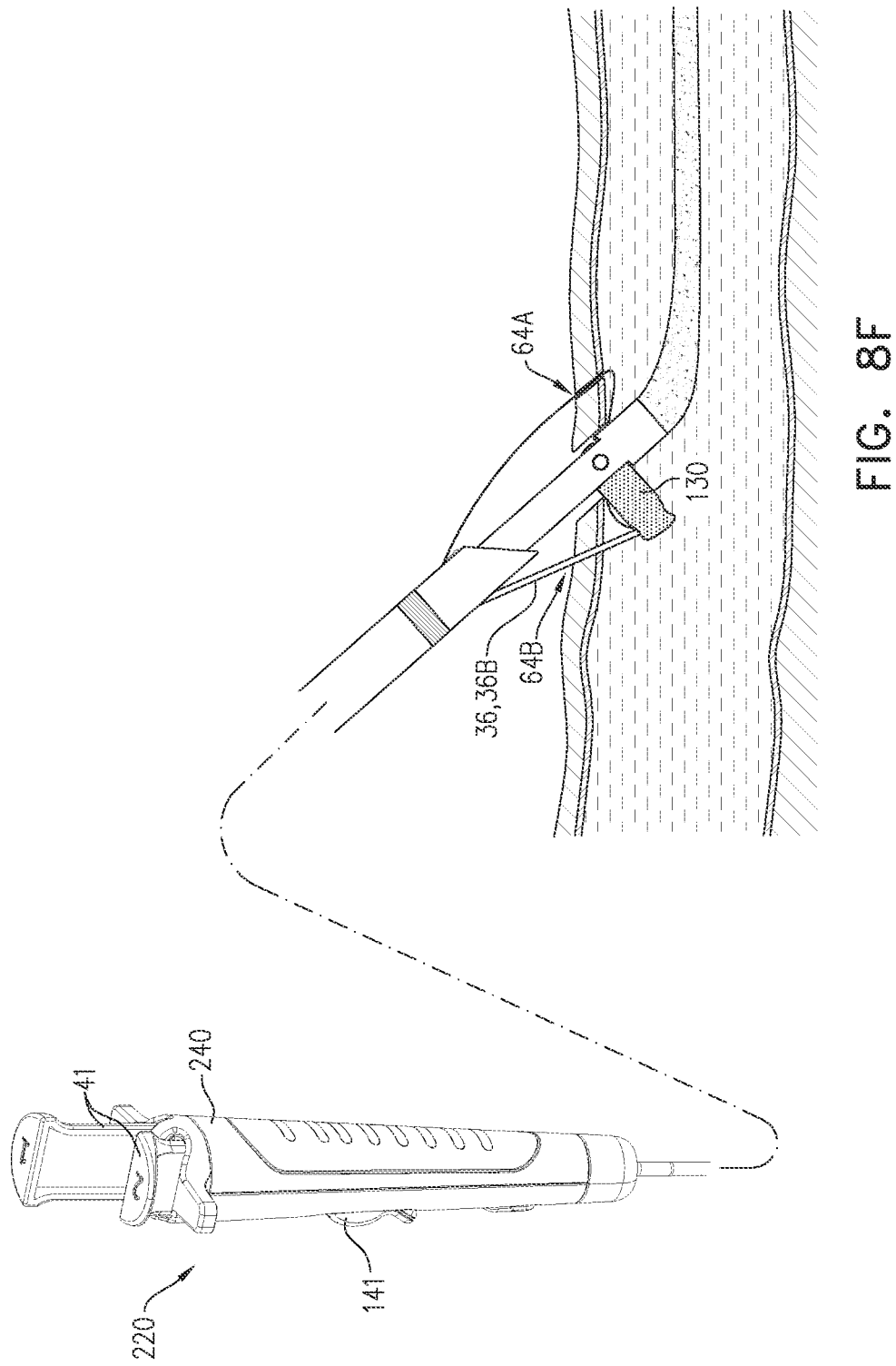

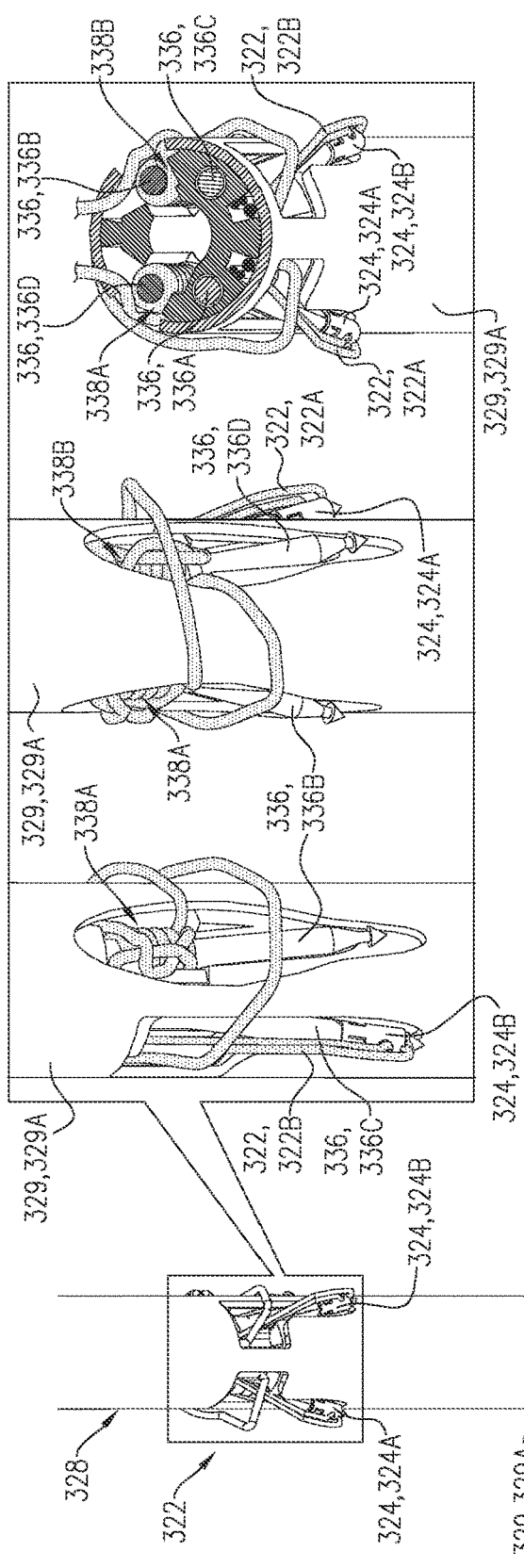
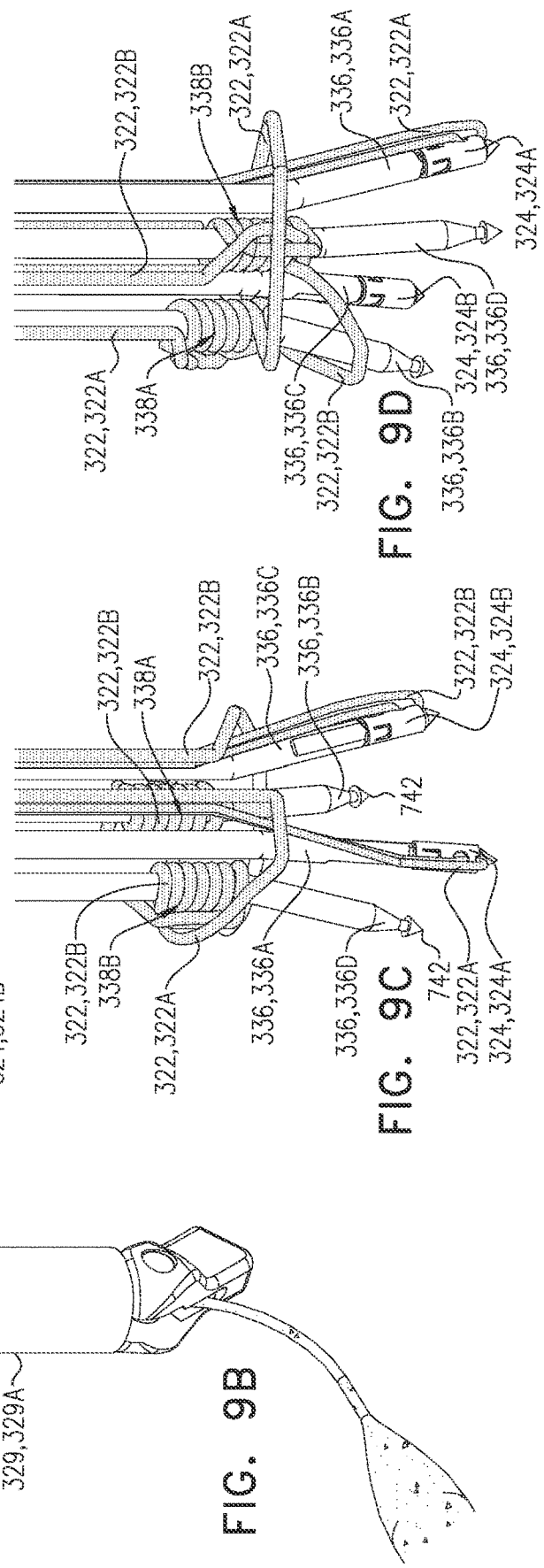

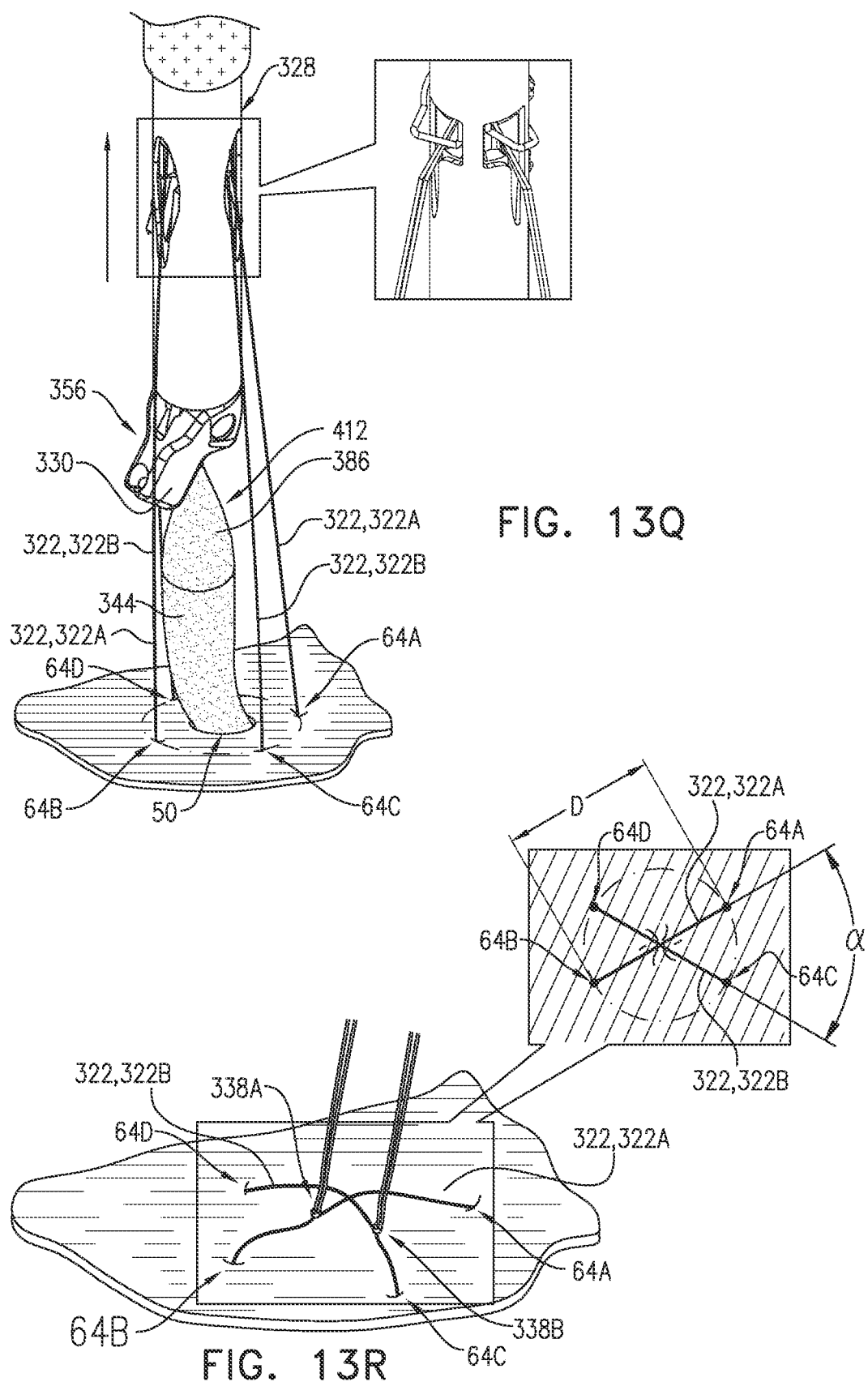

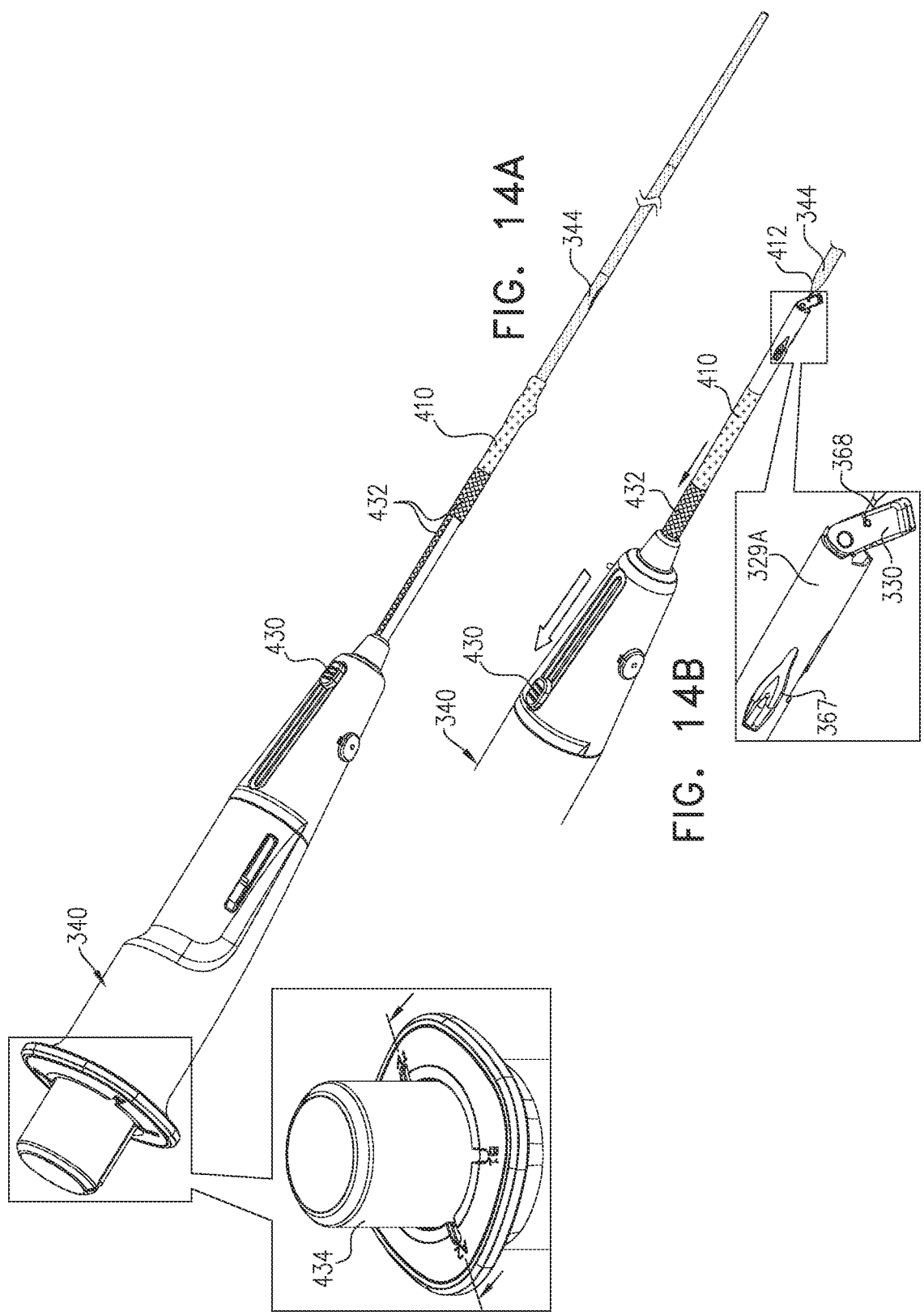

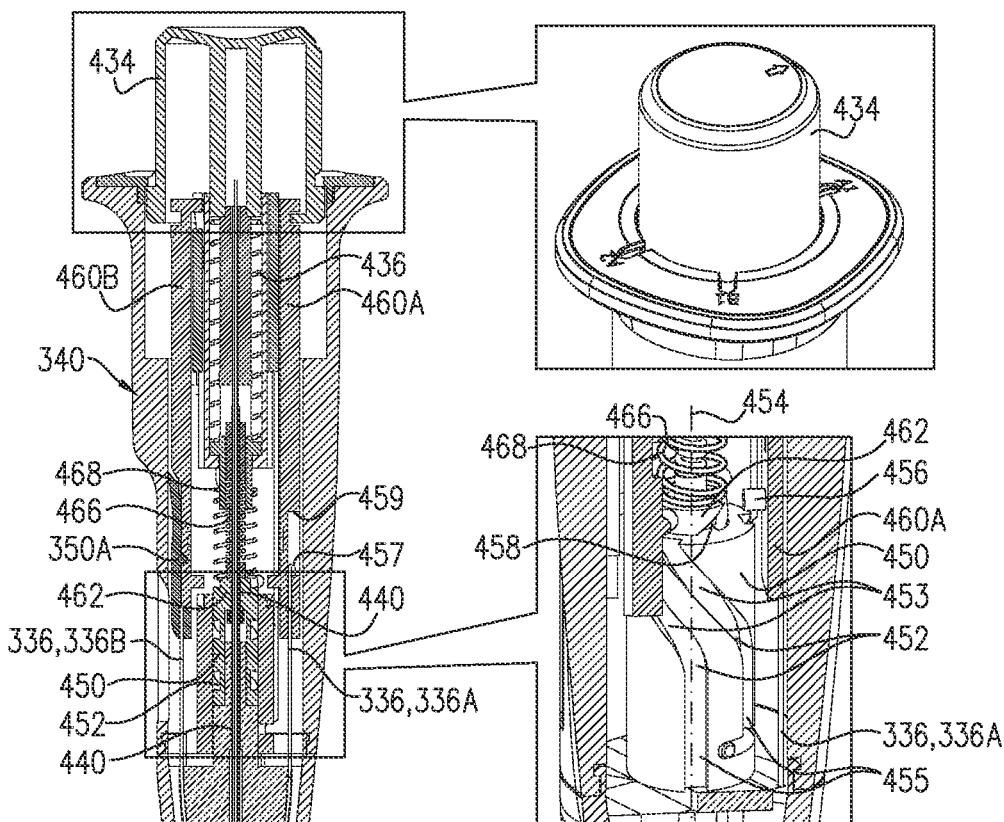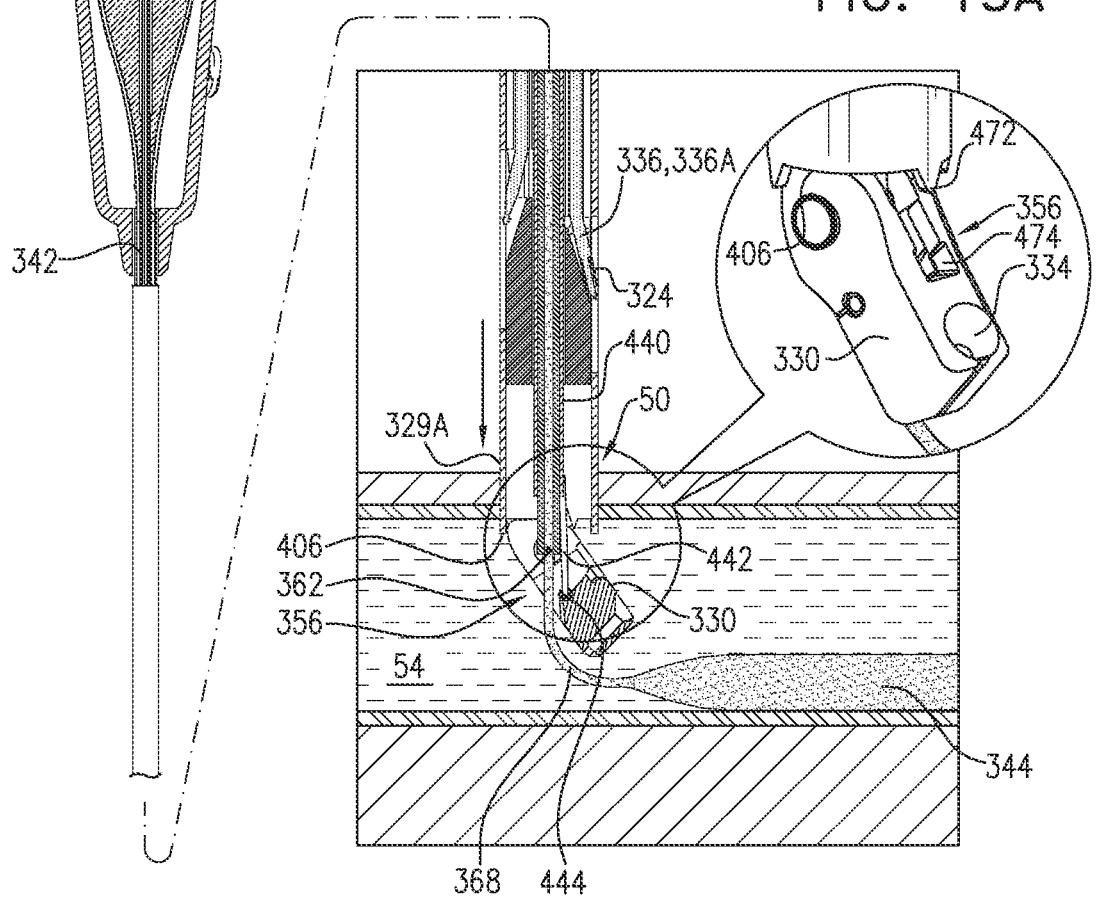
FIG. 15A

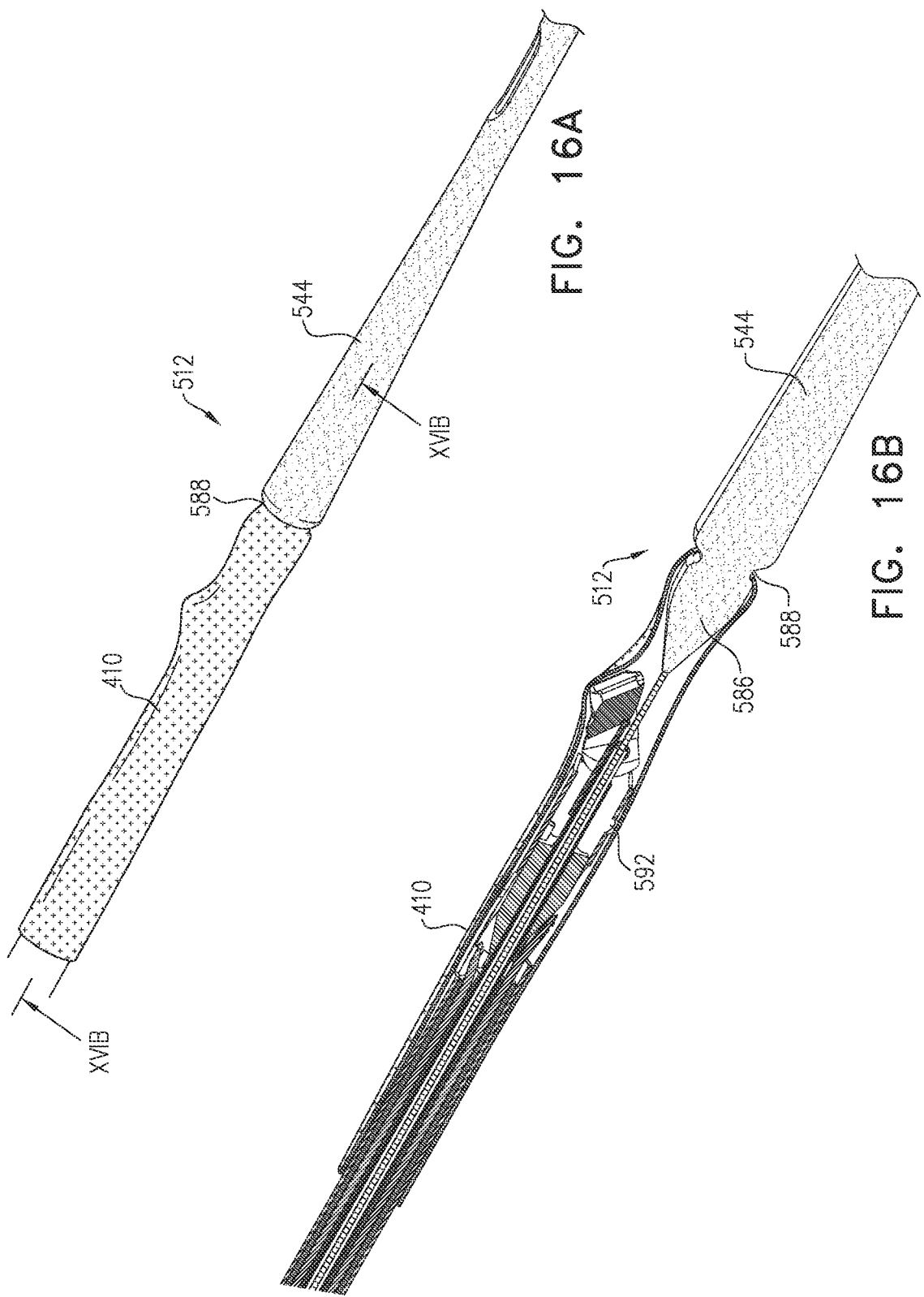

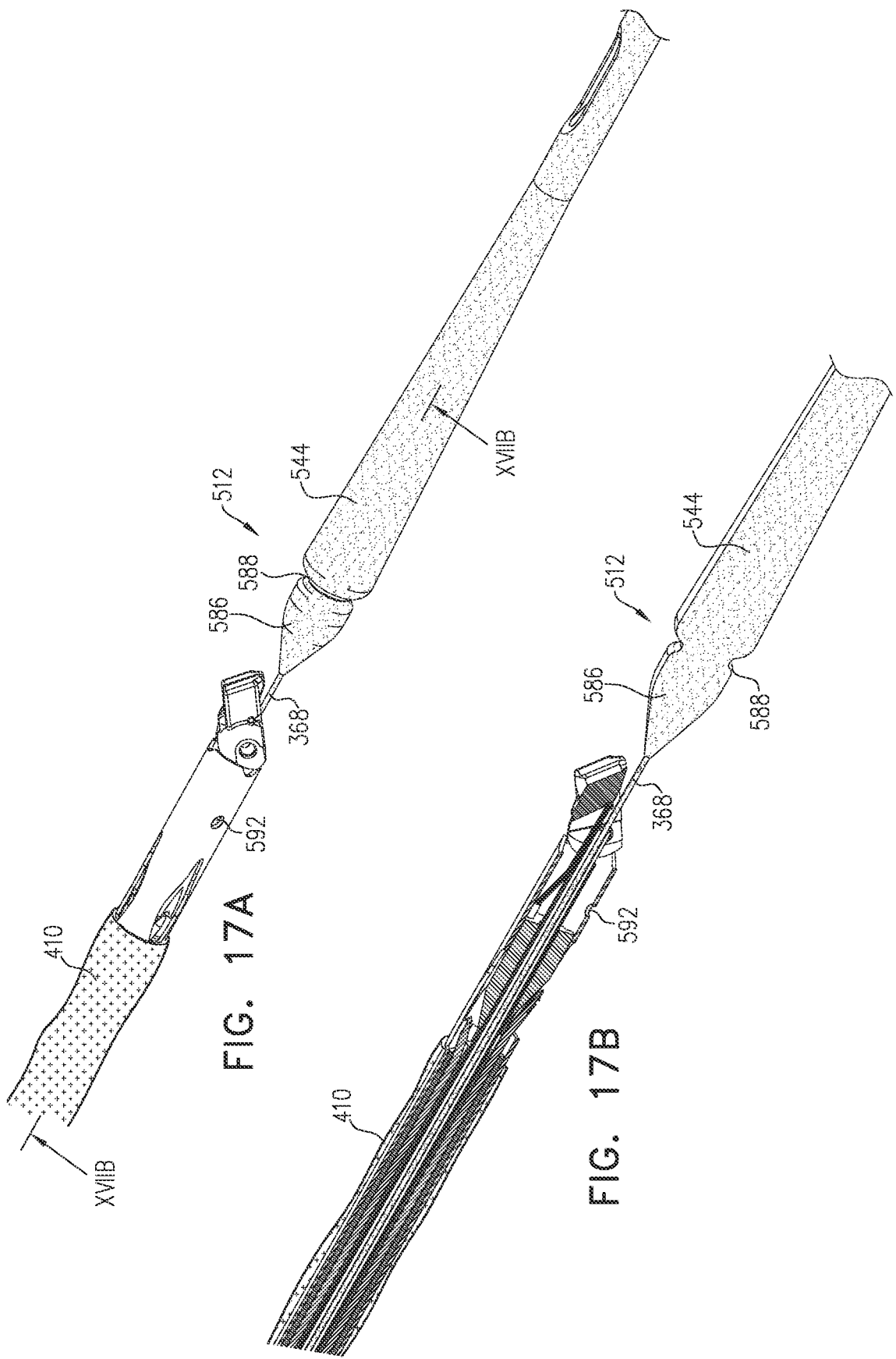

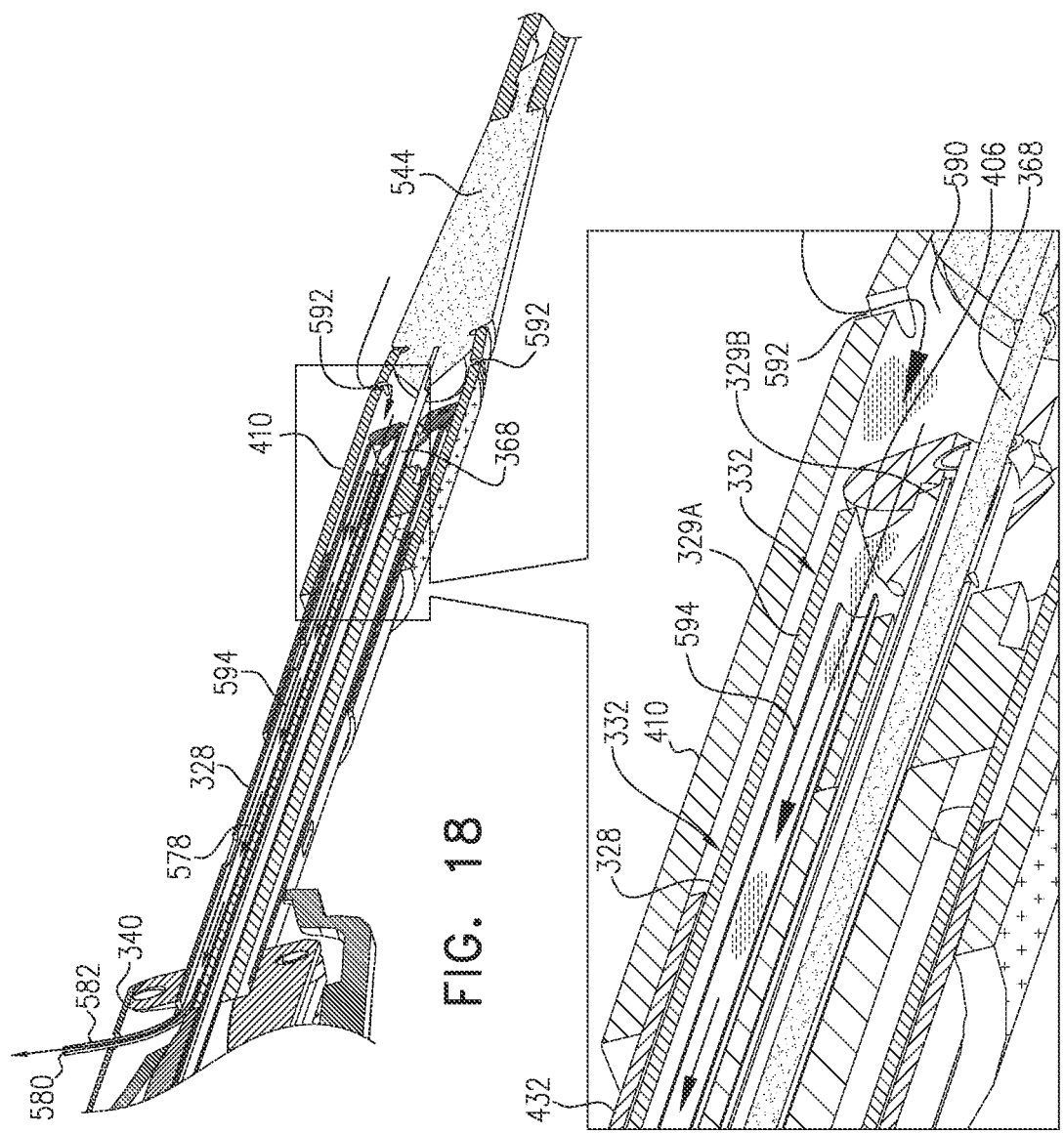

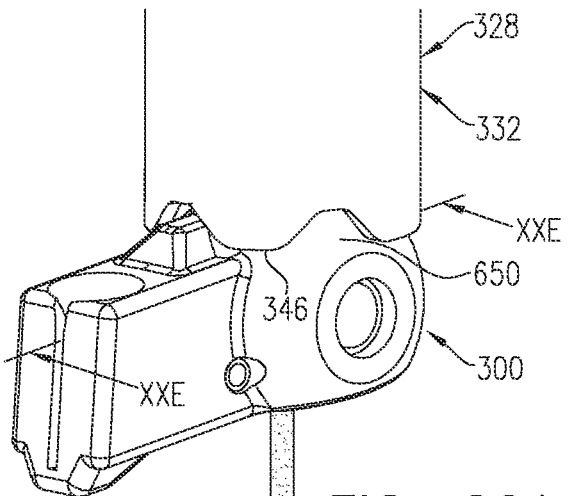
FIG. 20A
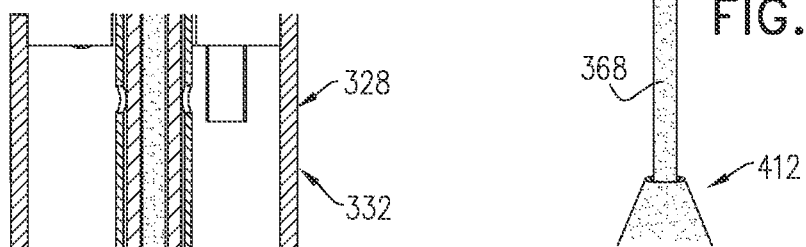
FIG. 20B
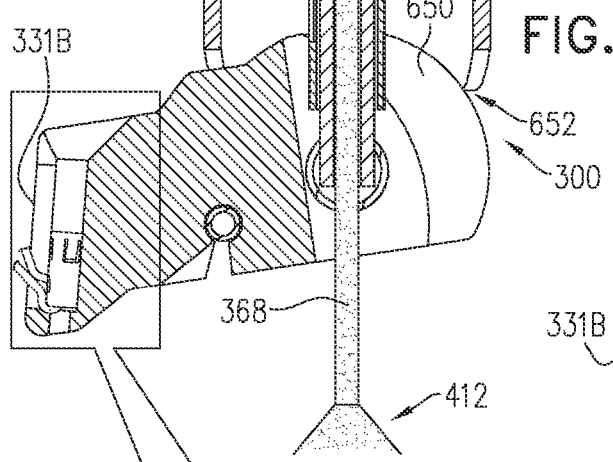
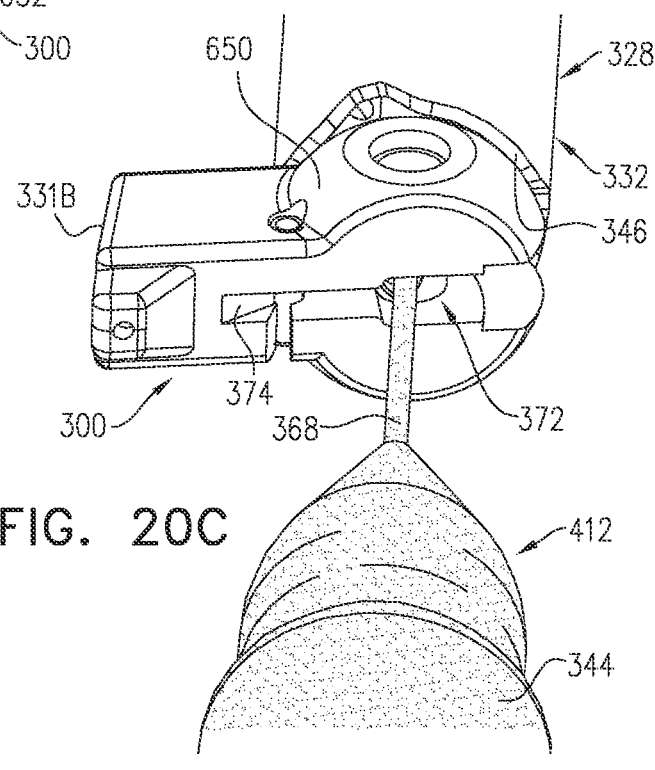
FIG. 20C
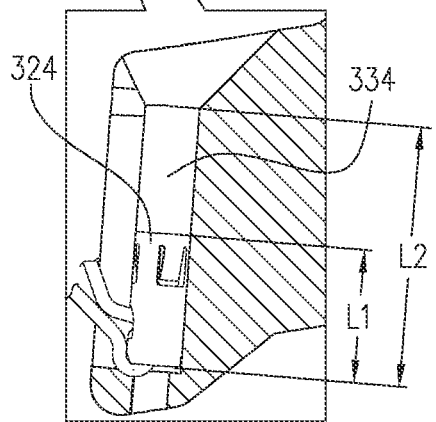

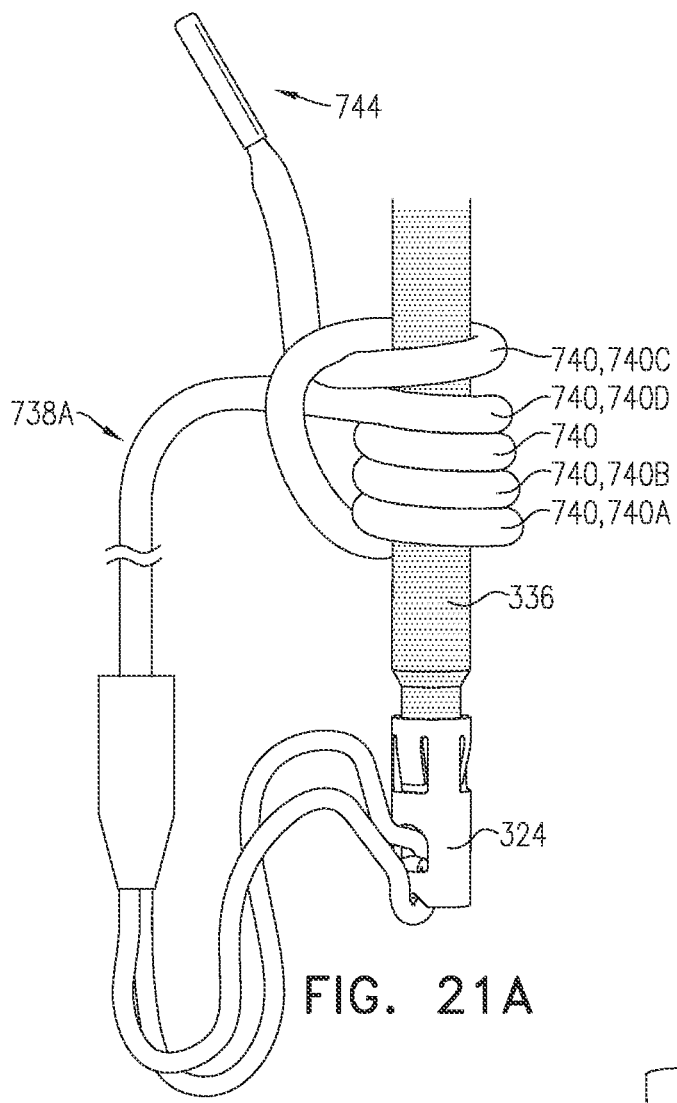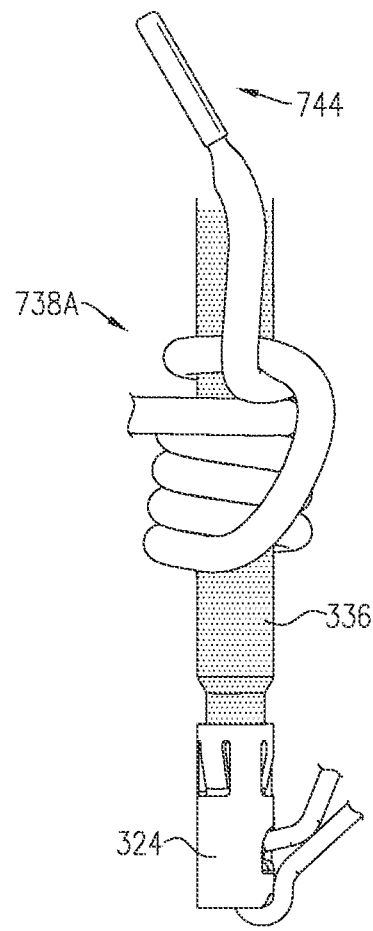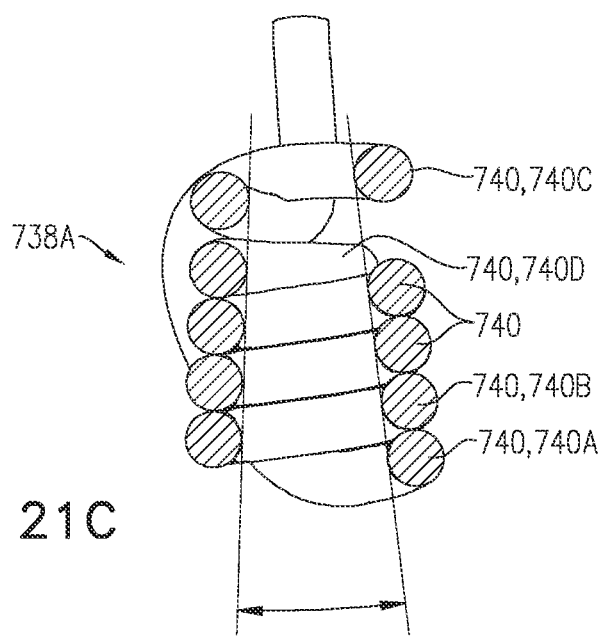
FIG. 21A
FIG. 21B
FIG. 21C

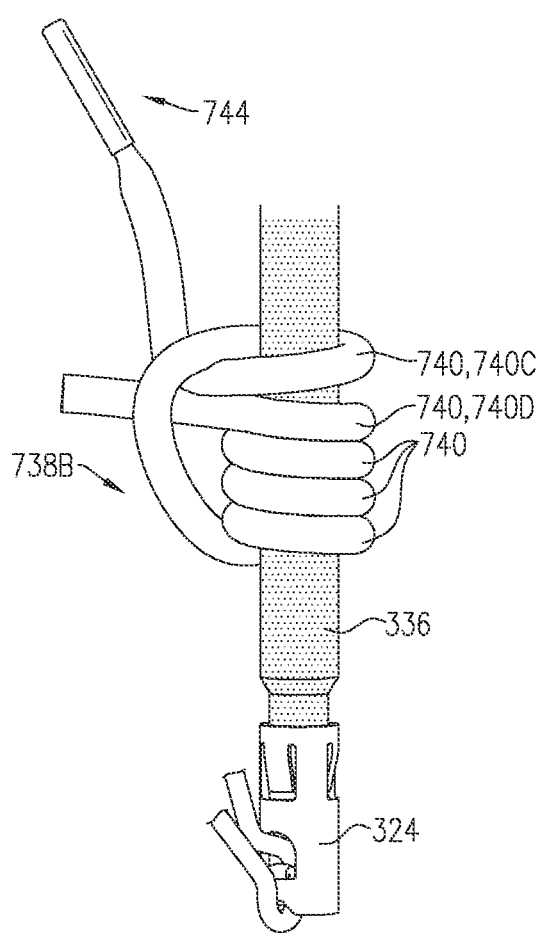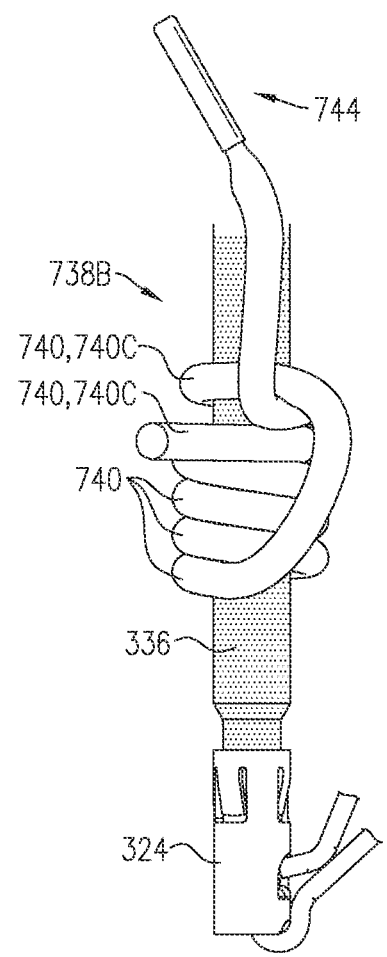
FIG. 22A  FIG. 22B
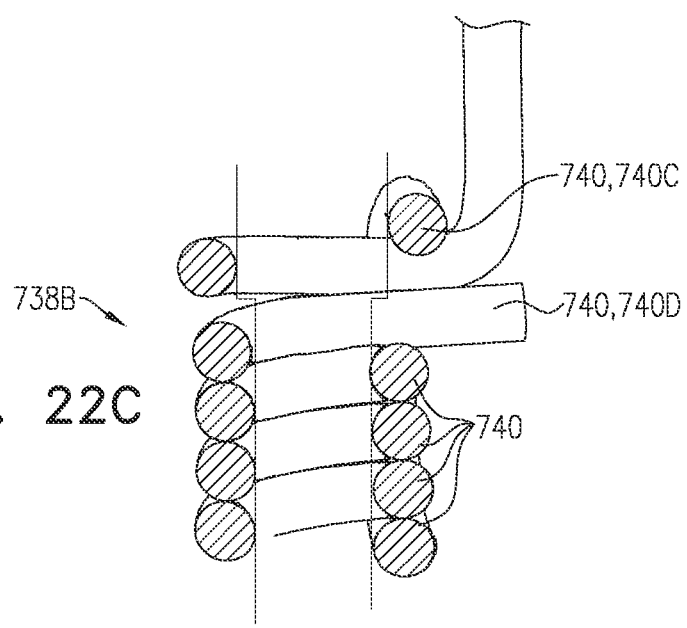
FIG. 22C

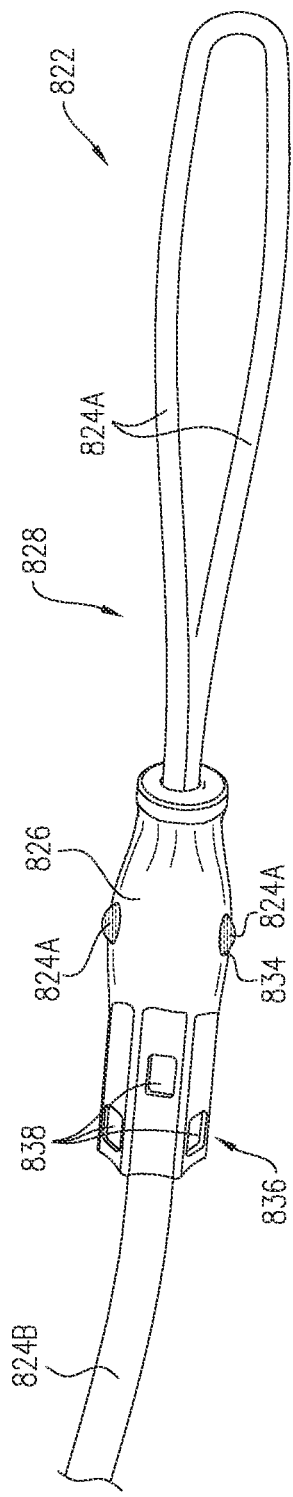
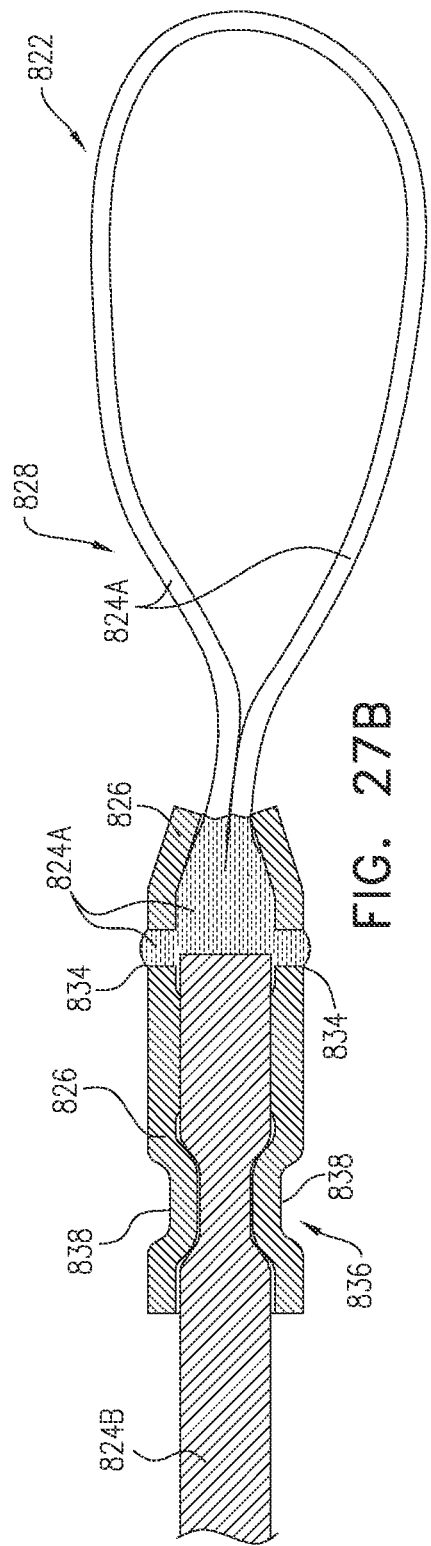
FIG. 27A
FIG. 27B

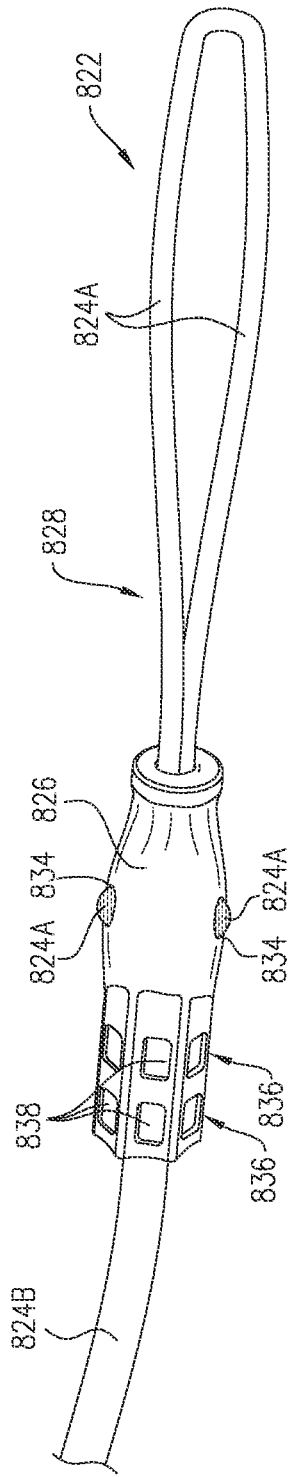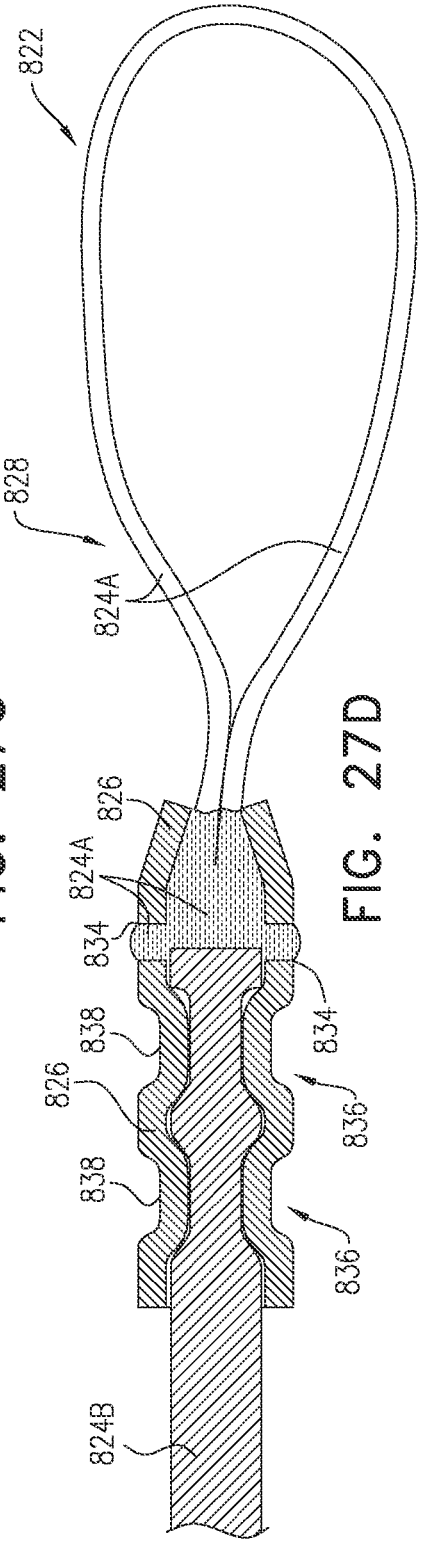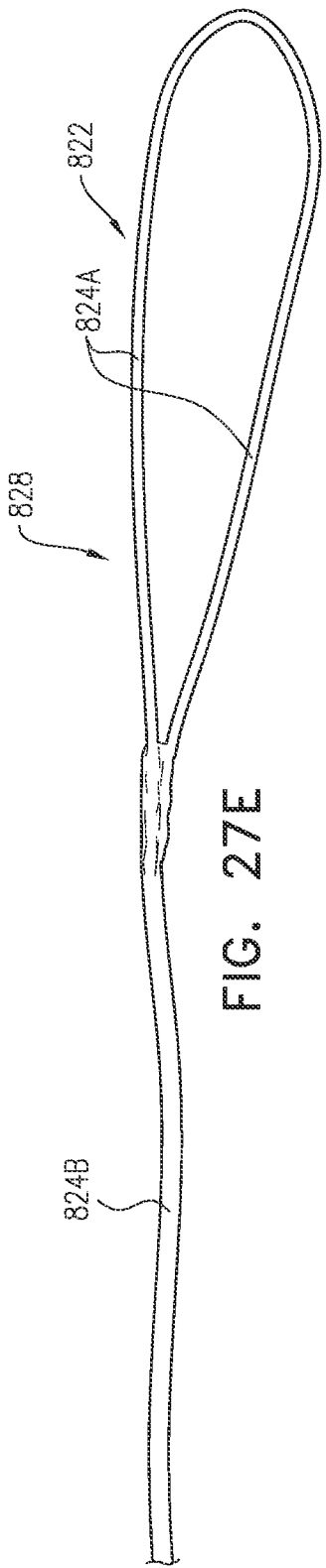
FIG. 27C
FIG. 27D
FIG. 27E

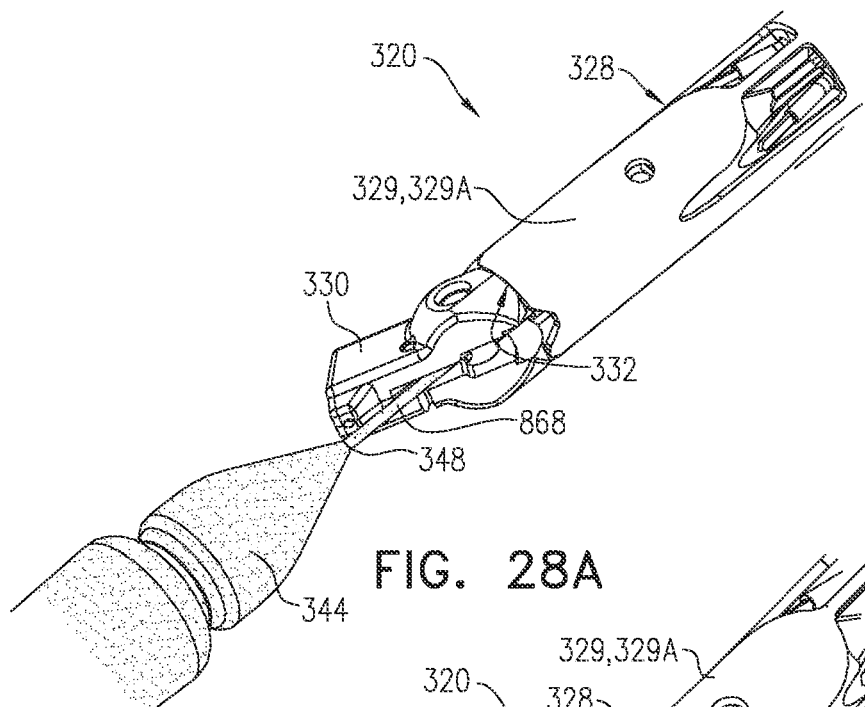
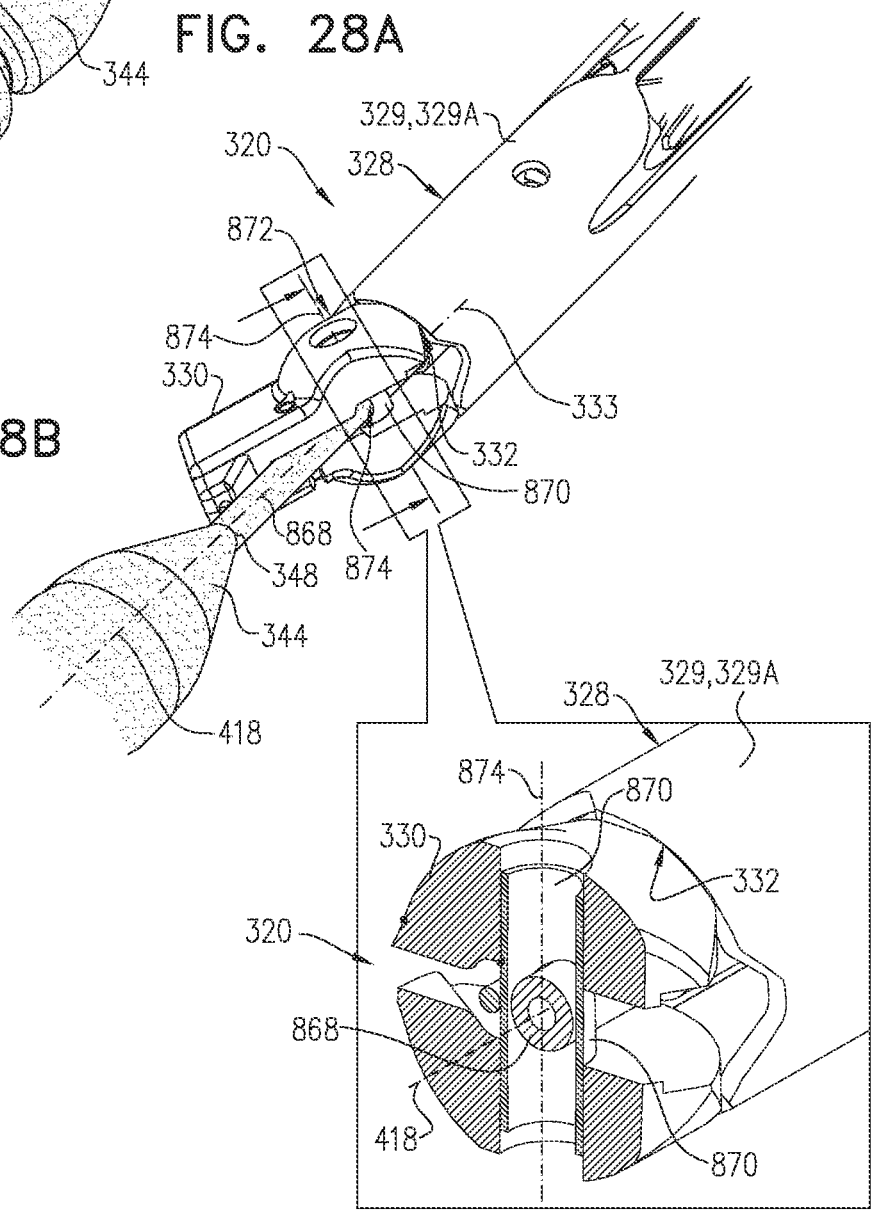

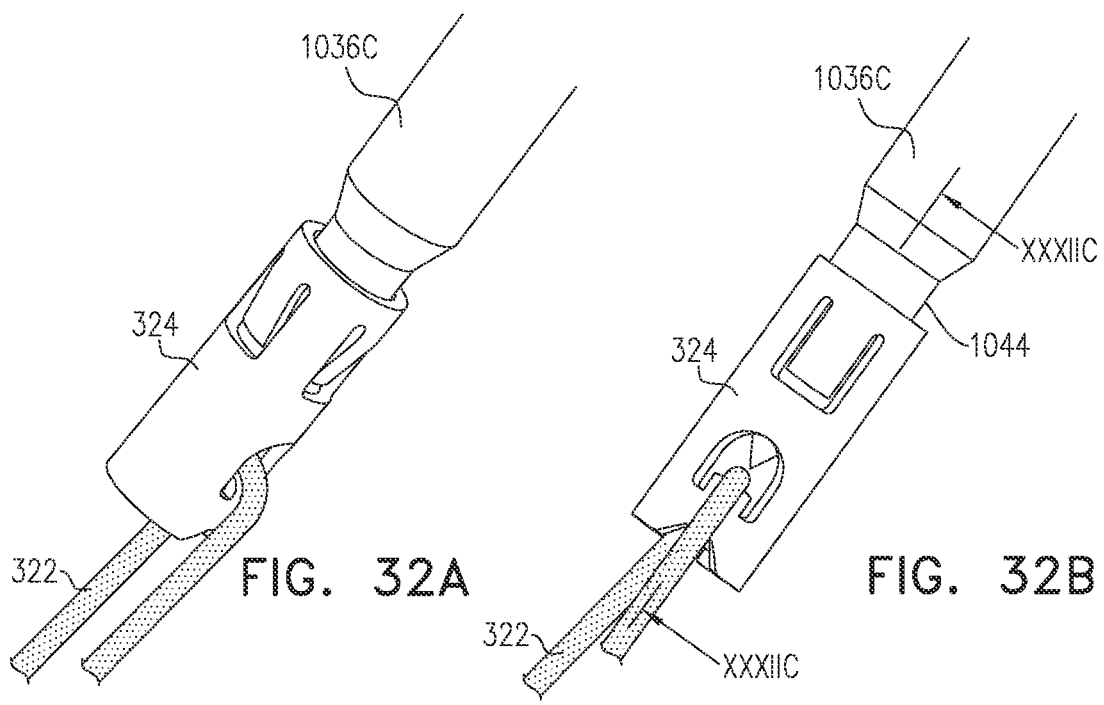
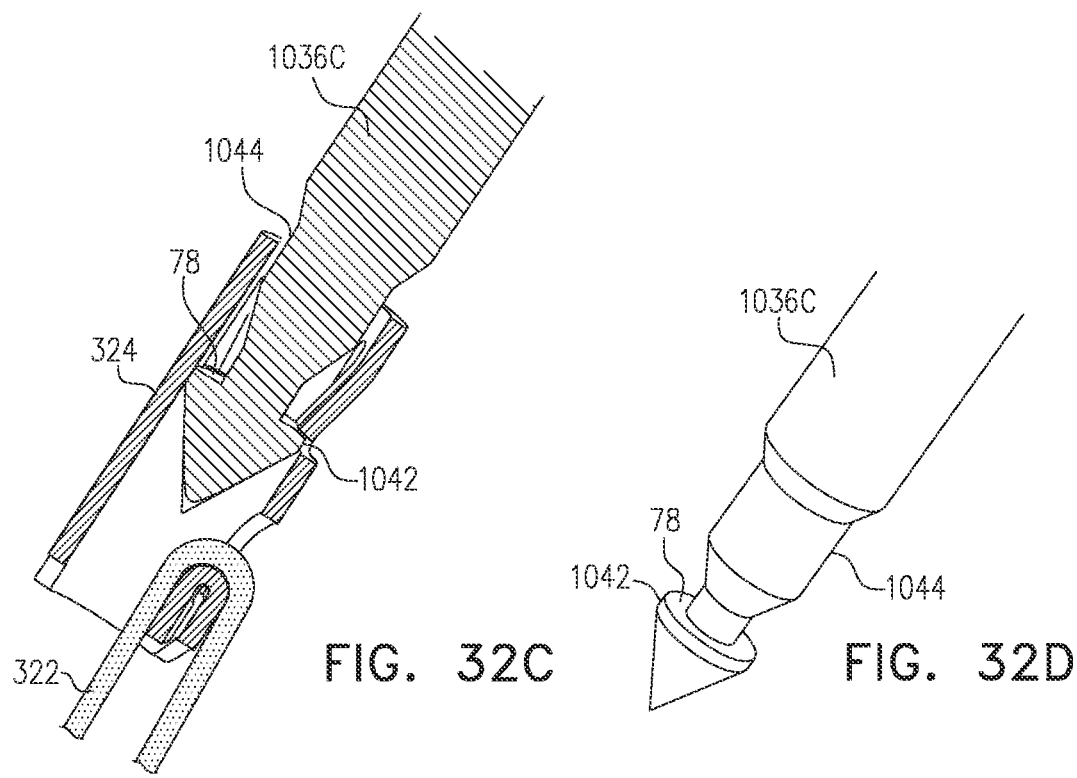

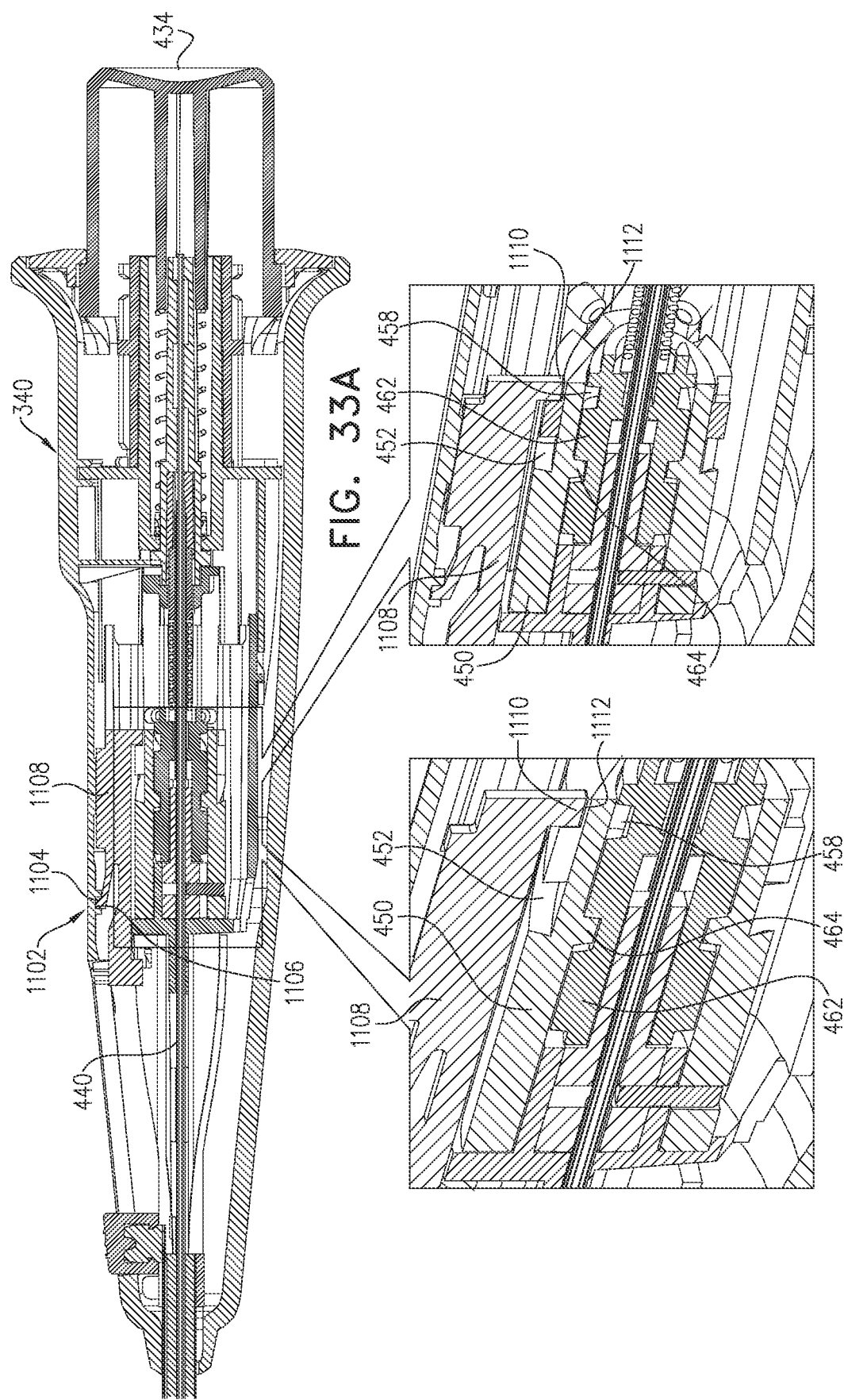

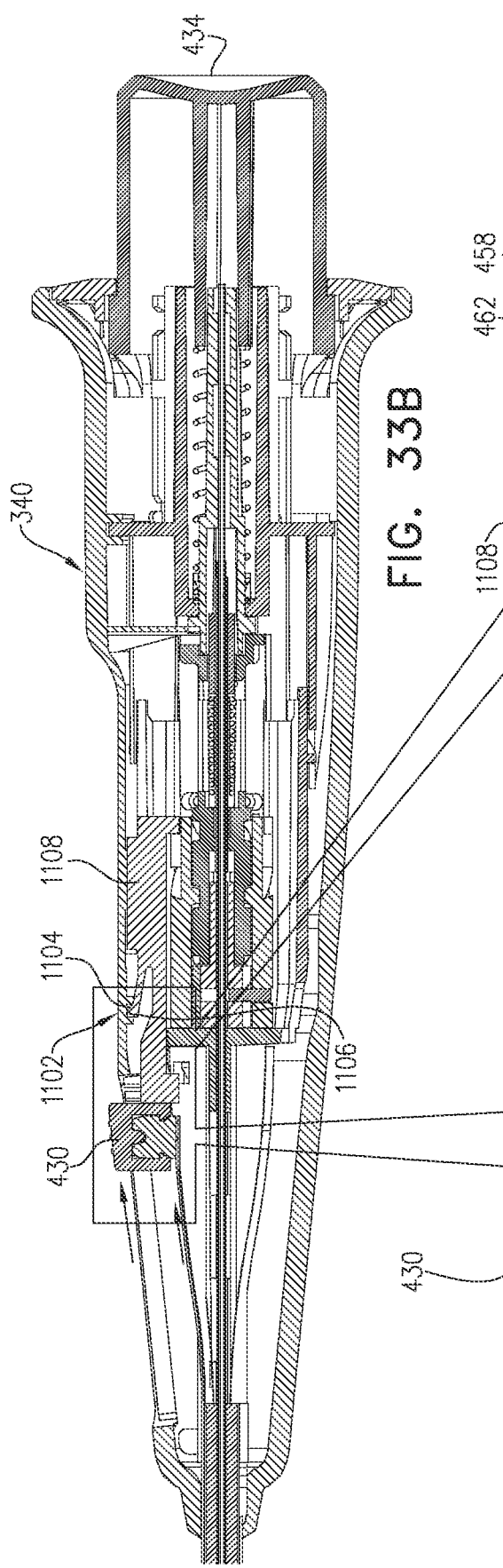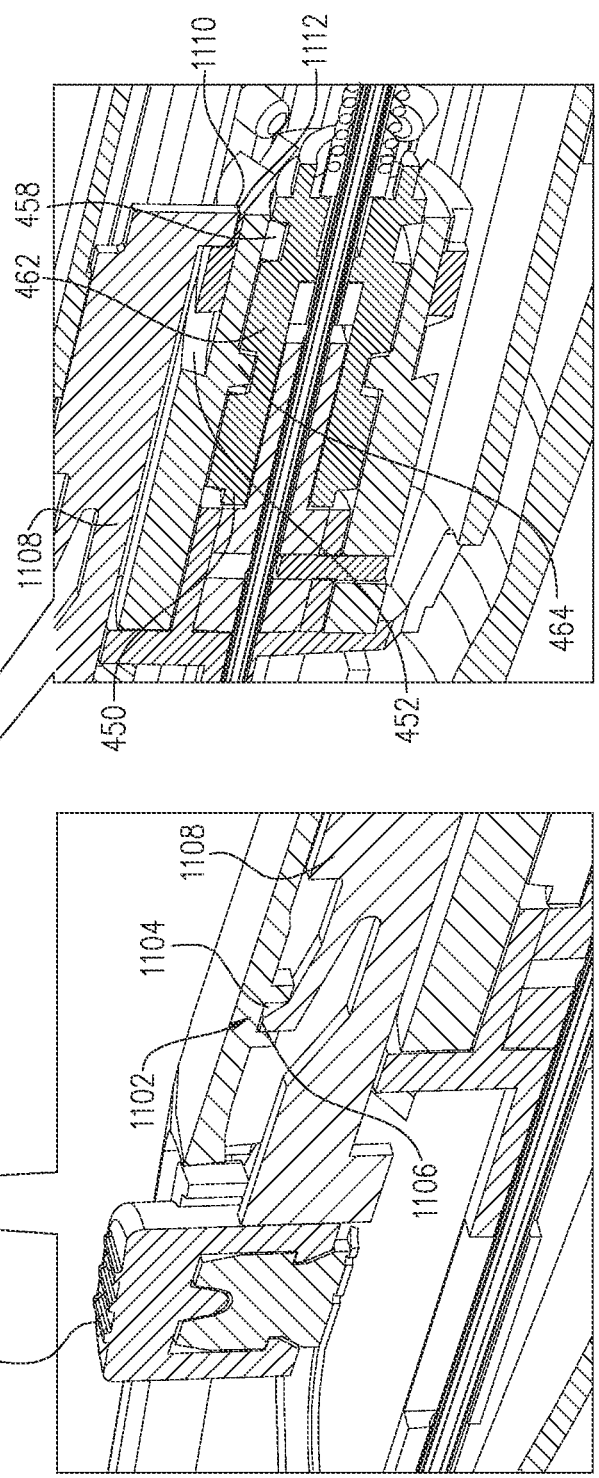
FIG. 33B

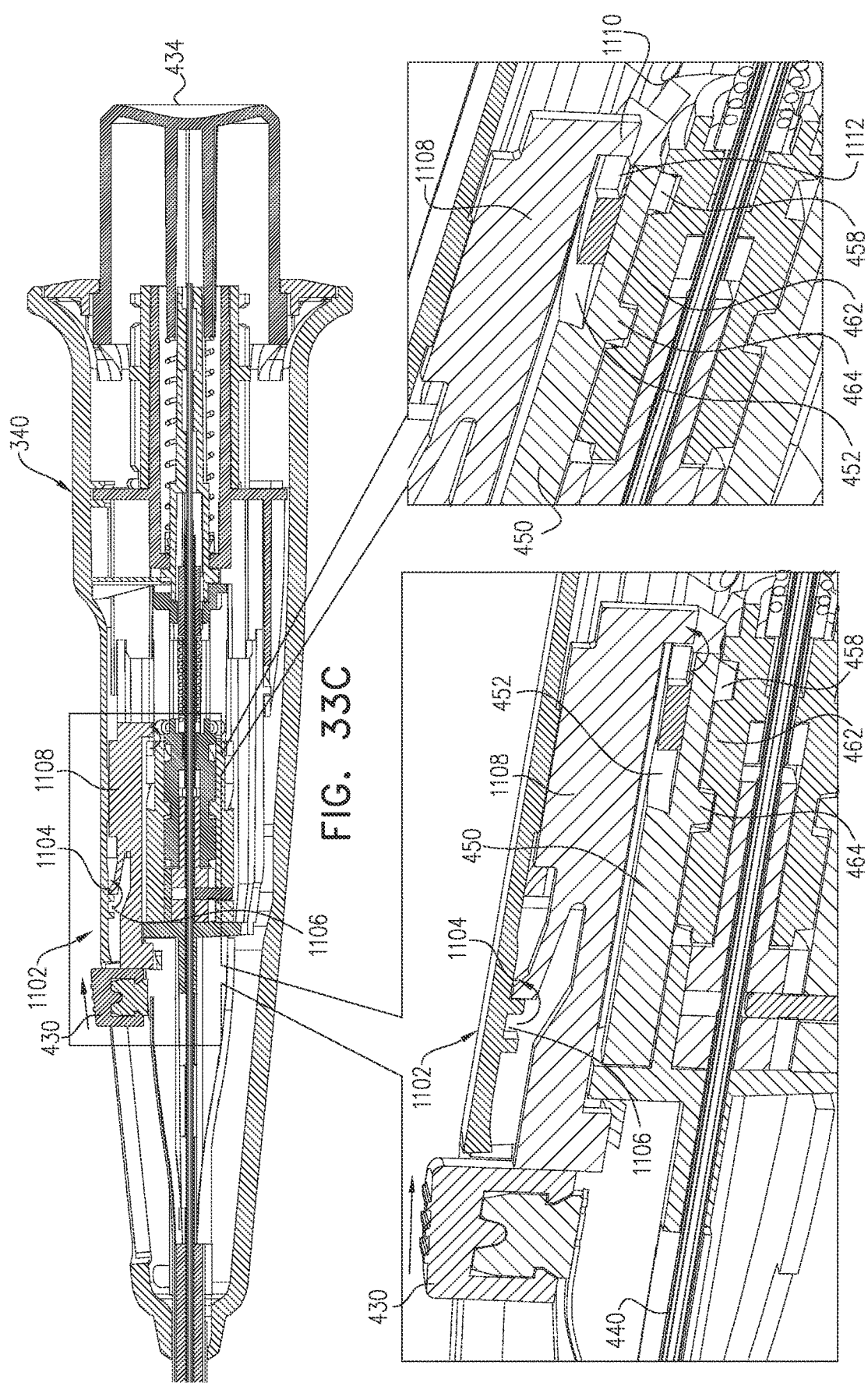

SUTURE CLOSURE DEVICES

CROSS-REFERENCE TO RELATED APPLICATIONS

The present application is a continuation of International Application PCT/IL2023/050966, filed Sep. 7, 2023, which published as PCT Publication WO 2024/052916 to Iamberger, and which claims priority from (i) U.S. Provisional Application 63/404,630, filed Sep. 8, 2022, and (ii) U.S. Provisional Application 63/526,765, filed Jul. 14, 2023. All of the above-mentioned applications are assigned to the assignee of the present application and incorporated herein by reference.

FIELD OF THE APPLICATION

The present invention relates generally to closure devices, and specifically to suture closure devices.

BACKGROUND OF THE APPLICATION

Vascular access for diagnostic and interventional vascular procedures is usually established using the Seldinger technique. Suture-applying devices are sometimes used to close the vascular access site upon completion of the procedure. These devices include a shaft that is inserted into the blood vessel through the vascular puncture, and one or more needles that are used to draw a suture through the blood vessel wall on opposite sides of the puncture. The suture is then secured outside the blood vessel to provide closure.

Closure devices are also used to deploy sutures within the body of a patient, such as to close surgical punctures, including endoscopic port site punctures. The devices are used to draw a suture through the fascia, muscle, and peritoneum layers of the endoscopic port site puncture on opposite sides of the puncture. The suture is then secured outside the fascia to close the fascia and peritoneum.

US Patent Application Publication 2013/0310856 to Sherts et al. describes suture passer guides and related kits and methods. In certain aspects, a suture passer guide includes an elongate member and a suture positioning member that can be radially extended from a distal end region of the elongate member and rotated relative to the elongate member such that the suture positioning member can reposition a suture from a first side area of the elongate member to a second side area of the elongate member.

US Patent Application Publication 2008/0045979 to Ma describes devices, systems, and methods for suturing of body lumens to allow the suturing of vascular puncture sites located at the distal end of a percutaneous tissue tract. An elongated articulated foot of the device can be inserted through the penetration and actuated so that the foot extends along the lumenal axis. The foot can carry suturing attachment cuffs with one end of the cuff adapted to receive a needle, while the other end receives suture. A portion of the foot and/or lumen of the shaft can receive a portion of the suture and can include friction reducing structure that aid with movement of the sutured during removal of the cuffs from within the penetration.

SUMMARY OF THE APPLICATION

Embodiments of the present invention provide closure devices for suturing a puncture through a wall of a hollow anatomical structure, such as a blood vessel, at an access site. The closure devices comprises one or more sutures; one or more ferrules, coupled to distal end portions of the one or more sutures, respectively; and an elongate support. A suture-positioning support is laterally extendable from a distal portion of the shaft, and is shaped so as to define a ferrule receptacle, which is configured to removably receive the one or more ferrules. A suturing needle is removably couplable to each of the one or more ferrules. The closure devices are configured to direct the one or more ferrules into the ferrule receptacle during distal advancement of the respective suturing needles removably coupled to the respective ferrules.

Methods are also provided for using the closure devices for suturing the puncture. The distal portion of the shaft inserted through the puncture and into the hollow anatomical structure while the suture-positioning support is in a delivery position. The suture-positioning support is transitioned from the delivery position to a first deployed position in which the suture-positioning support laterally extends in a first direction from the distal portion of the shaft. One of the one or more suturing needles is distally advanced through a first wall site of the wall and into the hollow anatomical structure, while the suturing needle is removably coupled to the ferrule, such that the closure device directs one of the one or more ferrules into the ferrule receptacle defined by the suture-positioning support and the ferrule receptacle removably receives the ferrule while the suture-positioning support is in the first deployed position. The suturing needle is proximally withdrawn from the ferrule and the hollow anatomical structure, while leaving the ferrule within the ferrule receptacle.

The suture-positioning support is transitioned from the first deployed position to a second deployed position in which the suture-positioning support laterally extends in a second direction from the distal portion of the shaft, the second direction different from the first direction. The ferrule is proximally withdrawn from the ferrule receptacle and out of the hollow anatomical structure via a second wall site of the wall, so as to proximally withdraw a portion of the suture, including the distal end portion thereof, out of the hollow anatomical structure via the second wall site. The portion of the suture drawn out of the hollow anatomical structure via the second wall site is secured to another portion of the suture outside the hollow anatomical structure.

There is therefore provided, in accordance with an Inventive Concept 1 of the present invention, a closure device for suturing a puncture, the closure device comprising:
   a suture;
   an elongate support, which comprises one or more shafts;
   a suture-positioning support, which is (a) coupled to a distal end portion of the elongate support, (b) laterally extendable with respect to the distal end portion of the elongate support, and (c) configured to removably receive the suture; and
   an elongate dilator, which is configured to be inserted through the puncture, and which has a proximal end that is coupled to the distal end portion of the elongate support,
   wherein the closure device is configured to allow movement of the distal end portion of the elongate support with respect to the proximal end of the dilator with at least two degrees of freedom.

Inventive Concept 2. The closure device according to Inventive Concept 1, wherein the at least two degrees of freedom include at least one rotational degree of freedom.

Inventive Concept 3. The closure device according to Inventive Concept 2, comprising:

a dilator-connection shaft; and a joint that couples the dilator-connection shaft to the distal end portion of the elongate support, so as to allow the movement of the distal end portion of the elongate support with respect to the proximal end of the dilator with the at least one rotational degree of freedom.

Inventive Concept 4. The closure device according to Inventive Concept 3, wherein the joint comprises a hinge.

Inventive Concept 5. The closure device according to Inventive Concept 2, wherein the at least two degrees of freedom include at least two rotational degrees of freedom.

Inventive Concept 6. The closure device according to Inventive Concept 5, comprising:

a dilator-connection shaft; and a joint that couples the dilator-connection shaft to the distal end portion of the elongate support, so as to allow the movement of the distal end portion of the elongate support with respect to the proximal end of the dilator with the at least two rotational degrees of freedom.

Inventive Concept 7. The closure device according to Inventive Concept 6, wherein the joint comprises a hinge and a twisting joint.

Inventive Concept 8. The closure device according to Inventive Concept 5, wherein the at least two degrees of freedom include three rotational degrees of freedom.

Inventive Concept 9. The closure device according to Inventive Concept 9, wherein the at least two degrees of freedom include at least one translational degree of freedom.

Inventive Concept 10. The closure device according to Inventive Concept 9, wherein the at least one translational degree of freedom includes a translational degree of freedom along a distal-support central longitudinal axis of the distal end portion of the elongate support.

Inventive Concept 11. The closure device according to Inventive Concept 9, wherein the at least two degrees of freedom include at least two translational degrees of freedom.

Inventive Concept 12. The closure device according to Inventive Concept 11, wherein the closure device is configured to allow the movement of the distal end portion of the elongate support with respect to the proximal end of the dilator with three translational degrees of freedom.

Inventive Concept 13. The closure device according to Inventive Concept 9, wherein the closure device is configured to allow the movement of the distal end portion of the elongate support with respect to the proximal end of the dilator with at least four degrees of freedom.

Inventive Concept 14. The closure device according to Inventive Concept 13, wherein the closure device is configured to allow the movement of the distal end portion of the elongate support with respect to the proximal end of the dilator with six degrees of freedom.

There is further provided, in accordance with an Inventive Concept 15 of the present invention, a closure device for suturing a puncture, the closure device comprising:

a suture;

an elongate support, which comprises one or more shafts;

a suture-positioning support, which is (a) coupled to a distal end portion of the elongate support, (b) laterally extendable with respect to the distal end portion of the elongate support, and (c) configured to removably receive the suture; and an elongate dilator, which is configured to be inserted through the puncture, and which has a proximal end that is coupled to the distal end portion of the elongate support, wherein the closure device is configured to allow movement of the distal end portion of the elongate support with respect to the proximal end of the dilator with at least one translational degree of freedom.

Inventive Concept 16. The closure device according to Inventive Concept 15, wherein the at least one translational degree of freedom includes a translational degree of freedom along a distal-support central longitudinal axis of the distal end portion of the elongate support.

Inventive Concept 17. The closure device according to Inventive Concept 15, wherein the at least one translational degree of freedom includes at least two translational degrees of freedom.

Inventive Concept 18. The closure device according to Inventive Concept 17, wherein the at least two translational degrees of freedom includes three translational degrees of freedom.

Inventive Concept 19. The closure device according to any one of Inventive Concepts 1 and 15, wherein the elongate support comprises an outer tubular shaft having a distal end, wherein the closure device further comprises a sheath that covers: the distal end of the outer tubular shaft, the suture-positioning support, and a proximal end portion of the dilator that includes the proximal end of the dilator, and wherein the sheath is proximally withdrawable along the outer tubular shaft so as to expose the suture-positioning support, and the proximal end portion of the dilator.

There is still further provided, in accordance with an Inventive Concept 20 of the present invention, a closure device for suturing a puncture, the closure device comprising:

a suture;

an elongate support, which comprises one or more shafts;

a suture-positioning support, which is (a) coupled to a distal end portion of the elongate support, (b) laterally extendable with respect to the distal end portion of the elongate support, and (c) configured to removably receive the suture;

an elongate dilator, which is configured to be inserted through the puncture, and which has a proximal end that is coupled to the distal end portion of the elongate support; and an elongate flexible dilator connector, which couples the proximal end of the dilator to the distal end portion of the elongate support so as to allow movement of the distal end portion of the elongate support with respect to the proximal end of the dilator, wherein an average outer diameter of the dilator connector is less than 20% of a greatest outer diameter of the dilator.

Inventive Concept 21. The closure device according to any one of Inventive Concepts 1, 15, and 20, wherein the closure device is configured to allow the movement without requiring the distal end portion of the elongate support to directly or indirectly apply a force to the proximal end of the dilator.

Inventive Concept 22. The closure device according to any one of Inventive Concepts 1, 15, and 20, wherein the closure device is configured to allow the movement without requiring bending of the dilator.

Inventive Concept 23. The closure device according to any one of Inventive Concepts 1, 15, and 20, wherein the closure device is configured to allow the movement without requiring deformation of the dilator.

Inventive Concept 24. The closure device according to any one of Inventive Concepts 1, 15, and 20, wherein the distal end portion of the elongate support defines a distal-support central longitudinal axis, and a proximal end portion of the dilator, which includes the proximal end of the dilator, defines a proximal-dilator central longitudinal axis, and wherein the closure device is configured to allow the distal end portion of the elongate support to move with respect to the proximal end of the dilator from defining a first angle to defining a second angle between the distal-support central longitudinal axis and the proximal-dilator central longitudinal axis, wherein the first angle is less than 30 degrees and the second angle is 45-90 degrees.

Inventive Concept 25. The closure device according to Inventive Concept 24, wherein the second angle is 60-90 degrees.

Inventive Concept 26. The closure device according to Inventive Concept 25, wherein the second angle is 75-90 degrees.

Inventive Concept 27. The closure device according to any one of Inventive Concepts 1, 15, and 20,
wherein the distal end portion of the elongate support defines a distal-support central longitudinal axis, and a proximal end portion of the dilator, which includes the proximal end of the dilator, defines a proximal-dilator central longitudinal axis, and
wherein the closure device is configured to allow the distal end portion of the elongate support to move with respect to the proximal end of the dilator from defining a first angle to defining a second angle between the distal-support central longitudinal axis and the proximal-dilator central longitudinal axis, wherein the second angle is at least 15 degrees greater than the first angle.

Inventive Concept 28. The closure device according to Inventive Concept 27, wherein the second angle is at least 30 degrees greater than the first angle.

Inventive Concept 29. The closure device according to Inventive Concept 28, wherein the second angle is at least 45 degrees greater than the first angle.

Inventive Concept 30. The closure device according to Inventive Concept 29, wherein the second angle is at least 60 degrees greater than the first angle.

Inventive Concept 31. The closure device according to any one of Inventive Concepts 1, 15, and 20, wherein the dilator comprises a flexible polymer.

Inventive Concept 32. The closure device according to any one of Inventive Concepts 1 and 15, further comprising an elongate flexible dilator connector, which couples the proximal end of the dilator to the distal end portion of the elongate support so as to allow the movement.

Inventive Concept 33. The closure device according to Inventive Concept 32, wherein an average outer diameter of the dilator connector is less than 20% of a greatest outer diameter of the dilator.

Inventive Concept 34. The closure device according to any one of Inventive Concepts 20 and 32,
wherein the distal end portion of the elongate support defines a distal-support central longitudinal axis, and a proximal end portion of the dilator, which includes the proximal end of the dilator, defines a proximal-dilator central longitudinal axis, and
wherein the elongate flexible dilator connector couples the proximal end of the dilator to the distal end portion of the elongate support so as to allow the distal end portion of the elongate support to move with respect to the proximal end of the dilator from defining a first angle to defining a second angle between the distal-support central longitudinal axis and the proximal-dilator central longitudinal axis, wherein the first angle is less than 30 degrees and the second angle is 45-90 degrees.

Inventive Concept 35. The closure device according to claim 34, wherein the second angle is 60-90 degrees.

Inventive Concept 36. The closure device according to Inventive Concept 35, wherein the second angle is 75-90 degrees.

Inventive Concept 37. The closure device according to any one of Inventive Concepts 20 and 32,
wherein the distal end portion of the elongate support defines a distal-support central longitudinal axis, and a proximal end portion of the dilator, which includes the proximal end of the dilator, defines a proximal-dilator central longitudinal axis, and
wherein the elongate flexible dilator connector couples the proximal end of the dilator to the distal end portion of the elongate support so as to allow the distal end portion of the elongate support to move with respect to the proximal end of the dilator from defining a first angle to defining a second angle between the distal-support central longitudinal axis and the proximal-dilator central longitudinal axis, wherein the second angle is at least 15 degrees greater than the first angle.

Inventive Concept 38. The closure device according to Inventive Concept 37, wherein the second angle is at least 30 degrees greater than the first angle.

Inventive Concept 39. The closure device according to Inventive Concept 38, wherein the second angle is at least 45 degrees greater than the first angle.

Inventive Concept 40. The closure device according to Inventive Concept 39, wherein the second angle is at least 60 degrees greater than the first angle.

Inventive Concept 41. The closure device according to any one of Inventive Concepts 20 and 32, wherein the dilator connector and the dilator comprise separate respective elements coupled together.

Inventive Concept 42. The closure device according to any one of Inventive Concepts 20 and 32, wherein the dilator connector and the dilator are integrally formed from a single element.

Inventive Concept 43. The closure device according to any one of Inventive Concepts 20 and 32, wherein the dilator connector comprises an element selected from the group of elements consisting of: a cable, a cord, a wire, and a string.

Inventive Concept 44. The closure device according to any one of Inventive Concepts 20 and 32, wherein the dilator connector comprises a tube.

Inventive Concept 45. The closure device according to any one of Inventive Concepts 20 and 32, wherein a flexural rigidity of the dilator is greater than a flexural rigidity of the dilator connector.

Inventive Concept 46. The closure device according to any one of Inventive Concepts 20 and 32, wherein a material of the dilator is harder than a material of the dilator connector.

Inventive Concept 47. The closure device according to any one of Inventive Concepts 20 and 32, wherein an average outer diameter of the dilator connector is 0.2-0.8 mm.

Inventive Concept 48. The closure device according to any one of Inventive Concepts 20 and 32, wherein the dilator connector has a length of 0.5-5 cm.

Inventive Concept 49. The closure device according to any one of Inventive Concepts 20 and 32, wherein the dilator connector comprises a material selected from the group of materials consisting of Nitinol and stainless steel.

Inventive Concept 50. The closure device according to any one of Inventive Concepts 20 and 28
 wherein the dilator connector is rotationally fixed to the distal end portion of the elongate support and the proximal end of the dilator, and
 wherein the dilator connector couples the proximal end of the dilator to the distal end portion of the elongate support so as to allow rotation of the distal end portion of the elongate support about a distal-support central longitudinal axis thereof without corresponding rotation of the dilator about a proximal-dilator central longitudinal axis of a proximal end portion of the dilator.

Inventive Concept 51. The closure device according to any one of Inventive Concepts 20 and 32, wherein the closure device is configured to allow lateral movement of the dilator while the distal end portion of the elongate support remains stationary with respect to the puncture.

Inventive Concept 52. The closure device according to any one of Inventive Concepts 20 and 32,
 wherein the elongate support comprises an outer tubular shaft having a distal end,
 wherein the closure device further comprises a sheath that covers: the distal end of the outer tubular shaft, the suture-positioning support, the dilator connector, and a proximal end portion of the dilator that includes the proximal end of the dilator, and
 wherein the sheath is proximally withdrawable along the outer tubular shaft so as to expose the suture-positioning support, the dilator connector, and the proximal end portion of the dilator.

Inventive Concept 53. The closure device according to any one of Inventive Concepts 20 and 32,
 wherein the suture-positioning support is shaped so as to define a passage therethrough, and
 wherein the dilator connector is disposed passing through the passage.

Inventive Concept 54. The closure device according to any one of Inventive Concepts 1, 15, and 20, wherein the dilator is shaped so as to define an atraumatic proximal tip.

Inventive Concept 55. The closure device according to Inventive Concept 54, wherein the atraumatic proximal tip is tapered.

Inventive Concept 56. The closure device according to any one of Inventive Concepts 1, 15, and 20,
 wherein the closure device further comprises:
  a ferrule, which is coupled to a distal end portion of the suture; and
  a suturing needle, which is removably couplable to the ferrule,
 wherein the suture-positioning support is shaped so as to define a ferrule receptacle, which is configured to removably receive the ferrule, such that the suture-positioning support is configured to removably receive the suture, and
 wherein the closure device is configured to direct the ferrule into the ferrule receptacle during distal advancement of the suturing needle removably coupled to the ferrule.

Inventive Concept 57. The closure device according to Inventive Concept 56, wherein the ferrule is shaped so as to define a blunt interface with the distal end portion of the suture.

Inventive Concept 58. The closure device according to Inventive Concept 57,
 wherein the blunt interface is defined by a flap defined by at least a portion of material cut from a wall of the ferrule to define an opening through the wall,
 wherein the at least a portion of the material is bent so as to define the flap having a curved bend, and
 wherein the suture passes through the opening.

Inventive Concept 59. The closure device according to Inventive Concept 58, wherein the suture is looped through the opening.

Inventive Concept 60. The closure device according to Inventive Concept 57, wherein the blunt interface is defined by a curved surface of a rod fixed to a perimeter of an opening through a wall of the ferrule, and wherein the suture passes through the opening around the rod.

Inventive Concept 61. The closure device according to Inventive Concept 60, wherein the suture is looped through the opening around the rod.

Inventive Concept 62. The closure device according to any one of Inventive Concepts 1, 15, and 20,
 wherein the elongate support comprises an outer tubular shaft having a distal end,
 wherein the suture-positioning support has proximal and distal end portions at opposite ends of the suture-positioning support,
 wherein the proximal end portion of the suture-positioning support is coupled to the elongate support, and
 wherein the distal end portion of the suture-positioning support is disposed distally to the distal end of the outer tubular shaft.

Inventive Concept 63. The closure device according to Inventive Concept 62, wherein the elongate support further comprises an inner shaft nested within the outer tubular shaft, and wherein the suture-positioning support is coupled to the inner shaft of the elongate support.

Inventive Concept 64. The closure device according to any one of Inventive Concepts 1, 15, and 20, wherein the suture-positioning support is configured to assume:
 a delivery position, in which a suture-positioning support axis of the suture-positioning support (a) forms a first angle of less than 45 degrees with a distal-support central longitudinal axis of the distal end portion of the elongate support, or (b) is parallel with the distal-support central longitudinal axis, and
 one or more deployed positions, in which the suture-positioning support is laterally extended with respect to the distal end portion of the elongate support such that the suture-positioning support axis forms a second angle of at least 60 degrees with the distal-support central longitudinal axis.

Inventive Concept 65. The closure device according to Inventive Concept 64, wherein the first angle is less than 30 degrees.

Inventive Concept 66. The closure device according to any one of Inventive Concepts 1, 15, and 20, wherein the puncture is an endoscopic puncture through a wall of a body cavity.

Inventive Concept 67. The closure device according to any one of Inventive Concepts 1, 15, and 20, wherein the puncture is a puncture through a wall of a blood vessel, and wherein the dilator is configured to be inserted through the puncture into the blood vessel.

Inventive Concept 68. The closure device according to Inventive Concept 67, wherein the closure device is configured to allow the movement without application by the dilator of a force to the wall of the blood vessel.

Inventive Concept 69. The closure device according to any one of Inventive Concepts 1, 15, and 20, wherein the suture-positioning support is disposed distally beyond a distal end of the elongate support.

Inventive Concept 70. The closure device according to any one of Inventive Concepts 1, 15, and 20,
wherein the suture is a first suture, and wherein the closure device further comprises a second suture, and wherein the suture-positioning support is configured to removably receive the second suture.

Inventive Concept 71. The closure device according to any one of Inventive Concepts 1, 15, and 20, further comprising a control handle, coupled to a proximal end portion of the elongate support.

Inventive Concept 72. The closure device according to any one of Inventive Concepts 1, 15, and 20, wherein the dilator is shaped so as to define a guidewire channel.

Inventive Concept 73. The closure device according to any one of Inventive Concepts 1, 15, and 20, wherein an external portion of the suture-positioning support that interfaces with the distal end portion of the elongate support is shaped so as to define one or more partial spherical surfaces.

There is additionally provided, in accordance with an Inventive Concept 73 of the present invention, a method for suturing a puncture through a wall of a blood vessel, the method comprising:
inserting an elongate dilator of a closure device through the puncture and into the blood vessel;
inserting, through the puncture and into the blood vessel, (a) a distal end portion of an elongate support of the closure device and (b) a suture-positioning support that is coupled to the distal end portion of the elongate support, wherein a proximal end of the dilator is coupled to the distal end portion of the elongate support, and wherein the closure device is configured to allow movement of the distal end portion of the elongate support with respect to the proximal end of the dilator with at least two degrees of freedom;
thereafter, laterally extending the suture-positioning support with respect to the distal end portion of the elongate support; and
distally advancing a suture through a portion of the elongate support and a wall site of the wall and into the blood vessel, and into the suture-positioning support.

Inventive Concept 75. The method according to Inventive Concept 74, further comprising moving the distal end portion of the elongate support with respect to the proximal end of the dilator with the at least two degrees of freedom.

Inventive Concept 76. The method according to Inventive Concept 75, wherein moving the distal end portion of the elongate support with respect to the proximal end of the dilator comprises moving the distal end portion of the elongate support with respect to the proximal end of the dilator without causing the dilator to apply a force to the wall of the blood vessel.

Inventive Concept 77. The method according to Inventive Concept 75, wherein moving the distal end portion of the elongate support with respect to the proximal end of the dilator comprises moving the distal end portion of the elongate support with respect to the proximal end of the dilator with at least one rotational degree of freedom.

Inventive Concept 78. The method according to Inventive Concept 77, wherein moving the distal end portion of the elongate support with respect to the proximal end of the dilator comprises moving the distal end portion of the elongate support with respect to the proximal end of the dilator with at least two rotational degrees of freedom.

Inventive Concept 79. The method according to Inventive Concept 78, wherein moving the distal end portion of the elongate support with respect to the proximal end of the dilator comprises moving the distal end portion of the elongate support with respect to the proximal end of the dilator with three rotational degrees of freedom.

Inventive Concept 80. The method according to Inventive Concept 80, wherein moving the distal end portion of the elongate support with respect to the proximal end of the dilator comprises moving the distal end portion of the elongate support with respect to the proximal end of the dilator with at least one translational degree of freedom.

Inventive Concept 81. The method according to Inventive Concept 80, wherein the at least one translational degree of freedom includes a translational degree of freedom along a distal-support central longitudinal axis of the distal end portion of the elongate support.

Inventive Concept 82. The method according to Inventive Concept 80, wherein moving the distal end portion of the elongate support with respect to the proximal end of the dilator comprises moving the distal end portion of the elongate support with respect to the proximal end of the dilator with at least two translational degrees of freedom.

Inventive Concept 83. The method according to Inventive Concept 82, wherein moving the distal end portion of the elongate support with respect to the proximal end of the dilator comprises moving the distal end portion of the elongate support with respect to the proximal end of the dilator with three translational degrees of freedom.

Inventive Concept 84. The method according to Inventive Concept 80, wherein moving the distal end portion of the elongate support with respect to the proximal end of the dilator comprises moving the distal end portion of the elongate support with respect to the proximal end of the dilator with at least four degrees of freedom.

Inventive Concept 85. The method according to Inventive Concept 84, wherein moving the distal end portion of the elongate support with respect to the proximal end of the dilator comprises moving the distal end portion of the elongate support with respect to the proximal end of the dilator with six degrees of freedom.

There is yet additionally provided, in accordance with an Inventive Concept 86 of the present invention, a method for suturing a puncture through a wall of a blood vessel, the method comprising:
inserting an elongate dilator of a closure device through the puncture and into the blood vessel;
inserting, through the puncture and into the blood vessel, (a) a distal end portion of an elongate support of the closure device and (b) a suture-positioning support that is coupled to the distal end portion of the elongate support, wherein a proximal end of the dilator is coupled to the distal end portion of the elongate support, and wherein the closure device is configured to allow movement of the distal end portion of the elongate support with respect to the proximal end of the dilator with at least one translational degree of freedom;
thereafter, laterally extending the suture-positioning support with respect to the distal end portion of the elongate support; and
distally advancing a suture through a portion of the elongate support and a wall site of the wall and into the blood vessel, and into the suture-positioning support.

Inventive Concept 87. The method according to Inventive Concept 86, further comprising moving the distal end portion of the elongate support with respect to the proximal end of the dilator with the at least one translational degree of freedom.

Inventive Concept 88. The method according to Inventive Concept 87, wherein moving the distal end portion of the elongate support with respect to the proximal end of the dilator comprises moving the distal end portion of the elongate support with respect to the proximal end of the dilator without causing the dilator to apply a force to the wall of the blood vessel.

Inventive Concept 89. The method according to any one of Inventive Concepts 74 and 86,
 wherein the elongate support includes an outer tubular shaft having a distal end,
 wherein inserting the distal end portion of the elongate support and the suture-positioning support through the puncture and into the blood vessel comprises inserting the distal end portion of the elongate support and the suture-positioning support through the puncture and into the blood vessel while a sheath of the closure device covers: the distal end of the outer tubular shaft, the suture-positioning support, and a proximal end portion of the dilator that includes the proximal end of the dilator, and
 wherein the method further comprises, after inserting the distal end portion of the elongate support and the suture-positioning support, and before laterally extending the suture-positioning support:
  proximally withdrawing the sheath along the outer tubular shaft so as to expose the suture-positioning support and the proximal end portion of the dilator.

There is also provided, in accordance with an Inventive Concept 90 of the present invention, a method for suturing a puncture through a wall of a blood vessel, the method comprising:
 inserting an elongate dilator of a closure device through the puncture and into the blood vessel;
 inserting, through the puncture and into the blood vessel, (a) a distal end portion of an elongate support of the closure device and (b) a suture-positioning support that is coupled to the distal end portion of the elongate support, wherein an elongate flexible dilator connector of the closure device couples the proximal end of the dilator to the distal end portion of the elongate support so as to allow movement of the distal end portion of the elongate support with respect to the proximal end of the dilator, wherein an average outer diameter of the dilator connector is less than 20% of a greatest outer diameter of the dilator;
 thereafter, laterally extending the suture-positioning support with respect to the distal end portion of the elongate support; and
 distally advancing a suture through a portion of the elongate support and a wall site of the wall and into the blood vessel, and into the suture-positioning support.

Inventive Concept 91. The method according to any one of Inventive Concepts 74, 86, and 90, further comprising moving the distal end portion of the elongate support with respect to the proximal end of the dilator without causing the distal end portion of the elongate support to directly or indirectly apply a force to the proximal end of the dilator.

Inventive Concept 92. The method according to any one of Inventive Concepts 74, 86, and 90, further comprising moving the distal end portion of the elongate support with respect to the proximal end of the dilator without bending the dilator.

Inventive Concept 93. The method according to any one of Inventive Concepts 74, 86, and 90, further comprising moving the distal end portion of the elongate support with respect to the proximal end of the dilator without deforming the dilator.

Inventive Concept 94. The method according to any one of Inventive Concepts 74, 86, and 90, wherein inserting the dilator through the puncture and into the blood vessel comprises:
 inserting a guidewire through the puncture and into the blood vessel;
 advancing the dilator over the guidewire and through the puncture and into the blood vessel; and
 removing the guidewire from the blood vessel.

Inventive Concept 95. The method according to any one of Inventive Concepts 74 and 86, wherein an elongate flexible dilator connector couples the proximal end of the dilator to the distal end portion of the elongate support so as to allow the movement.

Inventive Concept 96. The method according to Inventive Concept 95, wherein an average outer diameter of the dilator connector is less than 20% of a greatest outer diameter of the dilator.

Inventive Concept 97. The method according to any one of Inventive Concepts 90 and 95, wherein the dilator connector and the dilator include separate respective elements coupled together.

Inventive Concept 98. The method according to any one of Inventive Concepts 90 and 95, wherein the dilator connector and the dilator are integrally formed from a single element.

Inventive Concept 99. The method according to any one of Inventive Concepts 90 and 95, wherein the dilator connector includes an element selected from the group of elements consisting of: a cable, a cord, a wire, and a string.

Inventive Concept 100. The method according to any one of Inventive Concepts 90 and 95, wherein the dilator connector includes a tube.

Inventive Concept 101. The method according to any one of Inventive Concepts 90 and 95, wherein a flexural rigidity of the dilator is greater than a flexural rigidity of the dilator connector.

Inventive Concept 102. The method according to any one of Inventive Concepts 90 and 95, wherein a material of the dilator is harder than a material of the dilator connector.

Inventive Concept 103. The method according to any one of Inventive Concepts 90 and 95, wherein an average outer diameter of the dilator connector is less than 20% of a greatest outer diameter of the dilator.

Inventive Concept 104. The method according to any one of Inventive Concepts 90 and 95, wherein an average outer diameter of the dilator connector is 0.2-0.8 mm.

Inventive Concept 105. The method according to any one of Inventive Concepts 90 and 95, wherein the dilator connector has a length of 0.5-5 cm.

Inventive Concept 106. The method according to any one of Inventive Concepts 90 and 95,
 wherein the dilator connector is rotationally fixed to the distal end portion of the elongate support and the proximal end of the dilator, and
 wherein the method further comprises rotating the distal end portion of the elongate support about a distal-support central longitudinal axis of the distal end portion of the elongate support without corresponding rotation of the dilator about a proximal-dilator central longitudinal axis of a proximal end portion of the dilator.

Inventive Concept 107. The method according to any one of Inventive Concepts 90 and 95, further comprising laterally moving the dilator while the distal end portion of the elongate support remains stationary with respect to the puncture.

Inventive Concept 108. The method according to any one of Inventive Concepts 90 and 95,
- wherein the elongate support includes an outer tubular shaft having a distal end,
- wherein inserting the distal end portion of the elongate support and the suture-positioning support through the puncture and into the blood vessel comprises inserting the distal end portion of the elongate support and the suture-positioning support through the puncture and into the blood vessel while a sheath of the closure device covers: the distal end of the outer tubular shaft, the suture-positioning support, the dilator connector, and a proximal end portion of the dilator that includes the proximal end of the dilator, and
- wherein the method further comprises, after inserting the distal end portion of the elongate support and the suture-positioning support, and before laterally extending the suture-positioning support:
  - proximally withdrawing the sheath along the outer tubular shaft so as to expose the suture-positioning support, the dilator connector, and the proximal end portion of the dilator.

Inventive Concept 109. The method according to any one of Inventive Concepts 74, 86, and 90, wherein the dilator is shaped so as to define an atraumatic proximal tip.

Inventive Concept 110. The method according to Inventive Concept 109, wherein the atraumatic proximal tip is tapered.

Inventive Concept 111. The method according to any one of Inventive Concepts 74, 86, and 90, wherein the suture-positioning support is disposed distally beyond a distal end of the elongate support.

Inventive Concept 112. The method according to any one of Inventive Concepts 74, 86, and 90, wherein a control handle is coupled to a proximal end portion of the elongate support.

Inventive Concept 113. The method according to any one of Inventive Concepts 74, 86, and 90, wherein distally advancing the suture into the suture-positioning support comprises distally advancing a suturing needle of the closure device through the wall site of the wall and into the blood vessel, while the suturing needle is removably coupled to a ferrule, such that the closure device directs the ferrule into a ferrule receptacle defined by the suture-positioning support and the ferrule receptacle removably receives the ferrule.

There is further provided, in accordance with an Inventive Concept 114 of the present invention, a closure device for suturing a puncture, the closure device comprising:
- a suture;
- an elongate support, which comprises one or more shafts;
- a suture-positioning support, which is (a) coupled to a distal end portion of the elongate support, (b) laterally extendable with respect to the distal end portion of the elongate support, and (c) configured to removably receive the suture; and
- an elongate dilator, which is configured to be inserted through the puncture, and which has a proximal end that is coupled to the distal end portion of the elongate support,
- wherein the distal end portion of the elongate support defines a distal-support central longitudinal axis, and a proximal end portion of the dilator, which includes the proximal end of the dilator, defines a proximal-dilator central longitudinal axis, and
- wherein the closure device is configured to allow the distal end portion of the elongate support to move with respect to the proximal end of the dilator from defining a first angle to defining a second angle between the distal-support central longitudinal axis and the proximal-dilator central longitudinal axis, wherein the second angle is at least 15 degrees greater than the first angle.

Inventive Concept 115. The closure device according to Inventive Concept 114, wherein the second angle is at least 30 degrees greater than the first angle.

Inventive Concept 116. The closure device according to Inventive Concept 115, wherein the second angle is at least 45 degrees greater than the first angle.

Inventive Concept 117. The closure device according to Inventive Concept 116, wherein the second angle is at least 60 degrees greater than the first angle.

Inventive Concept 118. The closure device according to Inventive Concept 114, wherein the first angle is less than 30 degrees and the second angle is 45-90 degrees.

Inventive Concept 119. The closure device according to Inventive Concept 118, wherein the second angle is 60-90 degrees.

Inventive Concept 120. The closure device according to Inventive Concept 119, wherein the second angle is 75-90 degrees.

Inventive Concept 121. The closure device according to Inventive Concept 114, wherein the closure device further comprises:
- a ferrule, which is coupled to a distal end portion of the suture; and
  - a suturing needle, which is removably couplable to the ferrule,
  - wherein the suture-positioning support is shaped so as to define a ferrule receptacle,
- which is configured to removably receive the ferrule, such that the suture-positioning support is configured to removably receive the suture, and
- wherein the closure device is configured to direct the ferrule into the ferrule receptacle during distal advancement of the suturing needle removably coupled to the ferrule.

Inventive Concept 122. The closure device according to Inventive Concept 114,
- wherein the elongate support comprises an outer tubular shaft having a distal end,
- wherein the suture-positioning support has proximal and distal end portions at opposite ends of the suture-positioning support,
- wherein the proximal end portion of the suture-positioning support is coupled to the elongate support, and
- wherein the distal end portion of the suture-positioning support is disposed distally to the distal end of the outer tubular shaft.

Inventive Concept 123. The closure device according to Inventive Concept 122, wherein the elongate support further comprises an inner shaft nested within the outer tubular shaft, and wherein the suture-positioning support is coupled to the inner shaft of the elongate support.

Inventive Concept 124. The closure device according to Inventive Concept 114, wherein the suture-positioning support is configured to assume:
- a delivery position, in which a suture-positioning support axis of the suture-positioning support (a) forms a first angle of less than 45 degrees with a distal-support central longitudinal axis of the distal end portion of the elongate support, or (b) is parallel with the distal-support central longitudinal axis, and one or more deployed positions, in which the suture-positioning support is laterally extended with respect to the distal end portion of the elongate support such that the suture-positioning support axis forms a second angle of at least 60 degrees with the distal-support central longitudinal axis.

Inventive Concept 125. The closure device according to Inventive Concept 124, wherein the first angle is less than 30 degrees.

Inventive Concept 126. The closure device according to Inventive Concept 114,
  wherein the suture is a first suture, and wherein the closure device further comprises a second suture, and
  wherein the suture-positioning support is configured to removably receive the second suture.

Inventive Concept 127. The closure device according to Inventive Concept 114, wherein the suture-positioning support is disposed distally beyond a distal end of the elongate support.

There is still further provided, in accordance with an Inventive Concept 128 of the present invention, a closure device for suturing a puncture, the closure device comprising:
  an elongate support, which comprises one or more shafts; and
  an elongate dilator, which is configured to be inserted through the puncture, and which has a proximal end that is coupled to the distal end portion of the elongate support,
  wherein the distal end portion of the elongate support defines a distal-support central longitudinal axis, and a proximal end portion of the dilator, which includes the proximal end of the dilator, defines a proximal-dilator central longitudinal axis, and
  wherein the closure device is configured to allow the distal end portion of the elongate support to move with respect to the proximal end of the dilator from defining a first angle to defining a second angle between the distal-support central longitudinal axis and the proximal-dilator central longitudinal axis, wherein the first angle is less than 30 degrees and the second angle is 60-90 degrees.

Inventive Concept 129. The closure device according to Inventive Concept 128, wherein the second angle is 75-90 degrees.

Inventive Concept 130. The closure device according to any one of Inventive Concepts 114 and 128, wherein the dilator comprises a flexible polymer.

Inventive Concept 131. The closure device according to any one of Inventive Concepts 114 and 128, further comprising an elongate flexible dilator connector, which couples the proximal end of the dilator to the distal end portion of the elongate support so as to allow the distal end portion of the elongate support to move with respect to the proximal end of the dilator.

Inventive Concept 132. The closure device according to Inventive Concept 131, wherein an average outer diameter of the dilator connector is less than 20% of a greatest outer diameter of the dilator.

Inventive Concept 133. The closure device according to Inventive Concept 131,
  wherein the distal end portion of the elongate support defines a distal-support central longitudinal axis, and a proximal end portion of the dilator, which includes the proximal end of the dilator, defines a proximal-dilator central longitudinal axis, and
  wherein the elongate flexible dilator connector couples the proximal end of the dilator to the distal end portion of the elongate support so as to allow the distal end portion of the elongate support to move with respect to the proximal end of the dilator from defining a first angle to defining a second angle between the distal-support central longitudinal axis and the proximal-dilator central longitudinal axis, wherein the first angle is less than 30 degrees and the second angle is 45-90 degrees.

Inventive Concept 134. The closure device according to Inventive Concept 133, wherein the second angle is 60-90 degrees.

Inventive Concept 135. The closure device according to Inventive Concept 134, wherein the second angle is 75-90 degrees.

Inventive Concept 136. The closure device according to Inventive Concept 131, wherein the dilator connector and the dilator comprise separate respective elements coupled together.

Inventive Concept 137. The closure device according to Inventive Concept 131, wherein the dilator connector and the dilator are integrally formed from a single element.

Inventive Concept 138. The closure device according to Inventive Concept 131, wherein the dilator connector comprises an element selected from the group of elements consisting of: a cable, a cord, a wire, and a string.

Inventive Concept 139. The closure device according to Inventive Concept 131, wherein the dilator connector comprises a tube.

Inventive Concept 140. The closure device according to Inventive Concept 131, wherein a flexural rigidity of the dilator is greater than a flexural rigidity of the dilator connector.

Inventive Concept 141. The closure device according to Inventive Concept 131, wherein a material of the dilator is harder than a material of the dilator connector.

Inventive Concept 142. The closure device according to Inventive Concept 131, wherein an average outer diameter of the dilator connector is 0.2-0.8 mm.

Inventive Concept 143. The closure device according to Inventive Concept 131, wherein the dilator connector has a length of 0.5-5 cm.

Inventive Concept 144. The closure device according to Inventive Concept 131, wherein the dilator connector comprises a material selected from the group of materials consisting of Nitinol and stainless steel.

Inventive Concept 145. The closure device according to Inventive Concept 131,
  wherein the dilator connector is rotationally fixed to the distal end portion of the elongate support and the proximal end of the dilator, and
  wherein the dilator connector couples the proximal end of the dilator to the distal end portion of the elongate support so as to allow rotation of the distal portion of the elongate support about a distal-support central longitudinal axis of the distal portion of the elongate support without corresponding rotation of the dilator about a proximal-dilator central longitudinal axis of a proximal end portion of the dilator.

Inventive Concept 146. The closure device according to Inventive Concept 131, wherein the closure device is configured to allow lateral movement of the dilator while the distal end portion of the elongate support remains stationary with respect to the puncture.

Inventive Concept 147. The closure device according to any one of Inventive Concepts 114 and 128, wherein the dilator is shaped so as to define an atraumatic proximal tip.

Inventive Concept 148. The closure device according to Inventive Concept 147, wherein the atraumatic proximal tip is tapered.

Inventive Concept 149. The closure device according to any one of Inventive Concepts 114 and 128, wherein the puncture is an endoscopic puncture through a wall of a body cavity.

Inventive Concept 150. The closure device according to any one of Inventive Concepts 114 and 128, wherein the puncture is a puncture through a wall of a blood vessel, and wherein the dilator is configured to be inserted through the puncture into the blood vessel.

Inventive Concept 151. The closure device according to Inventive Concept 150, wherein the closure device is configured to allow the distal end portion of the elongate support to move with respect to the proximal end of the dilator without application by the dilator of a force to the wall of the blood vessel.

Inventive Concept 152. The closure device according to any one of Inventive Concepts 114 and 128, further comprising a control handle, coupled to a proximal end portion of the elongate support.

There is additionally provided, in accordance with an Inventive Concept 153 of the present invention, a method for suturing a puncture through a wall of a blood vessel, the method comprising:
  inserting an elongate dilator of a closure device through the puncture and into the blood vessel;
  inserting, through the puncture and into the blood vessel, (a) a distal end portion of an elongate support of the closure device and (b) a suture-positioning support that is coupled to the distal end portion of the elongate support, while a distal-support central longitudinal axis of the distal end portion of the elongate support forms a first angle of less than 30 degrees with respect to a blood-vessel central longitudinal axis of the blood vessel at a site of the puncture, wherein a proximal end of the dilator is coupled to the distal end portion of the elongate support;
  thereafter, moving the distal end portion of the elongate support with respect to the blood vessel to define a second angle between the distal-support central longitudinal axis and the blood-vessel central longitudinal axis, wherein the second angle is at least 15 degrees greater than the first angle;
  thereafter, laterally extending the suture-positioning support with respect to the distal end portion of the elongate support; and
  distally advancing a suture through a portion of the elongate support and a wall site of the wall and into the blood vessel, and into the suture-positioning support.

Inventive Concept 154. The method according to Inventive Concept 153, wherein the second angle is at least 30 degrees greater than the first angle.

Inventive Concept 155. The method according to Inventive Concept 154, wherein the second angle is at least 45 degrees greater than the first angle.

Inventive Concept 156. The method according to Inventive Concept 155, wherein the second angle is at least 60 degrees greater than the first angle.

Inventive Concept 157. The method according to Inventive Concept 153, wherein the first angle is less than 30 degrees and the second angle is 45-90 degrees.

Inventive Concept 158. The method according to Inventive Concept 157, wherein the second angle is 60-90 degrees.

Inventive Concept 159. The method according to Inventive Concept 158, wherein the second angle is 75-90 degrees.

Inventive Concept 160. The method according to Inventive Concept 153, wherein distally advancing the suture into the suture-positioning support comprises distally advancing a suturing needle of the closure device through the wall site of the wall and into the blood vessel, while the suturing needle is removably coupled to a ferrule, such that the closure device directs the ferrule into a ferrule receptacle defined by the suture-positioning support and the ferrule receptacle removably receives the ferrule.

Inventive Concept 161. The method according to Inventive Concept 153,
  wherein the elongate support includes an outer tubular shaft having a distal end,
  wherein inserting the distal end portion of the elongate support and the suture-positioning support through the puncture and into the blood vessel comprises inserting the distal end portion of the elongate support and the suture-positioning support through the puncture and into the blood vessel while a sheath of the closure device covers: the distal end of the outer tubular shaft, the suture-positioning support, the dilator connector, and a proximal end portion of the dilator that includes the proximal end of the dilator, and
  wherein the method further comprises, after inserting the distal end portion of the elongate support and the suture-positioning support, and before laterally extending the suture-positioning support:
    proximally withdrawing the sheath along the outer tubular shaft so as to expose the suture-positioning support, the dilator connector, and the proximal end portion of the dilator.

Inventive Concept 162. The method according to Inventive Concept 153, wherein the suture-positioning support is disposed distally beyond a distal end of the elongate support.

There is yet additionally provided, in accordance with an Inventive Concept 163 of the present invention, a method for suturing a puncture through a wall of a blood vessel, the method comprising:
  inserting an elongate dilator of a closure device through the puncture and into the blood vessel;
  inserting a distal end portion of an elongate support of the closure device through the puncture and into the blood vessel, while a distal-support central longitudinal axis of the distal end portion of the elongate support forms a first angle of less than 30 degrees with respect to a blood-vessel central longitudinal axis of the blood vessel at a site of the puncture, wherein a proximal end of the dilator is coupled to the distal end portion of the elongate support; and
  thereafter, moving the distal end portion of the elongate support with respect to the blood vessel to define a second angle between the distal-support central longitudinal axis and the blood-vessel central longitudinal axis, wherein the second angle is at least 60 degrees.

Inventive Concept 164. The method according to Inventive Concept 163, wherein the second angle is at least 75 degrees.

Inventive Concept 165. The method according to any one of Inventive Concepts 153 and 163, further comprising moving the distal end portion of the elongate support with respect to the proximal end of the dilator without causing the distal end portion of the elongate support to directly or indirectly apply a force to the proximal end of the dilator.

Inventive Concept 166. The method according to any one of Inventive Concepts 153 and 163, further comprising moving the distal end portion of the elongate support with respect to the proximal end of the dilator without bending the dilator.

Inventive Concept 167. The method according to any one of Inventive Concepts 153 and 163, further comprising moving the distal end portion of the elongate support with respect to the proximal end of the dilator without deforming the dilator.

Inventive Concept 168. The method according to any one of Inventive Concepts 153 and 163, wherein inserting the dilator through the puncture and into the blood vessel comprises: inserting a guidewire through the puncture and into the blood vessel;
  advancing the dilator over the guidewire and through the puncture and into the blood vessel; and
  removing the guidewire from the blood vessel.

Inventive Concept 169. The method according to any one of Inventive Concepts 153 and 163, wherein an elongate flexible dilator connector couples the proximal end of the dilator to the distal end portion of the elongate support so as to allow the movement.

Inventive Concept 170. The method according to Inventive Concept 169, wherein an average outer diameter of the dilator connector is less than 20% of a greatest outer diameter of the dilator.

Inventive Concept 171. The method according to Inventive Concept 169, wherein the dilator connector and the dilator include separate respective elements coupled together.

Inventive Concept 172. The method according to Inventive Concept 169, wherein the dilator connector and the dilator are integrally formed from a single element.

Inventive Concept 173. The method according to Inventive Concept 169, wherein the dilator connector includes an element selected from the group of elements consisting of: a cable, a cord, a wire, and a string.

Inventive Concept 174. The method according to Inventive Concept 169, wherein the dilator connector includes a tube.

Inventive Concept 175. The method according to Inventive Concept 169, wherein a flexural rigidity of the dilator is greater than a flexural rigidity of the dilator connector.

Inventive Concept 176. The method according to Inventive Concept 169, wherein a material of the dilator is harder than a material of the dilator connector.

Inventive Concept 177. The method according to Inventive Concept 169, wherein an average outer diameter of the dilator connector is less than 20% of a greatest outer diameter of the dilator.

Inventive Concept 178. The method according to Inventive Concept 169, wherein an average outer diameter of the dilator connector is 0.2-0.8 mm.

Inventive Concept 179. The method according to Inventive Concept 169, wherein the dilator connector has a length of 0.5-5 cm.

Inventive Concept 180. The method according to Inventive Concept 169,
  wherein the dilator connector is rotationally fixed to the distal end portion of the elongate support and the proximal end of the dilator, and
  wherein the method further comprises rotating the distal portion of the elongate support about a distal-support central longitudinal axis of the distal portion of the elongate support without corresponding rotation of the dilator about a proximal-dilator central longitudinal axis of a proximal end portion of the dilator.

Inventive Concept 181. The method according to Inventive Concept 169, further comprising laterally moving the dilator while the distal end portion of the elongate support remains stationary with respect to the puncture.

Inventive Concept 182. The method according to any one of Inventive Concepts 153 and 163, wherein the dilator is shaped so as to define an atraumatic proximal tip.

Inventive Concept 183. The method according to Inventive Concept 182, wherein the atraumatic proximal tip is tapered.

Inventive Concept 184. The method according to any one of Inventive Concepts 153 and 163, wherein a control handle is coupled to a proximal end portion of the elongate support.

There is also provided, in accordance with an Inventive Concept 185 of the present invention, a closure device for suturing a puncture, the closure device comprising:
  first and second sutures;
  first and second ferrules, coupled to respective distal end portions of the first and the second sutures;
  an elongate support, which comprises one or more shafts;
  a suture-positioning support, which is (a) coupled to a distal end portion of the elongate support, (b) laterally extendable with respect to the elongate support, and (c) shaped so as to define a ferrule receptacle, which is configured to removably receive the first and the second ferrules, one at a time;
  first and second ferrule-advancing suturing needles, which are removably couplable to the first and the second ferrules, respectively; and
  first and second ferrule-withdrawing suturing needles, which are removably couplable to the first and the second ferrules, respectively,
  wherein the closure device is configured to direct the first ferrule into the ferrule receptacle during distal advancement of the first suturing ferrule-advancing needle removably coupled to the first ferrule,
  wherein the closure device is configured to direct the first ferrule-withdrawing suturing needle to the first ferrule during distal advancement of the first ferrule-withdrawing suturing needle,
  wherein the closure device is configured such that after the distal advancement of the first ferrule-withdrawing suturing needle to the first ferrule, proximal withdrawal of the first ferrule-withdrawing suturing needle coupled to the first ferrule removes the first ferrule from the ferrule receptacle,
  wherein the closure device is configured to direct the second ferrule into the ferrule receptacle during distal advancement of the second suturing ferrule-advancing needle removably coupled to the second ferrule,
  wherein the closure device is configured to direct the second ferrule-withdrawing suturing needle to the second ferrule during distal advancement of the second ferrule-withdrawing suturing needle, and
  wherein the closure device is configured such that after the distal advancement of the second ferrule-withdrawing suturing needle to the second ferrule, proximal withdrawal of the second ferrule-withdrawing suturing needle coupled to the second ferrule removes the second ferrule from the ferrule receptacle.

Inventive Concept 186. The closure device according to Inventive Concept 185,
  wherein the first and the second sutures are pre-knotted so as to form first and second pre-tied knots, respectively, which are disposed at least partially within the closure device,
  wherein the closure device is configured such that:
    the proximal withdrawal of the first ferrule-withdrawing suturing needle coupled to the first ferrule pulls the first ferrule-withdrawing suturing needle, the distal end portion of the first suture, and the first ferrule through the first pre-tied knot, and the proximal withdrawal of the second ferrule-withdrawing suturing needle coupled to the second ferrule pulls the second ferrule-withdrawing suturing needle, the distal end portion of the second suture, and the second ferrule through the second pre-tied knot.

Inventive Concept 187. The closure device according to Inventive Concept 185, wherein the elongate support defines, through respective longitudinal portions of the elongate support, first, second, third, and fourth needle-guiding lumens, which are shaped so as to direct the first ferrule-advancing suturing needle, the second ferrule-advancing suturing needle, the first ferrule-withdrawing suturing needle, and the second ferrule-withdrawing suturing needle, respectively, toward the ferrule receptacle during the distal advancement of the respective suturing needles.

Inventive Concept 188. The closure device according to Inventive Concept 187, wherein the first, the second, the third, and the fourth needle-guiding lumens are arranged around a distal-support central longitudinal axis of the distal end portion of the elongate support such that (a) the second needle-guiding lumen is between the first and the third needle-guiding lumens, and (b) the fourth needle-guiding lumen is between the first and the third needle-guiding lumens.

Inventive Concept 189. The closure device according to Inventive Concept 188, wherein respective rays from the distal-support central longitudinal axis to the first and the third needle-guiding lumens form a vertex angle of 150-180 degrees.

Inventive Concept 190. The closure device according to Inventive Concept 185,
wherein the elongate support comprises an outer tubular shaft having a distal end,
wherein the suture-positioning support has proximal and distal end portions at opposite ends of the suture-positioning support,
wherein the proximal end portion of the suture-positioning support is coupled to the elongate support, and
wherein the distal end portion of the suture-positioning support is disposed distally to the distal end of the outer tubular shaft.

Inventive Concept 191. The closure device according to Inventive Concept 190, wherein the elongate support further comprises an inner shaft nested within the outer tubular shaft, and wherein the suture-positioning support is coupled to the inner shaft of the elongate support.

Inventive Concept 192. The closure device according to Inventive Concept 185, wherein the suture-positioning support is configured to assume:
a delivery position, in which a suture-positioning support axis of the suture-positioning support (a) forms a first angle of less than 45 degrees with a distal-support central longitudinal axis of the distal end portion of the elongate support, or (b) is parallel with the distal-support central longitudinal axis, and
one or more deployed positions, in which the suture-positioning support is laterally extended with respect to the elongate support such that the suture-positioning support axis forms a second angle of at least 60 degrees with the distal-support central longitudinal axis.

Inventive Concept 193. The closure device according to Inventive Concept 192, wherein the first angle is less than 30 degrees.

Inventive Concept 194. The closure device according to Inventive Concept 185, wherein the puncture is an endoscopic puncture through a wall of a body cavity.

Inventive Concept 195. The closure device according to Inventive Concept 185, wherein the puncture is a puncture through a wall of a blood vessel.

Inventive Concept 196. The closure device according to Inventive Concept 185, further comprising a control handle, coupled to a proximal end portion of the elongate support.

Inventive Concept 197. The closure device according to Inventive Concept 196, wherein the control handle comprises a needle-advancement safety control assembly, which is configured to prevent distal advancement of the second ferrule-advancing suturing needle until the first ferrule-withdrawing suturing needle has been distally advanced.

Inventive Concept 198. The closure device according to any one of Inventive Concepts 185 197, wherein the suture-positioning support is shaped so as to define exactly one ferrule receptacle.

Inventive Concept 199. The closure device according to any one of Inventive Concepts 185-197,
wherein the suture-positioning support is configured to assume first, second, third, and fourth deployed positions with respect to the distal end portion of the elongate support, in which the suture-positioning support laterally extends in first, second, third, and fourth directions from the distal end portion of the elongate support, the directions different from one another.

Inventive Concept 200. The closure device according to Inventive Concept 199, wherein the suture-positioning support is rotatable about a central longitudinal axis of the distal end portion of the elongate support so as to transition among the first, the second, the third, and the fourth deployed positions.

There is further provided, in accordance with an Inventive Concept 201 of the present invention, a method for suturing a puncture through a wall of a blood vessel, the method comprising:
distally advancing a first ferrule-advancing suturing needle of a closure device through a first wall site of the wall and into the blood vessel, while the first ferrule-advancing suturing needle is removably coupled to a first ferrule, such that the closure device directs the first ferrule into a ferrule receptacle defined by a suture-positioning support of the closure device and the ferrule receptacle removably receives the first ferrule,
wherein the first ferrule is coupled to a distal end portion of a first suture; distally advancing a first ferrule-withdrawing suturing needle of the closure device through a second wall site of the wall and into the blood vessel, to the first ferrule, coupling the first ferrule-withdrawing suturing needle to the first ferrule, and proximally withdrawing the first ferrule-withdrawing suturing needle while coupled to the first ferrule, so as to remove the first ferrule from the ferrule receptacle;
thereafter, distally advancing a second ferrule-advancing suturing needle of the closure device through a third wall site of the wall and into the blood vessel, while the second ferrule-advancing suturing needle is removably coupled to a second ferrule, such that the closure device directs the second ferrule into the ferrule receptacle defined by the suture-positioning support and the ferrule receptacle removably receives the second ferrule, wherein the second ferrule is coupled to a distal end portion of a second suture;
distally advancing a second ferrule-withdrawing suturing needle of the closure device through a fourth wall site of the wall and into the blood vessel, to the second ferrule, coupling the second ferrule-withdrawing suturing needle to the second ferrule, and proximally withdrawing the second ferrule-withdrawing suturing needle while coupled to the second ferrule, so as to remove the second ferrule from the ferrule receptacle.

Inventive Concept 202. The method according to Inventive Concept 201, wherein an elongate support of the closure device defines, through respective longitudinal portions of the elongate support, first, second, third, and fourth needle-guiding lumens, which are shaped so as to direct the first ferrule-advancing suturing needle, the second ferrule-advancing suturing needle, the first ferrule-withdrawing suturing needle, and the second ferrule-withdrawing suturing needle, respectively, toward the ferrule receptacle during the distal advancement of the respective suturing needles.

Inventive Concept 203. The method according to Inventive Concept 202, wherein the first, the second, the third, and the fourth needle-guiding lumens are arranged around a distal-support central longitudinal axis of the distal end portion of the elongate support such that (a) the second needle-guiding lumen is between the first and the third needle-guiding lumens, and (b) the fourth needle-guiding lumen is between the first and the third needle-guiding lumens.

Inventive Concept 204. The method according to Inventive Concept 203, wherein respective rays from the distal-support central longitudinal axis to the first and the third needle-guiding lumens form a vertex angle of 150-180 degrees.

Inventive Concept 205. The method according to any one of Inventive Concepts 201-204, wherein the suture-positioning support is configured to assume first, second, third, and fourth deployed positions with respect to the distal end portion of the elongate support, in which the suture-positioning support laterally extends in first, second, third, and fourth directions from the distal end portion of an elongate support of the closure device, the directions different from one another.

Inventive Concept 206. The method according to Inventive Concept 205, further comprising rotating the suture-positioning support about a central longitudinal axis of the distal end portion of the elongate support so as to transition among the first, the second, the third, and the fourth deployed positions.

There is still further provided, in accordance with an Inventive Concept 207 of the present invention, a closure device for suturing a puncture, the closure device comprising:
  a suture;
  an elongate support, which comprises one or more shafts;
  a ferrule, which is coupled to a distal end portion of the suture;
  a suturing needle, which is removably couplable to the ferrule;
  a suture-positioning support, which is (a) coupled to a distal end portion of the elongate support, (b) laterally extendable with respect to the distal end portion of the elongate support, and (c) shaped so as to define a ferrule receptacle, which is configured to removably receive the ferrule, such that the suture-positioning support is configured to removably receive the suture; and
  a control handle, which (i) comprises a support-and-needle user control, and (ii) is configured such that actuation of the support-and-needle user control causes:
    lateral extension of the suture-positioning support, with respect to a distal end portion of the elongate support, from (a) a delivery position, in which a suture-positioning support axis of the suture-positioning support forms a first angle of less than 45 degrees with a distal-support central longitudinal axis of the distal end portion of the elongate support, to (b) a deployed position in which the suture-positioning support laterally extends from the distal end portion of the elongate support, and
    distal advancement of the suturing needle, while the suturing needle is removably coupled to the ferrule, such that the closure device directs the ferrule into the ferrule receptacle and the ferrule receptacle removably receives the ferrule while the suture-positioning support is in the deployed position.

Inventive Concept 208. The closure device according to Inventive Concept 207, wherein the control handle is configured such that the actuation of the support-and-needle user control causes at least a portion of the distal advancement of the suturing needle to occur as the suture-positioning support is extended laterally.

Inventive Concept 209. The closure device according to Inventive Concept 208, wherein the control handle is configured such that the actuation of the support-and-needle user control causes the suture-positioning support to begin extending laterally before the suturing needle begins advancing distally.

Inventive Concept 210. The closure device according to Inventive Concept 207, wherein the control handle is configured such that the actuation of the support-and-needle user control non-electrically causes the distal advancement of the suturing needle and the lateral extension of the suture-positioning support.

Inventive Concept 211. The closure device according to Inventive Concept 207, wherein the support-and-needle user control is configured to be actuated by movement of the user control in a proximal-to-distal direction.

Inventive Concept 212. The closure device according to Inventive Concept 207, wherein the control handle is configured such that:
  the actuation of the support-and-needle user control to cause the lateral extension and the distal advancement of the suturing needle is initial actuation of the support-and-needle user control, and
  subsequent actuation of the support-and-needle user control, after the initial actuation of the support-and-needle user control, causes:
    proximal withdrawal of the suturing needle, a portion of which proximal withdrawal proximally withdraws the suturing needle from the ferrule while leaving the ferrule within the ferrule receptacle, and
    transitioning of the suture-positioning support from the deployed position back to the delivery position.

Inventive Concept 213. The closure device according to Inventive Concept 212, wherein the control handle is configured such that the subsequent actuation of the support-and-needle user control causes at least a portion of the transitioning of the suture-positioning support from the deployed position back to the delivery position distal advancement of the suturing needle to occur as the suturing needle is proximally withdrawn.

Inventive Concept 214. The closure device according to Inventive Concept 212,
  wherein the deployed position is a first deployed position in which the suture-positioning support laterally extends from the distal end portion of the elongate support in a first direction,
  wherein the suturing needle is a ferrule-advancing suturing needle, wherein the closure device further comprises a ferrule-withdrawing suturing needle, wherein the control handle is configured such that rotation of the support-and-needle user control rotates the suture-positioning support about the distal-support central longitudinal axis, and wherein the control handle is configured such that second subsequent actuation of the support-and-needle user control, after the rotation of the support-and-needle user control, causes:

lateral extension of the suture-positioning support, with respect to the distal end portion of the elongate support, from (a) the delivery position to (b) a second deployed position in which the suture-positioning support laterally extends from the distal end portion of the elongate support in a second direction different from the first direction, and distal advancement of the ferrule-withdrawing suturing needle, such that the closure device directs the ferrule-withdrawing suturing needle to the ferrule and couples the ferrule-withdrawing suturing needle to the ferrule while the suture-positioning support is in the second deployed position.

Inventive Concept 215. The closure device according to Inventive Concept 207, wherein the suture is a first suture, and wherein the closure device further comprises a second suture, wherein the ferrule is a first ferrule, and wherein the closure device further comprises a second ferrule, which is coupled to a distal end portion of the second suture, and wherein the ferrule receptacle of the suture-positioning support is configured to removably receive the second ferrule.

There is additionally provided, in accordance with an Inventive Concept 216 of the present invention, a method for suturing a puncture through a wall of a blood vessel, the method comprising:

inserting, through the puncture and into the blood vessel, (a) a distal end portion of an elongate support of a closure device and (b) a suture-positioning support that is coupled to the distal end portion of the elongate support, and is in a delivery position, in which a suture-positioning support axis of the suture-positioning support forms a first angle of less than 45 degrees with a distal-support central longitudinal axis of the distal end portion of the elongate support; and while a suturing needle of the closure device is removably coupled to a ferrule that is coupled to a distal end portion of a suture, actuating a support-and-needle user control of a control handle of the closure device to cause:

lateral extension of the suture-positioning support, with respect to the distal end portion of the elongate support, from the delivery position to a deployed position in which the suture-positioning support laterally extends from the distal end portion of the elongate support, and distal advancement of the suturing needle through the wall and into the blood vessel, such that the closure device directs the ferrule into a ferrule receptacle of the suture-positioning support and the ferrule receptacle removably receives the ferrule while the suture-positioning support is in the deployed position.

Inventive Concept 217. The method according to Inventive Concept 216, wherein actuating the support-and-needle user control causes at least a portion of the distal advancement of the suturing needle to occur as the suture-positioning support is extended laterally.

Inventive Concept 218. The method according to Inventive Concept 217, wherein actuating the support-and-needle user control causes the suture-positioning support to begin extending laterally before the suturing needle begins advancing distally.

Inventive Concept 219. The method according to Inventive Concept 216, wherein actuating the support-and-needle user control non-electrically causes the distal advancement of the suturing needle and the lateral extension of the suture-positioning support.

Inventive Concept 220. The method according to Inventive Concept 216, wherein actuating the support-and-needle user control comprises moving the user control in a proximal-to-distal direction.

Inventive Concept 221. The method according to Inventive Concept 216, wherein actuating the support-and-needle user control to cause the lateral extension and the distal advancement of the suturing needle comprises initially actuating the support-and-needle user control, and wherein the method further comprises subsequently actuating the support-and-needle user control, after initially actuating the support-and-needle user control to cause:

proximal withdrawal of the suturing needle, a portion of which proximal withdrawal proximally withdraws the suturing needle from the ferrule while leaving the ferrule within the ferrule receptacle, and transitioning of the suture-positioning support from the deployed position back to the delivery position.

Inventive Concept 222. The method according to Inventive Concept 221, wherein subsequently actuating the support-and-needle user control causes at least a portion of the transitioning of the suture-positioning support from the deployed position back to the delivery position distal advancement of the suturing needle to occur as the suturing needle is proximally withdrawn.

Inventive Concept 223. The method according to Inventive Concept 221, wherein the deployed position is a first deployed position in which the suture-positioning support laterally extends from the distal end portion of the elongate support in a first direction, wherein the suturing needle is a ferrule-advancing suturing needle, and wherein the method further comprises:

rotating the support-and-needle user control to rotate the suture-positioning support about the distal-support central longitudinal axis, and thereafter, again subsequently actuating the support-and-needle user control to cause:

lateral extension of the suture-positioning support, with respect to the distal end portion of the elongate support, from (a) the delivery position to (b) a second deployed position in which the suture-positioning support laterally extends from the distal end portion of the elongate support in a second direction different from the first direction, and distal advancement of a ferrule-withdrawing suturing needle of the closure device, such that the closure device directs the ferrule-withdrawing suturing needle to the ferrule and couples the ferrule-withdrawing suturing needle to the ferrule while the suture-positioning support is in the second deployed position.

There is yet additionally provided, in accordance with an Inventive Concept 224 of the present invention, a closure device for suturing a puncture, the closure device comprising:
- a suture;
- an elongate support, which comprises an outer tubular shaft having a distal end,
- a suture-positioning support, which is (a) coupled to a distal end portion of the elongate support, (b) laterally extendable with respect to the elongate support, and (c) configured to removably receive the suture;
- an elongate dilator; and
- a sheath that covers: the distal end of the outer tubular shaft, the suture-positioning support, and a proximal end portion of the dilator that includes the proximal end of the dilator,
- wherein the sheath is proximally withdrawable along the outer tubular shaft so as to expose the suture-positioning support and the proximal end portion of the dilator.

Inventive Concept 225. The closure device according to Inventive Concept 224,
- further comprising an elongate flexible dilator connector, which couples the proximal end of the dilator to the distal end portion of the elongate support so as to allow the distal end portion of the elongate support to move with respect to the proximal end of the dilator,
- wherein the sheath covers: the distal end of the outer tubular shaft, the suture-positioning support, the proximal end portion of the dilator, and the dilator connector, and
- wherein the sheath is proximally withdrawable along the outer tubular shaft so as to expose the suture-positioning support, the proximal end portion of the dilator, and the dilator connector.

Inventive Concept 226. The closure device according to Inventive Concept 224,
- wherein the suture is a first suture, and wherein the closure device further comprises a second suture, and
- wherein the suture-positioning support is configured to removably receive the second suture.

Inventive Concept 227. The closure device according to Inventive Concept 224, wherein the dilator is shaped so as to define an atraumatic proximal tip.

Inventive Concept 228. The closure device according to Inventive Concept 227, wherein the proximal end portion of the dilator is shaped so as to define an indentation at least partially around the dilator longitudinally between the atraumatic proximal tip and the remaining more distal portion of the dilator.

Inventive Concept 229. The closure device according to Inventive Concept 224,
- wherein the closure device further comprises a control handle, which is coupled to a proximal end portion of the elongate support, and which comprises a sheath-control user control, and
- wherein the closure device is configured such that actuation of the sheath-control user control proximally withdraws sheath along the outer tubular shaft.

Inventive Concept 230. The closure device according to Inventive Concept 229,
- wherein the control handle (i) comprises a support-and-needle user control, and (ii) is configured such that actuation of the support-and-needle user control causes lateral extension of the suture-positioning support, with respect to a distal end portion of the elongate support, from (a) a delivery position, in which a suture-positioning support axis of the suture-positioning support forms a first angle of less than 45 degrees with a distal-support central longitudinal axis of the distal end portion of the elongate support, to (b) a deployed position in which the suture-positioning support laterally extends from the distal end portion of the elongate support, and
- wherein the control handle is configured to lock the support-and-needle user control, thereby preventing the actuation thereof, until the actuation of the sheath-control user control.

There is also provided, in accordance with an Inventive Concept 231 of the present invention, a method for suturing a puncture through a wall of a blood vessel, the method comprising:
- inserting an elongate dilator of a closure device through the puncture and into the blood vessel;
- inserting, through the puncture and into the blood vessel, (a) a distal end portion of an elongate support of the closure device and (b) a suture-positioning support that is coupled to the distal end portion of the elongate support, while a sheath of the closure device covers:
  - a distal end of an outer tubular shaft of the elongate support, the suture-positioning support, and a proximal end portion of the dilator including a proximal end of the dilator, wherein the proximal end of the dilator is coupled to the distal end portion of the elongate support;
- thereafter, proximally withdrawing the sheath along the outer tubular shaft so as to expose the suture-positioning support and the proximal end portion of the dilator;
- thereafter, laterally extending the suture-positioning support with respect to the distal end portion of the elongate support; and
- thereafter, distally advancing a suture through a portion of the elongate support and a wall site of the wall and into the blood vessel, and into the suture-positioning support.

Inventive Concept 232. The method according to Inventive Concept 231,
- wherein an elongate flexible dilator connector of the closure device couples the proximal end of the dilator to the distal end portion of the elongate support so as to allow movement of the distal end portion of the elongate support with respect to the proximal end of the dilator,
- wherein inserting the distal end portion of the elongate support and the suture-positioning support through the puncture comprises inserting the distal end portion of the elongate support and the suture-positioning support through the puncture and into the blood vessel while the sheath covers: the distal end of the outer tubular shaft of the elongate support, the suture-positioning support, the dilator connector, and the proximal end portion of the dilator, and
- wherein proximally withdrawing the sheath comprises proximally withdrawing the sheath along the outer tubular shaft so as to expose the suture-positioning support, the dilator connector, and the proximal end portion of the dilator.

Inventive Concept 233. The method according to Inventive Concept 231, wherein inserting the dilator through the puncture and into the blood vessel comprises:
- inserting a guidewire through the puncture and into the blood vessel;
- advancing the dilator over the guidewire and through the puncture and into the blood vessel; and
- removing the guidewire from the blood vessel.

There is further provided, in accordance with an Inventive Concept 234 of the present invention, a closure device for suturing a puncture, the closure device comprising:
a suture;
an elongate support; and
a suture-positioning support, which is coupled to a distal end portion of the elongate support, and which is configured to assume:
(i) a delivery position, in which a suture-positioning support axis of the suture-positioning support (a) forms a first angle of less than 45 degrees with a distal-support central longitudinal axis of the distal end portion of the elongate support, or (b) is parallel with the distal-support central longitudinal axis, and
(ii) a plurality of deployed positions, in which the suture-positioning support is laterally extended with respect to the distal end portion of the elongate support such that the suture-positioning support axis forms a second angle of at least 60 degrees with the distal-support central longitudinal axis,
wherein the closure device is configured to:
transition the suture-positioning support from the delivery position to a first one of the deployed positions, in which the suture-positioning support laterally extends in a first direction from the distal end portion of the elongate support,
couple the suture to the suture-positioning support while the suture-positioning support is in the first deployed position,
thereafter, transition the suture-positioning support from the first deployed position back to the delivery position,
thereafter, rotate the suture-positioning support about a distal-support central longitudinal axis of the distal portion of the elongate support,
thereafter, transition the suture-positioning support from the delivery position to a second one of the deployed positions, in which the suture-positioning support laterally extends in a second direction from the distal end portion of the elongate support, the second direction different from the first direction, and
proximally withdraw the suture from the suture-positioning support while the suture-positioning support is in the second deployed position.

Inventive Concept 235. The closure device according to Inventive Concept 234, wherein the first angle is less than 30 degrees.

Inventive Concept 236. The closure device according to Inventive Concept 234, wherein the puncture is a puncture through a wall of a blood vessel.

Inventive Concept 237. The closure device according to Inventive Concept 234, wherein the puncture is an endoscopic puncture through a wall of a body cavity.

Inventive Concept 238. The closure device according to Inventive Concept 234,
wherein the closure device further comprises:
a ferrule, which is coupled to a distal end portion of the suture;
a ferrule-advancing suturing needle, which is removably couplable to the ferrule; and
a ferrule-withdrawing suturing needle,
wherein the suture-positioning support is shaped so as to define a ferrule receptacle, which is configured to removably receive the ferrule,
wherein the elongate support defines, through a longitudinal portion of the elongate support, first and second needle lumens having first and second distal lumen openings, respectively, and
wherein the closure device is configured to:
couple the suture to the suture-positioning support by distally advancing, within the first needle lumen and out of the first distal lumen opening, the ferrule-advancing suturing needle removably coupled to the ferrule, and inserting the ferrule into the ferrule receptacle, and
proximally withdraw the suture from the suture-positioning support by distally advancing, within the second needle lumen and out of the second distal lumen opening, the ferrule-withdrawing suturing needle to the ferrule, coupling the ferrule-withdrawing suturing needle to the ferrule, and proximally withdrawing the ferrule-withdrawing suturing needle while coupled to the ferrule, so as to remove the ferrule from the ferrule receptacle.

Inventive Concept 239. The closure device according to Inventive Concept 234,
wherein the elongate support comprises an outer tubular shaft having a distal end,
wherein the suture-positioning support has proximal and distal end portions at opposite ends of the suture-positioning support,
wherein the proximal end portion of the suture-positioning support is coupled to the elongate support, and
wherein the distal end portion of the suture-positioning support is disposed distally to the distal end of the outer tubular shaft.

Inventive Concept 240. The closure device according to Inventive Concept 239, wherein the elongate support further comprises an inner shaft nested within the outer tubular shaft, and wherein the suture-positioning support is coupled to the inner shaft of the elongate support.

Inventive Concept 241. The closure device according to Inventive Concept 234,
wherein the suture-positioning support is pivotably coupled to the distal end portion of the elongate support such that the suture-positioning support is rotatable about a pivot axis that is not coaxial with the distal-support central longitudinal axis, and
wherein the closure device is configured to transition the suture-positioning support from the delivery position to the first deployed position by rotating the suture-positioning support about the pivot axis.

Inventive Concept 242. The closure device according to Inventive Concept 241, wherein the closure device is configured to transition the suture-positioning support from the first deployed position back to the delivery position by rotating the suture-positioning support about the pivot axis.

Inventive Concept 243. The closure device according to Inventive Concept 234, wherein the elongate support comprises one or more shafts, and wherein the elongate support is configured to rotate the suture-positioning support about the distal-support central longitudinal axis by rotating at least one of the one or more of the shafts of the elongate support.

There is still further provided, in accordance with an Inventive Concept 244 of the present invention, a method for suturing a puncture through a wall of a blood vessel, the method comprising:
inserting, through the puncture and into the blood vessel, (a) a distal end portion of an elongate support of a closure device and (b) a suture-positioning support that is coupled to the distal end portion of the elongate support, while the suture-positioning support is in a delivery position, in which a suture-positioning support axis of the suture-positioning support (a) forms a first angle of less than 45 degrees with a distal-support central longitudinal axis of the distal end portion of the elongate support, or (b) is parallel with the distal-support central longitudinal axis, wherein the elongate support is configured to assume a plurality of deployed positions, in which the suture-positioning support is laterally extended with respect to the distal end portion of the elongate support such that the suture-positioning support axis forms a second angle of at least 60 degrees with the distal-support central longitudinal axis;

thereafter, actuating the closure device to:
transition the suture-positioning support from the delivery position to a first one of the deployed positions, in which the suture-positioning support laterally extends in a first direction from the distal end portion of the elongate support, and thereafter, couple the suture to the suture-positioning support while the suture-positioning support is in the first deployed position; and thereafter, actuating the closure device to:
transition the suture-positioning support from the first deployed position back to the delivery position,
thereafter, rotate the suture-positioning support about the distal-support central longitudinal axis,
thereafter, transition the suture-positioning support from the delivery position to a second one of the deployed positions, in which the suture-positioning support laterally extends in a second direction from the distal end portion of the elongate support, the second direction different from the first direction, and
thereafter, proximally withdraw the suture from the suture-positioning support while the suture-positioning support is in the second deployed position.

Inventive Concept 245. The method according to Inventive Concept 244, wherein the first angle is less than 30 degrees.

Inventive Concept 246. The method according to Inventive Concept 244,
wherein the closure device further includes:
a ferrule, which is coupled to a distal end portion of the suture;
a ferrule-advancing suturing needle, which is removably couplable to the ferrule; and
a ferrule-withdrawing suturing needle,
wherein the suture-positioning support is shaped so as to define a ferrule receptacle, which is configured to removably receive the ferrule,
wherein the elongate support defines, through a longitudinal portion of the elongate support, first and second needle lumens having first and second distal lumen openings, respectively, and
wherein actuating the closure device to couple the suture to the suture-positioning support comprises actuating the closure device to couple the suture to the suture-positioning support by:
distally advancing, within the first needle lumen and out of the first distal lumen opening, the ferrule-advancing suturing needle removably coupled to the ferrule, and inserting the ferrule into the ferrule receptacle, and
wherein actuating the closure device to proximally withdraw the suture from the suture-positioning support comprises actuating the closure device to proximally withdraw the suture from the suture-positioning support by:

distally advancing, within the second needle lumen and out of the second distal lumen opening, the ferrule-withdrawing suturing needle to the ferrule, coupling the ferrule-withdrawing suturing needle to the ferrule, and proximally withdrawing the ferrule-withdrawing suturing needle while coupled to the ferrule, so as to remove the ferrule from the ferrule receptacle.

Inventive Concept 247. The method according to Inventive Concept 244,
wherein the elongate support includes an outer tubular shaft having a distal end,
wherein the suture-positioning support has proximal and distal end portions at opposite ends of the suture-positioning support,
wherein the proximal end portion of the suture-positioning support is coupled to the elongate support, and
wherein the distal end portion of the suture-positioning support is disposed distally to the distal end of the outer tubular shaft.

Inventive Concept 248. The method according to Inventive Concept 247, wherein the elongate support further includes an inner shaft nested within the outer tubular shaft, and wherein the suture-positioning support is coupled to the inner shaft of the elongate support.

Inventive Concept 249. The method according to Inventive Concept 244,
wherein the suture-positioning support is pivotably coupled to the distal end portion of the elongate support such that the suture-positioning support is rotatable about a pivot axis that is not coaxial with the distal-support central longitudinal axis, and
wherein actuating the closure device to transition the suture-positioning support from the delivery position to the first deployed position comprises actuating the closure device to transition the suture-positioning support from the delivery position to the first deployed position by rotating the suture-positioning support about the pivot axis.

Inventive Concept 250. The method according to Inventive Concept 249, wherein actuating the closure device to transition the suture-positioning support from the first deployed position back to the delivery position comprises actuating the closure device to transition the suture-positioning support from the first deployed position back to the delivery position by rotating the suture-positioning support about the pivot axis.

Inventive Concept 251. The method according to Inventive Concept 244, wherein the suture-positioning support is disposed distally beyond a distal end of the elongate support.

There is additionally provided, in accordance with an Inventive Concept 252 of the present invention, a closure device for suturing a puncture, the closure device comprising:
first and second suturing needles;
a first suture, which is pre-knotted so as to form a first pre-tied knot, which is disposed at least partially within the closure device; and
a second suture, which is pre-knotted so as to form a second pre-tied knot, which is disposed at least partially within the closure device,
wherein the closure device is configured such that:
proximal withdrawal of the first suturing needle pulls the first suturing needle and a distal end portion of the first suture through the first pre-tied knot, and proximal withdrawal of the second suturing needle pulls the second suturing needle and a distal portion of the second suture through the second pre-tied knot.

Inventive Concept 253. The closure device according to Inventive Concept 252, further comprising an elongate support, which comprises one or more shafts, wherein the first and the second pre-tied knots are disposed at least partially within the elongate support.

Inventive Concept 254. The closure device according to Inventive Concept 252, further comprising:
  an elongate support, which comprises one or more shafts;
  first and second ferrules, coupled to respective distal end portions of the first and the second sutures; and
  a suture-positioning support, which is (a) coupled to a distal end portion of the elongate support, (b) laterally extendable with respect to the elongate support, and (c) shaped so as to define a ferrule receptacle, which is configured to removably receive the first and the second ferrules, one at a time.

Inventive Concept 255. The closure device according to Inventive Concept 254,
  wherein the first and the second suturing needles are first and second ferrule-withdrawing suturing needles, respectively, and
  wherein the closure device is configured such that:
    the proximal withdrawal of the first ferrule-withdrawing suturing needle coupled to the first ferrule pulls the first suturing needle, the distal end portion of the first suture, and the first ferrule through the first pre-tied knot, and
    the proximal withdrawal of the second ferrule-withdrawing suturing needle coupled to the second ferrule pulls the second suturing needle, the distal end portion of the second suture, and the second ferrule through the second pre-tied knot.

Inventive Concept 256. The closure device according to Inventive Concept 255,
  wherein the closure device further comprises first and second ferrule-advancing suturing needles, which are removably couplable to the first and the second ferrules, respectively, and
  wherein the closure device is configured to:
    direct the first ferrule into the ferrule receptacle during distal advancement of the first suturing ferrule-advancing needle removably coupled to the first ferrule,
    direct the second ferrule into the ferrule receptacle during distal advancement of the second suturing ferrule-advancing needle removably coupled to the second ferrule.

Inventive Concept 257. The closure device according to Inventive Concept 255,
  wherein the first ferrule-withdrawing suturing needle is initially disposed passing through the first pre-tied knot,
  wherein the first pre-tied knot defines a plurality of turns, and
  wherein at least two of the turns have different respective inner diameters.

Inventive Concept 258. The closure device according to Inventive Concept 257, wherein an inner diameter of a distal-most turn of the first pre-tied knot is greater than an inner diameter of a second-to-distal-most turn of the first pre-tied knot, the distal-most turn being the turn of the first pre-tied knot located closest to a distal pointed end of the first ferrule-withdrawing suturing needle.

Inventive Concept 259. The closure device according to Inventive Concept 258, wherein respective inner diameters of all of the turns of the first pre-tied knot decrease in a distal-to-proximal direction.

Inventive Concept 260. The closure device according to Inventive Concept 257, wherein an inner diameter of a proximal-most turn of the first pre-tied knot is greater than an inner diameter of a second-to-proximal-most turn of the pre-tied knot, the proximal-most turn being the turn of the first pre-tied knot located farthest from a distal pointed end of the first ferrule-withdrawing suturing needle.

There is yet additionally provided, in accordance with an Inventive Concept 261 of the present invention, a method for suturing a puncture through a wall of a blood vessel, the method comprising:
  inserting, through the puncture and into the blood vessel, a distal end portion of an elongate support of a closure device, while first and second pre-tied knots formed by first and second sutures, respectively, are disposed at least partially within the closure device;
  distally advancing the first suture through a portion of the elongate support and a first wall site of the wall and into the blood vessel;
  distally advancing a first suturing needle of the closure device through a second wall site of the wall and into the blood vessel, and coupling the first suturing needle to a distal portion of the first suture;
  proximally withdrawing the first suturing needle from the blood vessel and pulling the first suturing needle and the distal end portion of the first suture through the first pre-tied knot;
  distally advancing the second suture through a portion of the elongate support and a third wall site of the wall and into the blood vessel;
  distally advancing a second suturing needle of the closure device through a second wall site of the wall and into the blood vessel, and coupling the second suturing needle to a distal portion of the second suture; and
  proximally withdrawing the second suturing needle from the blood vessel and pulling the second suturing needle and the distal end portion of the second suture through the second pre-tied knot.

Inventive Concept 262. The method according to Inventive Concept 261, wherein inserting the distal end portion of the elongate support comprises inserting the distal end portion of the elongate support while the first and the second pre-tied knots are disposed at least partially within the elongate support.

There is also provided, in accordance with an Inventive Concept 263 of the present invention, a closure device for suturing a puncture, the closure device comprising:
  a suture;
  an elongate support, which comprises one or more shafts;
  a suture-positioning support, which is (a) coupled to a distal end portion of the elongate support, (b) laterally extendable with respect to the distal end portion of the elongate support, and (c) configured to removably receive the suture;
  a ferrule, which is coupled to a distal end portion of the suture, wherein the ferrule is shaped so as to define a blunt interface with the distal end portion of the suture; and
  a suturing needle, which is removably couplable to the ferrule,
  wherein the suture-positioning support is shaped so as to define a ferrule receptacle, which is configured to removably receive the ferrule, such that the suture-positioning support is configured to removably receive the suture, and wherein the closure device is configured to direct the ferrule into the ferrule receptacle during distal advancement of the suturing needle removably coupled to the ferrule.

Inventive Concept 264. The closure device according to Inventive Concept 263, wherein the blunt interface is defined by a flap defined by at least a portion of material cut from a wall of the ferrule to define an opening through the wall, wherein the at least a portion of the material is bent so as to define the flap having a curved bend, and wherein the suture passes through the opening.

Inventive Concept 265. The closure device according to Inventive Concept 264, wherein the suture is looped through the opening.

Inventive Concept 266. The closure device according to Inventive Concept 263, wherein the blunt interface is defined by a curved surface of a rod fixed to a perimeter of an opening through a wall of the ferrule, and wherein the suture passes through the opening around the rod.

Inventive Concept 267. The closure device according to Inventive Concept 266, wherein the suture is looped through the opening around the rod.

There is further provided, in accordance with an Inventive Concept 268 of the present invention, a closure device for suturing a puncture, the closure device comprising:

a suture;

exactly one ferrule, coupled to a distal end portion of the suture;

an elongate support, which comprises one or more shafts;

a suture-positioning support, which is laterally extendable from a distal portion of the elongate support, and is shaped so as to define a ferrule receptacle, which is configured to removably receive the ferrule; and a suturing needle, which is removably couplable to the ferrule, wherein the closure device is configured to direct the ferrule into the ferrule receptacle during distal advancement of the suturing needle removably coupled to the ferrule.

Inventive Concept 269. The closure device according to Inventive Concept 268, wherein the suture-positioning support is configured to assume a delivery position, in which the suture-positioning support is substantially aligned with a central longitudinal axis of the elongate support, and one or more deployed positions, in which the suture-positioning support is laterally extended from the distal portion of the elongate support.

Inventive Concept 270. The closure device according to Inventive Concept 268, wherein the puncture is an endoscopic puncture through a wall of a body cavity.

Inventive Concept 271. The closure device according to Inventive Concept 268, wherein the puncture is a puncture through a wall of a blood vessel.

Inventive Concept 272. The closure device according to Inventive Concept 271, further comprising an elongate guidebody, which extends distally from a distal end of the elongate support, in order to facilitate alignment of the suture-positioning support in the blood vessel.

Inventive Concept 273. The closure device according to Inventive Concept 268, wherein the elongate support defines a needle lumen through a longitudinal portion of the elongate support, and wherein the needle lumen is shaped so as to direct the suturing needle toward the ferrule receptacle during the distal advancement of the suturing needle.

Inventive Concept 274. The closure device according to Inventive Concept 268, further comprising a control handle, coupled to a proximal end portion of the elongate support.

Inventive Concept 275. The closure device according to any one of Inventive Concepts 268 274, wherein the suture-positioning support is shaped so as to define exactly one ferrule receptacle.

Inventive Concept 276. The closure device according to any one of Inventive Concepts 268-274, wherein the ferrule receptacle is a first ferrule receptacle located at a first location along the suture-positioning support, and wherein the suture-positioning support is shaped so as to further define a second ferrule receptacle located at a second location along the suture-positioning support.

Inventive Concept 277. The closure device according to Inventive Concept 276, further comprising a control handle, which is coupled to a proximal end portion of the elongate support, and which comprises a user control that is configured to select one of the first and the second ferrule receptacles, and to set a direction of the distal advancement of the suturing needle to the selected ferrule receptacle.

Inventive Concept 278. The closure device according to any one of Inventive Concepts 268-274, wherein the suturing needle is a first suturing needle, and wherein the closure device further comprises a second suturing needle, which is couplable to the ferrule, wherein the closure device is configured to direct the ferrule into the ferrule receptacle during distal advancement of the first suturing needle removably coupled to the ferrule, wherein the closure device is configured to direct the second suturing needle to the ferrule during distal advancement of the second suturing needle, and wherein the closure device is configured such that after the distal advancement of the second suturing needle to the ferrule, proximal withdrawal of the second suturing needle coupled to the ferrule removes the ferrule from the ferrule receptacle.

Inventive Concept 279. The closure device according to Inventive Concept 278, wherein the ferrule is shaped to define a ferrule lumen having first and second end openings, wherein the first suturing needle is removably couplable to the ferrule by insertion of the first suturing needle into the first end opening of the ferrule lumen such that proximal withdrawal of the first suturing needle from the ferrule when the ferrule is within the ferrule receptacle withdraws the first suturing needle from the first end opening of the ferrule lumen, leaving the ferrule within the ferrule receptacle, and wherein the second suturing needle is couplable to the ferrule by insertion of the second suturing needle into the second end opening of the ferrule lumen such that proximal withdrawal of the second suturing needle from the ferrule when the ferrule is within the ferrule receptacle withdraws the ferrule from the ferrule receptacle.

Inventive Concept 280. The closure device according to Inventive Concept 279, wherein the ferrule is shaped so as to define one or more tabs that are biased to protrude radially inward within the ferrule lumen and to engage the second suturing needle upon the insertion of the second suturing needle into the second end opening of the ferrule lumen, so as to inhibit withdrawal of the second suturing needle from the ferrule lumen.

Inventive Concept 281. The closure device according to Inventive Concept 279, wherein a distal end portion of the second suturing needle is shaped so as to define one or more lateral protrusions that are configured to engage the ferrule upon the insertion of the second suturing needle into the second end opening of the ferrule lumen, so as to inhibit withdrawal of the second suturing needle from the ferrule lumen.

Inventive Concept 282. The closure device according to Inventive Concept 278, wherein the elongate support defines first and second needle lumens through respective longitudinal portions of the elongate support, and wherein the first and the second needle lumens are shaped so as to direct the first and the second suturing needles toward the ferrule receptacle during the distal advancement of the first suturing needle and the distal advancement of the second suturing needle, respectively.

Inventive Concept 283. The closure device according to any one of Inventive Concepts 268 274,
- wherein the suture-positioning support is configured to assume first and second deployed positions with respect to the distal portion of the elongate support, and
- wherein in the first deployed position the suture-positioning support laterally extends in a first direction from the distal portion of the elongate support, and in the second deployed position the suture-positioning support laterally extends in a second direction from the distal portion of the elongate support, the second direction different from the first direction.

Inventive Concept 284. The closure device according to Inventive Concept 283, wherein the suture-positioning support is rotatable about a central longitudinal axis of the distal portion of the elongate support so as to transition from the first deployed position to the second deployed position.

Inventive Concept 285. The closure device according to Inventive Concept 283,
- wherein the suture-positioning support is pivotably coupled to the distal portion of the elongate support such that the suture-positioning support is rotatable about a pivot axis to transition from the first deployed position and to the second deployed position, and
- wherein the pivot axis is not coaxial with a central longitudinal axis of the elongate support.

Inventive Concept 286. The closure device according to Inventive Concept 285, wherein the suture-positioning support is rotatable to assume a delivery position, in which the suture-positioning support is substantially aligned with a central longitudinal axis of the elongate support.

Inventive Concept 287. The closure device according to Inventive Concept 286, wherein the suture-positioning support is pivotably coupled to the distal portion of the elongate support such that the suture-positioning support is rotatable about the pivot axis to transition from the first deployed position to the second deployed position via the delivery position.

Inventive Concept 288. The closure device according to Inventive Concept 285,
- wherein the ferrule receptacle is shaped to define a ferrule-receiving lumen having first and second end openings open to first and second sides of the suture-positioning support, respectively,
- wherein the ferrule receptacle is configured to removably receive the ferrule via the first end opening of the ferrule-receiving lumen and to release the ferrule via the second end opening of the ferrule-receiving lumen, and
- wherein when the suture-positioning support is in the first deployed position, the first end opening of the ferrule-receiving lumen faces proximally, and when the suture-positioning support is in the second deployed position, the second end opening of the ferrule-receiving lumen faces proximally.

Inventive Concept 289. The closure device according to Inventive Concept 288,
- wherein the ferrule is shaped to define a ferrule lumen having first and second end openings,
- wherein the suturing needle is removably coupled to the ferrule by insertion of the suturing needle into the first end opening of the ferrule lumen such that proximal withdrawal of the suturing needle from the ferrule when the ferrule is within the ferrule receptacle withdraws the suturing needle from the first end opening of the ferrule lumen, leaving the ferrule within the ferrule receptacle, and
- wherein the suturing needle is couplable to the ferrule by insertion of the suturing needle into the second end opening of the ferrule lumen such that proximal withdrawal of the suturing needle from the ferrule when the ferrule is within the ferrule receptacle withdraws the ferrule from the second end opening of the ferrule lumen.

Inventive Concept 290. The closure device according to Inventive Concept 289, wherein the ferrule is shaped so as to define one or more tabs that are biased to protrude radially inward within the ferrule lumen and to engage the suturing needle upon the insertion of the suturing needle into the second end opening of the ferrule lumen, so as to inhibit withdrawal of the suturing needle from the ferrule lumen.

Inventive Concept 291. The closure device according to Inventive Concept 288,
- wherein the suturing needle is a first suturing needle, and wherein the closure device further comprises a second suturing needle, which is couplable to the ferrule,
- wherein the ferrule is shaped to define a ferrule lumen having first and second end openings,
- wherein the first suturing needle is removably couplable to the ferrule by insertion of the first suturing needle into the first end opening of the ferrule lumen such that proximal withdrawal of the first suturing needle from the ferrule when the ferrule is within the ferrule receptacle withdraws the first suturing needle from the first end opening of the ferrule lumen, leaving the ferrule within the ferrule receptacle, and
- wherein the second suturing needle is couplable to the ferrule by insertion of the second suturing needle into the second end opening of the ferrule lumen such that proximal withdrawal of the second suturing needle from the ferrule when the ferrule is within the ferrule receptacle withdraws the ferrule from the second end opening of the ferrule lumen.

There is still further provided, in accordance with an Inventive Concept 292 of the present invention, a method for suturing a puncture through a wall of a hollow anatomical structure, the method comprising:
- inserting a distal portion of an elongate support of a closure device through the puncture and into the hollow anatomical structure while a suture-positioning support of the closure device is in a delivery position coupled to the distal portion of the elongate support,
- wherein the closure device includes exactly one ferrule coupled to a distal end portion of a suture, and wherein the elongate support includes one or more shafts;

transitioning the suture-positioning support from the delivery position to a first deployed position in which the suture-positioning support laterally extends in a first direction from the distal portion of the elongate support;

distally advancing a suturing needle of the closure device through a first wall site of the wall and into the hollow anatomical structure, while the suturing needle is removably coupled to the ferrule, such that the closure device directs the ferrule into a ferrule receptacle defined by the suture-positioning support and the ferrule receptacle removably receives the ferrule while the suture-positioning support is in the first deployed position;

proximally withdrawing the suturing needle from the ferrule and the hollow anatomical structure, while leaving the ferrule within the ferrule receptacle;

transitioning the suture-positioning support from the first deployed position to a second deployed position in which the suture-positioning support laterally extends in a second direction from the distal portion of the elongate support, the second direction different from the first direction;

while the suture-positioning support is in the second deployed position, proximally withdrawing the ferrule from the ferrule receptacle and out of the hollow anatomical structure via a second wall site of the wall, so as to proximally withdraw a portion of the suture, including the distal end portion thereof, out of the hollow anatomical structure via the second wall site; and securing the portion of the suture drawn out of the hollow anatomical structure via the second wall site to another portion of the suture outside the hollow anatomical structure.

Inventive Concept 293. The method according to Inventive Concept 292, wherein the hollow anatomical structure is a body cavity, and wherein inserting the distal portion of the elongate support comprises inserting the distal portion of the elongate support through the puncture and into the body cavity.

Inventive Concept 294. The method according to Inventive Concept 292, wherein the hollow anatomical structure is a blood vessel, and wherein inserting the distal portion of the elongate support comprises inserting the distal portion of the elongate support through the puncture and into the blood vessel.

Inventive Concept 295. The method according to Inventive Concept 294, wherein inserting the distal portion of the elongate support through the puncture and into the blood vessel comprises aligning the suture-positioning support in the blood vessel by inserting, through the puncture and into the blood vessel, an elongate guidebody that extends distally from a distal end of the elongate support.

Inventive Concept 296. The method according to Inventive Concept 292,
wherein the elongate support defines a needle lumen through a longitudinal portion of the elongate support, and
wherein distally advancing the suturing needle comprises distally advancing the suturing needle through the first wall site and into the hollow anatomical structure while a portion of the suturing needle is disposed within the needle lumen, such that the needle lumen directs the suturing needle toward the ferrule receptacle while the suture-positioning support is in the first deployed position.

Inventive Concept 297. The method according to Inventive Concept 292, wherein transitioning the suture-positioning support from the delivery position to the first deployed position comprises actuating a user control of a control handle coupled to a proximal end portion of the elongate support.

Inventive Concept 298. The method according to Inventive Concept 292, wherein the suture-positioning support is shaped so as to define exactly one ferrule receptacle.

Inventive Concept 299. The method according to Inventive Concept 292, wherein the ferrule receptacle is a first ferrule receptacle located at a first location along the suture-positioning support, and wherein the suture-positioning support is shaped so as to further define a second ferrule receptacle located at a second location along the suture-positioning support.

Inventive Concept 300. The method according to Inventive Concept 299, wherein distally advancing the suturing needle comprises:
selecting one of the first and the second ferrule receptacles using a user control of a control handle coupled to a proximal end portion of the elongate support; and
distally advancing the suturing needle through the first wall site and into the hollow anatomical structure such that the closure device sets a direction of distal advancement of the suturing needle to the selected ferrule receptacle.

Inventive Concept 301. The method according to Inventive Concept 292,
wherein the suturing needle is a first suturing needle,
wherein distally advancing the suturing needle comprises distally advancing the first suturing needle through the first wall site and into the hollow anatomical structure, while the first suturing needle is removably coupled to the ferrule,
wherein proximally withdrawing the suturing needle comprises proximally withdrawing the first suturing needle from the ferrule and the hollow anatomical structure, while leaving the ferrule within the ferrule receptacle, and
wherein proximally withdrawing the ferrule from the ferrule receptacle and out of the hollow anatomical structure while the suture-positioning support is in the second deployed position comprises:
distally advancing a second suturing needle of the closure device through the second wall site and into the hollow anatomical structure, such that the closure device directs the second suturing needle to the ferrule and the second suturing needle becomes coupled to the ferrule; and
proximally withdrawing the second suturing needle from the hollow anatomical structure via the second wall site, so as to remove the ferrule from the ferrule receptacle and to proximally withdraw the distal end portion of the suture out of the hollow anatomical structure via the second wall site.

Inventive Concept 302. The method according to Inventive Concept 301,
wherein the ferrule is shaped to define a ferrule lumen having first and second end openings,
wherein distally advancing the first suturing needle comprises distally advancing the first suturing needle through the first wall site and into the hollow anatomical structure, while the first suturing needle is removably coupled to the ferrule by insertion of the first suturing needle into the first end opening of the ferrule lumen, wherein proximally withdrawing the first suturing needle from the ferrule comprises proximally withdrawing the first suturing needle from the first end opening of the ferrule lumen, leaving the ferrule within the ferrule receptacle, wherein distally advancing the second suturing needle comprises inserting the second suturing needle into the second end opening of the ferrule lumen, and wherein proximally withdrawing the second suturing needle removes the ferrule from the ferrule receptacle.

Inventive Concept 303. The method according to Inventive Concept 302, wherein the ferrule is shaped so as to define one or more tabs that are biased to protrude radially inward within the ferrule lumen and to engage the second suturing needle upon the insertion of the second suturing needle into the second end opening of the ferrule lumen, so as to inhibit withdrawal of the second suturing needle from the ferrule lumen.

Inventive Concept 304. The method according to Inventive Concept 302, wherein a distal end portion of the second suturing needle is shaped so as to define one or more lateral protrusions that are configured to engage the ferrule upon the insertion of the second suturing needle into the second end opening of the ferrule lumen, so as to inhibit withdrawal of the second suturing needle from the ferrule lumen.

Inventive Concept 305. The method according to Inventive Concept 301,
wherein the elongate support defines first and second needle lumens through respective longitudinal portions of the elongate support,
wherein distally advancing the first suturing needle comprises distally advancing the first suturing needle through the first wall site and into the hollow anatomical structure while a portion of the suturing needle is disposed within the first needle lumen, such that the first needle lumen directs the suturing needle toward the ferrule receptacle while the suture-positioning support is in the first deployed position, and
wherein distally advancing the second suturing needle comprises distally advancing the second suturing needle through the second wall site and into the hollow anatomical structure while a portion of the second suturing needle is disposed within the second needle lumen, such that the second needle lumen directs the second suturing needle toward the ferrule receptacle while the suture-positioning support is in the second deployed position.

Inventive Concept 306. The method according to Inventive Concept 292, wherein transitioning the suture-positioning support from the first deployed position to the second deployed position comprises rotating the suture-positioning support about a central longitudinal axis of the distal portion of the elongate support.

Inventive Concept 307. The method according to Inventive Concept 292,
wherein the suture-positioning support is pivotably coupled to the distal portion of the elongate support such that the suture-positioning support is rotatable about a pivot axis, wherein the pivot axis is not coaxial with a central longitudinal axis of the elongate support, and
wherein transitioning the suture-positioning support from the first deployed position to the second deployed comprises rotating the suture-positioning support about the pivot axis.

Inventive Concept 308. The method according to Inventive Concept 307, wherein inserting the distal portion of the elongate support comprises inserting the distal portion of the elongate support through the puncture and into the hollow anatomical structure while the suture-positioning support of the closure device is in the delivery position in which the suture-positioning support is substantially aligned with a central longitudinal axis of the elongate support.

Inventive Concept 309. The method according to Inventive Concept 308, wherein transitioning the suture-positioning support comprises rotating the suture-positioning support about the pivot axis to transition the suture-positioning support from the first deployed position to the second deployed position via the delivery position.

Inventive Concept 310. The method according to Inventive Concept 307,
wherein the ferrule receptacle is shaped to define a ferrule-receiving lumen having first and second end openings open to first and second sides of the suture-positioning support, respectively,
wherein the ferrule receptacle is configured to removably receive the ferrule via the first end opening of the ferrule-receiving lumen and to release the ferrule via the second end opening of the ferrule-receiving lumen,
wherein transitioning the suture-positioning support from the delivery position to the first deployed position comprises transitioning the suture-positioning support from the delivery position to the first deployed position in which the first end opening of the ferrule-receiving lumen faces proximally, and
transitioning the suture-positioning support from the first deployed position to the second deployed position comprises transitioning the suture-positioning support from the first deployed position to the second deployed position in which the second end opening of the ferrule-receiving lumen faces proximally.

There is additionally provided, in accordance with an Inventive Concept 311 of the present invention, a suture assembly comprising:
distal and proximal suture segments, which are non-integral with each other;
a crimp ferrule, which fixes the distal and the proximal suture segments to each other within the crimp ferrule,
wherein a distal end portion of the proximal suture segment is disposed within a proximal portion of the crimp ferrule and is fixed to the crimp ferrule by crimping,
wherein a proximal end portion of the distal suture segment is disposed within a distal portion of the crimp ferrule, and
wherein the distal portion of the crimp ferrule is shaped so as to define one or more lateral holes.

Inventive Concept 312. The suture assembly according to Inventive Concept 311, wherein the distal suture segment is shaped as a loop having two proximal end portions that are fixed within the distal portion of the crimp ferrule.

Inventive Concept 313. The suture assembly according to Inventive Concept 312, wherein the two proximal end portions of the loop of the distal suture segment are melted together so as to be fixed within the distal portion of the crimp ferrule.

Inventive Concept 314. The suture assembly according to Inventive Concept 313, wherein a portion of the melted suture segment protrudes through the one or more lateral holes to outside the crimp ferrule.

Inventive Concept 315. The suture assembly according to Inventive Concept 311, wherein the proximal end portion of the distal suture segment is knotted into a knot so as to fix the proximal end portion within the distal portion of the crimp ferrule.

Inventive Concept 316. The suture assembly according to Inventive Concept 315, further comprising an adhesive disposed within the distal portion of the crimp ferrule so as to inhibit unknotting of the knot.

Inventive Concept 317. The suture assembly according to Inventive Concept 315,
- wherein the distal suture segment is shaped as a loop having two proximal end portions, and
- wherein the two proximal end portions of the loop are knotted to each other into the knot, so as to fix the two proximal end portions within the distal portion of the crimp ferrule.

Inventive Concept 318. The suture assembly according to Inventive Concept 317, wherein the knot is too large to pass through a distal opening of the crimp ferrule.

There is yet additionally provided, in accordance with an Inventive Concept 319 of the present invention, a suture assembly comprising:
- distal and proximal suture segments, which are non-integral with each other;
- a crimp ferrule, which fixes the distal and the proximal suture segments to each other within the crimp ferrule,
- wherein a distal end portion of the proximal suture segment is disposed within a proximal portion of the crimp ferrule and is fixed to the crimp ferrule by crimping, and
- wherein a proximal end portion of the distal suture segment is (i) disposed within a distal portion of the crimp ferrule, and (ii) knotted into a knot so as to fix the proximal end portion within the distal portion of the crimp ferrule.

Inventive Concept 320. The suture assembly according to Inventive Concept 319, further comprising an adhesive disposed at least partially within the distal portion of the crimp ferrule so as to inhibit unknotting of the knot.

Inventive Concept 321. The suture assembly according to Inventive Concept 320, wherein a portion of the adhesive protrudes through the one or more lateral holes to outside the crimp ferrule.

Inventive Concept 322. The suture assembly according to Inventive Concept 319,
- wherein the distal suture segment is shaped as a loop having two proximal end portions, and
- wherein the two proximal end portions of the loop are knotted to each other into the knot, so as to fix the two proximal end portions within the distal portion of the crimp ferrule.

Inventive Concept 323. The suture assembly according to Inventive Concept 322, wherein the knot is too large to pass through a distal opening of the crimp ferrule.

There is also provided, in accordance with an Inventive Concept 324 of the present invention, a suture assembly comprising:
- distal and proximal suture segments, which are non-integral with each other;
- a crimp ferrule, which fixes the distal and the proximal suture segments to each other within the crimp ferrule,
- wherein a distal end portion of the proximal suture segment is disposed within a proximal portion of the crimp ferrule and is fixed to the crimp ferrule by crimping,
- wherein a proximal end portion of the distal suture segment is disposed within a distal portion of the crimp ferrule, and
- wherein the distal suture segment is shaped as a loop having two proximal end portions that are (i) within the distal portion of the crimp ferrule, and (ii) melted together so as to be fixed within the distal portion of the crimp ferrule.

Inventive Concept 325. The suture assembly according to any one of Inventive Concepts 311, 319, and 324, wherein the distal and the proximal suture segments have different diameters.

Inventive Concept 326. The suture assembly according to Inventive Concept 325, wherein a diameter of the distal suture segment is less than a diameter of the proximal suture segment.

Inventive Concept 327. The suture assembly according to any one of Inventive Concepts 311, 319, and 324, wherein the distal and the proximal suture segments comprise different types of material.

Inventive Concept 328. The suture assembly according to any one of Inventive Concepts 311, 319, and 324, wherein the crimping indentations are arranged in two or more axial rows along a longitudinal axis of the crimp ferrule, wherein each axial row encircles the crimp ferrule, wherein each axial row includes two to ten crimping indentations, and wherein the crimping indentations in axially-adject axial rows are circumferentially offset from one another.

Inventive Concept 329. The suture assembly according to any one of Inventive Concepts 311, 319, and 324, wherein the distal portion of the crimp ferrule is shaped so as to define a tapered distal tip that is shaped so as to define a distal opening that is smaller than a proximal opening defined by a proximal end of the crimp ferrule.

The present invention will be more fully understood from the following detailed description of embodiments thereof, taken together with the drawings, in which:

BRIEF DESCRIPTION OF THE DRAWINGS

FIGS. 5A-J are schematic illustrations of a method for suturing a puncture through a wall of a hollow anatomical structure using the closure device of FIG. 1, in accordance with an application of the present invention;

FIGS. 7A-L are schematic illustrations of a method for suturing a puncture through a wall of a hollow anatomical structure using the closure device of FIG. 6, in accordance with an application of the present invention;

FIGS. 8A-H are schematic illustrations of yet another closure device for suturing a puncture, in accordance with an application of the present invention, and a method for suturing a puncture through a wall of a hollow anatomical structure using the closure device, in accordance with an application of the present invention;

FIG. 9B is a schematic illustration of a distal end portion of an elongate support of the closure device of FIG. 9A, in accordance with an application of the present invention;

FIGS. 9C-D are schematic illustrations of distal portions of suturing needles and sutures of the closure device of FIG. 9A, from two views, in accordance with an application of the present invention;

FIGS. 14A-B are schematic illustrations of a configuration of the closure device of FIG. 9A, including a control handle thereof, in accordance with an application of the present invention;

FIGS. 15A-H are schematic cross-sectional illustrations of a method of using the control handle of the closure device configuration of FIGS. 14A-B, in accordance with an application of the present invention;

FIGS. 16A and 16B are schematic isometric and cross-sectional views of an alternative configuration of a proximal end portion of a dilator of the closure device of FIG. 9A, with a sheath distally advanced, in accordance with an application of the present invention;

FIGS. 17A and 17B are schematic isometric and cross-sectional views of the alternative configuration of the proximal end portion of the dilator of FIGS. 16A and 16B, with the sheath proximally withdrawn, in accordance with an application of the present invention;

FIG. 18 is a schematic cross-sectional illustration of a configuration of a sheath, an elongate support, and a portion of a control handle of the closure device of FIG. 9A, in accordance with an application of the present invention;

FIGS. 20A-C are schematic illustrations of the alternative configuration of suture the positioning support shown in FIGS. 19A-C, as well as a distal end portion of an elongate support, an elongate flexible dilator connector, and a portion of a proximal end portion of a dilator of the closure device of FIG. 9A, in accordance with an application of the present invention;

FIGS. 21A-C are schematic isometric and cross-sectional illustrations of pre-tied knots, in accordance with an application of the present invention;

FIGS. 22A-C are schematic isometric and cross-sectional illustrations of additional pre-tied knots, in accordance with an application of the present invention;

FIGS. 27A-B and 27C-D are schematic isometric and cross-sectional views of additional crimping techniques using a crimp tube, in accordance with respective applications of the present invention;

FIG. 27E is a schematic illustration of another fixation of distal and proximal suture segments of a suture, in accordance with an application of the present invention;

FIGS. 28A-B are schematic illustrations of another configuration of the closure device of FIG. 9A, in accordance with an application of the present invention;

FIGS. 32A-D are schematic illustrations of still another ferrule-withdrawing suturing needle, in accordance with an application of the present invention;

FIGS. 33A-C are schematic illustrations of a configuration of a control handle of the closure device of FIG. 9A, in accordance with an application of the present invention;

DETAILED DESCRIPTION OF APPLICATIONS

Figure 1:
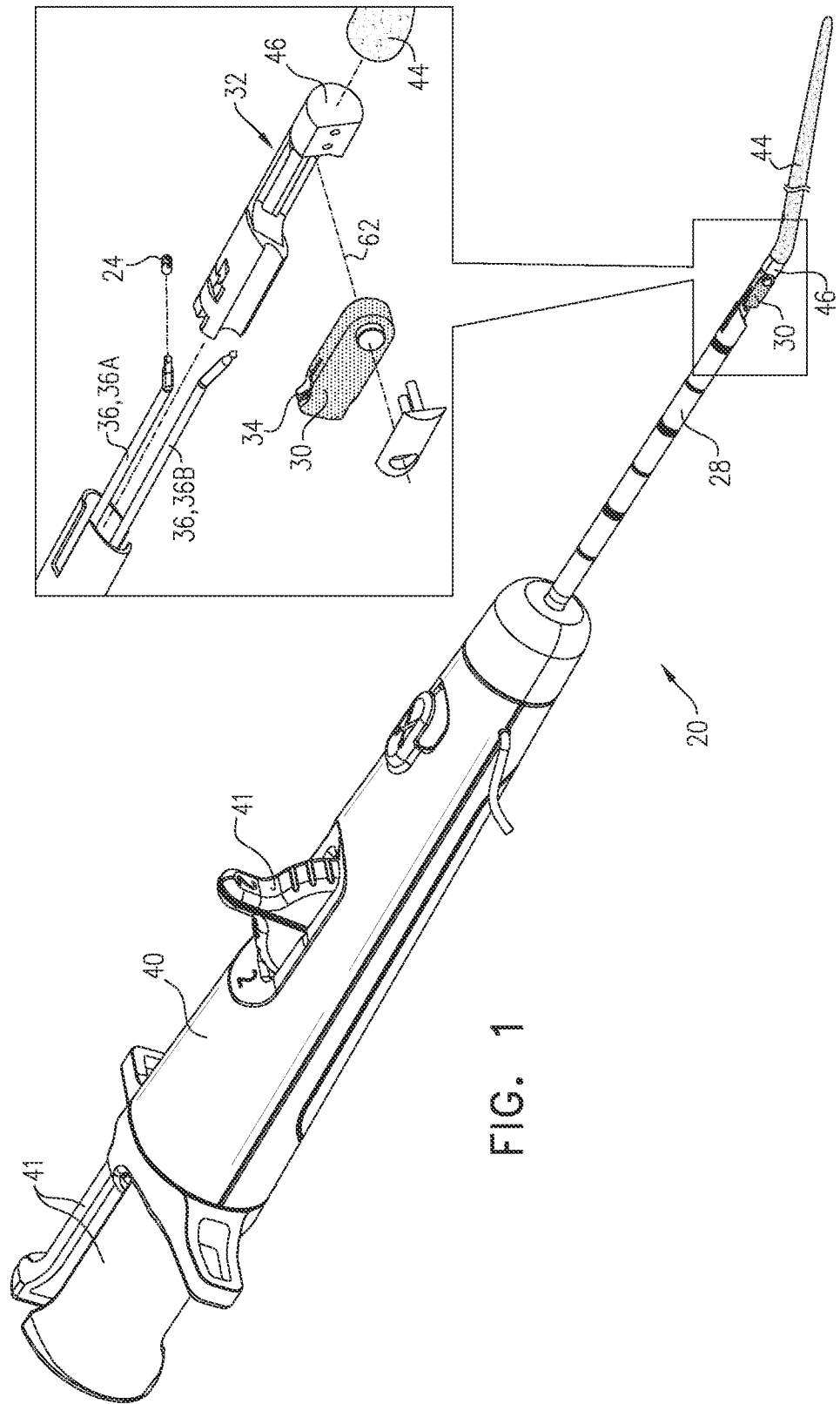
FIG. 1 is a schematic illustration of a closure device for suturing a puncture, in accordance with an application of the present invention.
Figure 2A:
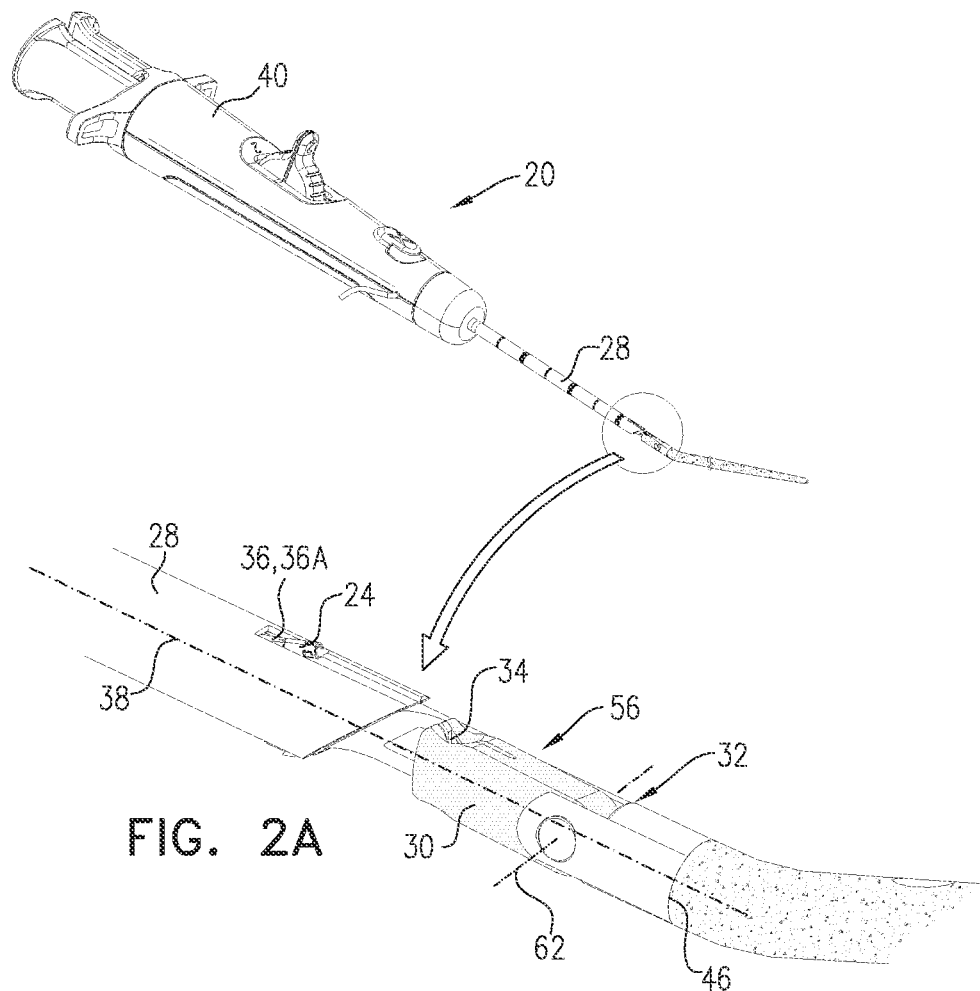
FIGS. 2A-D are several schematic views of a portion of the closure device of FIG. 1, in accordance with an application of the present invention.
Figure 2B:
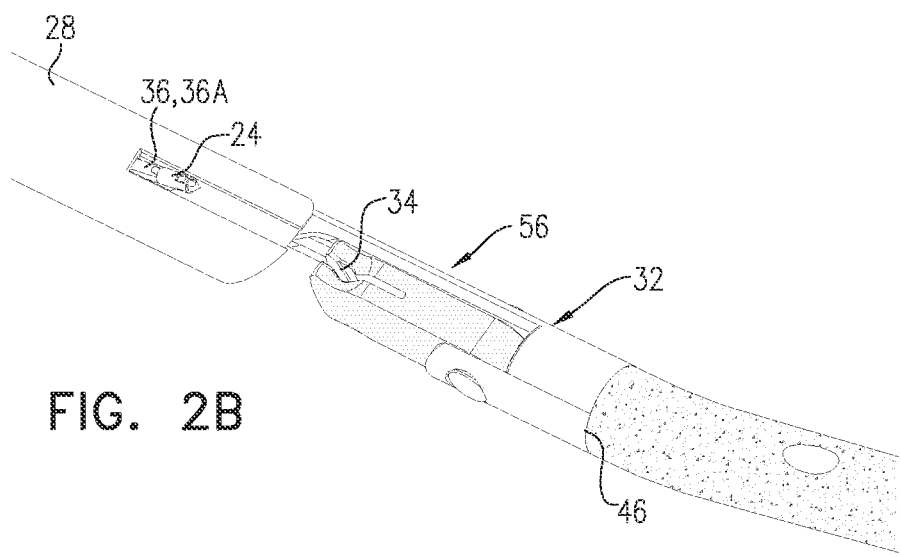
Figure 2C:
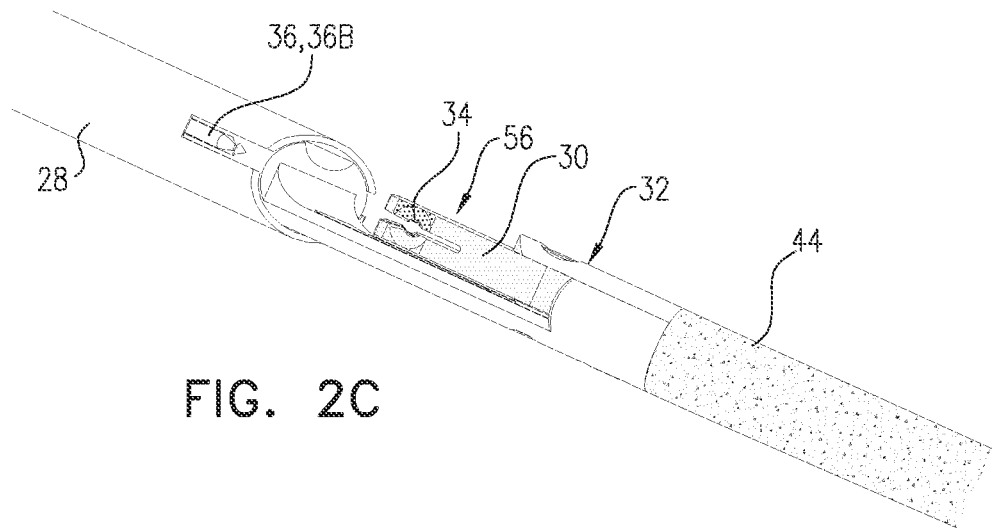
Figure 2D:
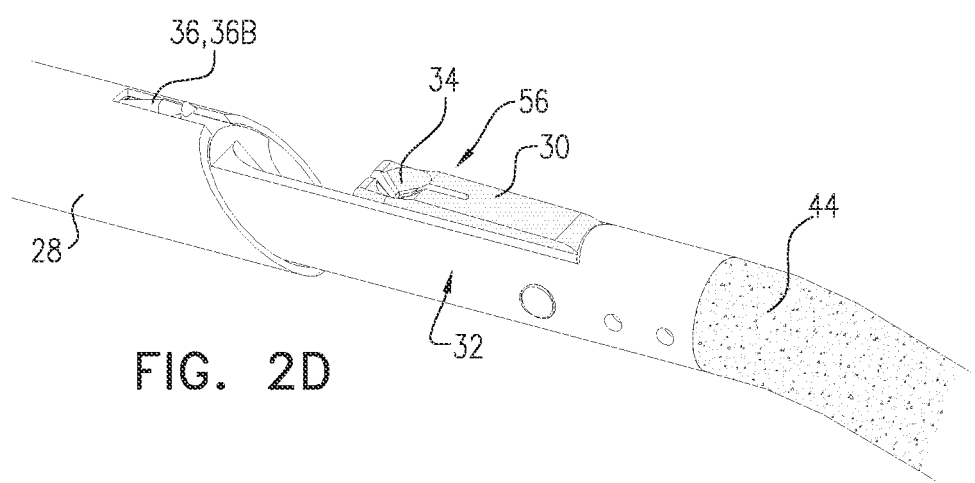

Reference is made to FIG. 1, which is a schematic illustration of a closure device 20 for suturing a puncture, in accordance with an application of the present invention.

Reference is further made to FIGS. 2A-D, which are several schematic views of a portion of closure device 20, in accordance with an application of the present invention.

Figure 3A:
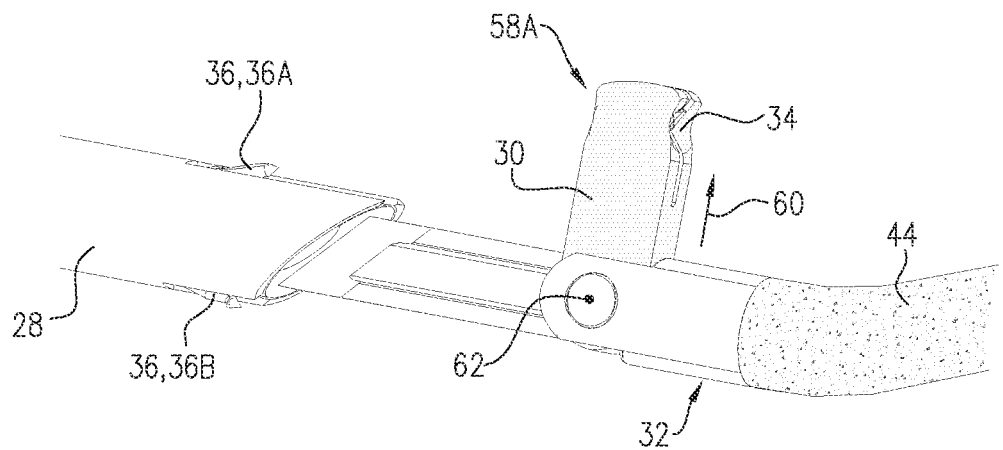
FIGS. 3A and 3B are schematic illustrations of a suture-positioning support of the closure device of FIG. 1 laterally extended in first and second directions from a distal portion of an elongate support of the closure device, respectively, in accordance with an application of the present invention.
Figure 3B:
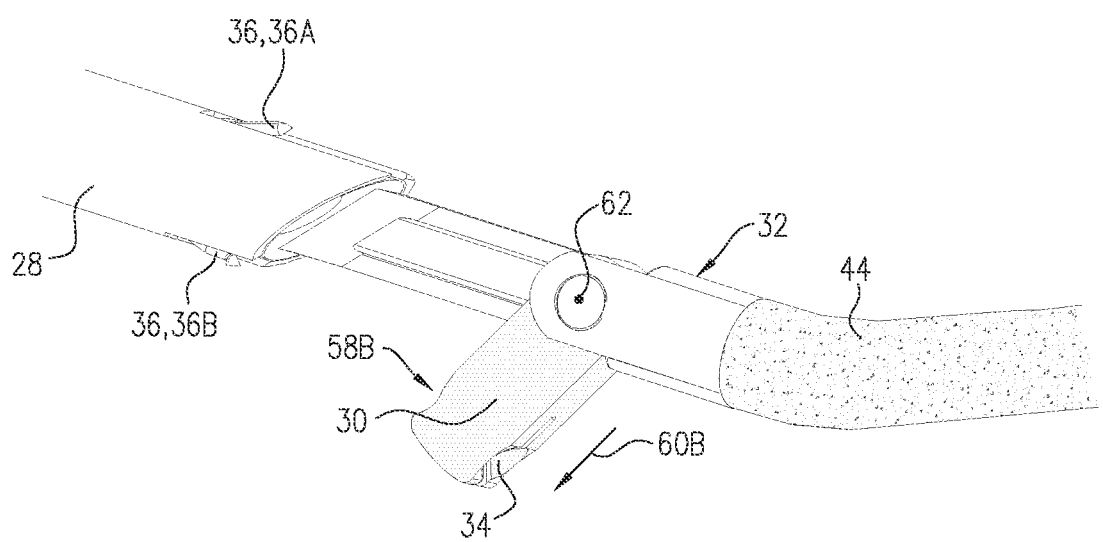

Reference is still further made to FIGS. 3A and 3B, which are schematic illustrations of a suture-positioning support 30 of closure device 20 laterally extended in first and second directions 60A and 60B from a distal portion 32 of an elongate support 28 of closure device 20, respectively, in accordance with an application of the present invention.

Figure 4:
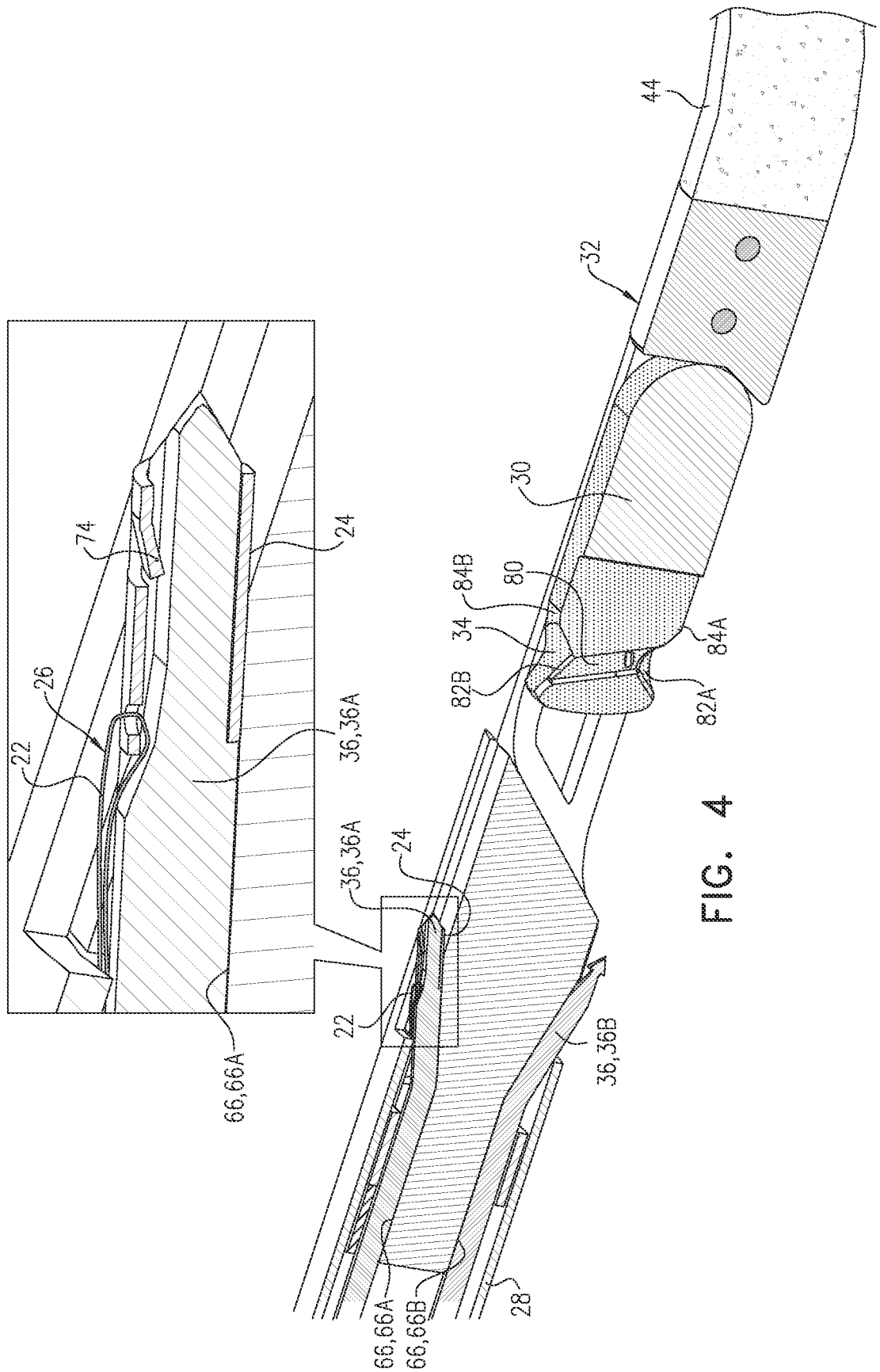
FIG. 4 is a schematic cross-sectional view of a portion of the closure device of FIG. 1, in accordance with an application of the present invention.

Reference is also made to FIG. 4, which is a schematic cross-sectional view of a portion of closure device 20, in accordance with an application of the present invention.

Closure device 20 is used for suturing a puncture at an access site through a wall of a hollow anatomical structure, such as a blood vessel (in which case the access site is a vascular access site), or another body cavity, e.g., an abdominal cavity.

Closure device 20 comprises:

a suture 22;

exactly one ferrule 24, coupled to a distal end portion 26 of suture 22 (labeled in FIG. 4), such as by being passed (e.g., looped) through an opening defined by a wall of ferrule 24 (such as shown), and/or by welding, knotting, gluing, or another technique (configurations not shown);

elongate support 28, which typically comprises one or more shafts;

suture-positioning support 30, which is laterally extendable from distal portion 32 of elongate support 28, and is shaped so as to define a ferrule receptacle 34, which is configured to removably receive ferrule 24; and a suturing needle 36, which is removably couplable to ferrule 24.

Closure device 20 is configured to direct ferrule 24 into ferrule receptacle 34 during distal advancement of suturing needle 36 removably coupled to ferrule 24, such as described hereinbelow with reference to FIG. 5D.

For some applications, suture-positioning support 30 is configured to assume (a) a delivery position 56, optionally in which suture-positioning support 30 is substantially aligned with longitudinal axis 38 of elongate support 28, such as shown in FIGS. 2A-D and 4, and (b) one or more deployed positions 58, in which suture-positioning support 30 is laterally extended from distal portion 32 of elongate support 28, such as shown in FIGS. 3A and 3B.

For some applications, suture-positioning support 30 is shaped so as to define exactly one ferrule receptacle 34. For other applications, the suture-positioning support is shaped so as to define two or more ferrule receptacles, such as described hereinbelow.

Typically, closure device 20 further comprises a control handle 40, coupled to a proximal end portion 42 of elongate support 28, such as shown in FIG. 1. Control handle 40 comprises one or more user controls 41, such as levers and/or buttons, that allow an operator to control the positions and states of one or more elements of closure device 20.

For some applications in which closure device 20 is configured to close a puncture through a wall of a blood vessel, closure device 20 further comprises an elongate guidebody 44 (also sometimes called a dilator in the art), which extends distally from a distal end 46 of elongate support 28, in order to facilitate alignment of suture-positioning support 30 in the blood vessel.

Reference is now made to FIGS. 5A-J, which are schematic illustrations of a method for suturing a puncture 50 through a wall 52 of a hollow anatomical structure 54 using closure device 20, in accordance with an application of the present invention. Although hollow anatomical structure 54 is illustrated as a blood vessel, and puncture 50 at a vascular access site, the method may alternatively be performed on other hollow anatomical structures, such as a body cavity, e.g., an abdominal cavity, mutatis mutandis., in which case closure device 320 may be configured to close an endoscopic puncture through a wall of the body cavity.

As shown in FIGS. 5A-B, distal portion 32 of elongate support 28 is inserted through puncture 50 and into hollow anatomical structure 54 while suture-positioning support 30 is in a delivery position 56 coupled to distal portion 32 of elongate support 28. As mentioned above, suture-positioning support 30 is also shown in delivery position 56 in FIGS. 2A-D and 4.

For some applications, when in delivery position 56, suture-positioning support 30 is substantially aligned with a longitudinal axis 38 of elongate support 28 (labeled in FIG. 2A), such as shown in FIGS. 2A-D, 4, and 5A-B.

For some applications in which closure device 20 is configured to close puncture 50 through wall 52 of a blood vessel, inserting distal portion 32 of elongate support 28 through puncture 50 and into the blood vessel comprises aligning suture-positioning support 30 in the blood vessel by inserting, through puncture 50 and into the blood vessel, elongate guidebody 44 that extends distally from distal end 46 of elongate support 28, such as shown in FIGS. 5A-B.

Figure 5C:
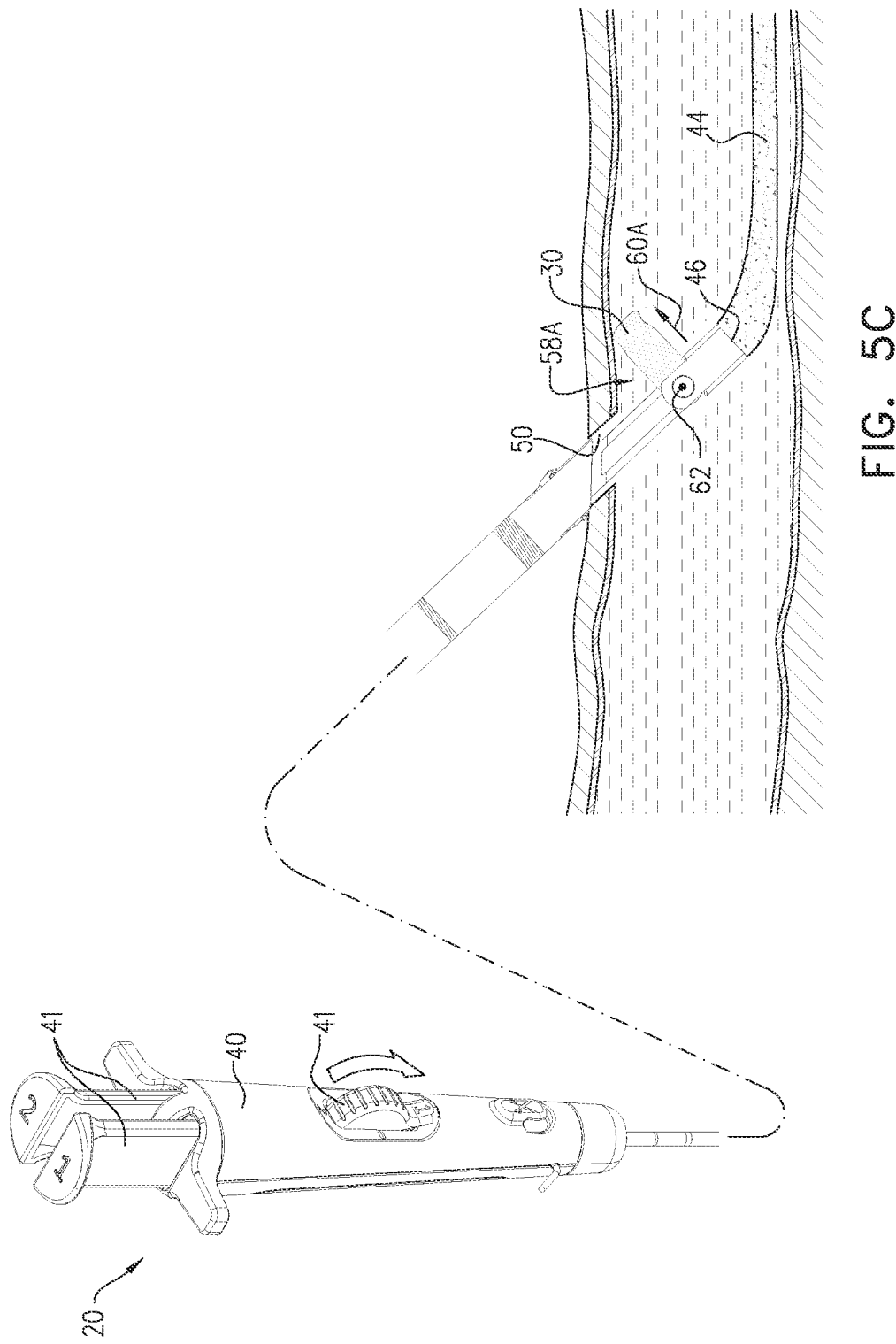

As shown in FIG. 5C, suture-positioning support 30 is transitioned from delivery position 56 to a first deployed position 58A in which suture-positioning support 30 laterally extends in a first direction 60A from distal portion 32 of elongate support 28. Suture-positioning support 30 is also shown in first deployed position 58A in FIG. 3A, described hereinabove.

For some applications, suture-positioning support 30 is transitioned from delivery position 56 to first deployed position 58A by activating one or more of user controls 41 of control handle 40 coupled to proximal end portion 42 of elongate support 28.

For some applications, such as shown in the transition between FIGS. 5A-B and FIG. 5C, suture-positioning support 30 is pivotably coupled to distal portion 32 of elongate support 28 such that suture-positioning support 30 is rotatable about a pivot axis 62 to transition from delivery position 56 to first deployed position 58A. Typically, pivot axis 62 is not coaxial with longitudinal axis 38 of elongate support 28 (as labeled in FIG. 2A).

Figure 5D:
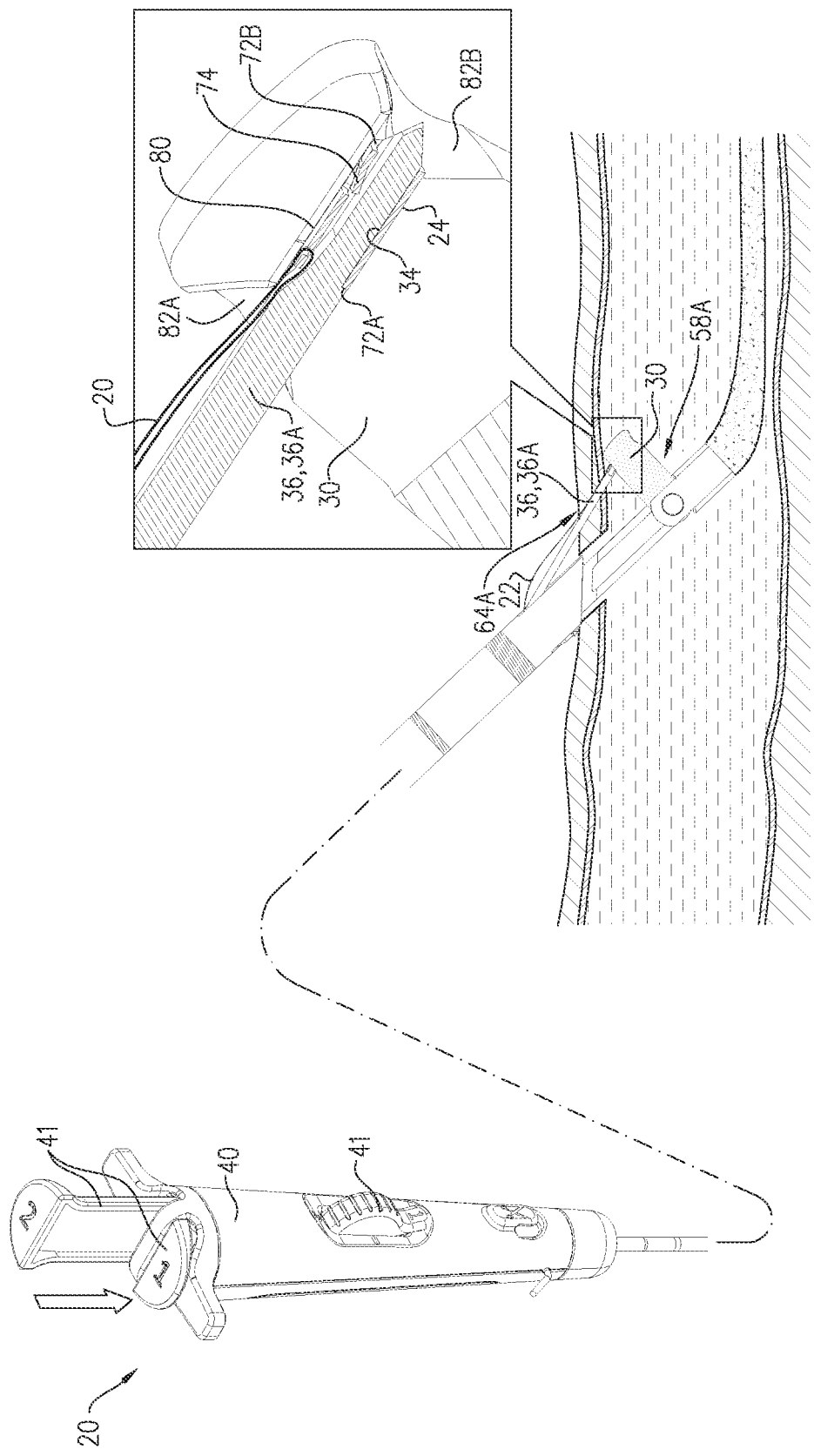

As shown in FIG. 5D, suturing needle 36 of closure device 20 is distally advanced through a first wall site 64A of wall 52 and into hollow anatomical structure 54, while suturing needle 36 is removably coupled to ferrule 24, such that closure device 20 directs ferrule 24 into ferrule receptacle 34 defined by suture-positioning support 30, and ferrule receptacle 34 removably receives ferrule 24 while suture-positioning support 30 is in first deployed position 58A. For some applications, suturing needle 36 is distally advanced by activating one or more of user controls 41 of control handle 40 coupled to a proximal portion of suturing needle 36. Typically, suturing needle 36 is removably coupled to ferrule 24 before the beginning of the procedure, although suturing needle 36 may alternatively become removably coupled to ferrule 24 during the procedure, such as during distal advancement of suturing needle 36 through or out of needle lumen 66, described immediately below. Optionally, the surgeon adjusts an axial position of elongate support 28 such that suture-positioning support 30 touches, or is near, an inner surface of wall 52, as shown in FIG. 5D.

Reference is still made to FIG. 5D, and is additionally again made to FIG. 4. For some applications, elongate support 28 defines a needle lumen 66 (labeled in FIG. 4) through a longitudinal portion of elongate support 28. Needle lumen 66 is shaped so as to direct suturing needle 36 toward ferrule receptacle 34 during the distal advancement of suturing needle 36 while suture-positioning support 30 is in first deployed position 58A. To this end, suturing needle 36 is typically sufficiently flexible to be bent and directed by needle lumen 66 in the proper direction of advancement.

Figure 5E:
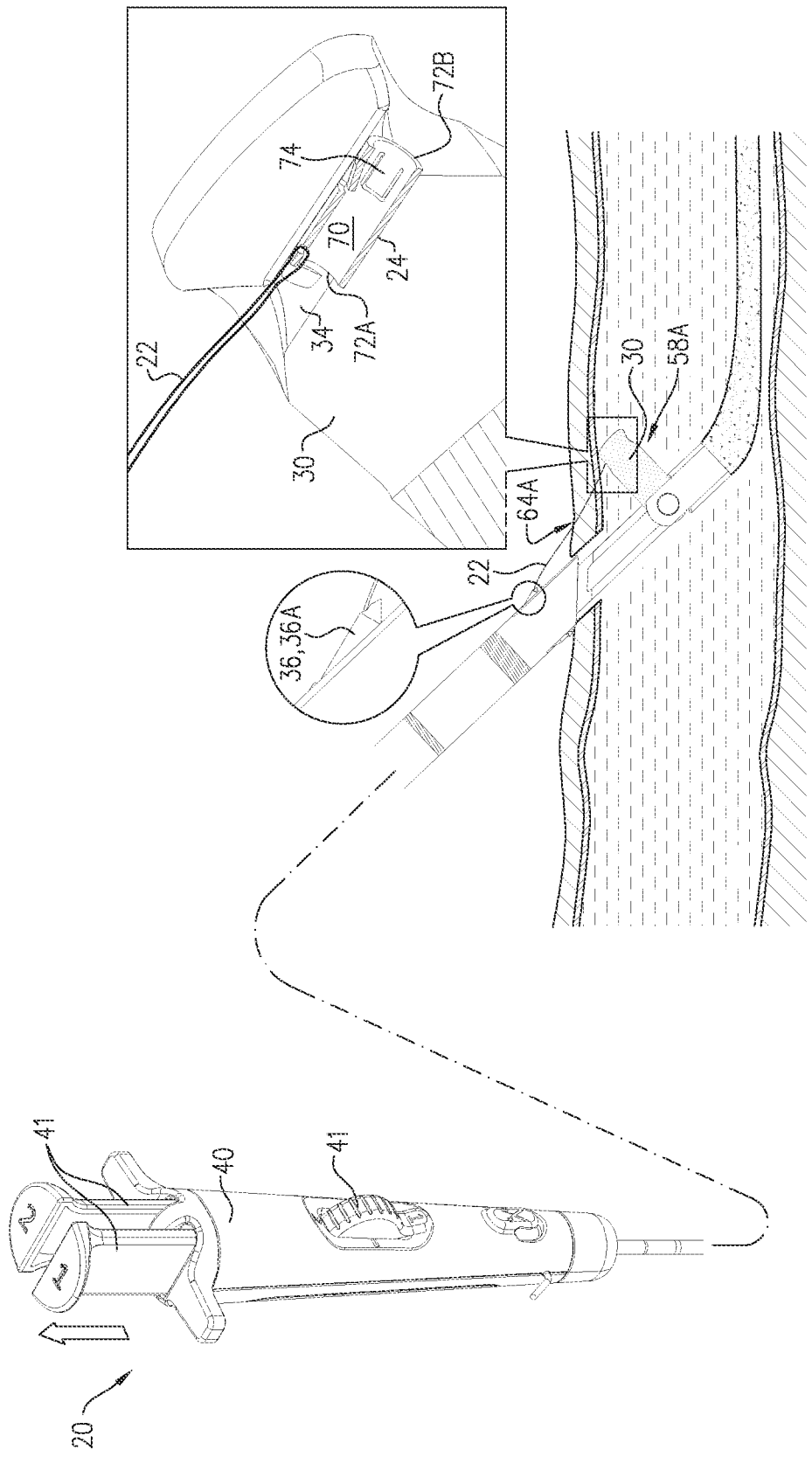

As shown in FIG. 5E, suturing needle 36 is proximally withdrawn from ferrule 24 and hollow anatomical structure 54, while leaving ferrule 24 within ferrule receptacle 34. For some applications, suturing needle 36 is proximally withdrawn by activating one or more of user controls 41 of control handle 40 coupled to a proximal portion of suturing needle 36.

As shown in FIGS. 5F, suture-positioning support 30 is transitioned from first deployed position 58A to a second deployed position 58B in which suture-positioning support 30 laterally extends in a second direction 60B from distal portion 32 of elongate support 28, second direction 60B different from first direction 60A.

Optionally, as shown in the transition shown in FIG. 5F, suture-positioning support 30 is transitioned from first deployed position 58A to second deployed position 58B by rotating suture-positioning support 30 about pivot axis 62 to transition suture-positioning support 30 from first deployed position 58A to second deployed position 58B via delivery position 56.

The step of the method shown in FIG. 5G is described hereinbelow.

Figure 5H:
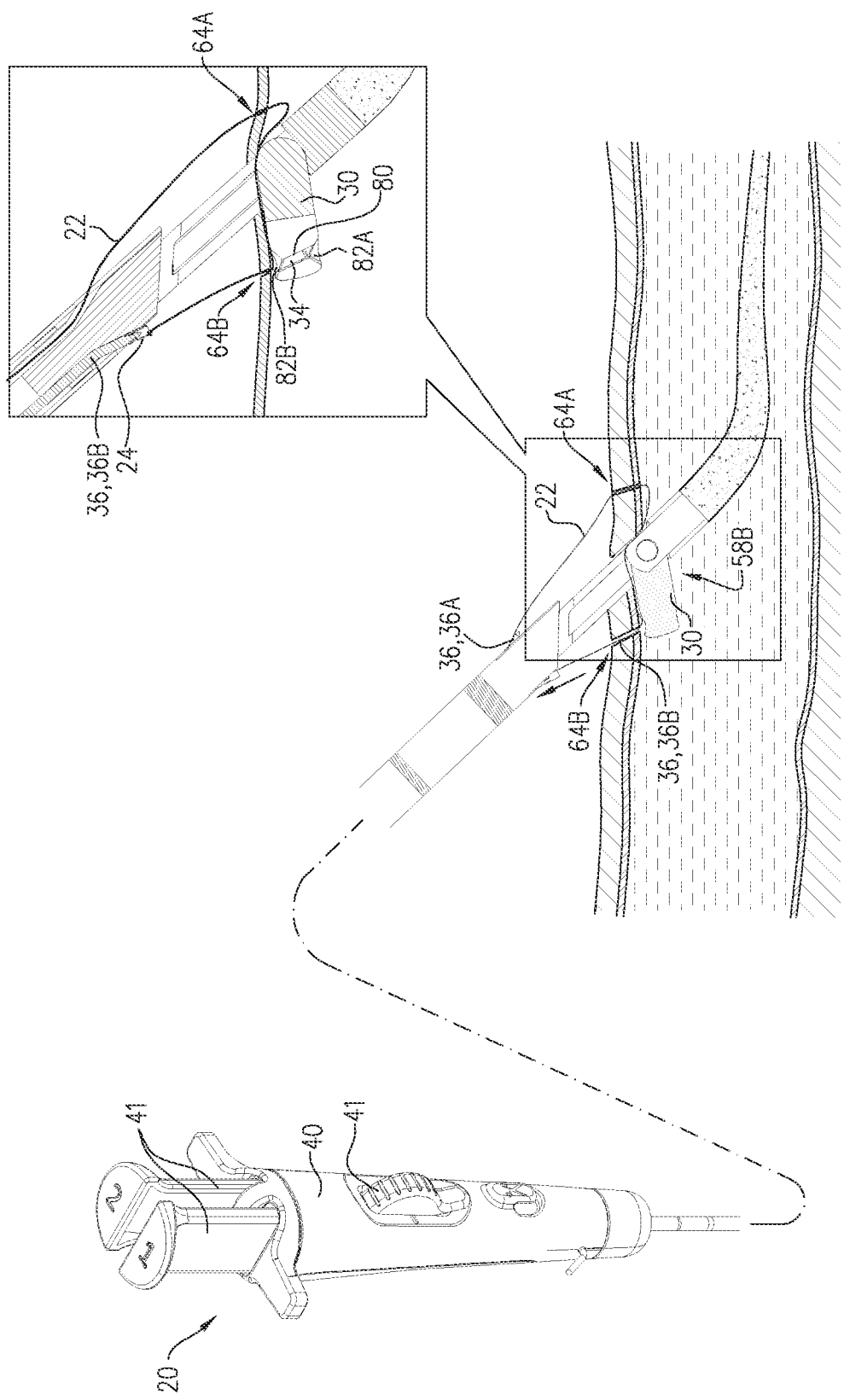
Figure 51:
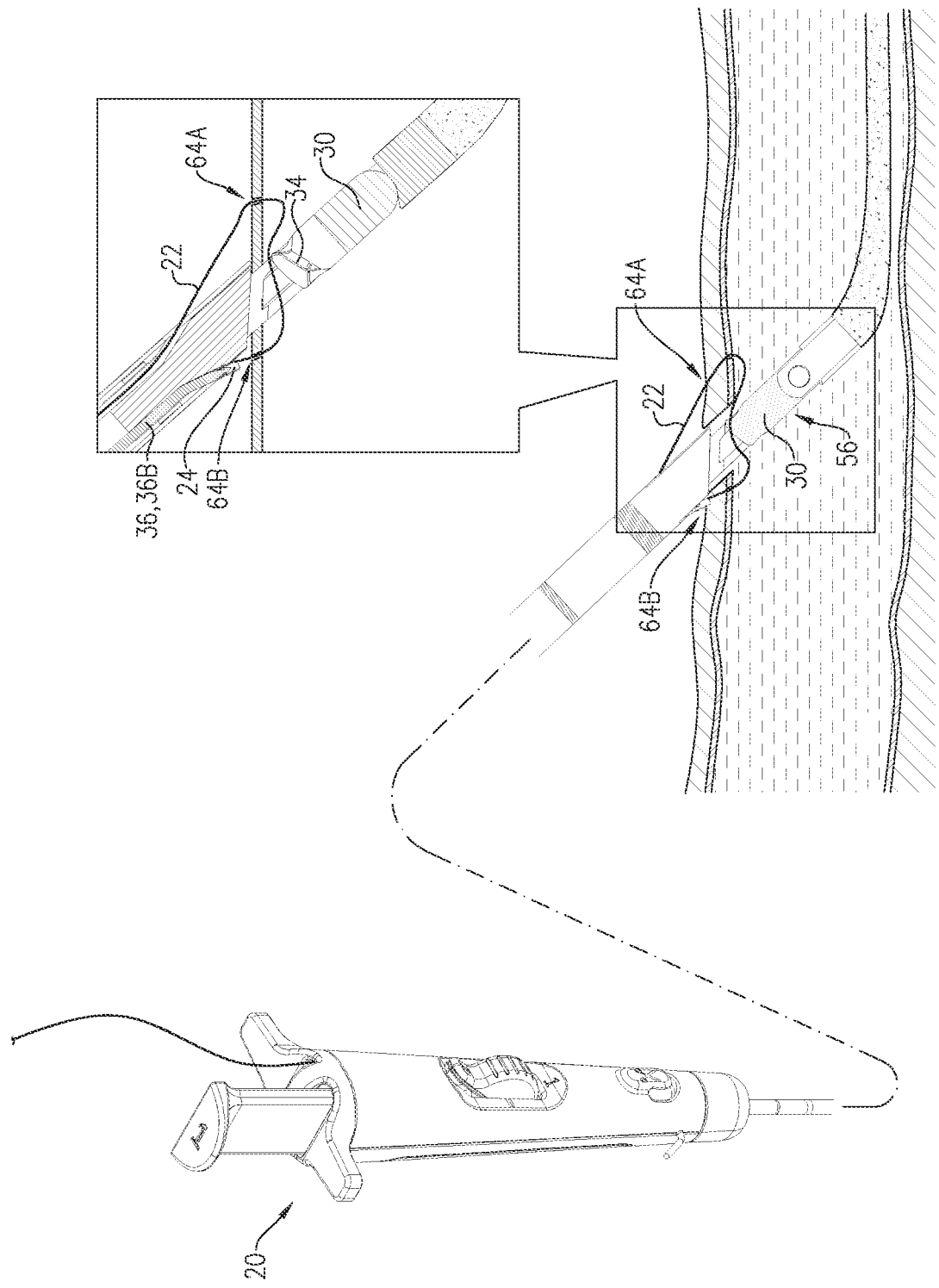
Figure 5J:
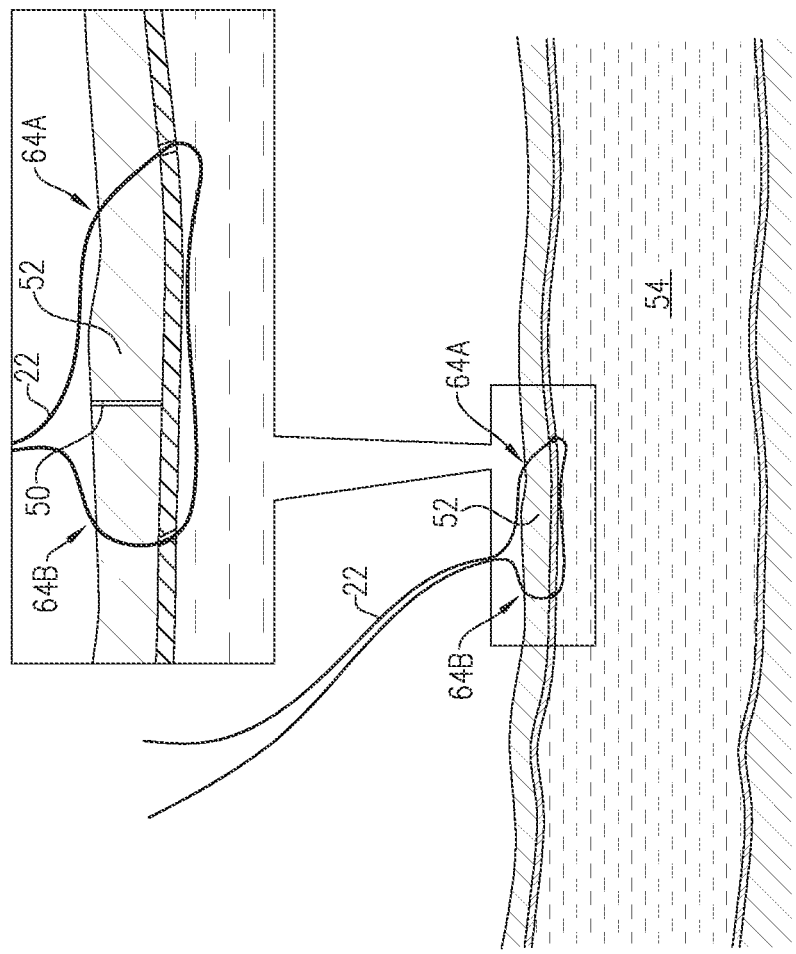

As shown in FIG. 5H, while suture-positioning support 30 is in second deployed position 58B, ferrule 24 is proximally withdrawn from ferrule receptacle 34 and out of hollow anatomical structure 54 via a second wall site 64B of wall 52, so as to proximally withdraw a portion of suture 22, including distal end portion 26 thereof, out of hollow anatomical structure 54 via second wall site 64B. The portion of suture 22 drawn out of hollow anatomical structure 54 via second wall site 64B is secured to another portion of suture 22 outside hollow anatomical structure 54.

Reference is made to FIGS. 2A-D, 3A-B, 4, 5D, and 5G-H. For some applications, suturing needle 36 is a first suturing needle 36, 36A, and closure device 20 further comprises a second suturing needle 36, 36B, which is couplable to ferrule 24. As shown in FIG. 5D, closure device 20 is configured to direct ferrule 24 into ferrule receptacle 34 during distal advancement of first suturing needle 36, 36A removably coupled to ferrule 24. As shown in FIG. 5G, closure device 20 is configured to direct second suturing needle 36, 36B to ferrule 24 during distal advancement of second suturing needle 36, 36B. Closure device 20 is configured such that after the distal advancement of second suturing needle 36, 36B to ferrule 24, proximal withdrawal of second suturing needle 36, 36B coupled to ferrule 24 removes ferrule 24 from ferrule receptacle 34, such as shown in FIG. 5H. For some applications, first suturing needle 36, 36A is distally advanced and proximally withdrawn by activating a first one of user controls 41 of control handle 40 coupled to a proximal portion of first suturing needle 36, 36A, and second suturing needle 36, 36B is distally advanced and proximally withdrawn by activating a second one of user controls 41 of control handle 40 coupled to a proximal portion of second suturing needle 36, 36B.

Alternatively, closure device 20 comprises only a single suturing needle 36, which is used twice during the procedure, both as described for first suturing needle 36, 36A, with reference to FIGS. 5D-E, and for second suturing needle 36, 36B, with reference to FIGS. 5G-H.

Reference is made to FIGS. 5G-H. For some applications, ferrule 24 is proximally withdrawn from ferrule receptacle 34 and out of hollow anatomical structure 54 while suture-positioning support 30 is in second deployed position 58B by:
- as shown in FIG. 5G, distally advancing second suturing needle 36, 36B through second wall site 64B and into hollow anatomical structure 54, such that closure device 20 directs second suturing needle 36, 36B to ferrule 24 and second suturing needle 36, 36B becomes coupled to ferrule 24, and
- as shown in FIG. 5H, proximally withdrawing second suturing needle 36, 36B from hollow anatomical structure 54 via second wall site 64B, so as to remove ferrule 24 from ferrule receptacle 34 and to proximally withdraw distal end portion 26 of suture 22 out of hollow anatomical structure 54 via second wall site 64B.

Optionally, the surgeon adjusts an axial position of elongate support 28 (e.g., by slightly proximally withdrawing elongate support 28) such that suture-positioning support 30 touches, or is near, an inner surface of wall 52, as shown in FIG. 5G.

Reference is made to FIGS. 2A-D, 3A-B, 4, and 5D-E. For some applications, ferrule 24 is shaped to define a ferrule lumen 70 having first and second end openings 72A and 72B (labeled in FIG. 5E). First suturing needle 36, 36A is removably couplable to ferrule 24 by insertion of first suturing needle 36, 36A into first end opening 72A of ferrule lumen 70, such as shown in FIG. 5D, such that proximal withdrawal of first suturing needle 36, 36A from ferrule 24 when ferrule 24 is within ferrule receptacle 34 withdraws first suturing needle 36, 36A from first end opening 72A of ferrule lumen 70, leaving ferrule 24 within ferrule receptacle 34, such as shown in FIG. 5E. Second suturing needle 36, 36B is couplable to ferrule 24 by insertion of second suturing needle 36, 36B into second end opening 72B of ferrule lumen 70, such as shown in FIG. 5G, such that proximal withdrawal of second suturing needle 36, 36B when ferrule 24 is within ferrule receptacle 34 (and while second suturing needle 36, 36B remains coupled to ferrule 24), such as shown in FIG. 5H, withdraws ferrule 24 from ferrule receptacle 34, such as from second end opening 82B of ferrule-receiving lumen 80, described hereinbelow with reference to FIGS. 2A-D, 3A-B, 4, 5D, and 5G-H.

For some of these applications, ferrule 24 is shaped so as to define one or more tabs 74 that are biased to protrude radially inward within ferrule lumen 70 and to engage second suturing needle 36, 36B upon the insertion of second suturing needle 36, 36B into second end opening 72B of ferrule lumen 70, so as to inhibit withdrawal of second suturing needle 36, 36B from ferrule lumen 70, such as shown in FIG. 5G.

Alternatively or additionally, for some of these applications, a distal end portion 76 of second suturing needle 36, 36B is shaped so as to define one or more lateral protrusions 78 (labeled in FIG. 5G) that are configured to engage ferrule 24 upon the insertion of second suturing needle 36, 36B into second end opening 72B of ferrule lumen 70, so as to inhibit withdrawal of second suturing needle 36, 36B from ferrule lumen 70, such as shown in FIG. 5G.

Reference is made to FIGS. 5D-E and 5G-H. For some applications, first suturing needle 36, 36A is distally advanced through first wall site 64A and into hollow anatomical structure 54, while first suturing needle 36, 36A is removably coupled to ferrule 24 by insertion of first suturing needle 36, 36A into first end opening 72A of ferrule lumen 70, such as shown in FIG. 5D. First suturing needle 36, 36A is proximally withdrawn from ferrule 24 by proximally withdrawing first suturing needle 36, 36A from first end opening 72A of ferrule lumen 70, leaving ferrule 24 within ferrule receptacle 34, such as shown in FIG. 5E. Distally advancing second suturing needle 36, 36B comprises inserting second suturing needle 36, 36B into second end opening 72B of ferrule lumen 70, such as shown in FIG. 5G. Proximally withdrawing second suturing needle 36, 36B removes ferrule 24 from ferrule receptacle 34, such as shown in FIG. 5H.

Reference is made to FIGS. 4, 5D, and 5G. For some applications, elongate support 28 defines a first needle lumen 66, 66A and a second needle lumen 66, 66B through respective longitudinal portions of elongate support 28 (labeled in FIG. 4). First needle lumen 66, 66A and second needle lumen 66, 66B are shaped so as to direct first suturing needle 36, 36A and second suturing needle 36, 36B toward ferrule receptacle 34 during the distal advancement of first suturing needle 36, 36A and the distal advancement of second suturing needle 36, 36B, respectively, such as shown in FIGS. 5D and 5G, respectively.

For some applications, first suturing needle 36, 36A is distally advanced through first wall site 64A and into hollow anatomical structure 54 while a portion of first suturing needle 36, 36A is disposed within first needle lumen 66, 66A, such that first needle lumen 66, 66A directs first suturing needle 36, 36A toward ferrule receptacle 34 while suture-positioning support 30 is in first deployed position 58A, such as shown in FIG. 5D. Second suturing needle 36, 36B is distally advanced through second wall site 64B and into hollow anatomical structure 54 while a portion of second suturing needle 36, 36B is disposed within second needle lumen 66, 66B, such that second needle lumen 66, 66B directs second suturing needle 36, 36B toward ferrule receptacle 34 while suture-positioning support 30 is in second deployed position 58B, such as shown in FIG. 5G.

Reference is made to FIGS. 2A-D, 3A-B, 4, 5D, and 5G-H. For some applications, ferrule receptacle 34 is shaped to define a ferrule-receiving lumen 80 having first and second end openings 82A and 82B open to first and second sides 84A and 84B of suture-positioning support 30, respectively (labeled in FIGS. 4, 5D, and 5H). Ferrule receptacle 34 is configured to removably receive ferrule 24 via first end opening 82A of ferrule-receiving lumen 80, such as shown in FIG. 5D, and to release ferrule 24 via second end opening 82B of ferrule-receiving lumen 80, such as shown in the transition between FIGS. 5G and 5H.

In these applications, typically:
when suture-positioning support 30 is in first deployed position 58A, first end opening 82A of ferrule-receiving lumen 80 faces proximally, such as shown in FIGS. 3A and 5C-E, and
when suture-positioning support 30 is in second deployed position 58B, second end opening 82B of ferrule-receiving lumen 80 faces proximally, such as shown in FIGS. 3B and 5G-H.

Reference is made to FIGS. 5B-C and 5F. For some applications, suture-positioning support 30 is transitioned from delivery position 56 to first deployed position 58A such that first end opening 82A of ferrule-receiving lumen 80 faces proximally, such as shown in the transition from FIG. 5B to FIG. 5C. Suture-positioning support 30 is transitioned from first deployed position 58A to second deployed position 58B such that second end opening 82B of ferrule-receiving lumen 80 faces proximally, such as shown in the transition shown in FIG. 5F.

As described above, for some applications, ferrule 24 is shaped to define ferrule lumen 70 having first and second end openings 72A and 72B. For some of these applications, suturing needle 36 is removably coupled to ferrule 24 by insertion of suturing needle 36 into first end opening 72A of ferrule lumen 70, such as shown in FIG. 5D, such that proximal withdrawal of suturing needle 36 from ferrule 24 when ferrule 24 is within ferrule receptacle 34 withdraws suturing needle 36 from first end opening 72A of ferrule lumen 70, leaving ferrule 24 within ferrule receptacle 34, such as shown in FIG. 5E. Suturing needle 36 (optionally, second suturing needle 36, 36B) is couplable to ferrule 24 by insertion of suturing needle 36 into second end opening 72B of ferrule lumen 70, such as shown FIG. 5G, such that proximal withdrawal of suturing needle 36 from ferrule 24 when ferrule 24 is within ferrule receptacle 34 withdraws ferrule 24 from second end opening 72B of ferrule lumen 70, such as shown in FIG. 5H.

Reference is again made to FIG. 5G. Typically, in applications in which ferrule receptacle 34 is shaped to define ferrule-receiving lumen 80, when suturing needle 36 (optionally, second suturing needle 36, 36B) is inserted into second end opening 82B of ferrule-receiving lumen 80 and into second end opening 72B of ferrule lumen 70, the suturing needle is not distally advanced so far as to push ferrule 24 out of first end opening 82A of ferrule-receiving lumen 80 (which is at the far side of suture-positioning support 30 at this stage of the procedure). However, if the suturing needle is advanced farther and pushes ferrule 24 out of first end opening 82A of ferrule-receiving lumen 80, during the first portion of the subsequent proximal withdrawal of the suturing needle, as shown in the transition between FIGS. 5G and 5H, the suturing needle proximally pulls ferrule 24 back into ferrule-receiving lumen 80 before subsequently pulling ferrule 24 out of second end opening 82B of ferrule-receiving lumen 80.

Figure 6:
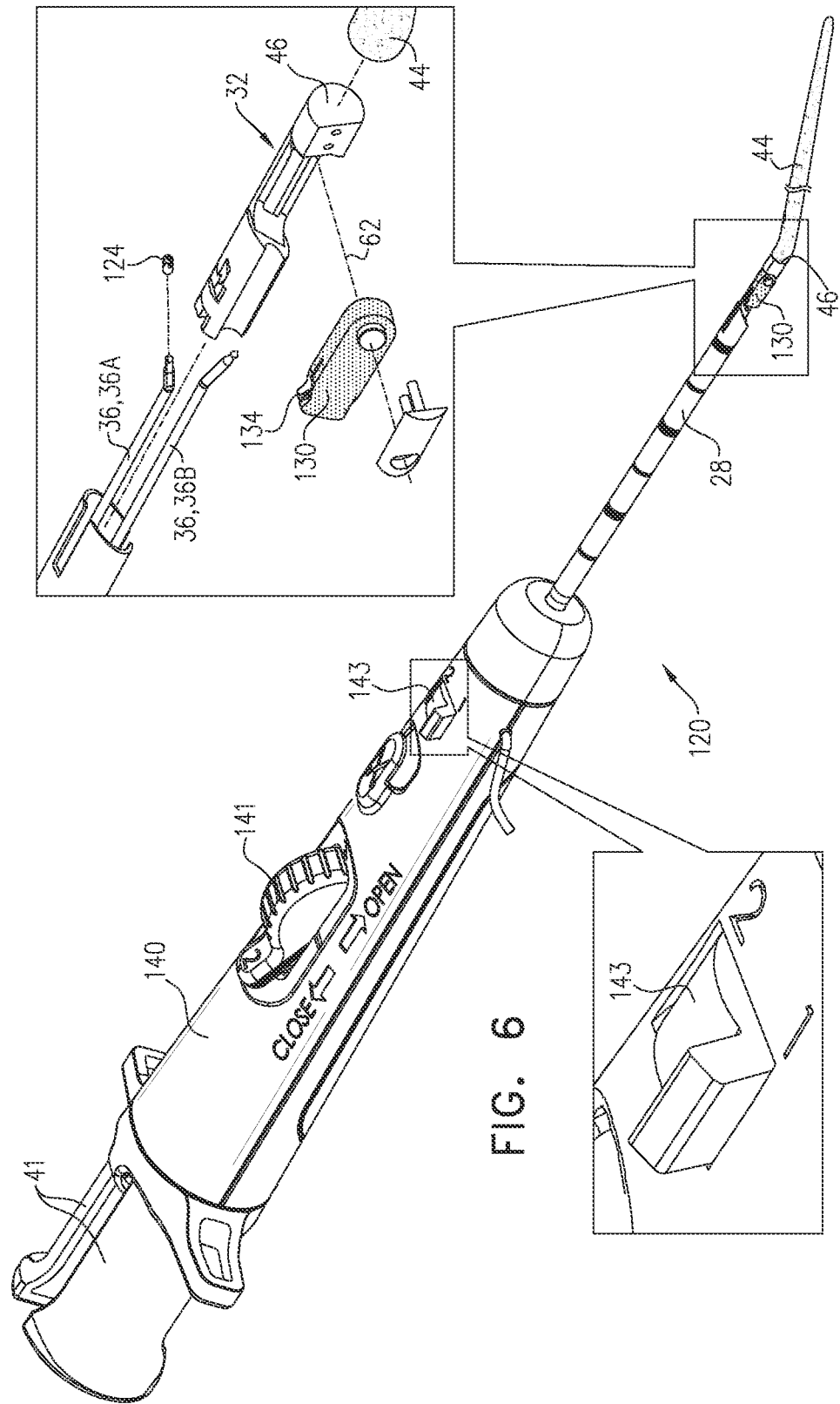
FIG. 6 is a schematic illustration of another closure device for suturing a puncture, in accordance with an application of the present invention.

Reference is made to FIG. 6, which is a schematic illustration of a closure device 120 for suturing a puncture, in accordance with an application of the present invention. Other than as described below, closure device 120 is generally similar to closure device 20, described hereinabove with reference to FIGS. 1-5J, and may implement any features thereof, mutatis mutandis.

Closure device 120 comprises:
suture 22;
exactly one ferrule 124, coupled to distal end portion 26 of suture 22, such as by being passed (e.g., looped) through an opening defined by a wall of ferrule 124 (such as shown), and/or by welding, knotting, gluing, or another technique (configurations not shown);
elongate support 28;
a suture-positioning support 130, which is laterally extendable from distal portion 32 of elongate support 28, and is shaped so as to define a ferrule receptacle 134 (labeled in FIGS. 7E and 7H), which is configured to removably receive ferrule 124; and
suturing needle 36, which is removably couplable to ferrule 124.

For some applications, suture-positioning support 130 is shaped so as to define exactly one ferrule receptacle 134. For other applications, the suture-positioning support is shaped so as to define two or more ferrule receptacles, such as described hereinbelow.

Typically, closure device 120 further comprises a control handle 140, coupled to proximal end portion 42 of elongate support 28, such as shown in FIG. 6. Control handle 140 comprises one or more user controls, such as user controls 41, 141, and 143, such as levers and/or buttons, that allow an operator to control the positions and states of one or more elements of closure device 120.

Reference is also made to FIGS. 7A-L, which are schematic illustrations of a method for suturing puncture 50 through wall 52 of hollow anatomical structure 54 using closure device 120, in accordance with an application of the present invention. Although hollow anatomical structure 54 is illustrated as a blood vessel, the method may alternatively be performed on other hollow anatomical structures, such as a body cavity, e.g., an abdominal cavity, mutatis mutandis. Other than as described below, the method of FIGS. 7A-L is generally similar to the method of FIGS. 5A-J, described hereinabove, and may implement any of the techniques thereof, mutatis mutandis.

Figure 7A:
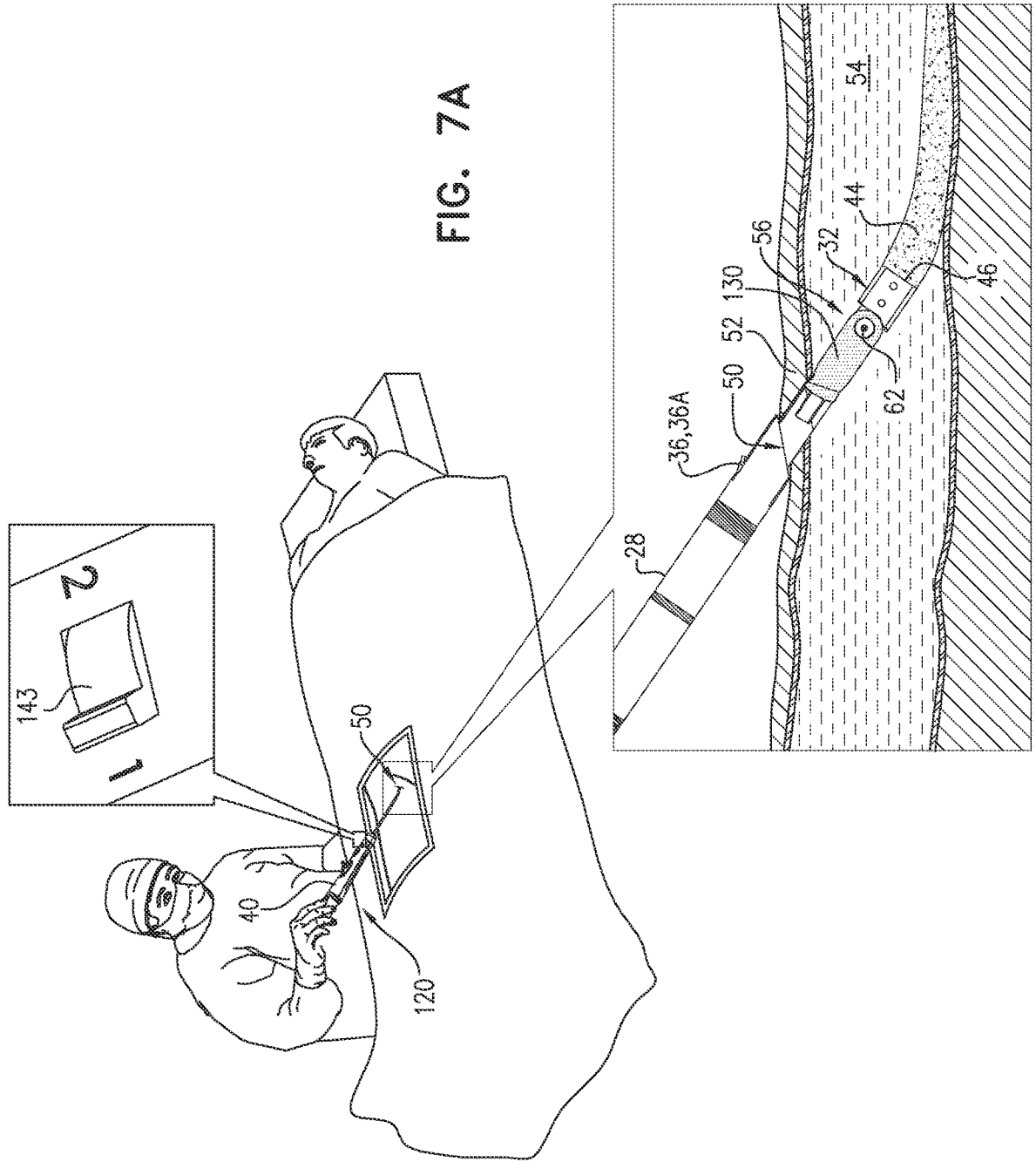

As shown in FIGS. 7A-B, distal portion 32 of elongate support 28 is inserted through puncture 50 and into hollow anatomical structure 54 while suture-positioning support 130 is in delivery position 56 coupled to distal portion 32 of elongate support 28.

As shown in FIG. 7C, suture-positioning support 130 is transitioned from delivery position 56 to first deployed position 58A in which suture-positioning support 130 laterally extends in first direction 60A from distal portion 32 of elongate support 28. For example, user control 141, which may comprise a knob, may be used to control the transition from delivery position 56 to first deployed position 58A. Another user control 143, which may also comprise a knob, may be in a first position at this stage of the method.

For some applications, such as shown in the transition between FIGS. 7A-B and FIG. 7C, suture-positioning support 130 is pivotably coupled to distal portion 32 of elongate support 28 such that suture-positioning support 130 is rotatable about pivot axis 62 to transition from delivery position 56 to first deployed position 58A. Typically, pivot axis 62 is not coaxial with longitudinal axis 38 of elongate support 28 (as labeled in FIG. 2A).

Figure 7D:
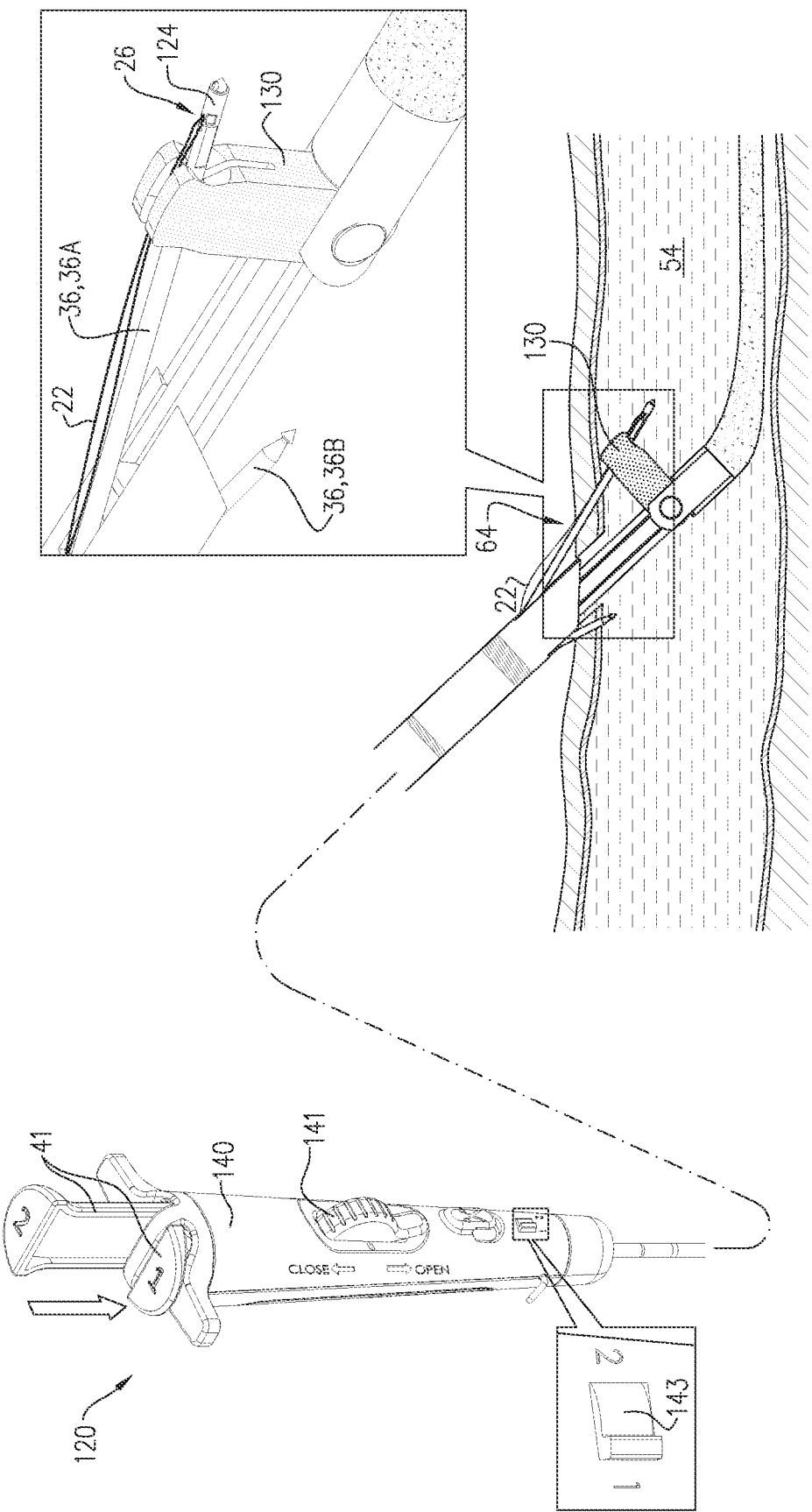

As shown in FIG. 7D, suturing needle 36 of closure device 120 is distally advanced through first wall site 64A of wall 52 and into hollow anatomical structure 54, while suturing needle 36 is removably coupled to ferrule 124, such that closure device 120 directs ferrule 124 into ferrule receptacle 134 (labeled in FIG. 7E) defined by suture-positioning support 130, and ferrule receptacle 134 removably receives ferrule 124 while suture-positioning support 130 is in first deployed position 58A. For some applications, suturing needle 36 is distally advanced by activating one or more of user controls 41 of control handle 140 coupled to a proximal portion of suturing needle 36. Typically, suturing needle 36 is removably coupled to ferrule 124 before the beginning of the procedure, although suturing needle 36 may alternatively become removably coupled to ferrule 124 during the procedure, such as during distal advancement of suturing needle 36 of needle lumen 66, described hereinabove with reference to FIG. 7D. Optionally, the surgeon adjusts an axial position of elongate support 28 such that suture-positioning support 130 touches, or is near, an inner surface of wall 52, as shown in FIG. 7D.

Figure 7E:
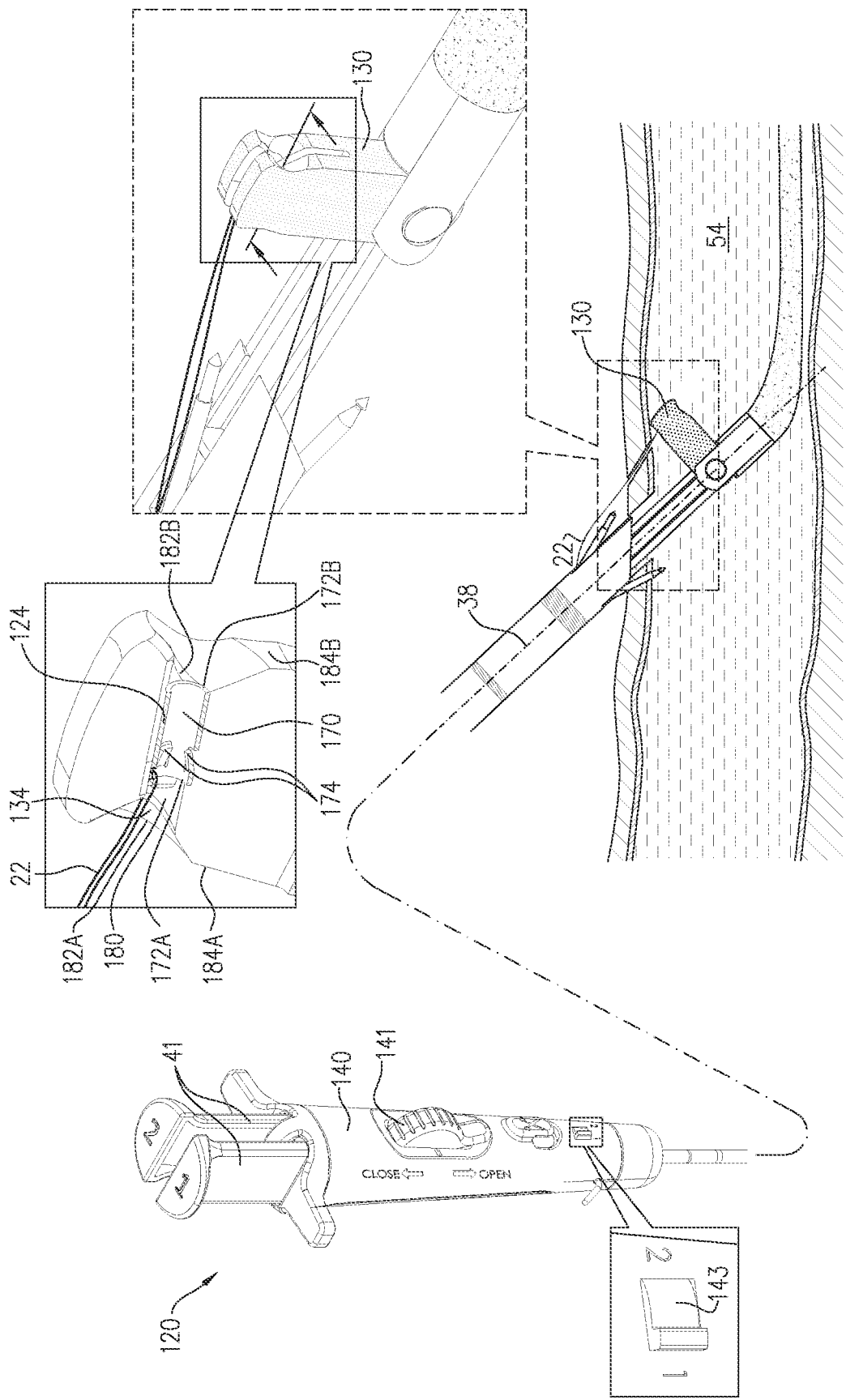

As shown in FIG. 7E, suturing needle 36 is proximally withdrawn from ferrule 124 and hollow anatomical structure 54, while leaving ferrule 124 within ferrule receptacle 134. For some applications, suturing needle 36 is proximally withdrawn by activating one or more of user controls 41 of control handle 140 coupled to a proximal portion of suturing needle 36.

Figure 7G:
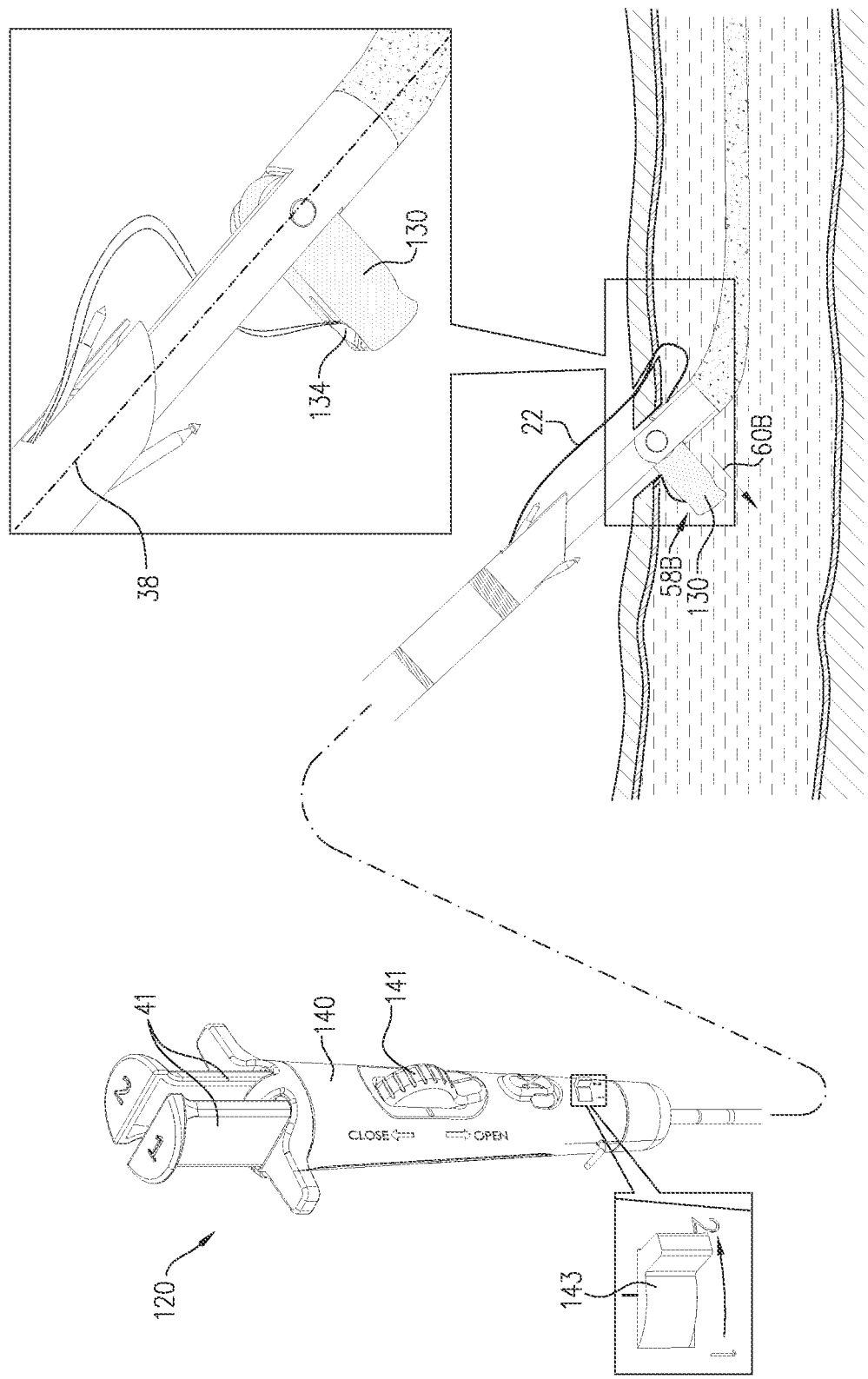

As shown in the transition from FIG. 7E to FIG. 7G, suture-positioning support 130 is transitioned from first deployed position 58A to second deployed position 58B in which suture-positioning support 130 laterally extends in second direction 60B from distal portion 32 of elongate support 28, second direction 60B different from first direction 60A. Optionally, this transition may be caused by transitioning user control 143 from its first position, described above, to a second position.

For some applications, as shown in the transition from FIG. 7E to FIG. 7G, suture-positioning support 130 is transitioned from first deployed position 58A to second deployed position 58B by rotating suture-positioning support 130 about longitudinal axis 38 of distal portion 32 of elongate support 28. For some of these applications, the rotation is achieved by rotation of one or more of the shafts of elongate support 28, with respect to handle 140, about longitudinal axis 38. For example, elongate support 28 may comprise outer and inner nested shafts 29A and 29B, and closure device 120 may be configured to rotate inner shaft 29B while holding outer shaft 29A fixed with respect to handle 140, such as shown. Alternatively, closure device 120 may be configured to rotate outer shaft 29A with respect to handle 140 (configuration not shown). Further alternatively, elongate support 28 may comprise only a single shaft, and closure device 120 may be configured to rotate the single shaft with respect to handle 140 (configuration not shown). In any of these configurations, distal end 46 of elongate support 28 may be pivotably coupled to guidebody 44, such that elongate support 28 rotates with respect to guidebody 44 during the rotation of elongate support 28 with respect to handle 140.

Figure 7H:
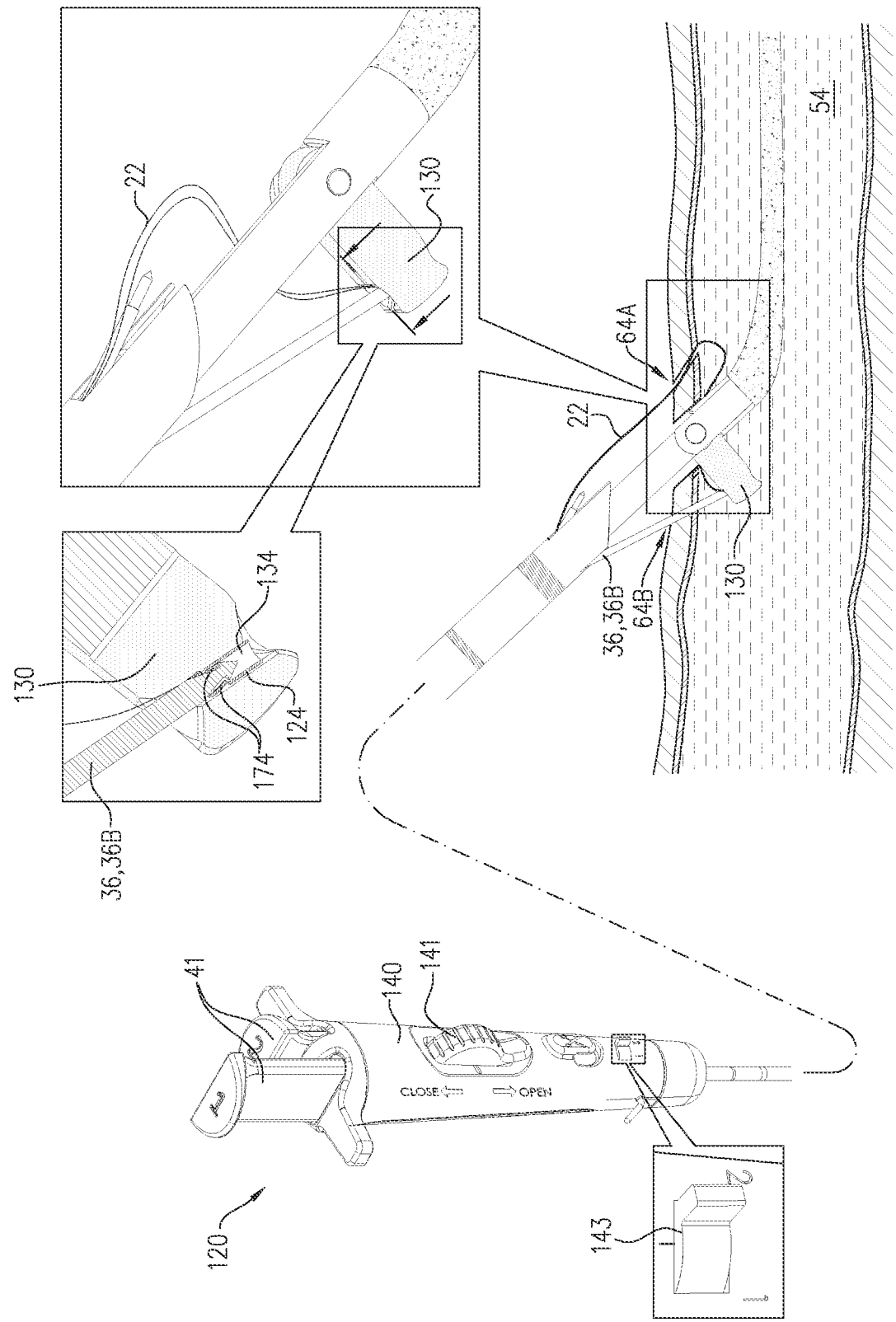

As shown in FIG. 7H, while suture-positioning support 130 is in second deployed position 58B, ferrule 124 is proximally withdrawn from ferrule receptacle 134 and out of hollow anatomical structure 54 via second wall site 64B of wall 52, so as to proximally withdraw a portion of suture 22, including distal end portion 26 thereof, out of hollow anatomical structure 54 via second wall site 64B. The portion of suture 22 drawn out of hollow anatomical structure 54 via second wall site 64B is secured to another portion of suture 22 outside hollow anatomical structure 54.

Figure 7I:
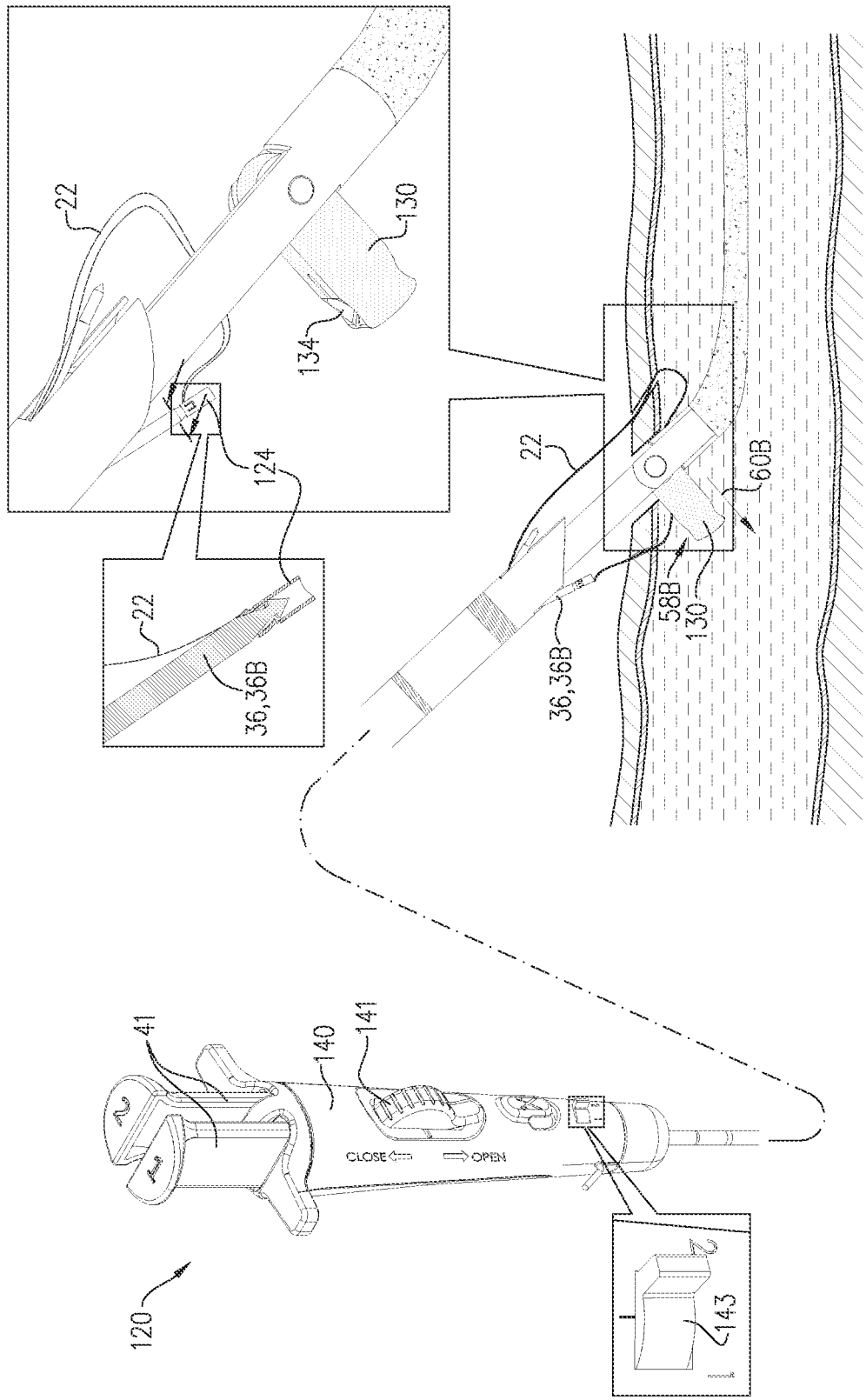
Figure 7J:
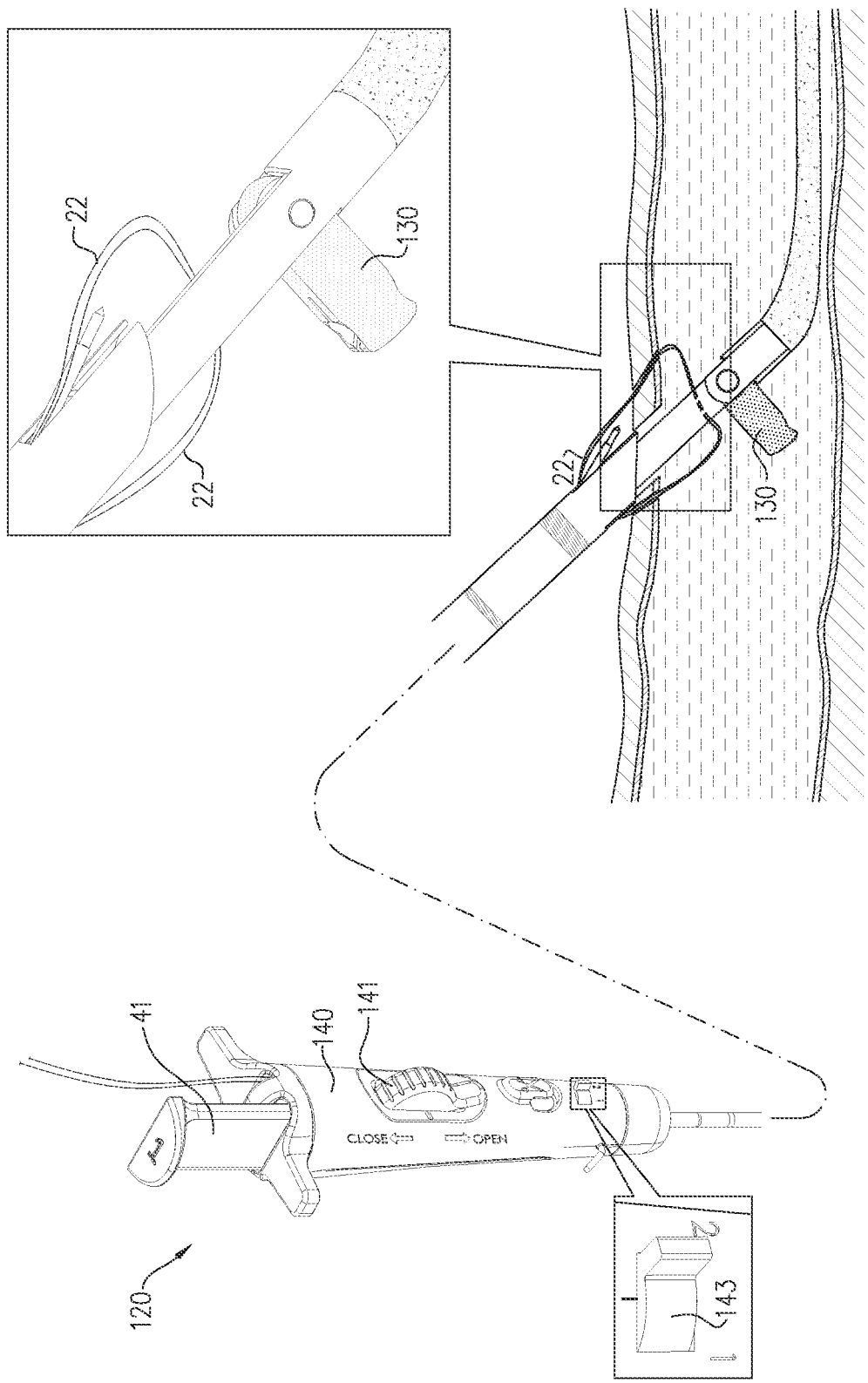
Figure 7K:
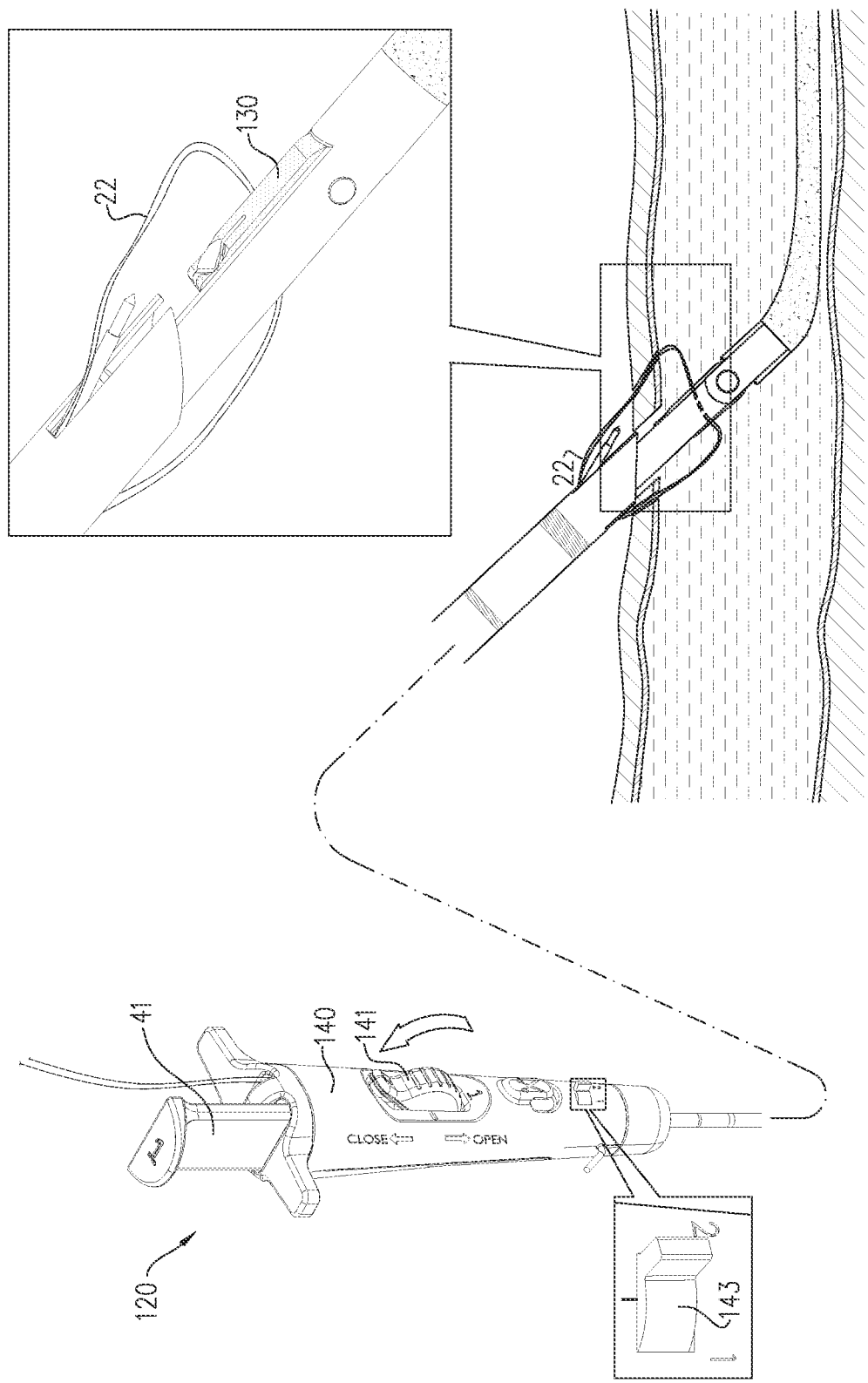
Figure 7L:
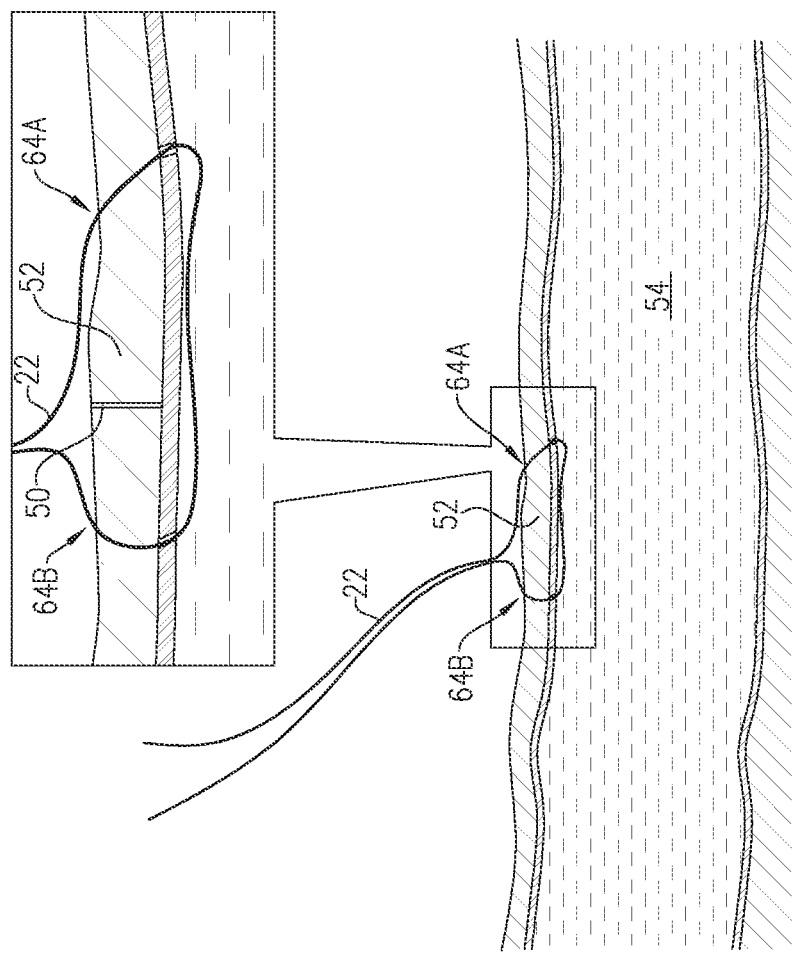

Reference is made to FIGS. 7D-E. For some applications, ferrule 124 is shaped to define a ferrule lumen 170 having first and second end openings 172A and 172B (labeled in FIG. 7E). First suturing needle 36, 36A is removably couplable to ferrule 124 by insertion of first suturing needle 36, 36A into first end opening 172A of ferrule lumen 170, such as shown in FIG. 7D, such that proximal withdrawal of first suturing needle 36, 36A from ferrule 124 when ferrule 124 is within ferrule receptacle 134 withdraws first suturing needle 36, 36A from first end opening 172A of ferrule lumen 170, leaving ferrule 124 within ferrule receptacle 134, such as shown in FIG. 7E. Second suturing needle 36, 36B is couplable to ferrule 124 by insertion of second suturing needle 36, 36B into first end opening 172A of ferrule lumen 170, such as shown in FIG. 7H, such that proximal withdrawal of second suturing needle 36, 36B when ferrule 124 is within ferrule receptacle 134 (and while second suturing needle 36, 36B remains coupled to ferrule 124), such as shown in FIG. 7I, withdraws ferrule 124 from ferrule receptacle 134, such as from first end opening 182A of ferrule-receiving lumen 180, described hereinbelow with reference to FIGS. 7D-E.

Optionally, the surgeon adjusts an axial position of elongate support 28 (e.g., by slightly proximally withdrawing elongate support 28) such that suture-positioning support 130 touches, or is near, an inner surface of wall 52, as shown in FIG. 7H.

For some of these applications, ferrule 124 is shaped so as to define one or more tabs 174 that are biased to protrude radially inward within ferrule lumen 170 and to engage second suturing needle 36, 36B upon the insertion of second suturing needle 36, 36B into first end opening 172A of ferrule lumen 170, so as to inhibit withdrawal of second suturing needle 36, 36B from ferrule lumen 170, such as shown in FIG. 7H.

Alternatively or additionally, for some of these applications, distal end portion 76 of second suturing needle 36, 36B is shaped so as to define one or more lateral protrusions 78 (labeled in FIG. 7G) that are configured to engage ferrule 124 upon the insertion of second suturing needle 36, 36B into first end opening 172A of ferrule lumen 170, so as to inhibit withdrawal of second suturing needle 36, 36B from ferrule lumen 170, such as shown in FIG. 7H.

Reference is made to FIGS. 7D-E and 7H-I. For some applications, first suturing needle 36, 36A is distally advanced through first wall site 64A and into hollow anatomical structure 54, while first suturing needle 36, 36A is removably coupled to ferrule 124 by insertion of first suturing needle 36, 36A into first end opening 172A of ferrule lumen 170, such as shown in FIG. 7D. First suturing needle 36, 36A is proximally withdrawn from ferrule 124 by proximally withdrawing first suturing needle 36, 36A from first end opening 172A of ferrule lumen 170, leaving ferrule 124 within ferrule receptacle 134, such as shown in FIG. 7E. Distally advancing second suturing needle 36, 36B comprises inserting second suturing needle 36, 36B into first end opening 172A of ferrule lumen 70, such as shown in FIG. 7H. Proximally withdrawing second suturing needle 36, 36B removes ferrule 124 from ferrule receptacle 134, such as shown in FIG. 7I.

Reference is made to FIGS. 7D-E. For some applications, ferrule receptacle 134 is shaped to define a ferrule-receiving lumen 180 having first and second end openings 182A and 182B open to first and second sides 184A and 184B of suture-positioning support 130, respectively (labeled in FIG. 7E). Ferrule receptacle 134 is configured to removably receive ferrule 124 via first end opening 182A of ferrule-receiving lumen 180, such as shown in FIG. 7D, and to release ferrule 124 via first end opening 182A of ferrule-receiving lumen 180, such as shown in FIG. 7E. Thus, in this configuration, ferrule receptacle 134 is configured to receive and release ferrule 124 via the same end opening (first end opening 182) of ferrule-receiving lumen 180.

Typically in these applications, both when suture-positioning support 130 is in first deployed position 58A and when suture-positioning support 130 is in second deployed position 58B, first end opening 182A of ferrule-receiving lumen 180 faces proximally, such as shown in FIGS. 7C-J.

Reference is again made to FIG. 7D. Typically, in applications in which ferrule receptacle 134 is shaped to define ferrule-receiving lumen 180, when suturing needle 36 (optionally, first suturing needle 36, 36A) is inserted into first end opening 182A of ferrule-receiving lumen 180 and into first end opening 172A of ferrule lumen 170, the suturing needle is not distally advanced so far as to push ferrule 124 out of second end opening 182B of ferrule-receiving lumen 180 (which is at the far side of suture-positioning support 130 at this stage of the procedure) (configuration not shown). However, if, as shown, the suturing needle is advanced farther and pushes ferrule 124 out of second end opening 182B of ferrule-receiving lumen 180, during the first portion of the subsequent proximal withdrawal of the suturing needle, as shown in the transition between FIGS. 7D and 7E, the suturing needle proximally pulls ferrule 124 back into ferrule-receiving lumen 180 before subsequently pulling ferrule 124 out of first end opening 182A of ferrule-receiving lumen 180.

Reference is made to FIGS. 8A-H, which are schematic illustrations of a closure device 220 for suturing a puncture, in accordance with an application of the present invention, and a method for suturing puncture 50 through wall 52 of hollow anatomical structure 54 using closure device 220, in accordance with an application of the present invention. Although hollow anatomical structure 54 is illustrated as a blood vessel, the method may alternatively be performed on other hollow anatomical structures, such as a body cavity, e.g., an abdominal cavity, mutatis mutandis.

Other than as described below, closure device 220 is generally similar to closure device 120, described hereinabove with reference to FIGS. 6 and 7A-L, and may implement any features thereof, mutatis mutandis, and is generally similar to closure device 20, described hereinabove with reference to FIGS. 1-5J, and may implement any features thereof, mutatis mutandis.

Closure device 220 comprises:
suture 22;
exactly one ferrule 124, coupled to distal end portion 26 of suture 22, such as by being passed (e.g., looped) through an opening defined by a wall of ferrule 124 (such as shown), and/or by welding, knotting, gluing, or another technique (configurations not shown);
elongate support 28;
a suture-positioning support 130, which is laterally extendable from distal portion 32 of elongate support 28, and is shaped so as to define a ferrule receptacle 134 (labeled in FIG. 8D), which is configured to removably receive ferrule 124; and
suturing needle 36, which is removably couplable to ferrule 124.

For some applications, suture-positioning support 130 is shaped so as to define exactly one ferrule receptacle 134. For other applications, the suture-positioning support is shaped so as to define two or more ferrule receptacles, such as described hereinbelow.

Typically, closure device 220 further comprises a control handle 240, coupled to proximal end portion 42 of elongate support 28, such as shown in FIGS. 8A-G. Control handle 240 comprises one or more user controls, such as user controls 41 and 141, such as levers and/or buttons, that allow an operator to control the positions and states of one or more elements of closure device 220.

Other than as described below, the method of FIGS. 8A-H is generally similar to the method of FIGS. 7A-L, described hereinabove, and may implement any of the techniques thereof, mutatis mutandis. For the sake of brevity, only steps of the method of FIGS. 8A-H that differ from those of the method of FIGS. 7A-L are described.

Figure 8B:
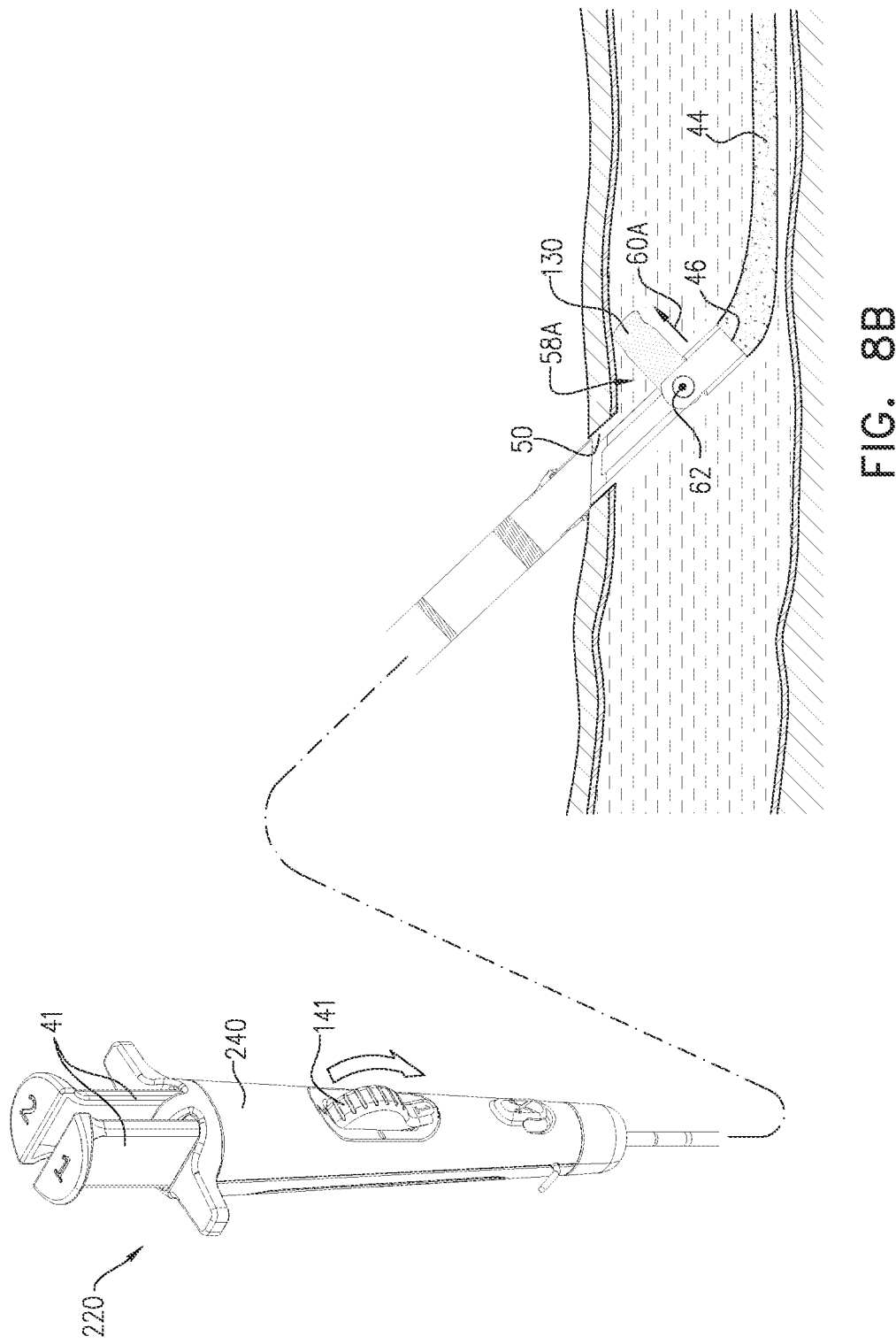
Figure 8C:
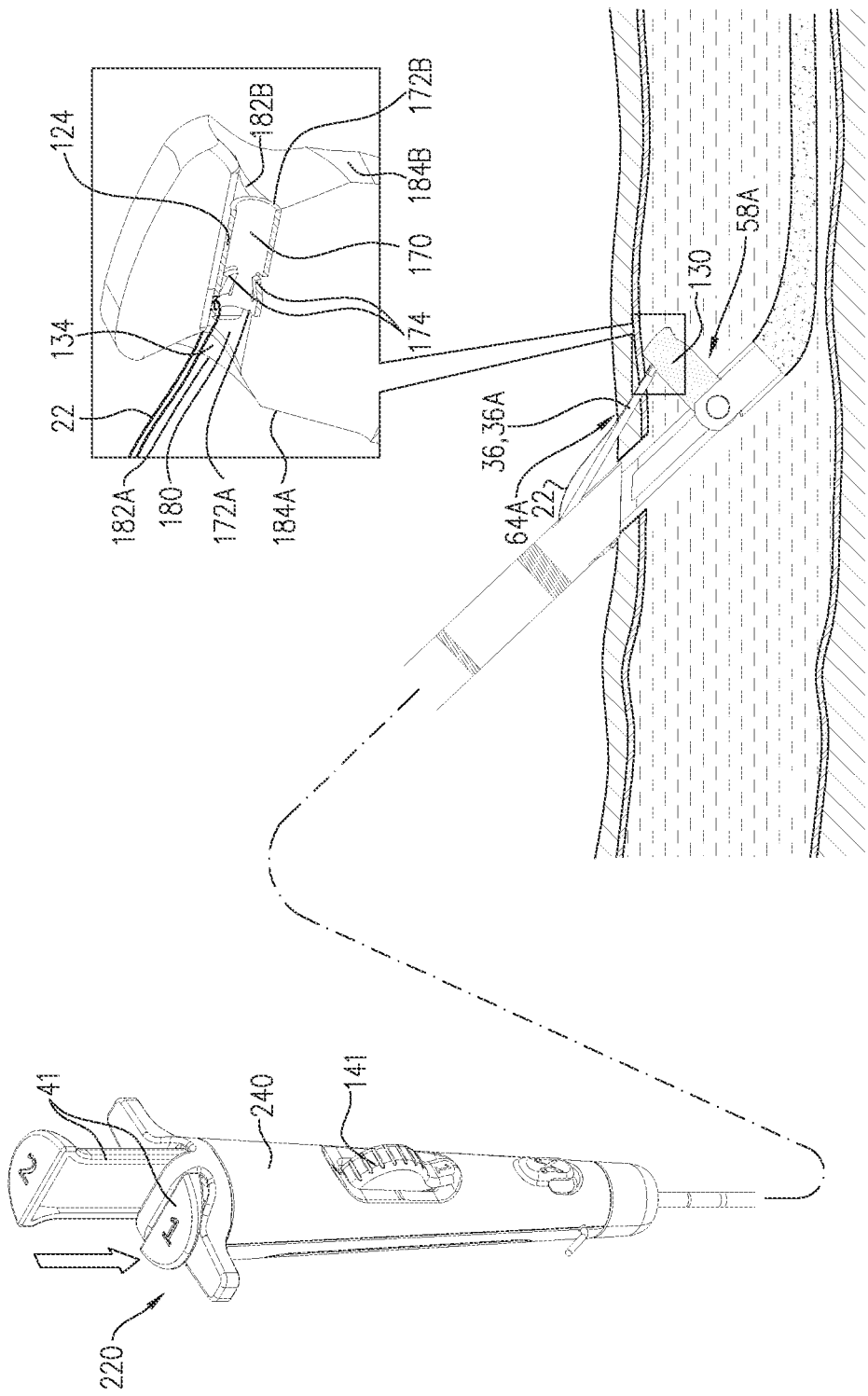
Figure 8D:
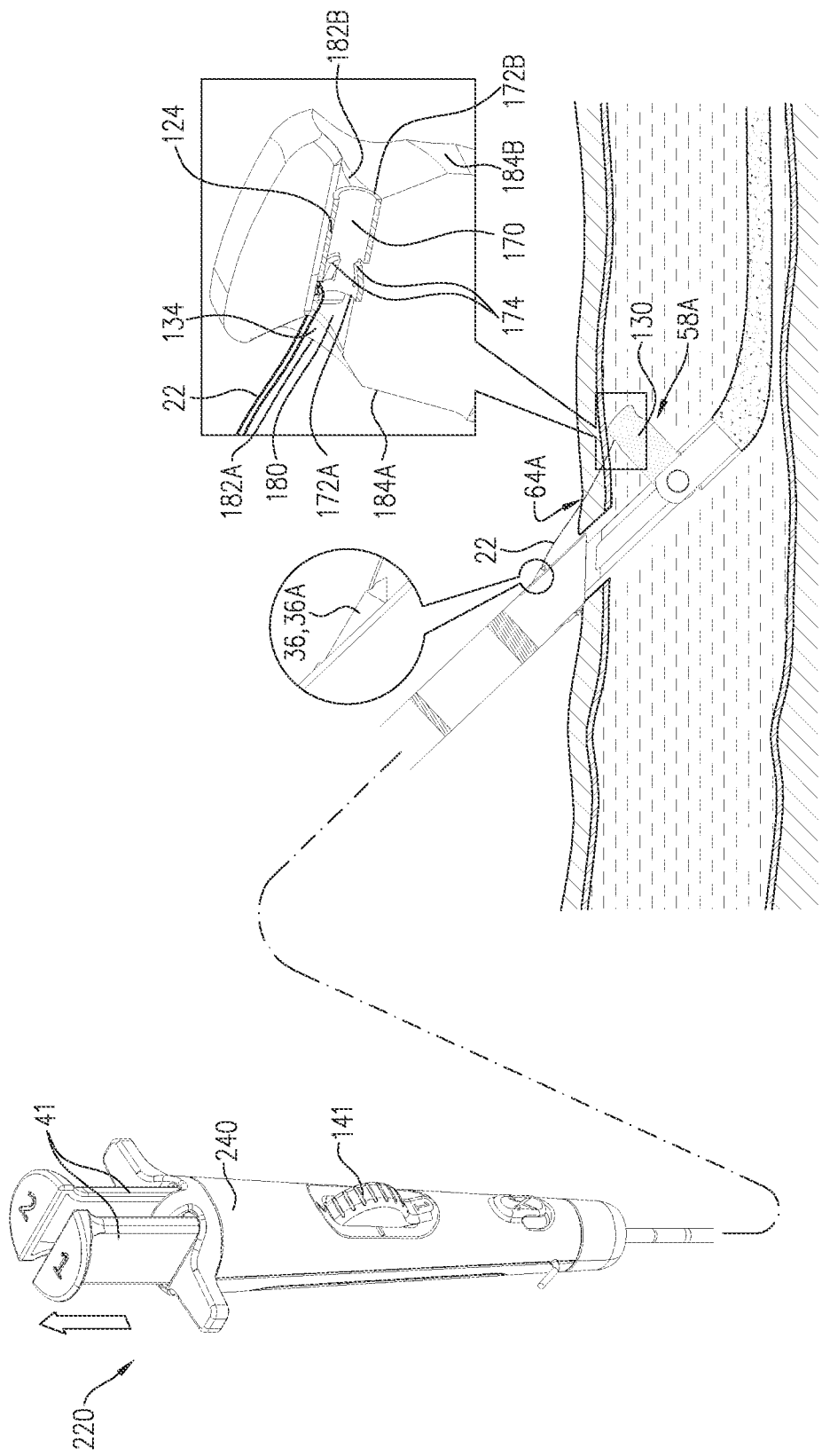
Figure 8E:
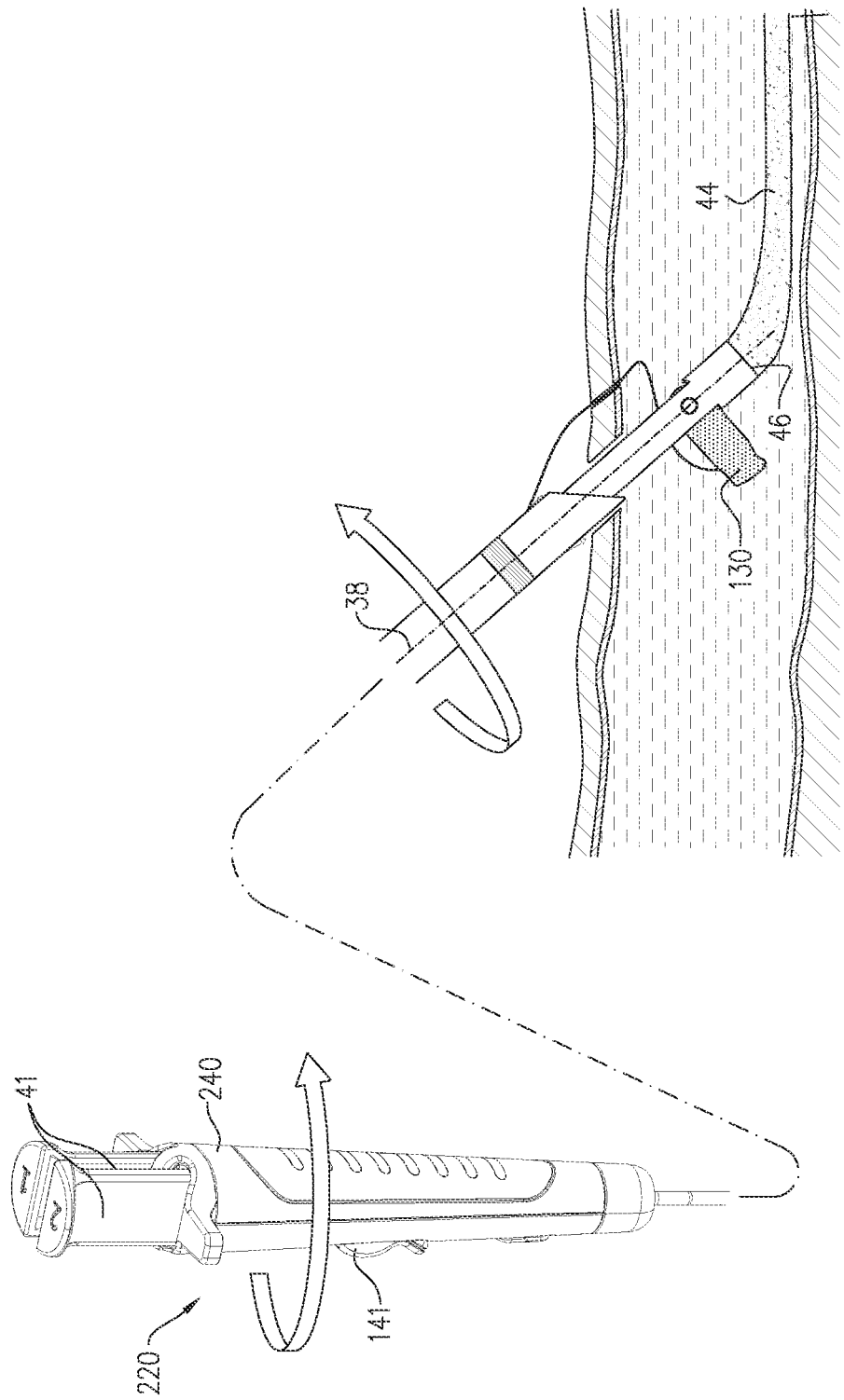
Figure 8G:
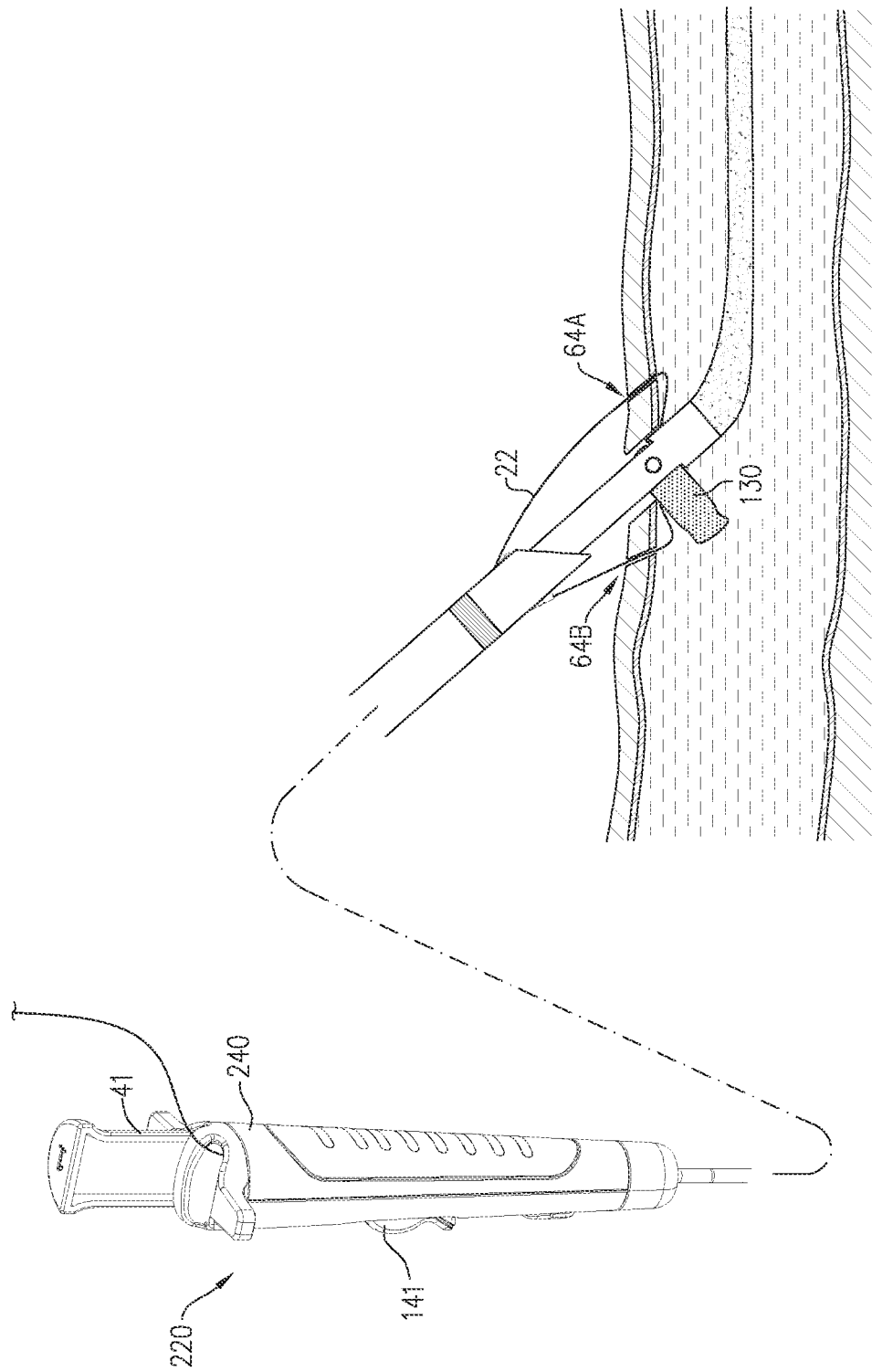
Figure 8H:
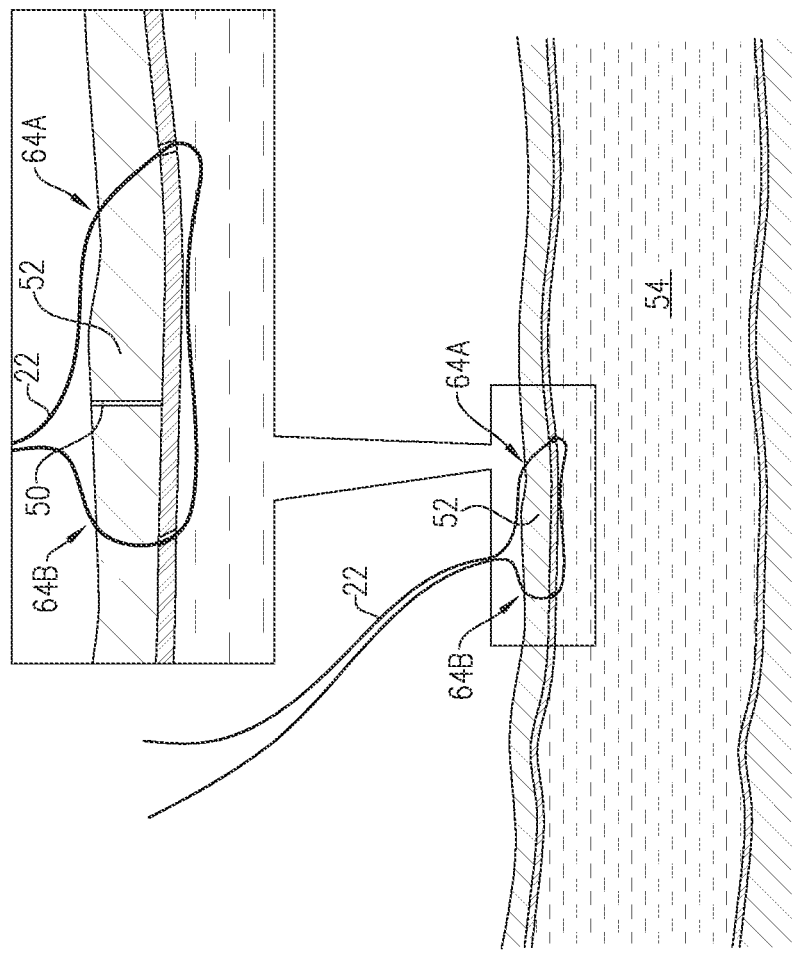

As shown in the transition from FIG. 8D to FIG. 8F, suture-positioning support 130 is transitioned from first deployed position 58A to second deployed position 58B in which suture-positioning support 130 laterally extends in second direction 60B from distal portion 32 of elongate support 28, second direction 60B different from first direction 60A. In this configuration, this transition is caused by rotating suture-positioning support 130 about longitudinal axis 38 of distal portion 32 of elongate support 28. The rotation is achieved by rotation of elongate support 28 by rotation of handle 240 about longitudinal axis 38 by the surgeon. Thus, user control 143, described hereinabove with reference to FIGS. 6 and 7A-L, is not necessary in this configuration. Optionally, distal end 46 of elongate support 28 may be pivotably coupled to guidebody 44, such that elongate support 28 rotates with respect to guidebody 44 during the rotation of elongate support 28 and handle 240.

In an application of the present invention, a closure device is provided for suturing a puncture at an access site. Other than as described below, the closure device is generally similar to the other closure devices described herein, and may implement any of the features thereof, mutatis mutandis.

The closure device comprises a suture-positioning support, which is laterally extendable from distal portion 32 of elongate support 28, and is shaped so as to define first and second ferrule receptacles at respective first and second locations along the suture-positioning support. Each of the first and the second ferrule receptacles is configured to removably receive the ferrule (but not at the same time). Typically, during any given closure procedure performed using the closure device, only one of the first and the second ferrule receptacles is used to receive the ferrule, and the other ferrule receptacle is not used at all during the closure procedure. Optionally, the suture-positioning support is configured to define yet additional ferrule receptacles at respective addition locations along the suture-positioning support.

The distance between first and second wall sites 64A and 64B will vary based on the selected ferrule receptacle; the farther the selected ferrule receptacle from longitudinal axis 38 of distal portion 32 of elongate support 28, the greater the distance between the first and the second wall sites at which suture 22 is passed through the vessel wall.

Typically, the closure device comprises a control handle, which is coupled to a proximal end portion of elongate support 28. The control handle typically comprises the one or more user controls described hereinabove, and typically further comprises a user control that is configured to select one of the first and the second ferrule receptacles, and to set a direction of the distal advancement of suturing needle 36 to the selected ferrule receptacle.

Figure 9A:
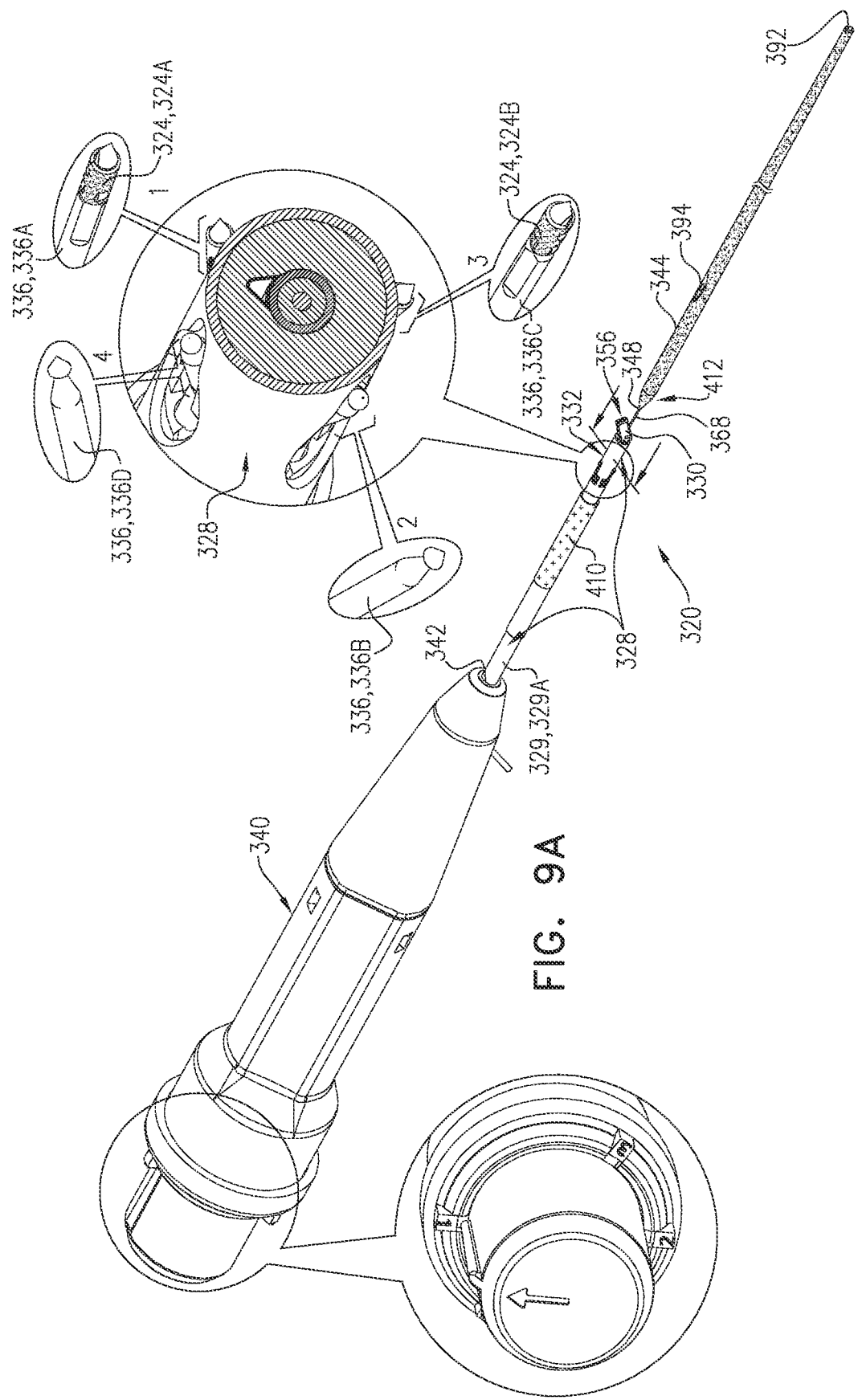
FIG. 9A is a schematic illustration of still another closure device for suturing a puncture with at least one suture, in accordance with an application of the present invention.

Reference is now made to FIG. 9A, which is a schematic illustration of a closure device 320 for suturing a puncture at an access site with at least one suture 322, in accordance with an application of the present invention. For the sake of clarity suture 322 is not shown in FIG. 9A, although the suture is present in practice; the suture is shown in many of the other figures described hereinbelow.

Reference is further made to FIG. 9B, which is a schematic illustration of a distal end portion 332 of an elongate support 328 of closure device 320, in accordance with an application of the present invention.

Reference is still further made to FIGS. 9C-D, which are schematic illustrations of distal portions of suturing needles 336 and sutures 322 of closure device 320, from two views, in accordance with an application of the present invention.

Reference is still further made to FIGS. 10A-D, which are several schematic views of a portion of closure device 320, in accordance with an application of the present invention.

Figure 11A:
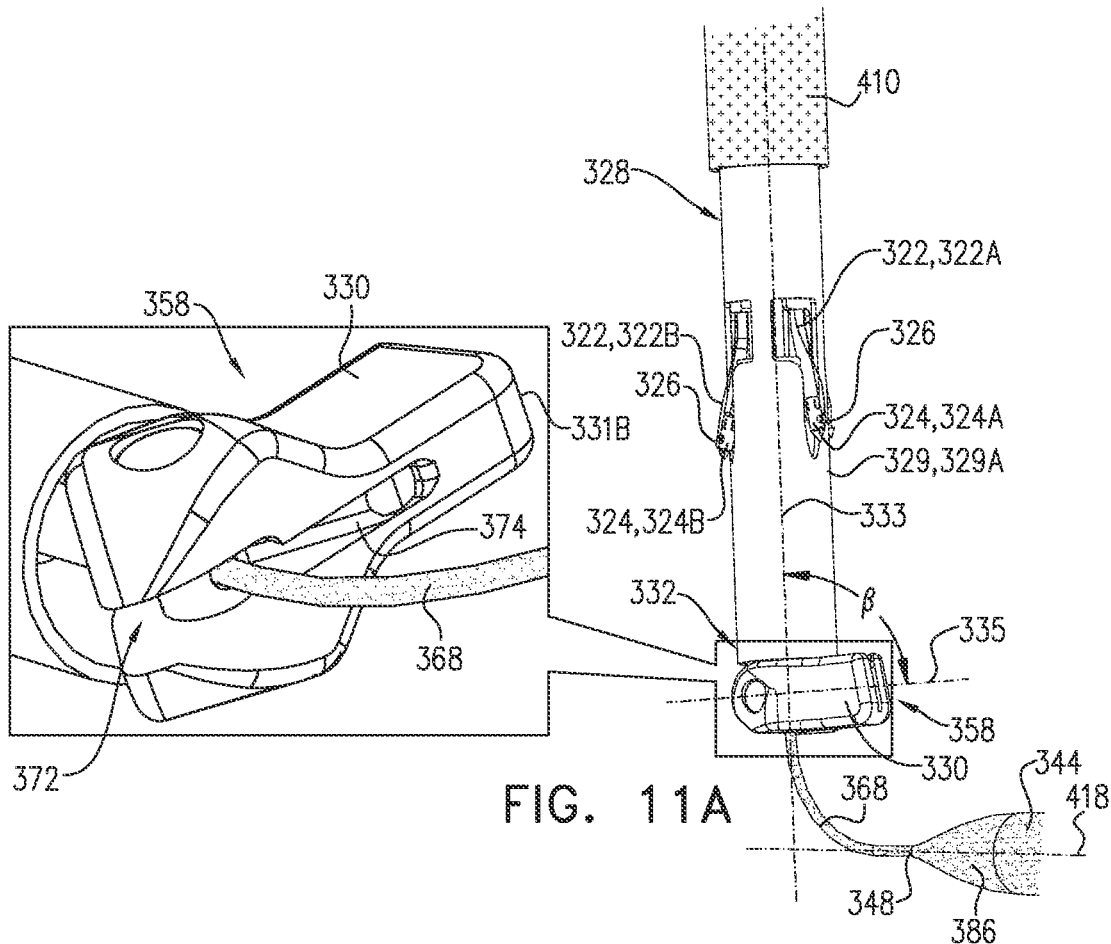
FIGS. 11A-B are schematic illustrations of a suture-positioning support of the closure device of FIG. 9A laterally extended from a distal end portion of an elongate support of the closure device of FIG. 9A, in accordance with an application of the present invention.
Figure 11B:
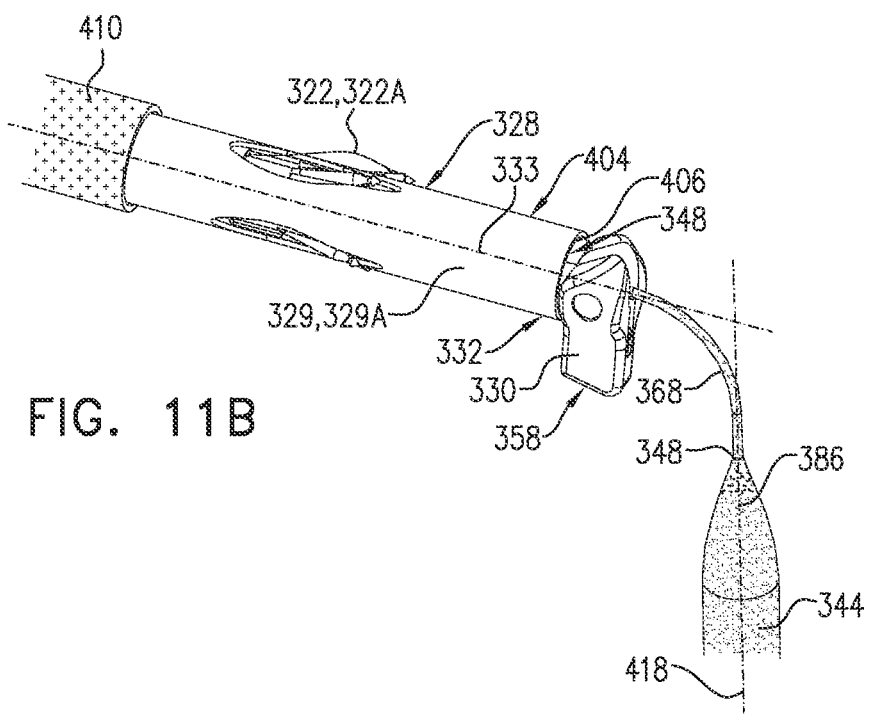

Reference is additionally made to FIGS. 11A-B, which are schematic illustrations of a suture-positioning support 330 of closure device 320 laterally extended from distal end portion 332 of elongate support 328, in accordance with an application of the present invention.

Figure 12:
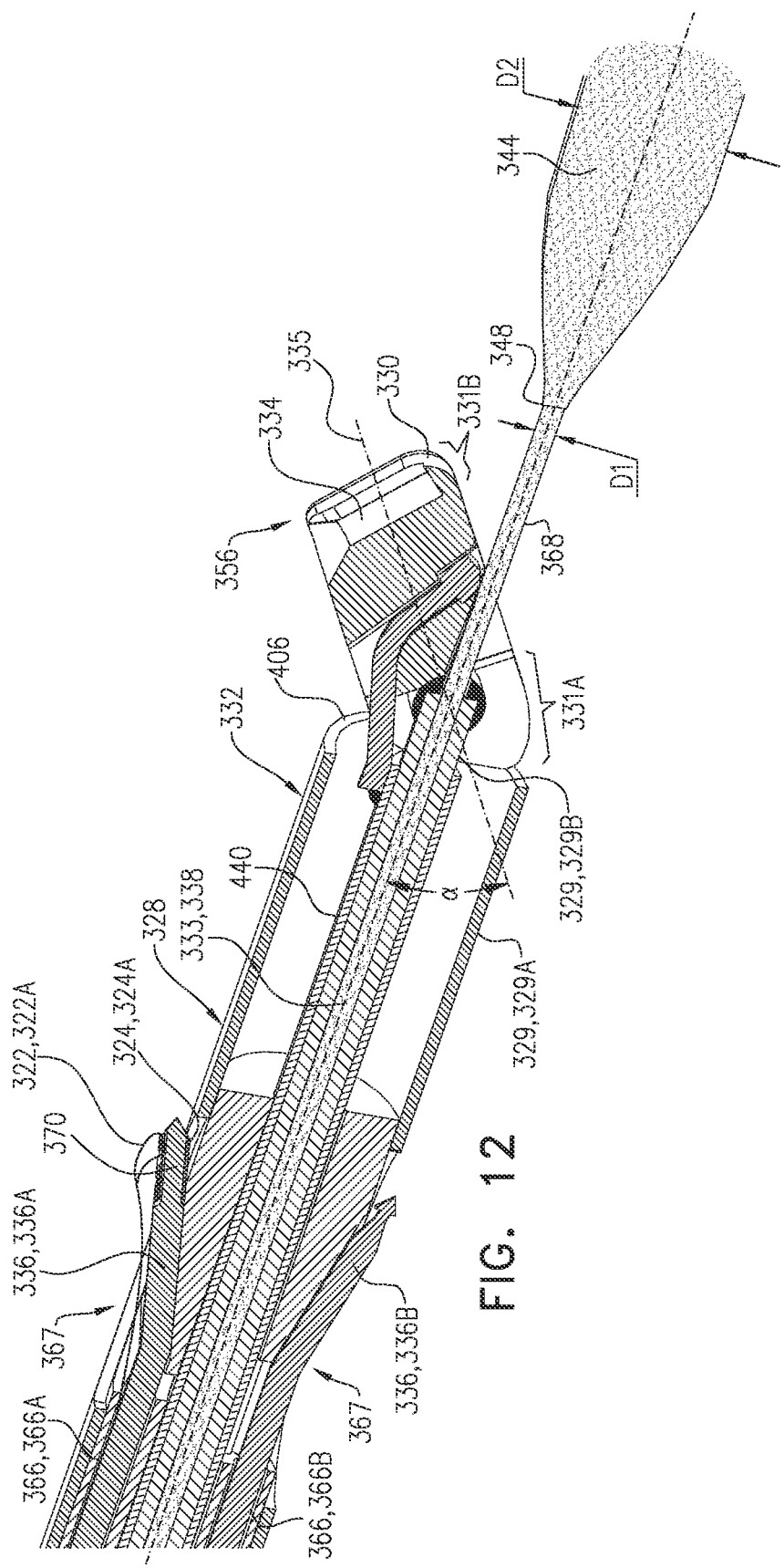
FIG. 12 is a schematic cross-sectional view of a portion of the closure device of FIG. 9A, in accordance with an application of the present invention.

Reference is also made to FIG. 12, which is a schematic cross-sectional view of a portion of closure device 320, in accordance with an application of the present invention.

Optionally, closure device 320 may implement, mutatis mutandis, any of the features of closure device 20, described hereinabove with reference to FIGS. 1-5J; closure device 120, described hereinabove with reference to FIGS. 6 and 7A-L; and/or closure device 220, described hereinabove with reference to FIGS. 8A-H.

Closure device 320 is used for suturing a puncture at an access site through a wall of a hollow anatomical structure, typically a blood vessel (in which case the access site is a vascular access site), or another body cavity, e.g., an abdominal cavity.

Closure device 320 comprises:
  elongate support 328, which typically comprises one or more shafts 329;
  suture-positioning support 330, which is (a) coupled to distal end portion 332 of elongate support 328, (b) laterally extendable with respect to distal end portion 332 of elongate support 328, and (c) configured to removably receive the suture 322; and
  an elongate dilator 344, which is configured to be inserted through the puncture, and which has a proximal end 348 that is coupled to distal end portion 332 of elongate support 328; dilator 344 typically facilitates insertion and alignment of suture-positioning support 330 in a blood vessel.

Typically, closure device 320 further comprises a control handle 340, coupled to a proximal end portion 342 of elongate support 28, such as shown in FIG. 9A. Control handle 340 comprises one or more user controls, such as levers and/or buttons, that allow an operator to control the positions and states of one or more elements of closure device 320, for example as described hereinbelow with reference to FIGS. 14A-B and 15A-H.

For some applications, closure device 320 is configured to allow movement of distal end portion 332 of elongate support 328 with respect to proximal end 348 of dilator 344:
  with at least two degrees of freedom, and/or
  with at least one translational degree of freedom.

The term "degrees of freedom" is used in the conventional sense in the present application, including in the claims and the Inventive Concepts, namely the six mechanical degrees of freedom of movement of an object in space, consisting of (a) three translational degrees of freedom in three perpendicular axes (forward/backward (surge), up/down (heave), left/right (sway)), resulting in change in position, and (b) three rotational degrees of freedom about three perpendicular axes (yaw (normal axis), pitch (transverse axis), and roll (longitudinal axis)), resulting in changes in orientation.

For some applications, closure device 320 is configured to allow the movement:
  without requiring distal end portion 332 of elongate support 328 to directly or indirectly apply a force to proximal end 348 of dilator 344,
  without requiring bending of dilator 344, and/or
  without requiring deformation of dilator 344.

For some applications, the above-mentioned at least two degrees of freedom include at least one rotational degree of freedom, e.g., at least two rotational degrees of freedom, such as three rotational degrees of freedom.

Alternatively or additionally, for some applications, the above-mentioned at least two degrees of freedom include at least one translational degree of freedom. Optionally, the at least one translational degree of freedom includes a translational degree of freedom along a distal-support central longitudinal axis 333 of distal end portion 332 of elongate support 328 (labeled in FIGS. 11A-B). For some applications, the at least two degrees of freedom include at least two translational degrees of freedom, such as three translational degrees of freedom.

For some applications, the above-mentioned at least one translational degree of freedom includes at least two translational degrees of freedom, such as three translational degrees of freedom.

For some applications, closure device 320 is configured to allow the movement of distal end portion 332 of elongate support 328 with respect to proximal end 348 of dilator 344 with at least four degrees of freedom, such as with six degrees of freedom.

Typically, closure device 320 is configured to allow the above-described movement without causing permanent deformation of any elements of closure device 320. Thus, the movement is reversable, such that distal end portion 332 of elongate support 328 can return to its prior position with respect to proximal end 348 of dilator 344.

Typically, dilator 344 has a length of at least 5 cm (e.g., at least 15 cm), no more than 30 cm (e.g., no more than 25 cm), and/or 5-30 cm (e.g., 15-25 cm), and/or a greatest diameter of at least 2 mm, no more than 6 mm, and/or 2-6 mm.

For some applications, dilator 344 comprises a flexible polymer, e.g., having a hardness of between 30-70 Shore D, optionally including a hydrophilic coating for minimal friction during insertion.

Figure 13A:
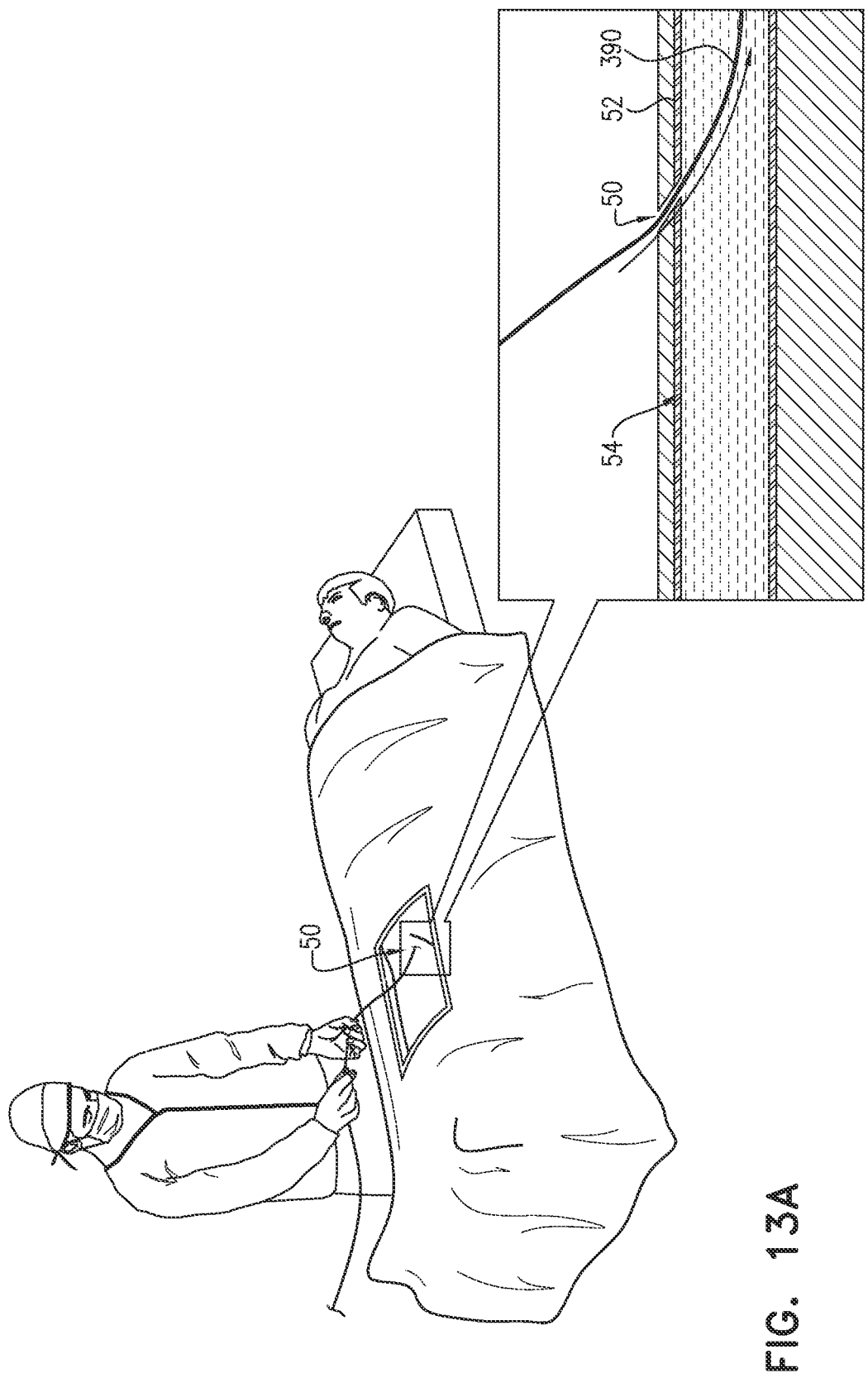
FIGS. 13A-R are schematic illustrations of a method for suturing a puncture through a wall of a hollow anatomical structure using the closure device of FIG. 9A, in accordance with an application of the present invention.
Figure 13B:
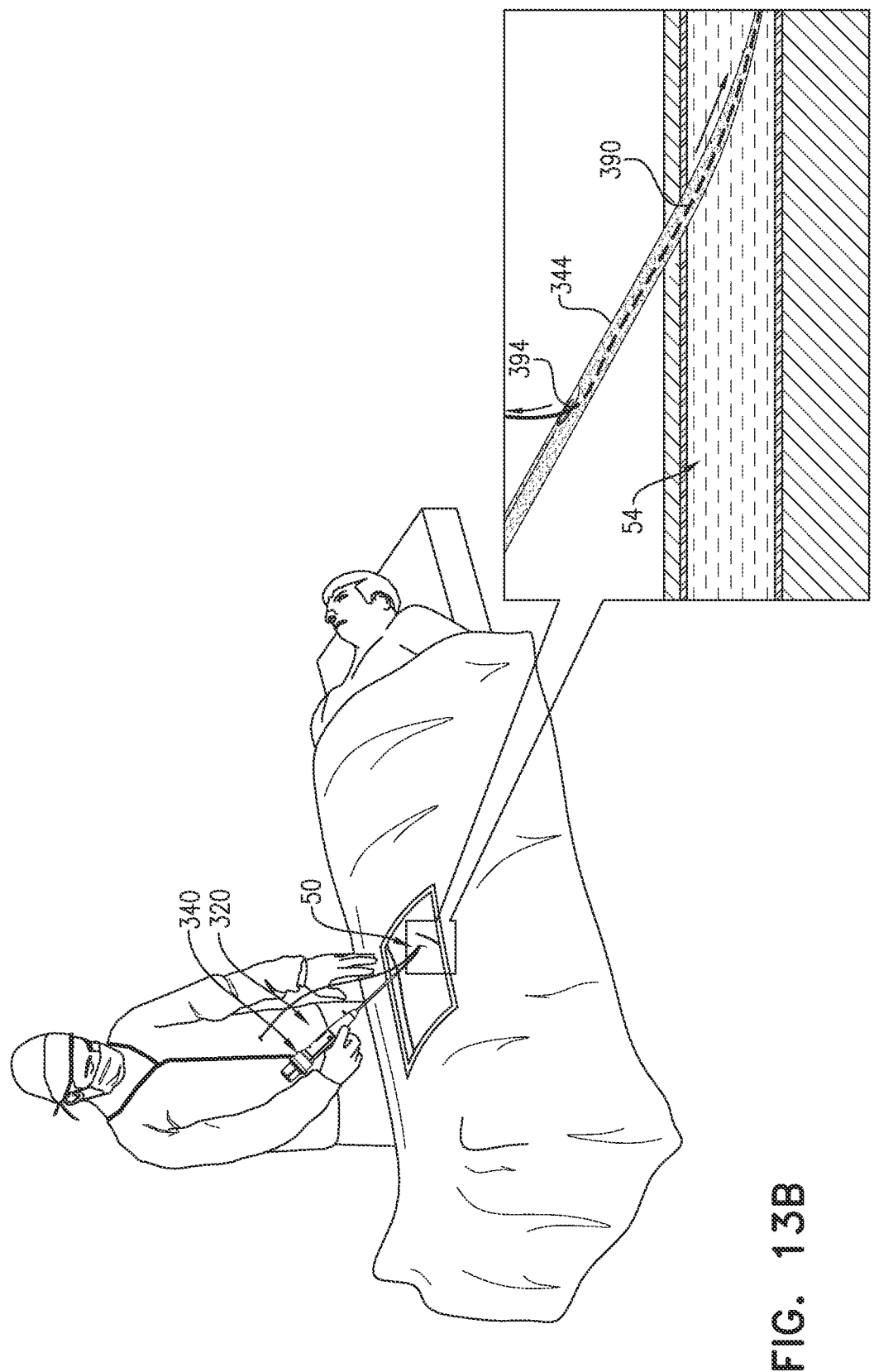
Figure 13C:
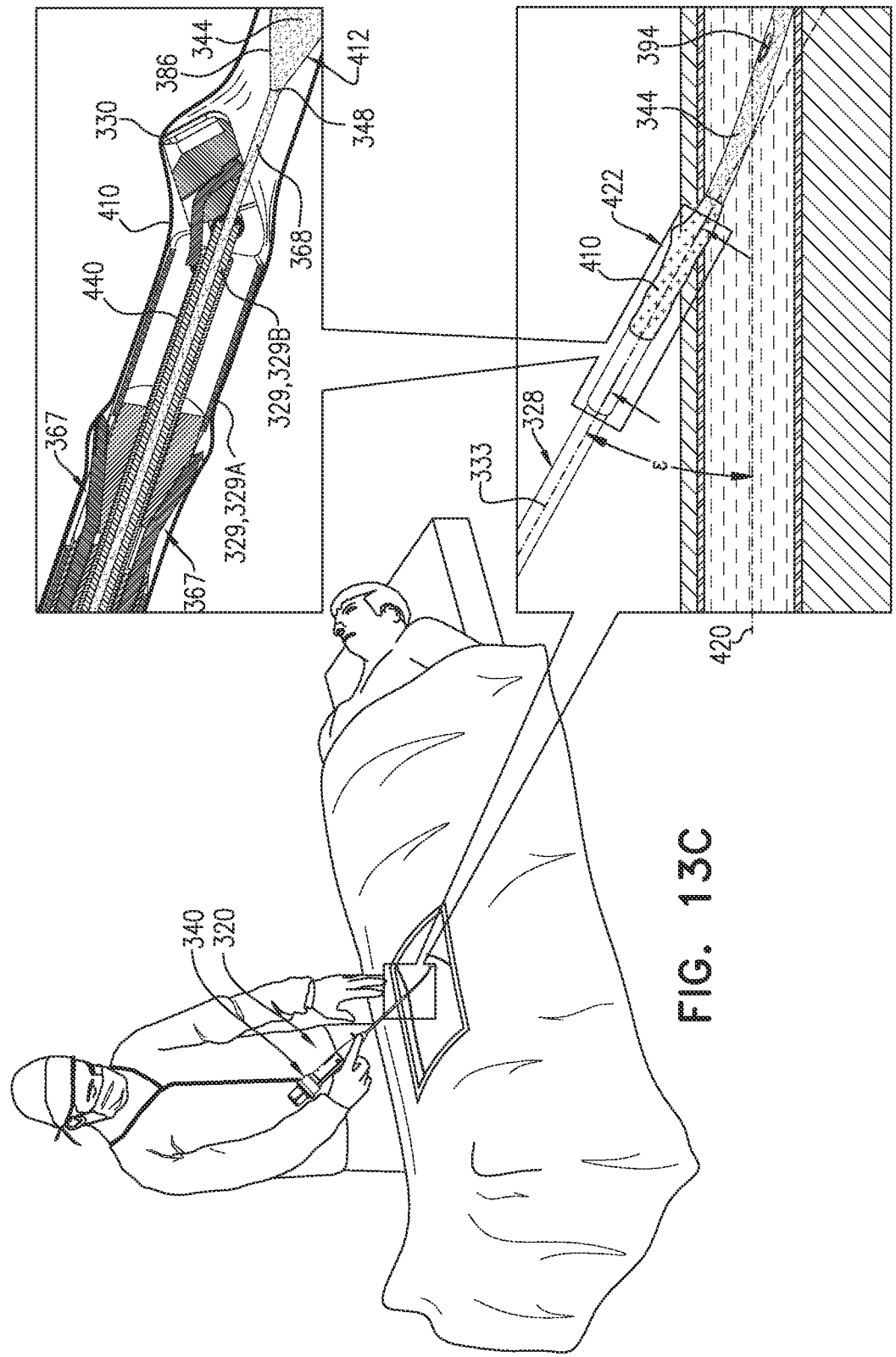

For some applications, dilator 344 is shaped so as to define an atraumatic proximal tip 386 (labeled in FIGS. 11A-B and 13C). Optionally, atraumatic proximal tip 386 is tapered.

For some applications, elongate support 328 comprises an outer tubular shaft 329A having a distal end portion 404 including a distal end 406 of outer tubular shaft 329A (labeled in FIG. 11B).

For some applications, elongate support 328 further comprises an inner shaft 329B (labeled in FIGS. 12 and 13C) nested within outer tubular shaft 329A, and suture-positioning support 330 is coupled to inner shaft 329B of elongate support 328.

For some applications, suture-positioning support 330 has proximal and distal end portions 331A and 331B at opposite ends of suture-positioning support 330 (labeled in FIG. 12). Proximal end portion 331A of suture-positioning support 330 is coupled to elongate support 328 (e.g., to inner shaft 329B of elongate support 328, as shown). Distal end portion 331B of suture-positioning support 330 is disposed distally to distal end 406 of outer tubular shaft 329A.

In some applications of the present invention, closure device 320 comprises an elongate flexible dilator connector 368, which couples proximal end 348 of dilator 344 to distal end portion 332 of elongate support 328 so as to allow movement of distal end portion 332 of elongate support 328 with respect to proximal end 348 of dilator 344, optionally with one or more of the above-mentioned degrees of freedom. Typically, proximal end 348 of dilator 344 and distal end portion 332 of elongate support 328 are connected by dilator connector 368 during manufacture of closure device 320, and remain connected throughout ordinary use of closure device 320. Thus, dilator connector 368 typically permanently connects proximal end 348 of dilator 344 to distal end portion 332 of elongate support 328, without enabling disconnection during ordinary use of closure device 320. Optionally, elongate flexible dilator connector 368 may alternatively be referred to as an elongate flexible dilator connecting member, an elongate flexible dilator coupling member, or an elongate flexible dilator linking member.

For some applications, dilator connector 368 and dilator 344 comprise separate respective elements coupled together. Alternatively, dilator connector 368 and dilator 344 are integrally formed from a single element.

For some applications, dilator connector 368 comprises a cable, a cord, a wire, a string, or a tube.

For some applications, dilator connector 368 comprises a metal (e.g., Nitinol or stainless steel) or a polymer.

For some applications, dilator connector 368 has a length of at least 0.5 cm (e.g., at least 1 cm), no more than 5 cm, and/or 0.5-5 cm, e.g., 1-5 cm. (Optionally, dilator connector 368 is anchored within at least a proximal portion of dilator 344 and/or within at least a distal portion of elongate support 328 (e.g., within inner shaft 329B of elongate support 328), such as shown in 13C; in this case, the length of dilator connector 368 includes only the exposed portion of the dilator connector outside the dilator and the elongate support.)

For some applications, a flexural rigidity of dilator 344 is greater than a flexural rigidity of dilator connector 368.

For some applications, a material of dilator 344 is harder than a material of dilator connector 368.

In some applications of the present invention (such as labeled in FIG. 12), an average outer diameter D1 of dilator connector 368 is:
- less than 20% of a greatest outer diameter D2 of dilator 344, such as less than 10% of D2,
- at least 3% of the greatest outer diameter D2 of dilator 344, such as at least 5% of D2, and/or
- at least 0.2 mm, no more than 0.8 mm, and/or 0.2-0.8 mm, e.g., 0.2-0.5 mm.

For some applications, dilator connector 368 is rotationally fixed to distal end portion 332 of elongate support 328 and proximal end 348 of dilator 344. Dilator connector 368 couples proximal end 348 of dilator 344 to distal end portion 332 of elongate support 328 so as to allow rotation of distal end portion 332 of elongate support 328 about distal-support central longitudinal axis 333 without corresponding rotation of dilator 344 about a proximal-dilator central longitudinal axis 418 of dilator 344 of a proximal end portion 412 of dilator 344 that includes proximal end 348 of dilator 344 (labeled in FIGS. 11A-B).

For some applications, suture-positioning support 330 is configured to assume:
- a delivery position 356, in which a suture-positioning support axis 335 of suture-positioning support 330 (a) forms a first angle α (alpha) of less than 45 degrees, e.g., less than 30 degrees, with distal-support central longitudinal axis 333 of distal end portion 332 of elongate support 328, such as shown in FIGS. 9A, 10A-D, and 12, and labeled in FIG. 12, or (b) is parallel with distal-support central longitudinal axis 333 (configuration not shown), and
- one or more deployed positions 358, in which suture-positioning support 330 is laterally extended with respect to distal end portion 332 of elongate support 328 such that suture-positioning support axis 335 forms a second angle β (beta) of at least 60 degrees, e.g., at least 75 degrees, such as 90 degrees with distal-support central longitudinal axis 333, such as shown in FIGS. 11A-B, and labeled in FIG. 11A.

As used in the present application, including in the claims and the Inventive Concepts, an angle between two elements is the smaller of the two supplementary angles between the two elements, or equals 90 degrees if the two elements are perpendicular.

Figure 10A:
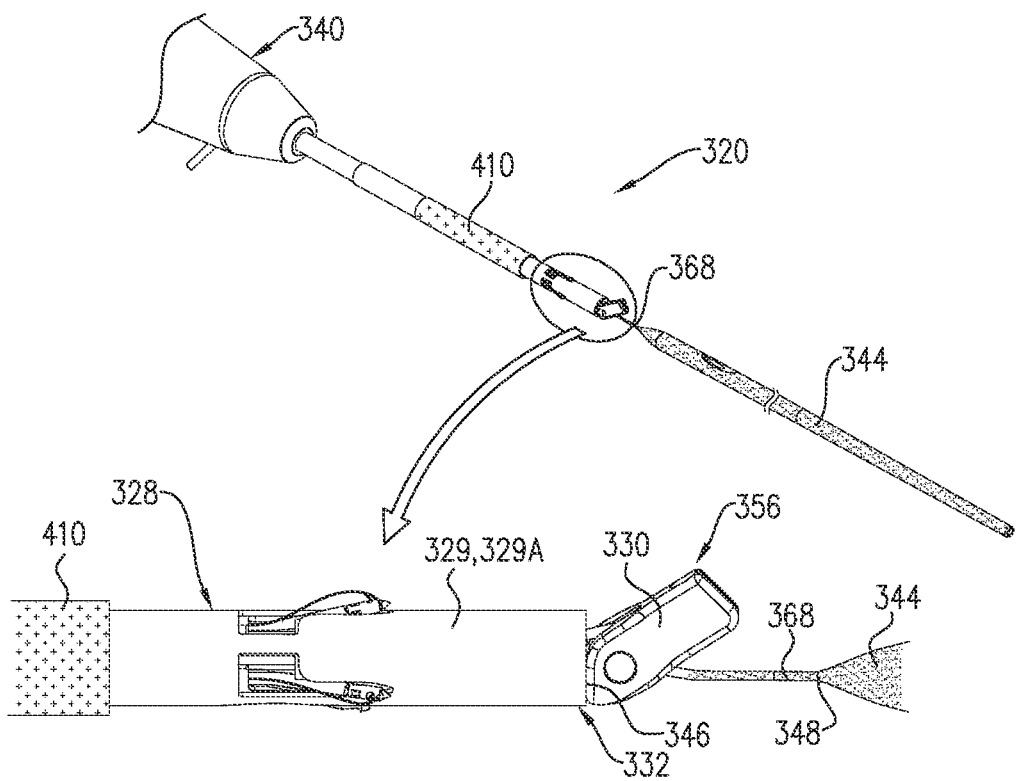
FIGS. 10A-D are several schematic views of a portion of the closure device of FIG. 9A, in accordance with an application of the present invention.
Figure 10B:
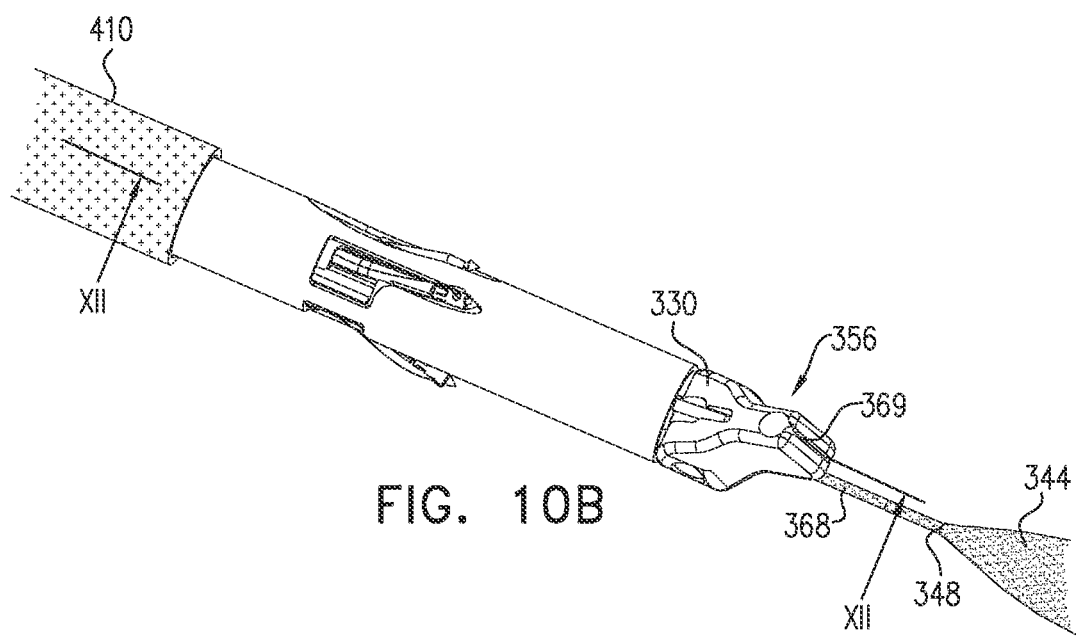

For some applications, suture-positioning support 330 is disposed distally beyond a distal end 346 of elongate support 328 (labeled in FIGS. 10A and 11B). Typically, but not necessarily, this is the case both when suture-positioning support 330 is in the above-mentioned delivery position 356 and in the above-mentioned one or more deployed positions 358.

Figure 10C:
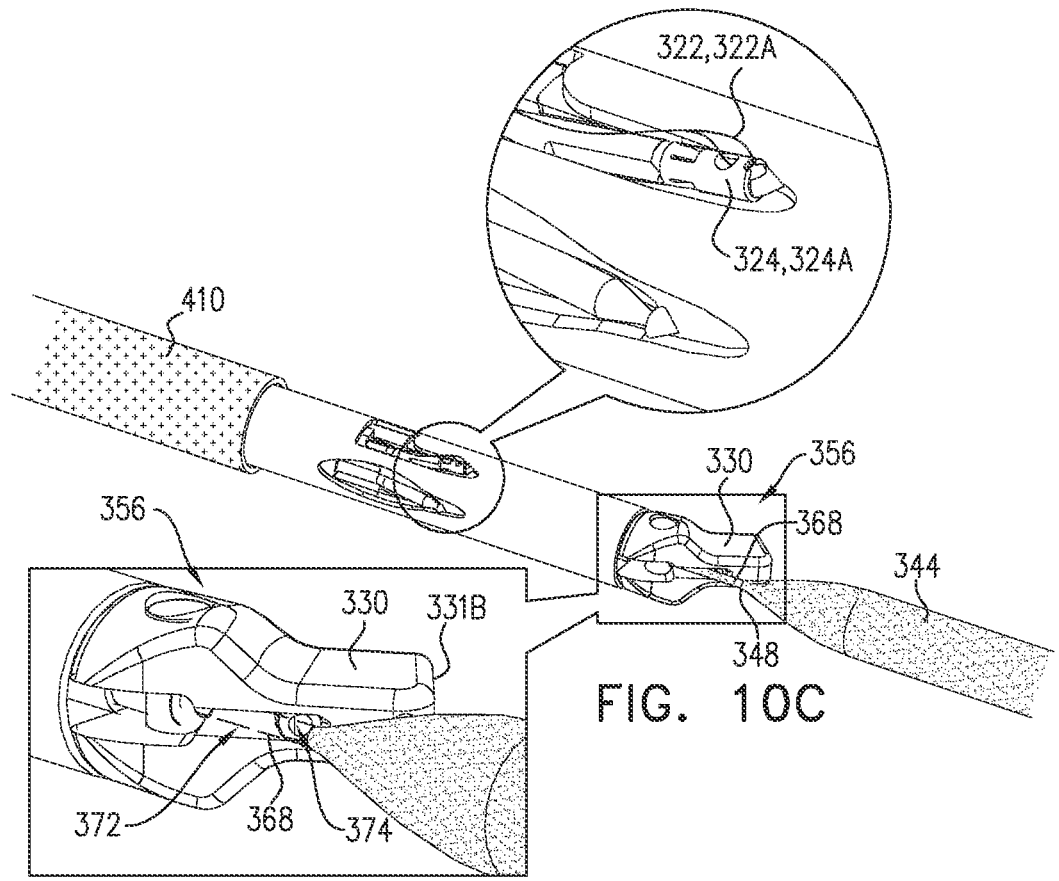
Figure 10D:
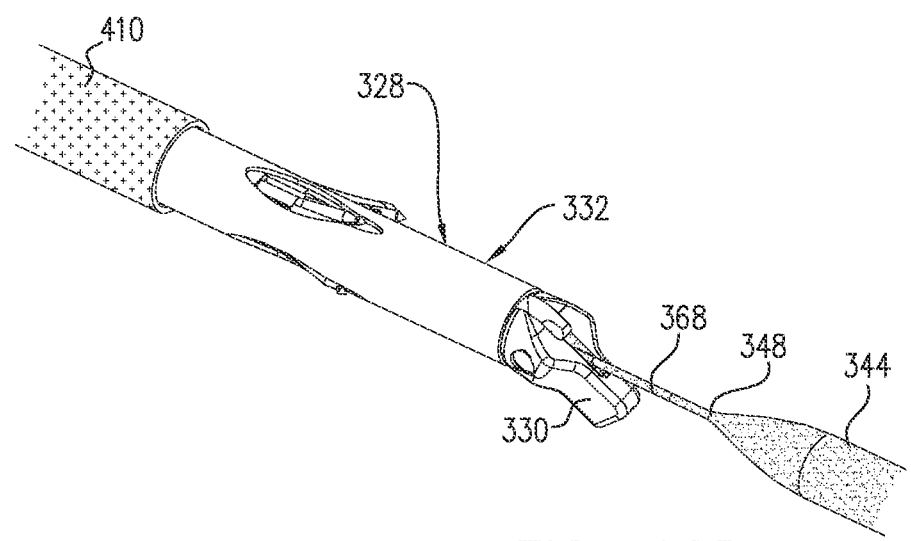

Reference is made to FIGS. 10C and 11A. For some applications, suture-positioning support 330 is shaped so as to define a passage 372 therethrough. Dilator connector 368 is disposed passing through passage 372. Passage 372 is typically shaped so as to allow the one or more of the above-mentioned degrees of freedom of movement of distal end portion 332 of elongate support 328 with respect to proximal end 348 of dilator 344, typically both when suture-positioning support 330 is in delivery position 356, such as shown in FIG. 10C, and when suture-positioning support 330 is the one or more deployed positions 358, such as shown in FIG. 11A.

For some applications, passage 372 is shaped so as to define an indentation 374 that slants toward distal end portion 331B of suture-positioning support 330. Indentation 374 may be shaped to receive dilator connector 368 when suture-positioning support 330 is in delivery position 356, such as shown in FIG. 10C, so as to avoid interfering with the freedom of movement of dilator connector 368.

(The configuration of suture-positioning support 330 described hereinbelow with reference to FIGS. 19A-C and 20A-C may also implement these features; optionally, passage 372 may be defined between partial spherical surfaces 650.)

Reference is still made to FIGS. 9A-12 and is additionally made to FIGS. 13A-R, which are schematic illustrations of a method for suturing puncture 50 through wall 52 of hollow anatomical structure 54 using closure device 320, in accordance with an application of the present invention. Although hollow anatomical structure 54 is illustrated as a blood vessel 54, the method may alternatively be performed on other hollow anatomical structures, such as a body cavity, e.g., an abdominal cavity, mutatis mutandis. Typically, the surgeon performed the medical procedure that made puncture 50 using the Selinger technique.

As shown in FIG. 13A, a guidewire 390 is inserted through puncture 50 and into the blood vessel 54.

As shown in FIGS. 13B, elongate dilator 344 is advanced over guidewire 390 and through puncture 50 and into blood vessel 54. Dilator 344 is shaped so as to define a guidewire channel through which the guidewire passes during the advancement. Typically, the guidewire channel has a distal opening 392 (labeled in FIG. 9A) through a distal end of dilator 344 and a proximal opening 394 through a lateral wall of dilator 344 near proximal end 348 of dilator 344 (labeled in FIGS. 9A and 13B). Optionally, the guidewire channel has a diameter of at least 0.8 mm, no more than 1.2 mm, and/or 0.8-1.2 mm. Guidewire 390 is removed from blood vessel 54.

As shown in FIG. 13C, distal end portion 332 of elongate support 328 is inserted through puncture 50 and into hollow anatomical structure 54 (e.g., the blood vessel), typically while suture-positioning support 330 is in delivery position 356.

Figure 13D:
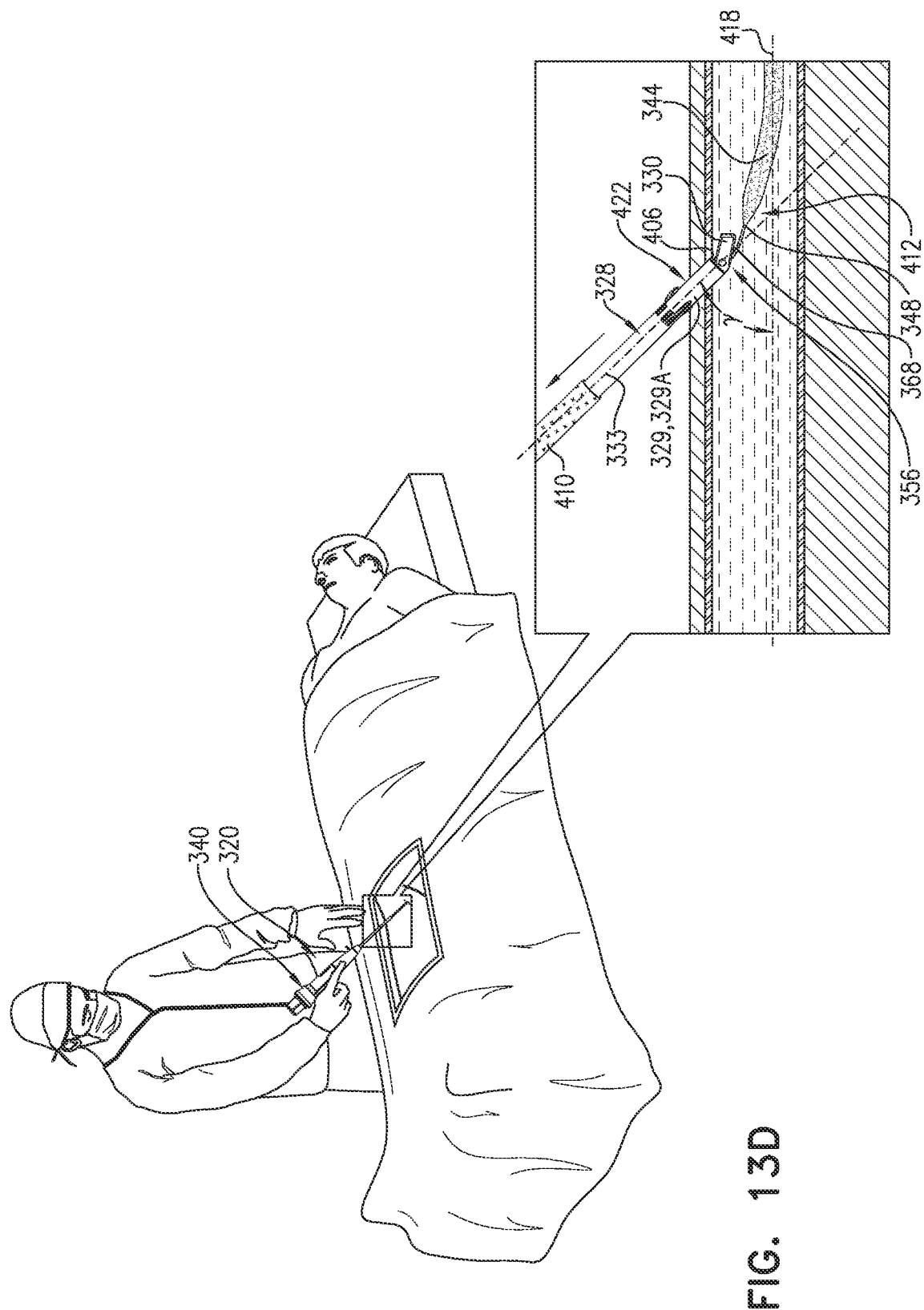

Reference is made to FIGS. 13C-D. As described hereinabove with reference to FIGS. 9A-12, for some applications elongate support 328 comprises outer tubular shaft 329A having a distal end 406 (labeled in FIG. 11B). In some applications of the present invention, closure device 320 further comprises a sheath 410 that covers: distal end 406 of outer tubular shaft 329A, suture-positioning support 330, dilator connector 368, and proximal end portion 412 of dilator 344 that includes proximal end 348 of dilator 344, such as shown in FIG. 13C. Sheath 410 thus may facilitate atraumatic insertion of distal end 406 of outer tubular shaft 329A and suture-positioning support 330 through puncture 50, despite the narrowing of closure device 320 along dilator connector 368 and atraumatic proximal tip 386 of dilator 344.

After distal end 406 of outer tubular shaft 329A and suture-positioning support 330 have been inserted through puncture 50 and into blood vessel 54, sheath 410 is proximally withdrawable along outer tubular shaft 329A so as to expose suture-positioning support 330, dilator connector 368, and proximal end portion 412 of dilator 344, such as shown in FIG. 13D. For example, control handle 340 may comprise a sheath-control user control 430, such as described hereinbelow with reference to FIGS. 14A-B. (For clarity of illustration, sheath 410 is shown proximally withdrawn in FIGS. 9A-B, even though sheath 410 is in practice not withdrawn until after insertion of outer tubular shaft 329A and suture-positioning support 330 through puncture 50 and into blood vessel 54.)

For some applications, sheath 410 is flexible enough to change diameter, e.g., to accommodate slight lateral protrusion of suture-positioning support 330 even while suture-positioning support 330 is in delivery position 356, such as shown in FIG. 13C. For some applications, sheath 410 comprises a material selected from the group of polymeric materials consisting of: silicone and polyether block amide (PEBA).

As shown in FIGS. 13C, in some applications of the present invention, distal end portion 332 of elongate support 328 is inserted of closure device 320 through puncture 50 and into blood vessel 54, while distal-support central longitudinal axis 333 of distal end portion 332 of elongate support 328 forms an angle ε (epsilon) of less than 30 degrees with respect to a blood-vessel central longitudinal axis 420 of blood vessel 54 at a site 422 of puncture 50. Thereafter, as shown in FIG. 13E, distal end portion 332 of elongate support 328 is moved with respect to blood vessel 54 to define a second angle θ (theta) between distal-support central longitudinal axis 333 and blood-vessel central longitudinal axis 420, such as shown in FIG. 13E.

For some applications:
the first angle ε (epsilon) is less than 30 degrees and the second angle θ (theta) is 45-90 degrees, such as 60-90 degrees, e.g., 75-90 degrees, such as 90 degrees, and/or
the second angle θ (theta) is at least 15 degrees greater than the first angle ε (epsilon), such as at least 30 degrees, e.g., at least 45 degrees, such as at least 60 degrees, greater than the first angle γ (gamma).

Figure 13E:
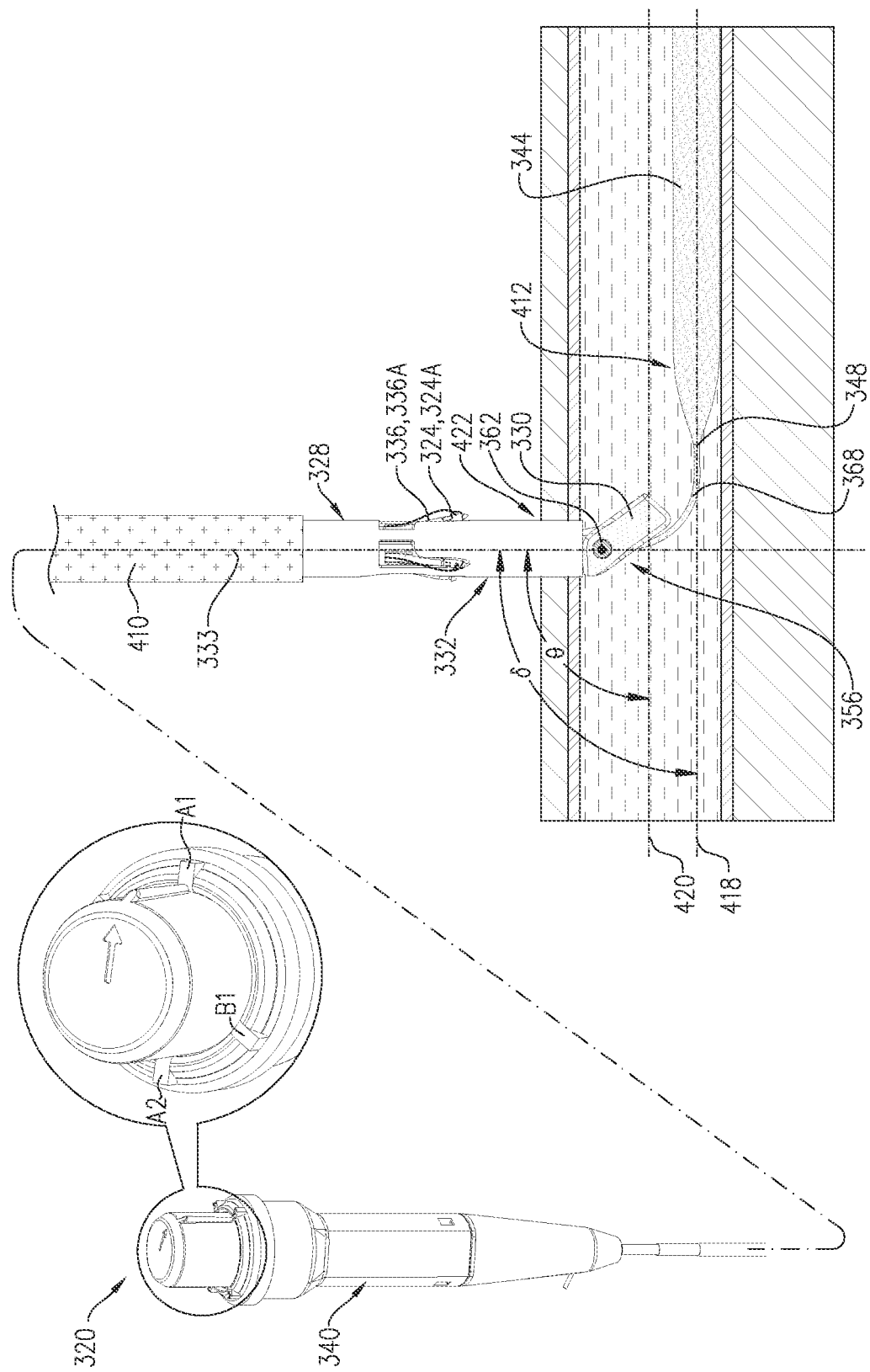

As also shown in FIGS. 13C and 13E, in some applications of the present invention, distal end portion 332 of elongate support 328 defines distal-support central longitudinal axis 333. Proximal end portion 412 of dilator 344, which includes proximal end 348 of dilator 344, defines proximal-dilator central longitudinal axis 418. Closure device 320 is configured to allow distal end portion 332 of elongate support 328 to move with respect to proximal end 348 of dilator 344 from defining a first angle γ (gamma) (as shown in FIG. 13D) to defining a second angle δ (delta) (as shown in FIG. 13E) between distal-support central longitudinal axis 333 and proximal-dilator central longitudinal axis 418.

For some applications:
the first angle γ (gamma) is less than 30 degrees and the second angle δ (delta) is 45-90 degrees, such as 60-90 degrees, e.g., 75-90 degrees, such as 90 degrees, and/or
the second angle δ (delta) is at least 15 degrees greater than the first angle γ (gamma), such as at least 30 degrees, e.g., at least 45 degrees, such as at least 60 degrees, greater than the first angle γ (gamma).

For some applications in which closure device 320 comprises elongate flexible dilator connector 368, the elongate flexible dilator connector couples proximal end 348 of dilator 344 to distal end portion 332 of elongate support 328 so as to allow the above-described movement.

For some applications, distal end portion 332 of elongate support 328 is moved with respect to proximal end 348 of dilator 344 without causing distal end portion 332 of elongate support 328 to directly or indirectly apply a force to proximal end 348 of dilator 344.

For some applications, distal end portion 332 of elongate support 328 is moved with respect to proximal end 348 of dilator 344 without bending dilator 344.

For some applications, distal end portion 332 of elongate support 328 is moved with respect to proximal end 348 of dilator 344 without deforming dilator 344.

For some applications, distal end portion 332 of elongate support 328 is moved with respect to proximal end 348 of dilator 344 with at least two degrees of freedom, such as:
- with at least one rotational degree of freedom, such as at least two rotational degrees of freedom, e.g., with three rotational degrees of freedom,
- with at least one translational degree of freedom, such as a translational degree of freedom along distal-support central longitudinal axis 333, and/or with at least two translational degrees of freedom, e.g., with three translational degrees of freedom, and/or
- with at least four degrees of freedom, e.g., with six degrees of freedom.

For some applications, distal end portion 332 of elongate support 328 is moved with respect to proximal end 348 of dilator 344 without causing dilator 344 to apply a force to wall 52 of blood vessel 54.

For some applications, dilator 344 is laterally moved while distal end portion 332 of elongate support 328 remains stationary with respect to puncture 50.

For any of the applications described above, elongate flexible dilator connector 368, described hereinabove with reference to FIGS. 9A-12, couples proximal end 348 of dilator 344 to distal end portion 332 of elongate support 328 so as to allow the described movement.

For some of these applications, dilator connector 368 is rotationally fixed to distal end portion 332 of elongate support 328 and proximal end 348 of dilator 344, and distal end portion 332 of elongate support 328 is rotated about distal-support central longitudinal axis 333 without corresponding rotation of dilator 344 about proximal-dilator central longitudinal axis 418. To allow this rotation, dilator connector 368 typically twists and/or bunches up, such as shown in FIG. 13H.

Figure 13F:
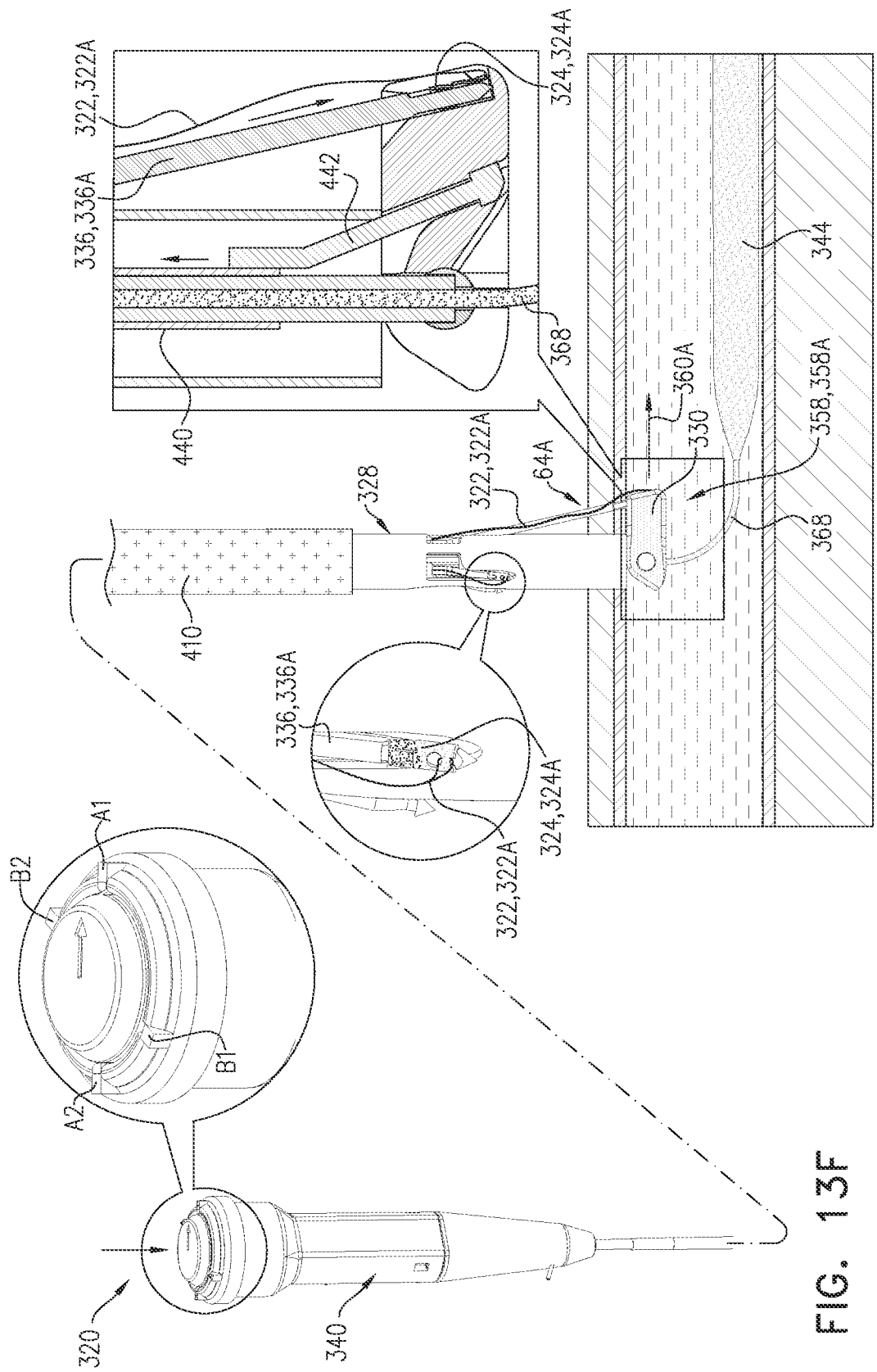

As shown in FIG. 13F, suture-positioning support 330 is laterally extended, with respect to distal end portion 332 of elongate support 328, to a first deployed position 358, 358A in which suture-positioning support 330 laterally extends in a first direction 360A from distal end portion 332 of elongate support 328. For example, suture-positioning support 330 may be laterally extended using control handle 340 as described hereinbelow with reference to FIGS. 15A-B.

A first suture 322, 322A is distally advanced through a portion of elongate support 328 and a first wall site 64A of wall 52 and into blood vessel 54, and into suture-positioning support 330.

For some applications, such as shown in the transition between FIG. 13E and FIG. 13F, suture-positioning support 330 is pivotably coupled to distal end portion 332 of elongate support 328 such that suture-positioning support 330 is rotatable about a pivot axis 362 to transition from delivery position 356 to first deployed position 358, 358A. Typically, pivot axis 362 is not coaxial with distal-support central longitudinal axis 333.

Reference is made to FIGS. 9A-D, 12, and 13F-O. For some applications, closure device 320 further comprises:
- a ferrule 324, which is coupled to a distal end portion 326 of first suture 322, 322A (labeled in FIG. 11A), such as by being passed (e.g., looped) through an opening defined by a wall of ferrule 324 (such as shown), and/or by welding, knotting, gluing, or another technique (configurations not shown); and
- one or more suturing needles 336, which are removably couplable to ferrule 324.

Suture-positioning support 330 is shaped so as to define a ferrule receptacle 334 (labeled in FIGS. 12 and 13G), which is configured to removably receive ferrule 324, such that suture-positioning support 330 is configured to removably receive first suture 322, 322A. For some applications, suture-positioning support 330 is shaped so as to define exactly one ferrule receptacle 334, such as shown. For other applications, suture-positioning support 330 is shaped so as to define two or more ferrule receptacles, such as described hereinabove.

Elongate support 328 defines, through a longitudinal portion of elongate support 328, one or more needle lumens 366 having respective distal lumen openings 367 (labeled in FIG. 12). Needle lumens 366 are shaped so as to direct respective suturing needles 336 out of respective distal lumen openings 367 and toward ferrule receptacle 334 during distal advancement of respective suturing needles 336, optionally removably coupled to ferrule 324. To this end, suturing needles 336 are typically sufficiently flexible to be bent and directed by needle lumens 366 in the proper direction of advancement, such as perhaps best seen in FIG. 12.

Reference is made to FIG. 13F. For some applications, first suture 322, 322A is distally advanced into suture-positioning support 330 by distally advancing a first ferrule-advancing suturing needle 336, 336A of suturing needles 336 through first wall site 64A of wall 52 and into blood vessel 54, while first ferrule-advancing suturing needle 336, 336A is removably coupled to ferrule 324, such that closure device 320 directs ferrule 324 into ferrule receptacle 334 defined by suture-positioning support 330 and ferrule receptacle 334 removably receives ferrule 324 while suture-positioning support 330 is in first deployed position 358, 358A. For example, first ferrule-advancing suturing needle 336, 336A may be distally advanced using control handle 340 as described hereinbelow with reference to FIGS. 15A-B.

Typically, first ferrule-advancing suturing needle 336, 336A is removably coupled to ferrule 324 before the beginning of the procedure, although first ferrule-advancing suturing needle 336, 336A may alternatively become removably coupled to ferrule 324 during the procedure, such as during distal advancement of first ferrule-advancing suturing needle 336, 336A through or out of a first one of needle lumens 366.

Optionally, the surgeon adjusts an axial position of elongate support 328 such that suture-positioning support 330 touches, or is near, an inner surface of wall 52, as shown in FIG. 13F. The various degrees of freedom of distal end portion 332 of elongate support 328 with respect to proximal end 348 of dilator 344 may facilitate this adjustment of the axial position of elongate support 328.

For some applications in which closure device 320 comprises sheath 410, such as described hereinabove with reference to FIGS. 13C-D, sheath 410 covers distal end 406 of outer tubular shaft 329A, suture-positioning support 330, dilator connector 368, proximal end portion 412 of dilator 344, and distal lumen opening 367. (Distal lumen opening 367 is sometimes introduced into the body, albeit not into the blood vessel.) Sheath 410 is proximally withdrawable along outer tubular shaft 329A so as to expose suture-positioning support 330, dilator connector 368, proximal end portion 412 of dilator 344, and distal lumen opening 367, such as shown in FIG. 13D.

For these applications, such as shown in FIG. 13B, distal end portion 332 of elongate support 328 is inserted through puncture 50 and into blood vessel 54 while sheath 410 covers: distal end 406 of outer tubular shaft 329A, suture-positioning support 330, dilator connector 368, and proximal end portion 412 of dilator 344. The method further comprises, after inserting distal end portion 332 of elongate support 328 and before laterally extending suture-positioning support 330: proximally withdrawing sheath 410 along outer tubular shaft 329A so as to expose suture-positioning support 330, dilator connector 368, proximal end portion 412 of dilator 344, and distal lumen opening 367, if provided and covered by sheath 410. For example, control handle 340 may comprise sheath-control user control 430, such as described hereinbelow with reference to FIGS. 14A-B.

Figure 13G:
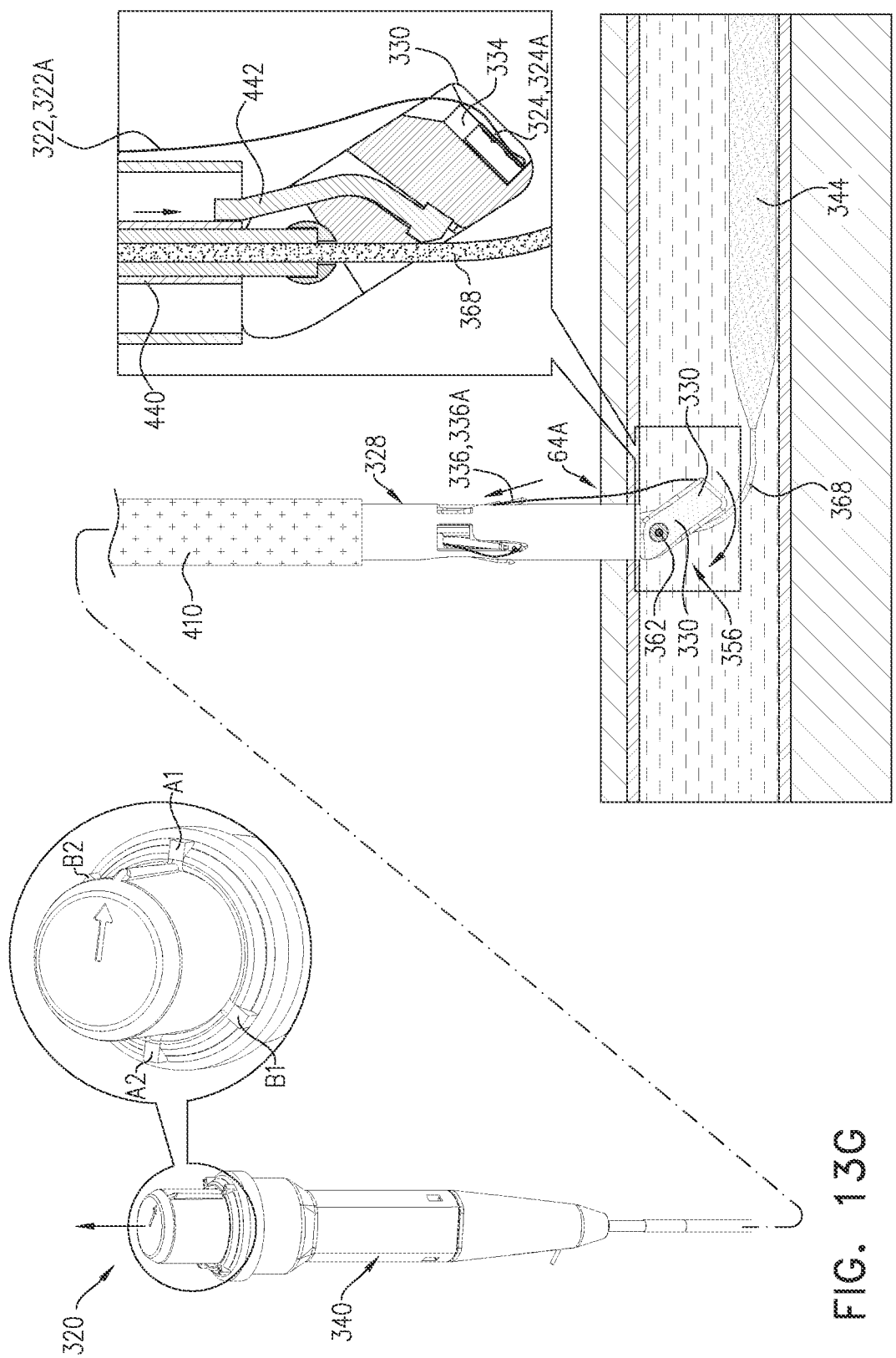
Figure 13H:
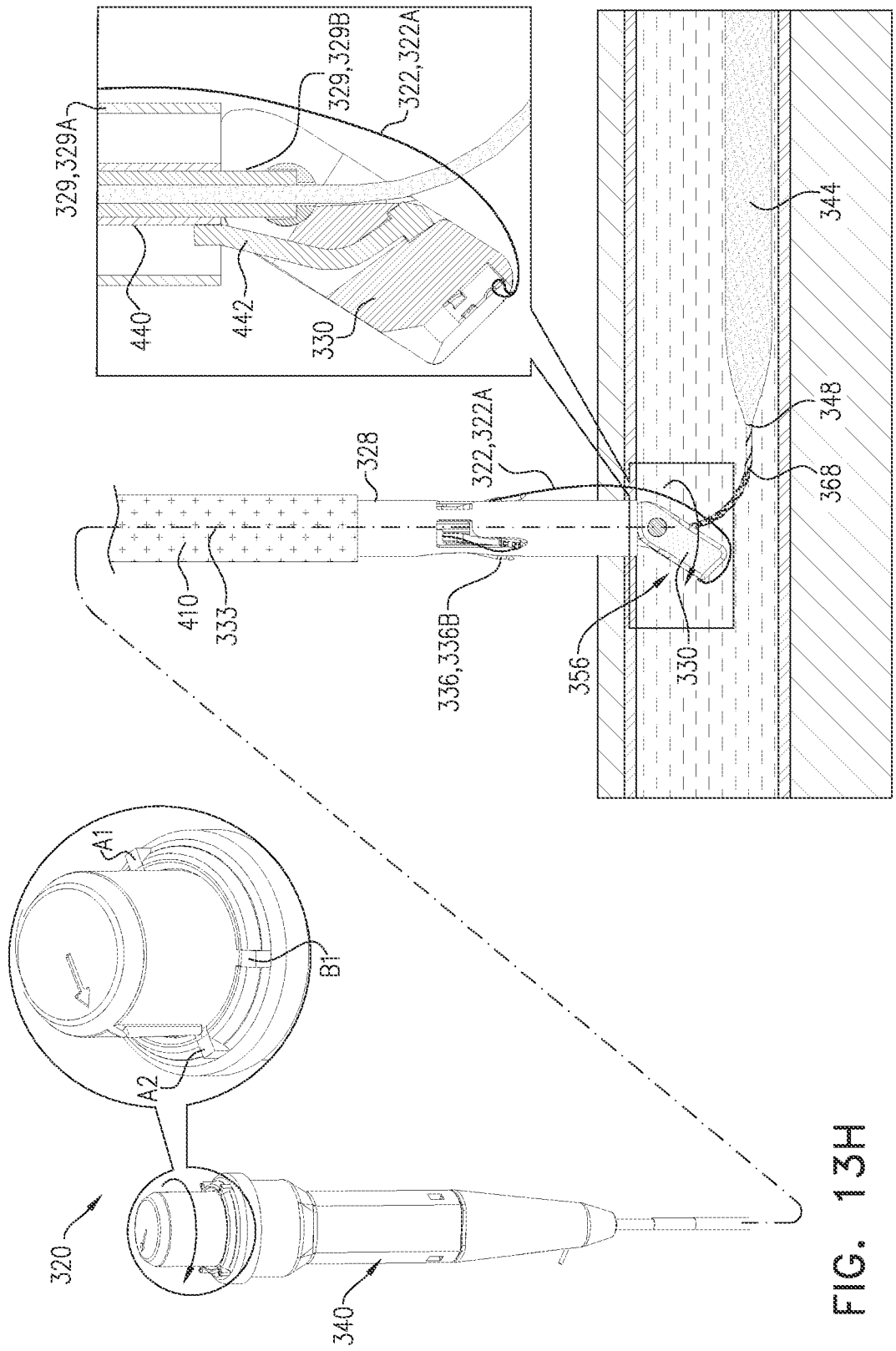
Figure 131:
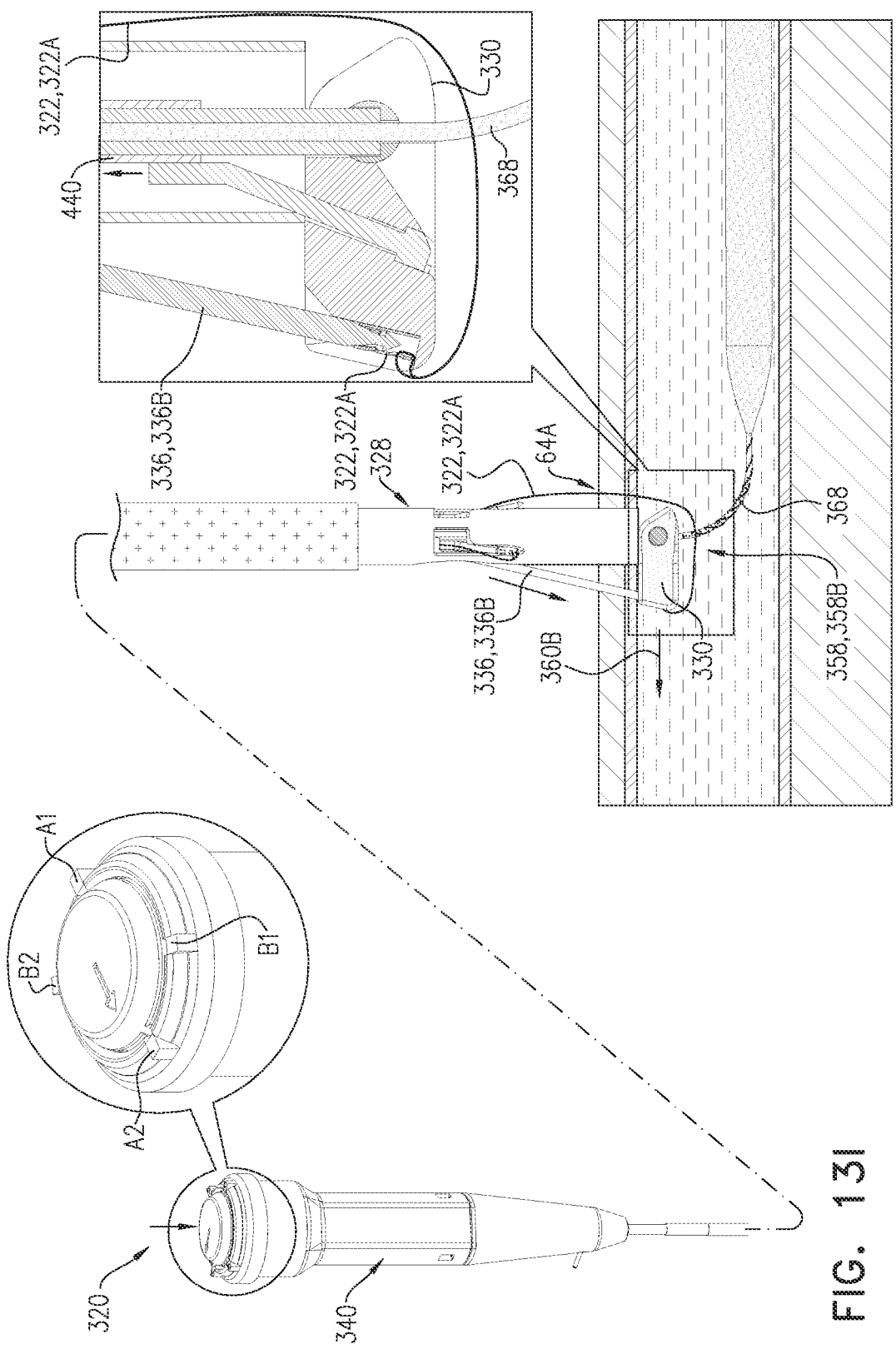

As shown in FIG. 13G, first ferrule-advancing suturing needle 336, 336A is proximally withdrawn from ferrule 324 and hollow anatomical structure 54, while leaving ferrule 324 within ferrule receptacle 334. For example, ferrule 324 may be held in ferrule receptacle 334 as first ferrule-advancing suturing needle 336, 336A is proximally withdrawn from ferrule 324 by one or more of the following features:

ferrule receptacle 334 may have a smaller cross-sectional area than that of ferrule 324; and/or ferrule receptacle 334 may be shaped so as to define a slit 369 (labeled in FIGS. 10B and 13L), e.g., through a wall of suture-positioning support 330, which allows ferrule receptacle 334 to expand slightly as ferrule 324 is inserted into the receptacle, applying friction and a spring-like effect to the ferrule.

For example, first ferrule-advancing suturing needle 336, 336A may be proximally withdrawn using control handle 340 as described hereinbelow with reference to FIG. 15D.

Also as shown in FIGS. 13G, suture-positioning support 330 is transitioned from first deployed position 358, 358A back to delivery position 356. (This position is called a "delivery" position, even though suture-positioning support 330 is not again delivered at this step, because the position is typically the same position as during initial delivery of suture-positioning support 330.) Optionally, as shown in the transition shown in FIG. 13G, suture-positioning support 330 is transitioned from first deployed position 358, 358A back to delivery position 356 by rotating suture-positioning support 330 about pivot axis 362. For example, suture-positioning support 330 may be transitioned from first deployed position 358, 358A back to delivery position 356 using control handle 340 as described hereinbelow with reference to FIG. 15E.

As shown in FIG. 13H, suture-positioning support 330, while in delivery position 356, is rotated about distal-support central longitudinal axis 333. Rotating suture-positioning support 330 while in delivery position 356 may help minimize the footprint of the device in the blood vessel. For some of these applications, the rotation is achieved by rotation of one or more of the shafts of elongate support 328, with respect to control handle 340, about distal-support central longitudinal axis 333. For example, elongate support 328 may comprise outer tubular shaft 329A and an inner shaft 329B, nested within outer tubular shaft 329A, and closure device 320 may be configured to rotate inner shaft 329B while holding outer tubular shaft 329A fixed with respect to control handle 340, such as shown. For example, suture-positioning support 330 may be rotated about distal-support central longitudinal axis 333 using control handle 340 (e.g., support-and-needle user control 434 thereof) as described hereinbelow with reference to FIGS. 15F.

Alternatively, closure device 320 may be configured to rotate outer tubular shaft 329A with respect to control handle 340 (configuration not shown).

Further alternatively, elongate support 328 may comprise only a single shaft, and closure device 320 may be configured to rotate the single shaft with respect to control handle 340 (configuration not shown). Further alternatively, the rotation is achieved by rotation of elongate support 328 by rotation of control handle 340 about distal-support central longitudinal axis 333 by the surgeon, such as described hereinbelow for the transition of suture-positioning support 130 of closure device 220, with reference to FIG. 8D through FIG. 8F, mutatis mutandis.

The one or more rotational degrees of freedom of distal end portion 332 of elongate support 328 with respect to proximal end 348 of dilator 344 may facilitate this adjustment of the axial position of elongate support 328, particularly in configurations in which dilator connector 368 is rotationally fixed to distal end portion 332 of elongate support 328 and proximal end 348 of dilator 344.

As shown in the transition between FIG. 13H and FIG. 13I, suture-positioning support 330 is again laterally extended, with respect to distal end portion 332 of elongate support 328, to a second deployed position 358, 358B in which suture-positioning support 330 laterally extends in a second direction 360B from distal end portion 332 of elongate support 328, second direction 360B different from first direction 360A. For example, first direction 360A and second direction 360B may be separated by an angle of 120-240 degrees, such as 175-185 degrees, e.g., 180 degrees, around distal-support central longitudinal axis 333 of distal end portion 332 of elongate support 328. For example, suture-positioning support 330 may be laterally extended using control handle 340 as described hereinbelow with reference to FIG. 15G.

Figure 13J:
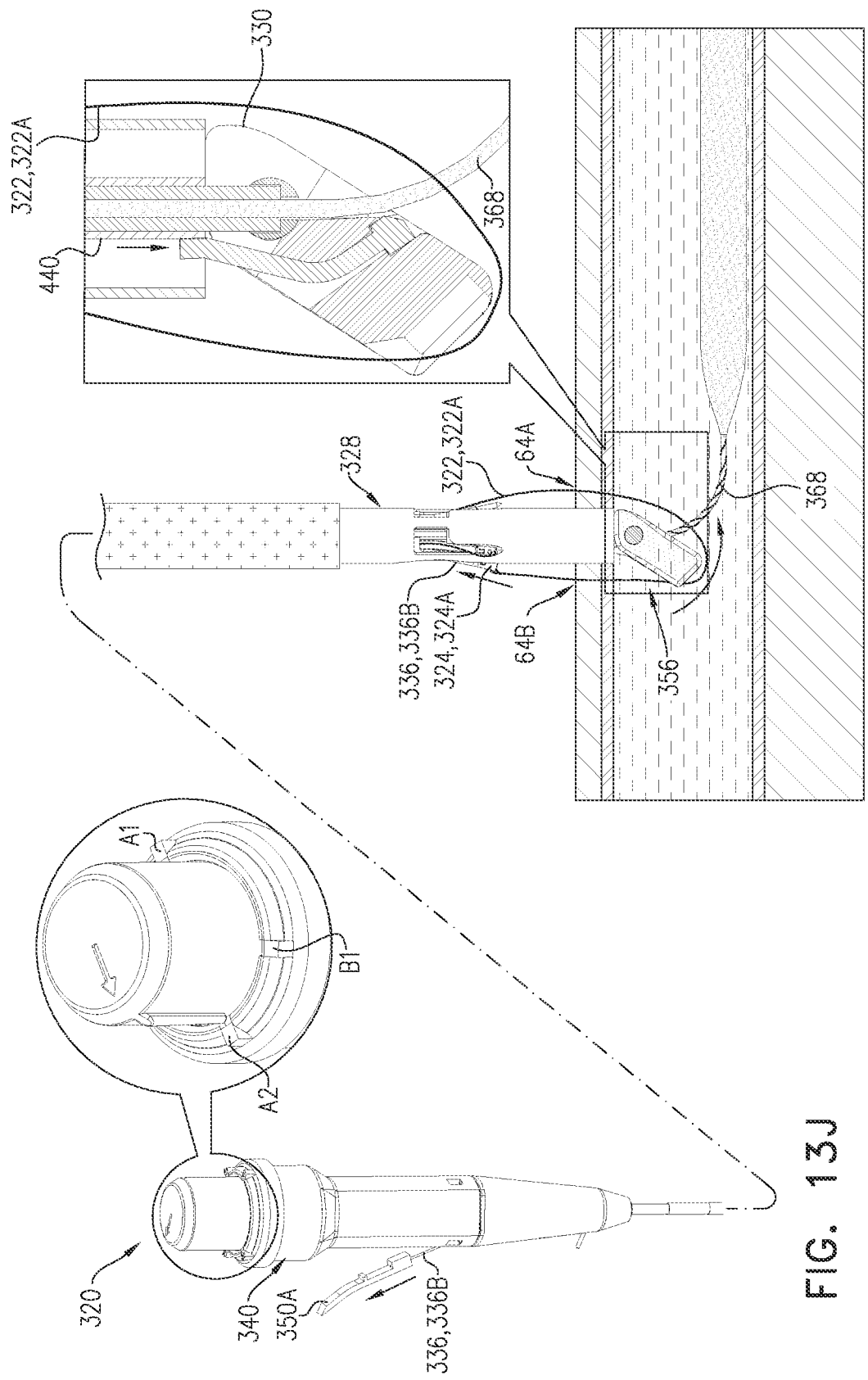

As shown in FIG. 13J, while suture-positioning support 330 is in second deployed position 358B, ferrule 324 is proximally withdrawn from ferrule receptacle 334 and out of hollow anatomical structure 54 via a second wall site 64B of wall 52, so as to proximally withdraw a portion of first suture 322, 322A, including distal end portion 326 thereof, out of hollow anatomical structure 54 via second wall site 64B. The portion of first suture 322, 322A drawn out of hollow anatomical structure 54 via second wall site 64B is secured to another portion of first suture 322, 322A, for example by a first pre-tied knot 338A, such as described hereinbelow with reference to FIGS. 9-D.

In some applications of the present invention, suturing needles 336 of closure device 320 further comprise a first ferrule-withdrawing suturing needle 336, 336B, which is couplable to ferrule 324. As shown in FIG. 13I, closure device 320 is configured to direct first ferrule-withdrawing suturing needle 336, 336B to ferrule 324 during distal advancement of first ferrule-withdrawing suturing needle 336, 336B. For example, first ferrule-withdrawing suturing needle 336, 336B may be distally advanced using control handle 340 as described hereinbelow with reference to FIG. 15G.

Closure device 320 is configured such that after the distal advancement of first ferrule-withdrawing suturing needle 336, 336B to ferrule 324, proximal withdrawal of first ferrule-withdrawing suturing needle 336, 336B coupled to ferrule 324 removes ferrule 324 from ferrule receptacle 334, such as shown in FIG. 13J. For example, first ferrule-withdrawing suturing needle 336, 336B may be proximally withdrawn using control handle 340 as described hereinbelow with reference to FIG. 15H.

Figure 13K:
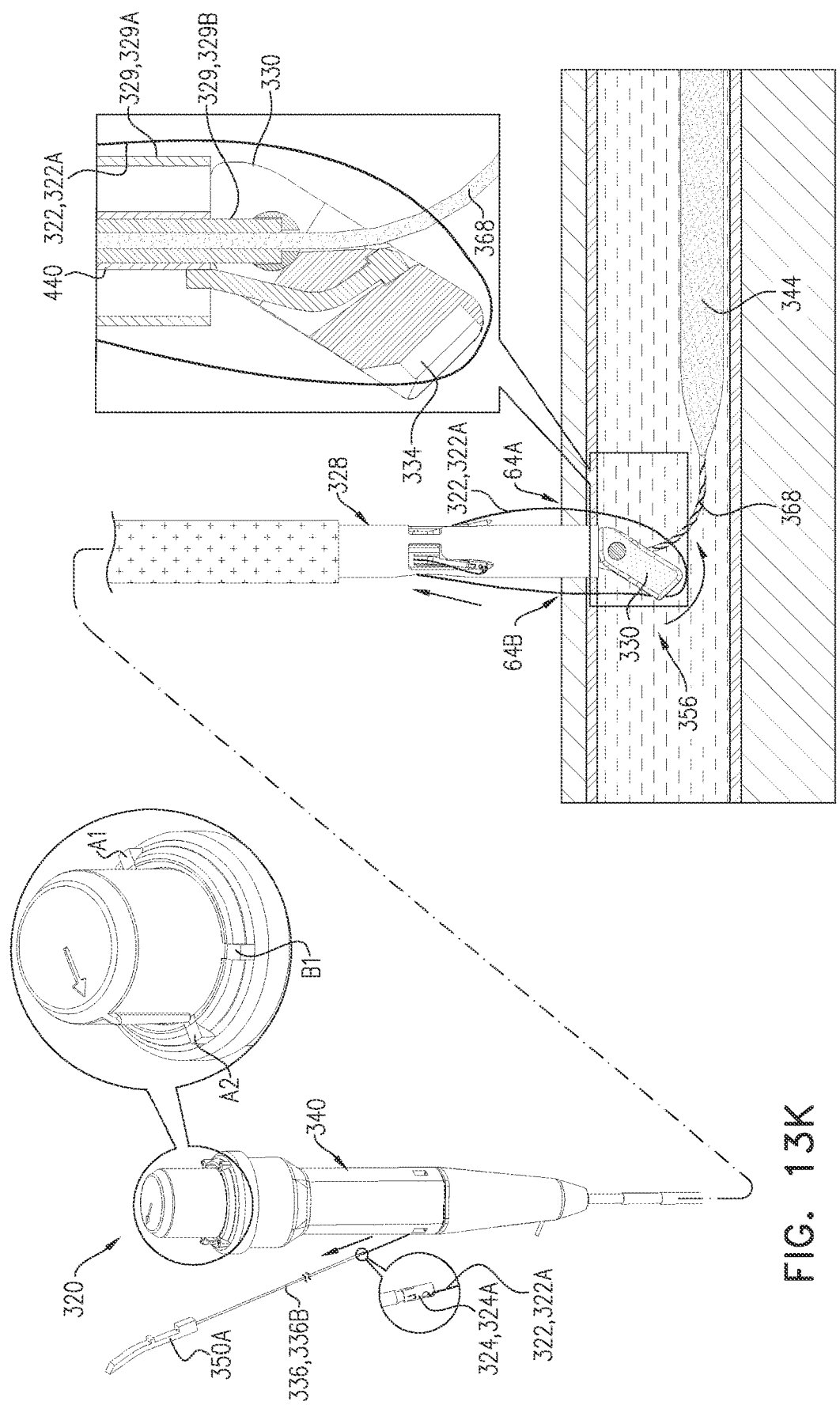

For some applications, such as shown in FIGS. 13J-K, after first ferrule-withdrawing suturing needle 336, 336B has been proximally withdrawn within control handle 340, first ferrule-withdrawing suturing needle 336, 336B is removed from control handle 340, such as by using a needle handle 350A that is coupled to a proximal end of first ferrule-withdrawing suturing needle 336, 336B. As mentioned above, at this stage of the procedure, first ferrule-withdrawing suturing needle 336, 336B is coupled to first suture 322, 322A via first ferrule 324, 324A. Therefore, removal of first ferrule-withdrawing suturing needle 336, 336B from control handle 340 pulls a portion of first suture 322, 322A out of the control handle. This removal of first ferrule-withdrawing suturing needle 336, 336B from control handle 340 is described in more detail hereinbelow with reference to FIGS. 15A-H.

Reference is made to FIGS. 13I-J. For some applications, ferrule 324 is proximally withdrawn from ferrule receptacle 334 and out of hollow anatomical structure 54 while suture-positioning support 330 is in second deployed position 358B by:
- as shown in FIG. 13I, distally advancing first ferrule-withdrawing suturing needle 336, 336B through second wall site 64B and into hollow anatomical structure 54, such that closure device 320 directs first ferrule-withdrawing suturing needle 336, 336B to ferrule 324 and first ferrule-withdrawing suturing needle 336, 336B becomes coupled to ferrule 324, and
- as shown in FIG. 13J, proximally withdrawing first ferrule-withdrawing suturing needle 336, 336B from hollow anatomical structure 54 via second wall site 64B, so as to remove ferrule 324 from ferrule receptacle 334 and to proximally withdraw distal end portion 326 of first suture 322A out of hollow anatomical structure 54 via second wall site 64B.

Figure 13L:
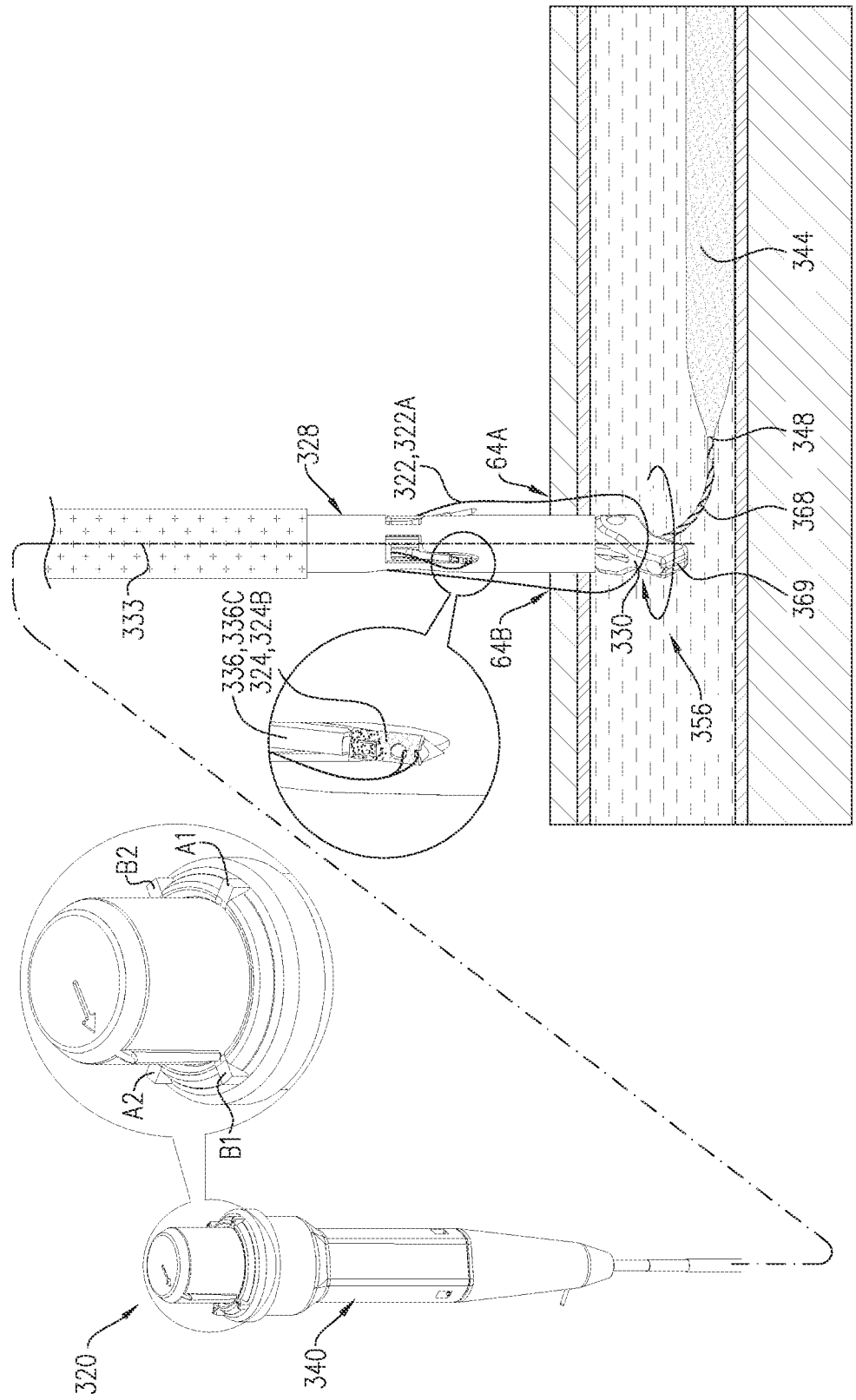

Optionally, the surgeon adjusts an axial position of elongate support 328 (e.g., by slightly proximally withdrawing elongate support 328) such that suture-positioning support 330 touches, or is near, an inner surface of wall 52, as shown in FIG. 13L The various degrees of freedom of distal end portion 332 of elongate support 328 with respect to proximal end 348 of dilator 344 may facilitate this adjustment of the axial position of elongate support 328.

Ferrule 324 is shaped so as to define a ferrule lumen 370 (labeled in FIG. 12). For some applications, ferrule lumen 370 is configured and used in the method as described hereinabove with reference to FIGS. 7D-E regarding ferrule lumen 170. Optionally, ferrule 324 is shaped so as to define the one or more tabs 174 described hereinabove with reference to FIGS. 7D-E, and/or a distal end portion of first ferrule-withdrawing suturing needle 336, 336B is shaped like distal end portion 76 of second suturing needle 36, 36B, as described hereinabove with reference to FIGS. 7D-E, so as to inhibit withdrawal of first ferrule-withdrawing suturing needle 336, 36B from ferrule lumen 370.

Reference is made to FIGS. 12 and 13L For some applications, elongate support 328 defines a first needle lumen 366, 366A and a second needle lumen 366, 366B through respective longitudinal portions of elongate support 328 (labeled in FIG. 12). First needle lumen 366, 366A and second needle lumen 366, 366B are shaped so as to direct first ferrule-advancing suturing needle 336, 336A and first ferrule-withdrawing suturing needle 336, 336B toward ferrule receptacle 334 during the distal advancement of first ferrule-advancing suturing needle 336, 336A and the distal advancement of first ferrule-withdrawing suturing needle 336, 336B, respectively, such as shown in FIGS. 13F and 13I, respectively.

For some applications, first ferrule-advancing suturing needle 336, 336A is distally advanced through first wall site 64A and into hollow anatomical structure 54 while a portion of first ferrule-advancing suturing needle 336, 336A is disposed within first needle lumen 366, 366A, such that first needle lumen 66, 366A directs first ferrule-advancing suturing needle 336, 336A toward ferrule receptacle 334 while suture-positioning support 330 is in first deployed position 358, 358A, such as shown in FIG. 13F. First ferrule-withdrawing suturing needle 336, 336B is distally advanced through second wall site 64B and into hollow anatomical structure 54 while a portion of first ferrule-withdrawing suturing needle 336, 336B is disposed within second needle lumen 366, 366B, such that second needle lumen 366, 366B directs first ferrule-withdrawing suturing needle 336, 336B toward ferrule receptacle 334 while suture-positioning support 330 is in second deployed position 358, 358B, such as shown in FIG. 13I.

Also as shown in FIGS. 13J, suture-positioning support 330 is transitioned from second deployed position 358, 358B back to delivery position 356, optionally by rotating suture-positioning support 330 about pivot axis 362. For example, suture-positioning support 330 may be transitioned from second deployed position 358, 358B back to delivery position 356 using control handle 340 as described hereinbelow with reference to FIG. 15H.

As shown in FIG. 13L, suture-positioning support 330 is rotated about distal-support central longitudinal axis 333, optionally as described hereinabove with reference to FIG. 13H. For example, suture-positioning support 330 may be rotated about distal-support central longitudinal axis 333 using control handle 340 as described hereinbelow with reference to FIGS. 15F.

Figure 13M:
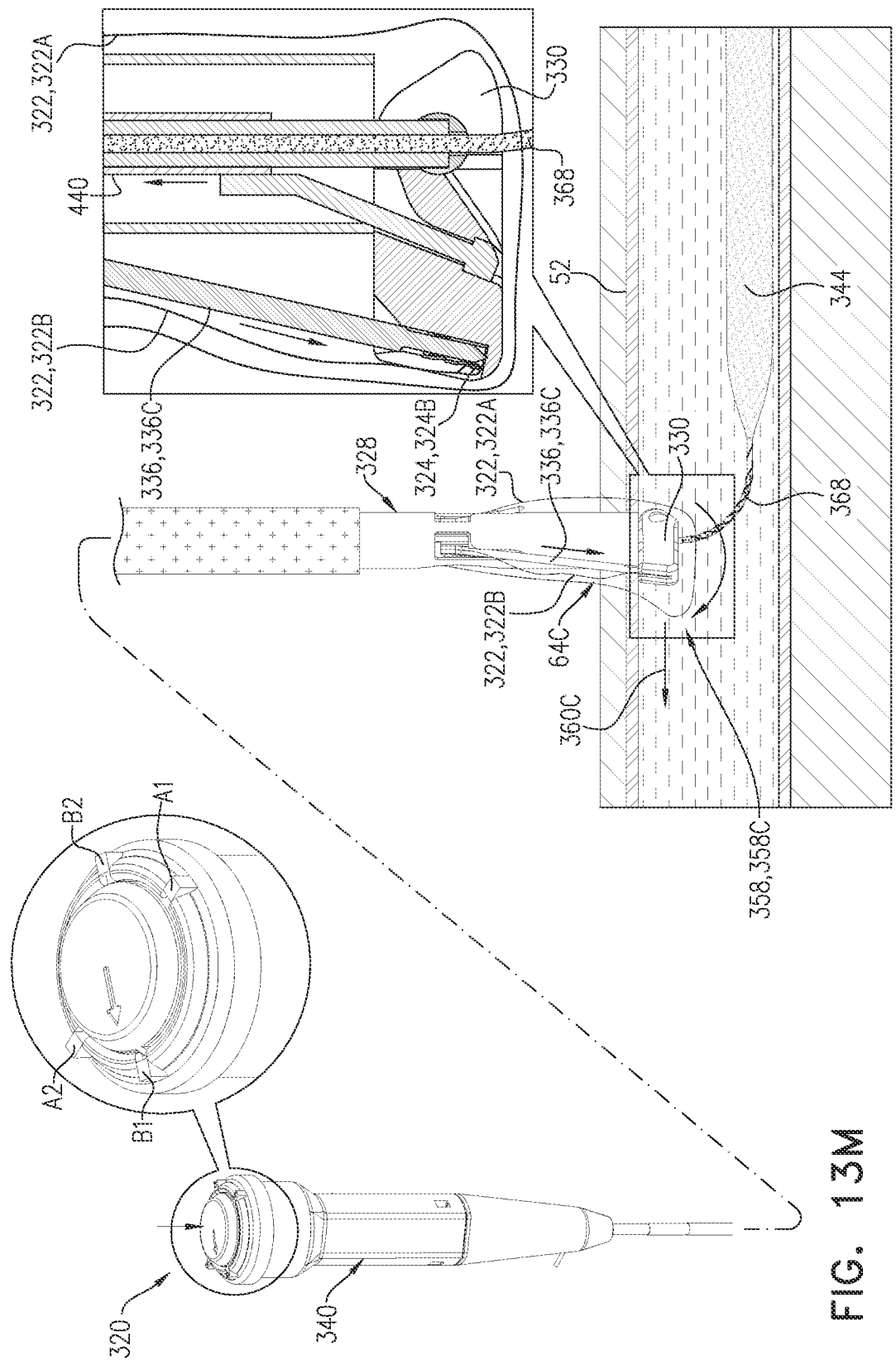

As shown in the transition between FIG. 13L and FIG. 13M, suture-positioning support 330 is again laterally extended, with respect to distal end portion 332 of elongate support 328, to a third deployed position 358, 358C in which suture-positioning support 330 laterally extends in a third direction 360C from distal end portion 332 of elongate support 328, third direction 360C different from first direction 360A and second direction 360B. For example, third direction 360C and first direction 360A may be separated by an angle of 30-150 degrees, e.g., 115-125 degrees, e.g., 120 degrees, around distal-support central longitudinal axis 333 of distal end portion 332 of elongate support 328. For example, suture-positioning support 330 may be laterally extended using control handle 340 as described hereinbelow with reference to FIGS. 15A-B regarding lateral extension to first deployed position 358, 358A, mutatis mutandis.

As shown in FIG. 13M, a second suture 322, 322B is distally advanced through a portion of elongate support 328 and a third wall site 64C of wall 52 and into blood vessel 54, and into suture-positioning support 330. Optionally, first and second sutures 322A and 32B are color-coded, i.e., have different colors, to aid the surgeon during the procedure.

Reference is still made to FIG. 13M. For some applications, ferrule 324, described hereinabove with reference to FIGS. 13C-L, is a first ferrule 324, 324A, and closure device 320 further comprises a second ferrule 324, 324B, which is coupled to a distal end portion of second suture 322, 322B, such as by being passed (e.g., looped) through an opening defined by a wall of ferrule 324, 324A (such as shown), and/or by welding, knotting, gluing, or another technique (configurations not shown). Second suture 322, 322B is distally advanced into suture-positioning support 330 by distally advancing a second ferrule-advancing suturing needle 336, 336C of suturing needles 336 through third wall site 64C of wall 52 and into blood vessel 54, while first ferrule-withdrawing suturing needle 336, 336B is removably coupled to second ferrule 324, 324B, such that closure device 320 directs second ferrule 324, 324B into ferrule receptacle 334 defined by suture-positioning support 330 and ferrule receptacle 334 removably receives second ferrule 324, 324B while suture-positioning support 330 is in third deployed position 358, 358C. For example, second ferrule-advancing suturing needle 336, 336C may be distally advanced using control handle 340 as described hereinbelow with reference to FIGS. 15A-B regarding first ferrule-advancing suturing needle 336, 336A, mutatis mutandis.

Typically, second ferrule-withdrawing suturing needle 336, 336C is removably coupled to second ferrule 324, 324B before the beginning of the procedure, although second ferrule-withdrawing suturing needle 336, 336C may alternatively become removably coupled to second ferrule 324, 324B during the procedure, such as during distal advancement of second ferrule-withdrawing suturing needle 336, 336C through or out of a third one of needle lumens 366. Optionally, the surgeon adjusts an axial position of elongate support 328 such that suture-positioning support 330 touches, or is near, an inner surface of wall 52, as shown in FIG. 13F. The various degrees of freedom of distal end portion 332 of elongate support 328 with respect to proximal end 348 of dilator 344 may facilitate this adjustment of the axial position of elongate support 328.

Figure 13N:
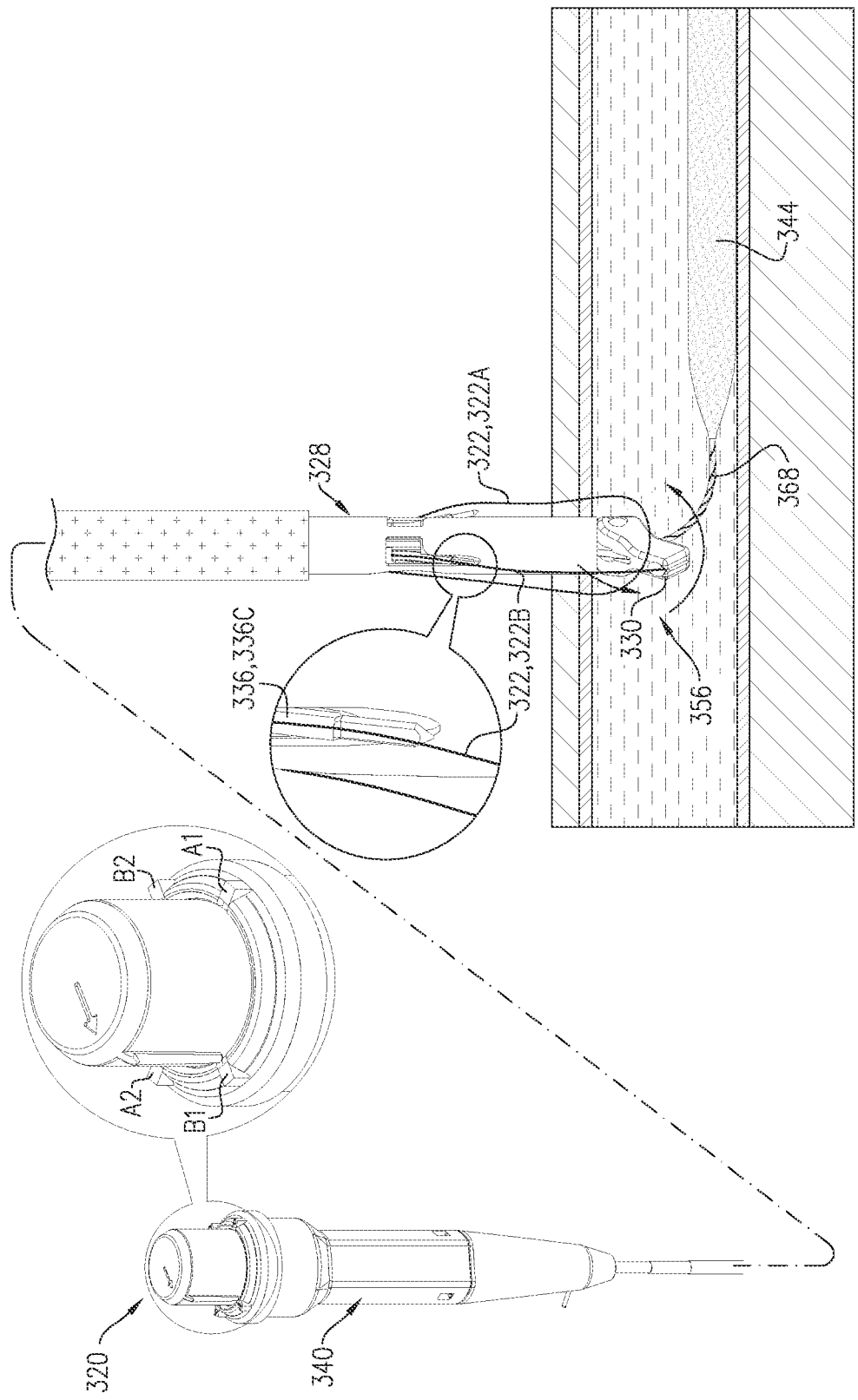
Figure 130:
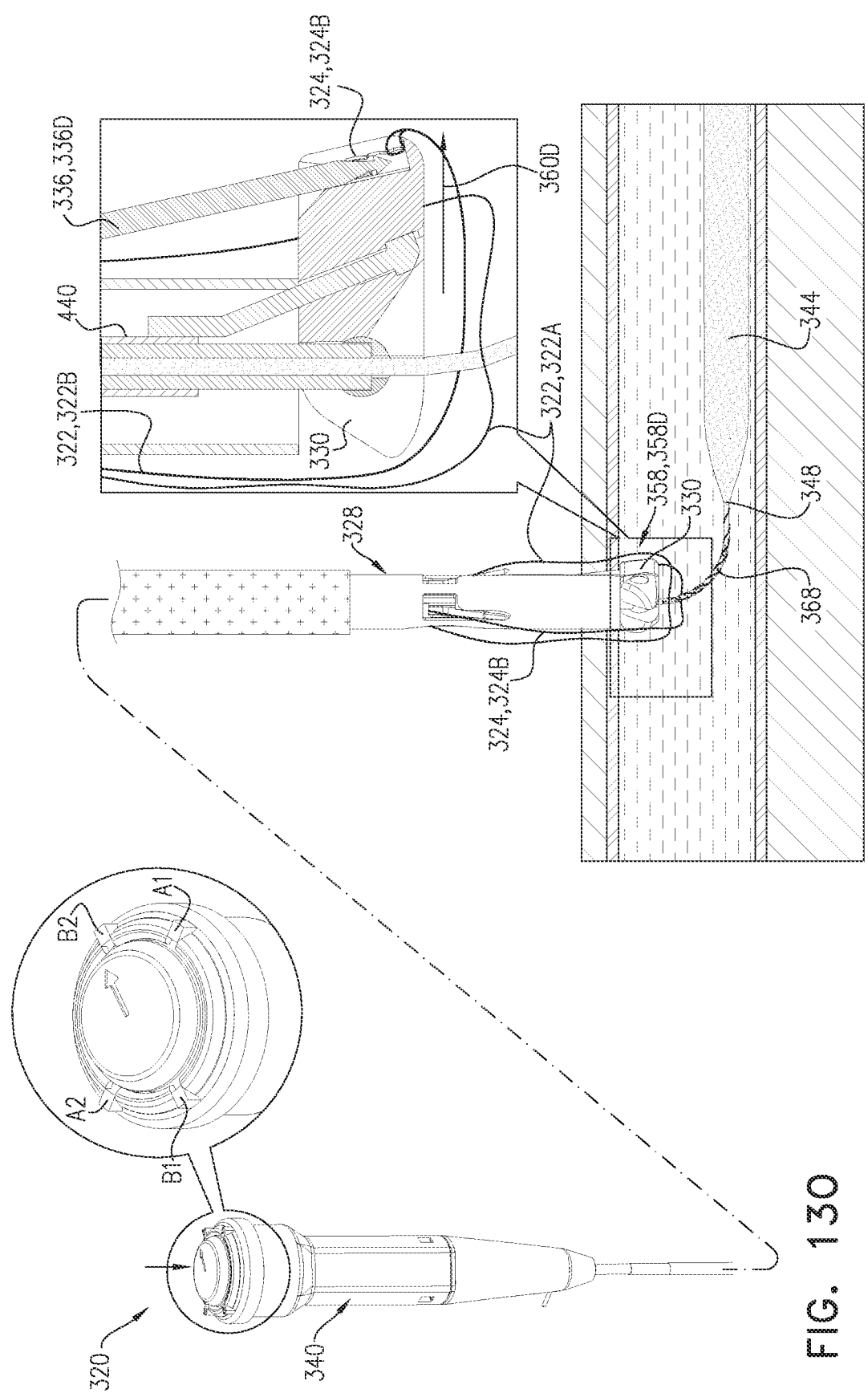

As shown in the transition between FIG. 13M and FIG. 13N, second ferrule-advancing suturing needle 336, 336C is proximally withdrawn from second ferrule 324, 324B and hollow anatomical structure 54, while leaving second ferrule 324, 324B within ferrule receptacle 334. For example, second ferrule-advancing suturing needle 336, 336C may be proximally withdrawn using control handle 340 as described hereinbelow with reference to FIG. 15D for first ferrule-advancing suturing needle 336, 336A, mutatis mutandis.

Also as shown in the transition between FIG. 13M and FIG. 13N, suture-positioning support 330 is transitioned from third deployed position 358, 358C back to delivery position 356, optionally by rotating suture-positioning support 330 about pivot axis 362. For example, suture-positioning support 330 may be transitioned from third deployed position 358, 358C back to delivery position 356 using control handle 340 as described hereinbelow with reference to FIG. 15E, mutatis mutandis.

As further shown in the transition between FIG. 13M and FIG. 13N, suture-positioning support 330 is rotated about distal-support central longitudinal axis 333, optionally as described hereinabove with reference to FIG. 13H. For example, suture-positioning support 330 may be rotated about distal-support central longitudinal axis 333 using control handle 340 as described hereinbelow with reference to FIGS. 15F.

As shown in the transition between FIG. 13N and FIG. 13O, suture-positioning support 330 is again rotated about distal-support central longitudinal axis 333. For example, suture-positioning support 330 may be rotated about distal-support central longitudinal axis 333 using control handle 340 as described hereinbelow with reference to FIGS. 15F. Suture-positioning support 330 is then laterally extended, with respect to distal end portion 332 of elongate support 328, to a fourth deployed position 358, 358D in which suture-positioning support 330 laterally extends in a fourth direction 360D from distal end portion 332 of elongate support 328, fourth direction 360D different from first direction 360A, second direction 360B, and third direction 360C. For example, third direction 360C and fourth direction 360D may be separated by an angle of 120-240 degrees, such as 175-185 degrees, e.g., 180 degrees, around distal-support central longitudinal axis 333 of distal end portion 332 of elongate support 328. For example, suture-positioning support 330 may be laterally extended using control handle 340 as described hereinbelow with reference to FIG. 15G, mutatis mutandis.

As shown in FIG. 13O, while suture-positioning support 330 is in fourth deployed position 358D, second ferrule 324, 324B is proximally withdrawn from ferrule receptacle 334 and out of hollow anatomical structure 54 via a fourth wall site 64D of wall 52, so as to proximally withdraw a portion of second suture 322, 322B, including the distal end portion thereof, out of hollow anatomical structure 54 via fourth wall site 64D. The portion of second suture 322, 322B drawn out of hollow anatomical structure 54 via fourth wall site 64D is secured to another portion of second suture 322, 322D, for example by a second pre-tied knot 338B, such as described hereinbelow with reference to FIGS. 9-D.

Figure 13P:
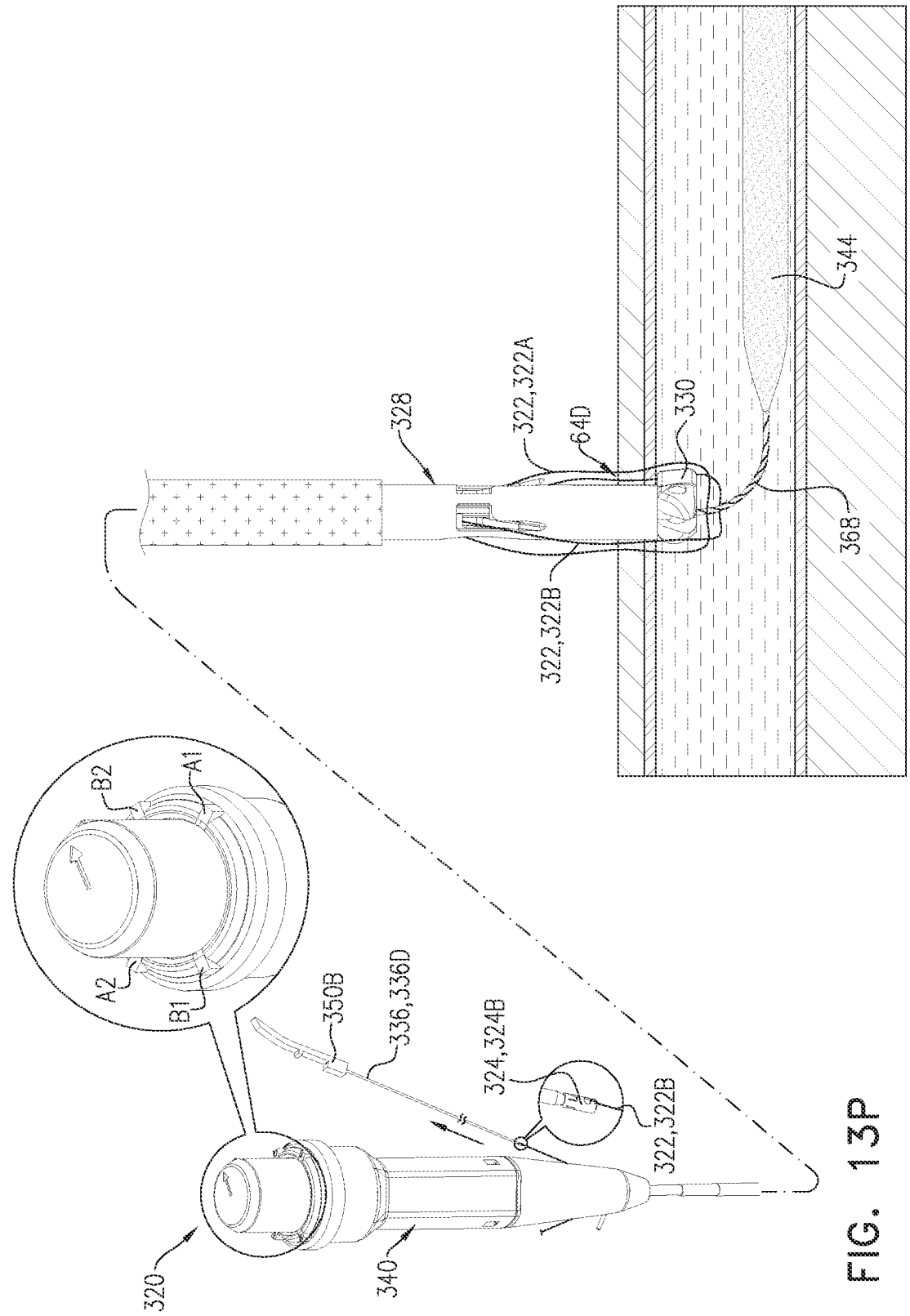

In some applications of the present invention, suturing needles 336 of closure device 320 further comprise a second ferrule-withdrawing suturing needle 336, 336D, which is couplable to second ferrule 324, 324B. As shown in FIG. 13O, closure device 320 is configured to direct second ferrule-withdrawing suturing needle 336, 336D to second ferrule 324, 324B during distal advancement of second ferrule-withdrawing suturing needle 336, 336D. Closure device 320 is configured such that after the distal advancement of second ferrule-withdrawing suturing needle 336, 336D to second ferrule 324, 324B, proximal withdrawal of second ferrule-withdrawing suturing needle 336, 336D coupled to second ferrule 324, 324B removes second ferrule 324, 324B from ferrule receptacle 334, such as shown in FIG. 13P. For example, second ferrule-withdrawing suturing needle 336, 336D may be proximally withdrawn using control handle 340 as described hereinbelow with reference to FIG. 15H regarding first ferrule-withdrawing suturing needle 336, 336B, mutatis mutandis.

For some applications, second ferrule-advancing suturing needle 336, 336C implements any of the features of first ferrule-advancing suturing needle 336, 336A, described hereinabove. For some applications, second ferrule-withdrawing suturing needle 336, 336D implements any of the features of first ferrule-withdrawing suturing needle 336, 336B, described hereinabove. For some applications, second ferrule 324, 324B implements any of the features of first ferrule 324, 324A.

In some applications of the present invention, closure device 320 comprises only a single first suture 322, 322A; a single first ferrule 324, 324A; a single first ferrule-advancing suturing needle 336, 336A; and single second ferrule-withdrawing suturing needle 336, 336B (configuration not shown). In these applications, closure device 320 does not further comprise second ferrule 324, 324B; second suture 322, 322B; second ferrule-advancing suturing needle 336, 336C; or second ferrule-withdrawing suturing needle 336, 336D. In this respect, closure device 320 is similar to closure device 20, described hereinabove with reference to FIGS. 1-5J; closure device 120, described hereinabove with reference to FIGS. 6-7L; and closure device 220, described hereinabove with reference to FIGS. 8A-H. In general, all of the features of closure device 320 described herein may implemented with only a single suture, ferrule, ferrule-advancing suturing needle, and ferrule-withdrawing suturing needle.

For some applications, such as shown in FIG. 13P, after second ferrule-withdrawing suturing needle 336, 336D has been proximally withdrawn within control handle 340, second ferrule-withdrawing suturing needle 336, 336D is removed from control handle 340, such as by using a needle handle 350B that is coupled to a proximal end of second ferrule-withdrawing suturing needle 336, 336D. As mentioned above, at this stage of the procedure, second ferrule-withdrawing suturing needle 336, 336D is coupled to second suture 322, 322B via second ferrule 324, 324B. Therefore, removal of second ferrule-withdrawing suturing needle 336, 336D from control handle 340 pulls a portion of second suture 322, 322B out of the control handle. This removal of second ferrule-withdrawing suturing needle 336, 336D from control handle 340 may optionally be implemented as described hereinbelow with reference to FIGS. 15A-H for first ferrule-withdrawing suturing needle 336, 336B, mutatis mutandis.

As shown in FIG. 13Q, closure device 320 is withdrawn from blood vessel 54 via puncture 50. In configurations in which dilator 344 is shaped so as to define atraumatic proximal tip 386, the atraumatic proximal tip may facilitate atraumatic maneuvering and passage of dilator 344 through puncture 50. Alternatively, in some configurations in which sheath 410 is provided, sheath 410 may distally advanced along outer tubular shaft 329A so as to cover suture-positioning support 330, dilator connector 368, and proximal end portion 412 of dilator 344, thereby facilitating atraumatic passage of suture-positioning support 330 and/or dilator 344 through puncture 50. Atraumatic proximal tip 386 may help facilitate insertion of proximal end portion 412 of dilator 344 into the distal end of sheath 410.

For some applications, such as shown in FIG. 13R, first suture 322, 322A and second suture 322, 322B are arranged so as to form an X-shaped suturing arrangement, i.e., such that first suture 322, 322A and second suture 322, 322B cross each other. This X-shaped suturing arrangement may provide stronger puncture closure than some alternative suture arrangements, such as arrangements in which a single suture extends around the perimeter of the puncture.

For some applications, such as labeled in FIG. 13R, a distance D between first wall site 64A and second wall site 64B is 5-10 mm, such as 6-8 mm, e.g., 7 mm. For some applications, such as labeled in FIG. 13R, a first line is defined between first wall site 64A and second wall site 64B and a second line is defined between third wall site 64C and fourth wall site 64D. The first and the second lines define an angle α (alpha) of 45-75 degrees, e.g., 60 degrees.

Reference is now made to FIGS. 14A-B, which are schematic illustrations of a configuration of closure device 320, including control handle 340 thereof, in accordance with an application of the present invention.

For some applications, control handle 340 comprises sheath-control user control 430. As shown in the transition between FIG. 14A and FIG. 14B, actuation of sheath-control user control 430 by a user (e.g., by proximal sliding the user control, such as shown), proximally withdraws sheath 410 along outer tubular shaft 329A so as to expose suture-positioning support 330, dilator connector 368, proximal end portion 412 of dilator 344, and distal lumen opening 367. Optionally, sheath-control user control 430 is coupled to sheath 410 by an elongate connector 432.

For some applications, sheath-control user control 430 may also be actuated by the user (e.g., by distal sliding the user control), to distally advance sheath 410 along outer tubular shaft 329A so as to cover suture-positioning support 330, dilator connector 368, proximal end portion 412 of dilator 344, and distal lumen opening 367, in order to facilitate atraumatic passage of suture-positioning support 330 and/or dilator 344 through puncture 50, such as described hereinabove with reference to FIG. 13Q.

Reference is still made to FIGS. 14A-B and is further made to FIGS. 15A-H, which are schematic cross-sectional illustrations of a method of using control handle 340 of closure device 320, in accordance with an application of the present invention. (For clarity of illustration, sutures 322 are not shown in FIGS. 15A-H, although they are provided in practice.) For some applications, control handle 340 comprises a support-and-needle user control 434, which may, for example, comprise a button, such as shown. For some applications, support-and-needle user control 434 is configured to be actuated by movement of the user control in a proximal-to-distal direction (such as by depressing the user control, e.g., a button) and/or movement of the user control in a distal-to-proximal direction (such as by releasing the user control, e.g., a button, such that a spring (e.g., a spring 436), moves the user control in the distal-to-proximal direction).

FIG. 15A shows closure device 320 after distal end 406 of outer tubular shaft 329A and suture-positioning support 330 have been inserted through puncture 50 and into blood vessel 54, such as described hereinabove with reference to FIGS. 13A-E, and sheath 410, if provided, has been proximally withdrawn along outer tubular shaft 329A, such as described hereinabove with reference to FIGS. 13D and 14A-B. FIG. 15A shows closure device 320 while (a) support-and-needle user control 434 is in an initial resting state, (b) suture-positioning support 330 is in initial delivery position 356, and (c) first ferrule-advancing suturing needle 336, 336A has not yet been deployed from elongate support 328.

Figure 15B:
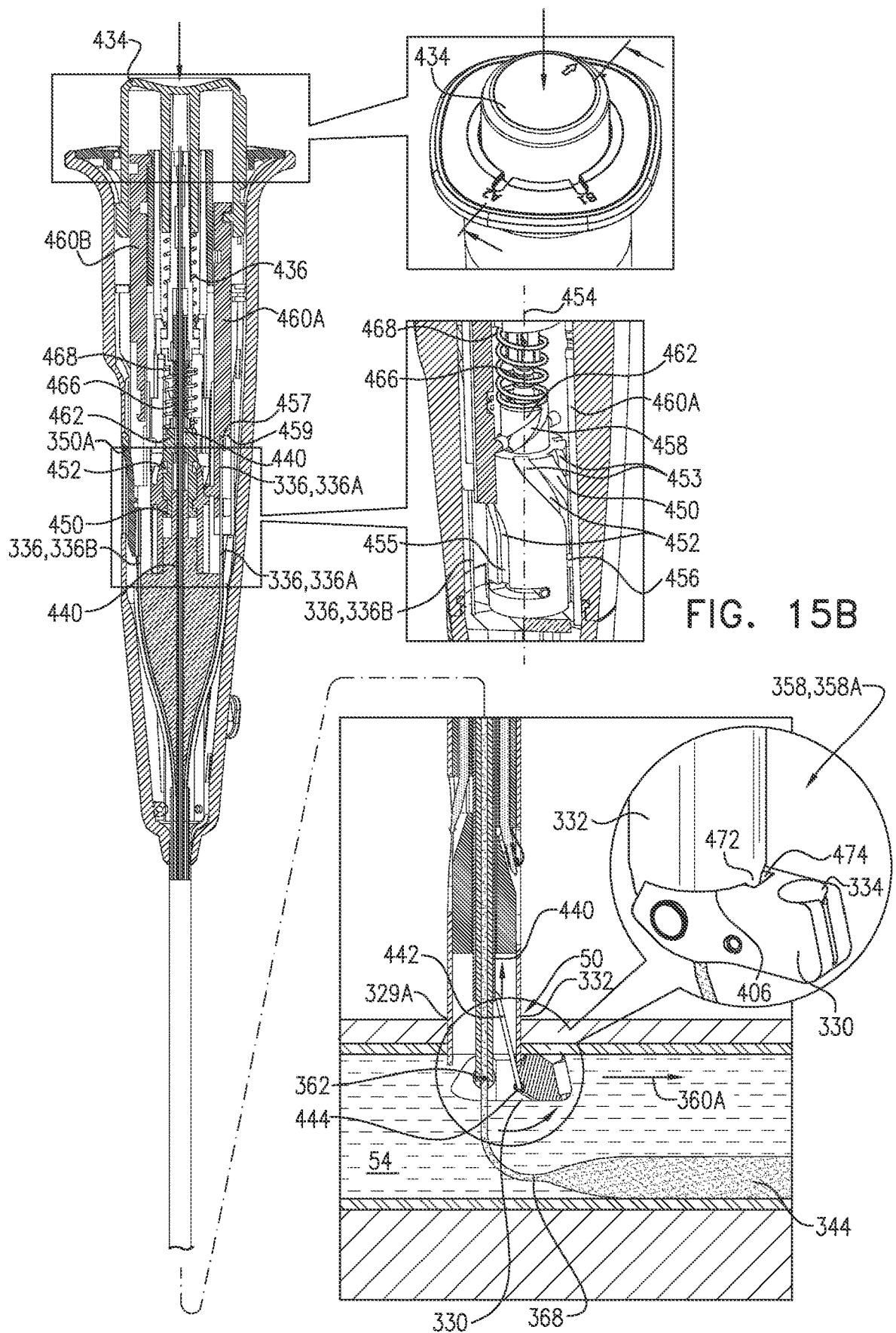
Figure 15C:
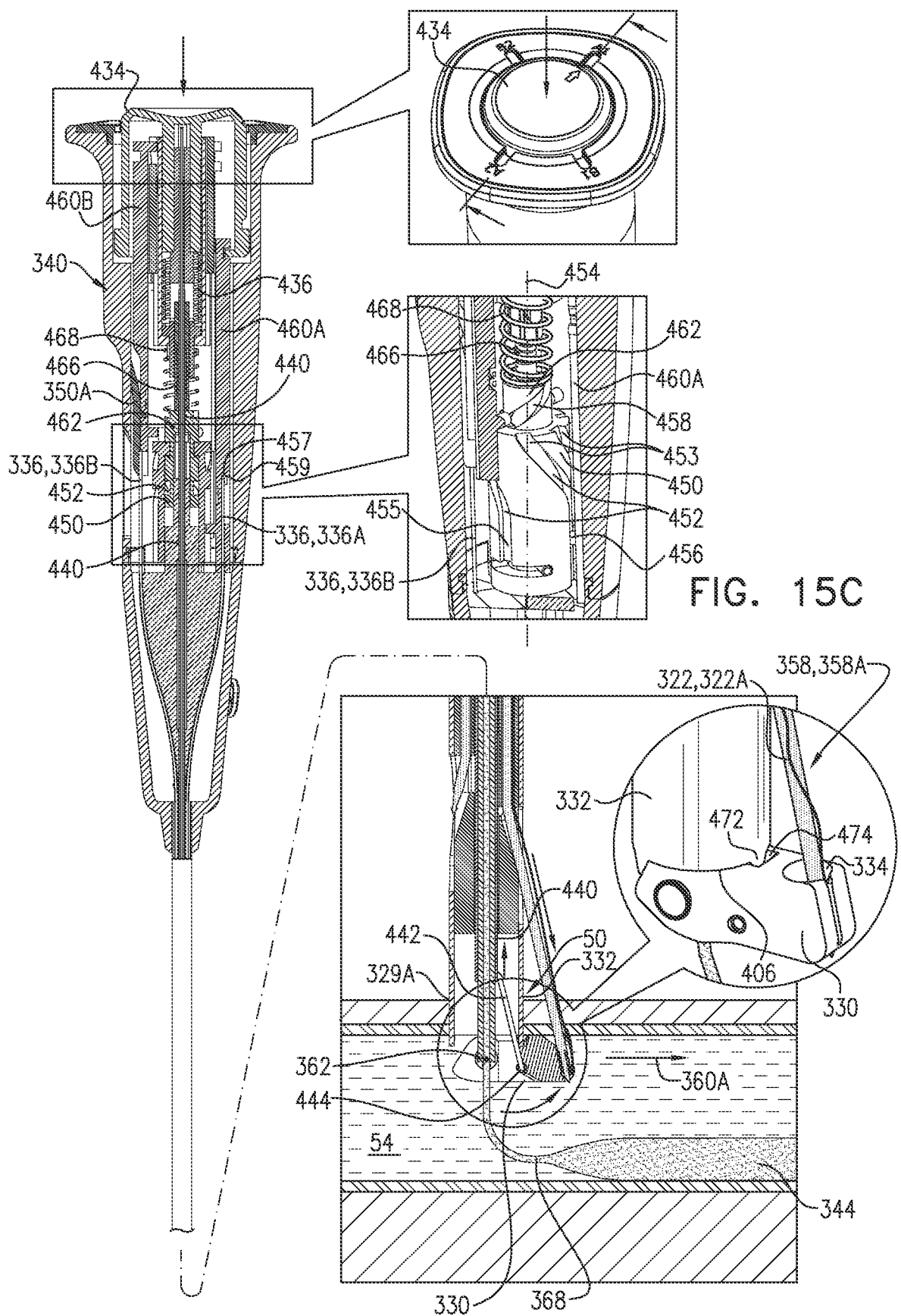

For some applications, such as shown in the transition between FIG. 15A and FIG. 15C, control handle 340 is configured such that actuation of support-and-needle user control 434 (such as by movement of the user control in a proximal-to-distal direction (such as by depressing the user control, e.g., a button)) causes:
lateral extension of suture-positioning support 330, with respect to distal end portion 332 of elongate support 328, to first deployed position 358, 358A in which suture-positioning support 330 laterally extends in first direction 360A from distal end portion 332 of elongate support 328, as shown in FIG. 15B, and such as described hereinabove with reference to FIG. 13F, and
distal advancement of first ferrule-advancing suturing needle 336, 336A, while first ferrule-advancing suturing needle 336, 336A is removably coupled to ferrule 324, such that closure device 320 directs ferrule 324 into ferrule receptacle 334 defined by suture-positioning support 330 and ferrule receptacle 334 removably receives ferrule 324 while suture-positioning support 330 is in first deployed position 358, 358A, as shown in FIG. 15C, and such as described hereinabove with reference to FIG. 13F; typically, this distal advancement of first ferrule-advancing suturing needle 336, 336A distally advances first suture 322, 322A into suture-positioning support 330.

For some applications, control handle 340 is configured such that the actuation of support-and-needle user control 434 causes at least a portion of the distal advancement of first ferrule-advancing suturing needle 336, 336A to occur as suture-positioning support 330 is extended laterally. Optionally, control handle 340 is configured such that the actuation of support-and-needle user control 434 causes suture-positioning support 330 to begin extending laterally before first ferrule-advancing suturing needle 336, 336A begins advancing distally; in this configuration, control handle 340 is typically configured such that the actuation of support-and-needle user control 434 causes suture-positioning support 330 to finish extending laterally, such as shown in FIG. 15B, before first ferrule-advancing suturing needle 336, 336A reaches suture-positioning support 330, such as shown in FIG. 15C. Typically, control handle 340 is configured to additionally provide the timing features described above when extending suture-positioning support 330 and distally advancing first ferrule-withdrawing suturing needle 336B, second ferrule-advancing suturing needle 336C, and second ferrule-withdrawing suturing needle 336D, respectively.

Typically, actuation of support-and-needle user control 434 non-electrically causes the distal advancement of first ferrule-advancing suturing needle 336, 336A and the lateral extension of suture-positioning support 330.

For some applications, such as shown in the transition between FIG. 15A and FIG. 15B, control handle 340 is configured such that the above-mentioned actuation of support-and-needle user control 434 causes the lateral extension of suture-positioning support 330 as follows. Distal motion of support-and-needle user control 434 causes proximal motion of an extension-control-shaft 440 that is coupled to a site 444 on suture-positioning support 330 (labeled in FIGS. 15A-B), the site away from pivot axis 362. For example, extension-control-shaft 440 may be coupled to site 444 by a rod 442 (which may be either flexible or rigid). The proximal motion of extension-control-shaft 440 pulls up site 444 (labeled in FIGS. 15A-B) on suture-positioning support 330, resulting in rotation of suture-positioning support 330 about pivot axis 362 and lateral extension of suture-positioning support 330. Optionally, extension-control-shaft 440 surrounds at least a portion of inner shaft 329B.

For some applications, control handle 340 comprises a plurality of needle-control shafts 460, including a first needle-control shaft 460A, second needle-control shaft 460B, a third needle-control shaft 460C, and a fourth needle-control shaft 460D (in the cross-sections shown in FIGS. 15A-H, only first and second needle-control shafts 460A and 460B can be seen; the other needle-control shafts 460 are labeled in FIGS. 34A-B, described hereinbelow). Support-and-needle user control 434 engages exactly one of needle-control shafts 460 when support-and-needle user control 434 is in each of its rotational positions. Distal motion (depression) of support-and-needle user control 434 distally advances the currently-engaged needle-control shaft 460, thereby distally advancing the corresponding suturing needle 336 and laterally extending suture-positioning support 330, such as described immediately hereinbelow.

Reference is made to FIGS. 15A-B. For some applications, in order to laterally extend suture-positioning support 330, control handle 340 comprises an outer cam 450 that is shaped so as to define four elongate indentations 452 that include (i) respective curved portions 453 that extend at least partially around a cam axis 454 of outer cam 450 and at least partially axially along outer cam 450, and (ii) respective straight portions 455 that extend axially long outer cam 450. Each of needle-control shafts 460 comprises a pin 456. As each of needle-control shafts 460 is separately distally advanced, as described above, pin 456 of the needle-control shaft 460 engages one of elongate indentations 452, thereby rotating outer cam 450 about cam axis 454 as pin 456 distally advances within curved portion 453 of the elongate indentation 452. Outer cam 450 is shaped so as to define an internal thread 464 (shown and labeled in FIGS. 33A-C, described hereinbelow), which is shaped so as to engage a corresponding external thread 458 defined by an inner cam 462 positioned partially within outer cam 450.

Outer cam 450 is held axially fixed within control handle 340. Inner cam 462 is axially movable within control handle 340. Rotation of outer cam 450 rotates internal thread 464 thereof, which engages external thread 458 of inner cam 462 and causes proximal motion of inner cam 462 with respect to outer cam 450 and control handle 340. Inner cam 462 is coupled to above-described extension-control-shaft 440, such that the proximal motion of inner cam 462 causes the above-described proximal motion of extension-control-shaft 440, and resulting lateral extension of suture-positioning support 330, such as described above.

All of the above-described rotation and motion are reversed as support-and-needle user control 434 is released and moves proximally to its original resting state (such as by spring 436, described hereinabove with reference to FIGS. 15A-H).

For some applications, control handle 340 further comprises:
a cam-stabilizing spring 466, which applies a distally-directed force to outer cam 450 and inner cam 462, to prevent proximal migration of the cams within the control handle; and/or
an inner-cam return spring 468, which applies a distally-directed force to inner cam 462, in order to ensure that inner cam 462 returns proximally to its initial position.

Reference is made to FIGS. 15B-C. As mentioned above, the plurality of needle-control shafts 460 are configured to distally advance respective suturing needles 336. Although the following description relates to first needle-control shaft 460A and first ferrule-advancing suturing needle 336, 336A, the same techniques are implemented for the other needle-control shafts 460 and suturing needles 336, mutatis mutandis. For some applications, in order to distally advance first ferrule-advancing suturing needle 336, 336A, first needle-control shaft 460A is shaped so as to define a distally-facing needle-pushing surface 459. During at least a portion of distal advancement of first needle-control shaft 460A, such as shown in the transition between FIG. 15B and FIG. 15C, distally-facing needle-pushing surface 459 is in contact with and distally pushes a proximal end surface 457 of first ferrule-advancing suturing needle 336, 336A, thereby distally advancing first ferrule-advancing suturing needle 336, 336A.

As described above, in some configurations, control handle 340 is configured such that the actuation of support-and-needle user control 434 causes suture-positioning support 330 to finish extending laterally, such as shown in FIG. 15B, before first ferrule-advancing suturing needle 336, 336A reaches suture-positioning support 330, such as shown in FIG. 15C. For some applications, this relative timing is achieved by the location of distally-facing needle-pushing surface 459 along first needle-control shaft 460A. A first portion of the distal advancement of first needle-control shaft 460A, as shown in the transition between FIG. 15A and FIG. 15B, does not cause distally-facing needle-pushing surface 459 to distally push proximal end surface 457 of first ferrule-advancing suturing needle 336, 336A. A second portion of the distal advancement of first needle-control shaft 460A, as shown in the transition between FIG. 15B and FIG. 15C causes distally-facing needle-pushing surface 459 to distally push proximal end surface 457 of first ferrule-advancing suturing needle 336, 336A. Typically, even though the second portion of the distal advancement of first needle-control shaft 460A causes further distal motion of pin 456, this distal motion does not continue to rotate outer cam 450, because the pin is within the above-mentioned straight portion 455 of elongate indentations 452 during this second portion of the distal advancement of first needle-control shaft 460A.

Typically, support-and-needle user control 434 is partially distally depressed to cause the transition between FIG. 15A and FIG. 15B, and further distally depressed to cause the subsequent transition between FIG. 15B and FIG. 15C.

Figure 15D:
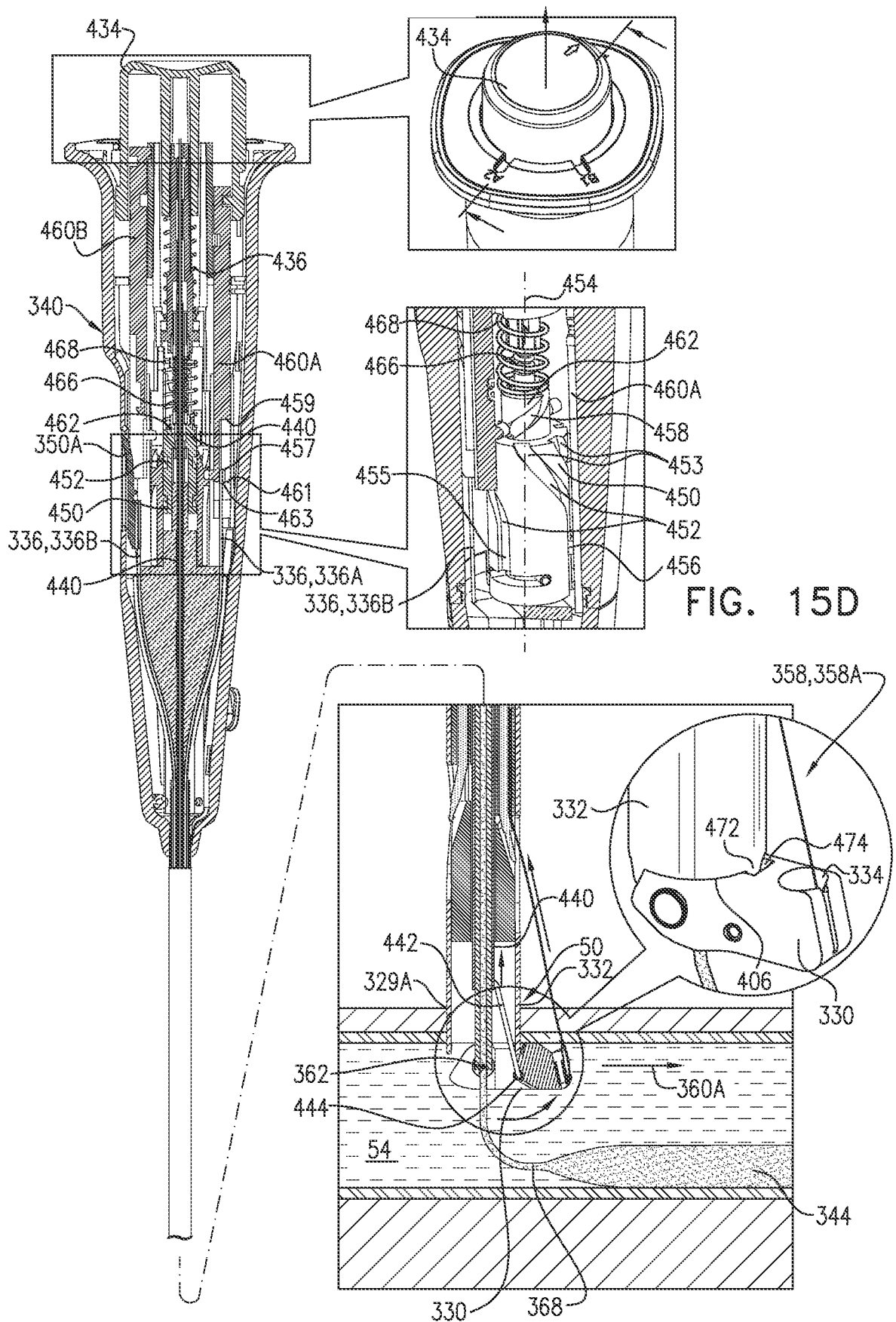
Figure 15E:
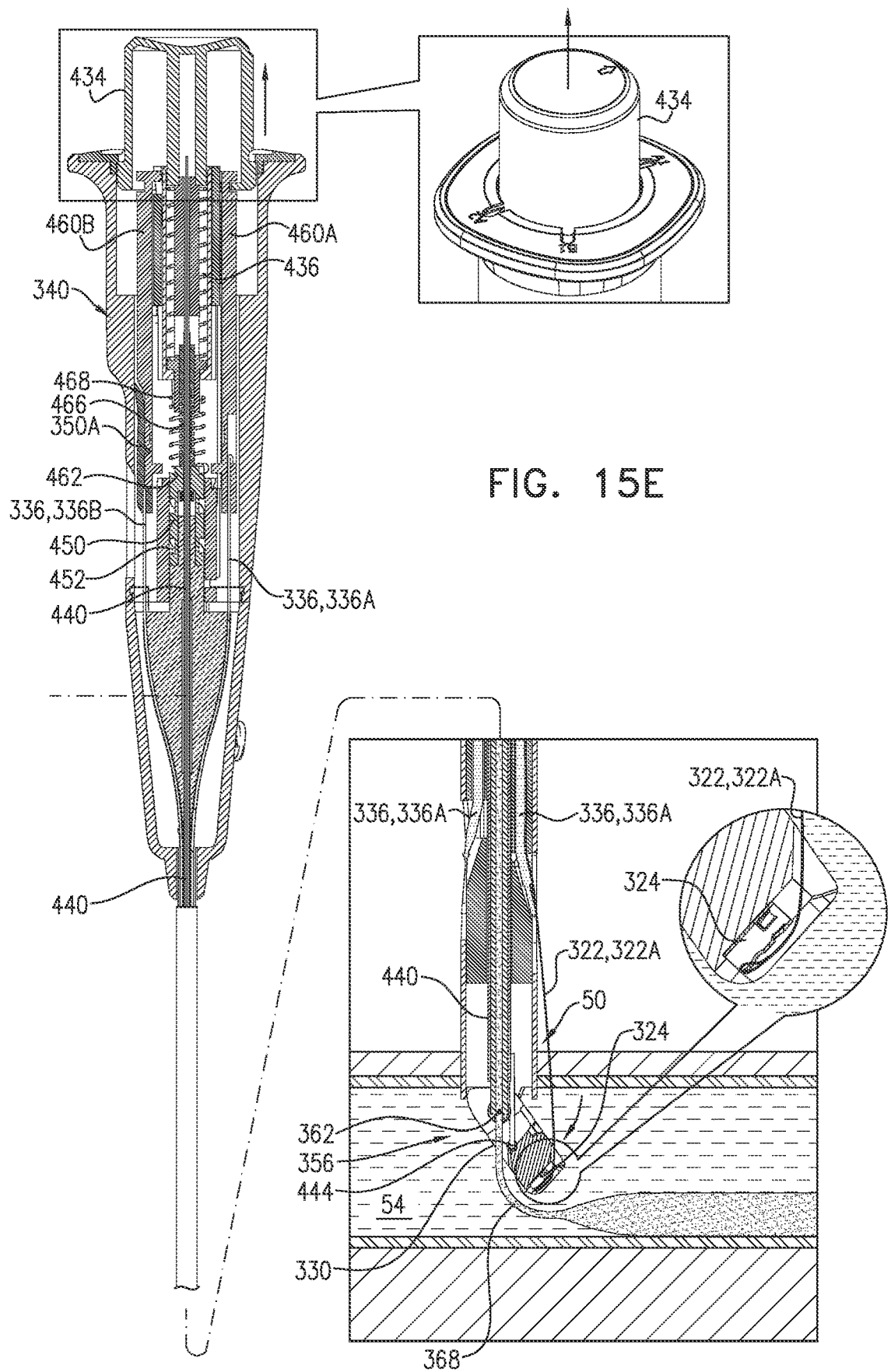

For some applications, such as shown in the transition between FIG. 15C and FIG. 15E, after the initial actuation of support-and-needle user control 434 to cause the lateral extension and distal advancement of the suturing needle, subsequent actuation of support-and-needle user control 434 (such as by movement of the user control in a distal-to-proximal direction (such as by releasing the user control, e.g., a button)) causes:

proximal withdrawal of first ferrule-advancing suturing needle 336, 336A, a portion of which proximal withdrawal proximally withdraws first ferrule-advancing suturing needle 336 from ferrule 324 while leaving ferrule 324 within ferrule receptacle 334, as shown in FIG. 15D, and such as described hereinabove with reference to FIG. 13G, and transitioning of suture-positioning support 330 from first deployed position 358, 358A back to delivery position 356, as shown in FIG. 15E, and such as described hereinabove with reference to FIG. 13G.

Proximal motion (release) of support-and-needle user control 434 proximally withdraws the currently-engaged needle-control shaft 460, thereby proximally withdrawing the corresponding suturing needle 336.

For some applications, the subsequent actuation of support-and-needle user control 434 causes at least a portion of the transitioning of suture-positioning support 330 from first deployed position 358, 358A back to delivery position 356 to occur as first ferrule-advancing suturing needle 336, 336A is proximally withdrawn. Optionally, control handle 340 is configured such that the subsequent actuation of support-and-needle user control 434 causes first ferrule-advancing suturing needle 336, 336A to begin proximally withdrawing before suture-positioning support 330 begins transitioning back to delivery position 356. Typically, control handle 340 is configured to additionally provide the timing features described above when transitioning suture-positioning support 330 back to delivery position 356 and proximally withdrawing first ferrule-withdrawing suturing needle 336B, second ferrule-advancing suturing needle 336C, and second ferrule-withdrawing suturing needle 336D.

Reference is made to FIGS. 15C-D. As mentioned above, the plurality of needle-control shafts 460 are configured to proximally withdraw respective suturing needles 336. Although the following description relates to first needle-control shaft 460A and first ferrule-advancing suturing needle 336, 336A, the same techniques are implemented for the other needle-control shafts 460 and suturing needles 336, mutatis mutandis. For some applications, in order to proximally withdraw first ferrule-advancing suturing needle 336, 336A, first needle-control shaft 460A is shaped so as to define a proximally-facing needle-pushing surface 461. During at least a portion of proximal withdrawal of first needle-control shaft 460A, such as shown in the transition between FIG. 15C and FIG. 15D, proximally-facing needle-pushing surface 461 is in contact with and proximally pushes a distally-facing surface 463 of first ferrule-advancing suturing needle 336, 336A, thereby proximally withdrawing first ferrule-advancing suturing needle 336, 336A. For example, a proximal end portion of first ferrule-advancing suturing needle 336, 336A may be bent distally to define distally-facing surface 463, such as shown.

As described above, in some configurations, control handle 340 is configured such that the subsequent actuation of support-and-needle user control 434 causes first ferrule-advancing suturing needle 336, 336A to begin proximally withdrawing, such as shown in FIG. 15D, before suture-positioning support 330 begins transitioning back to delivery position 356, such as shown in FIG. 15E. For some applications, this relative timing is achieved by the location of proximally-facing needle-pushing surface 461 along first needle-control shaft 460A. A first portion of the proximal withdrawal of first needle-control shaft 460A, as shown in the transition between FIG. 15C and FIG. 15D, causes proximally-facing needle-pushing surface 461 to proximally push distally-facing surface 463 of first ferrule-advancing suturing needle 336, 336A. A second portion of the proximal withdrawal of first needle-control shaft 460A, as shown in the transition between FIG. 15D and FIG. 15E causes suture-positioning support 330 to transition back to delivery position 356, and may optionally cause proximally-facing needle-pushing surface 461 to further proximally push distally-facing surface 463 of first ferrule-advancing suturing needle 336, 336A.

Typically, support-and-needle user control 434 is partially proximally released to cause the transition between FIG. 15C and FIG. 15D, and further proximally released to cause the subsequent transition between FIG. 15D and FIG. 15E.

Figure 15F:
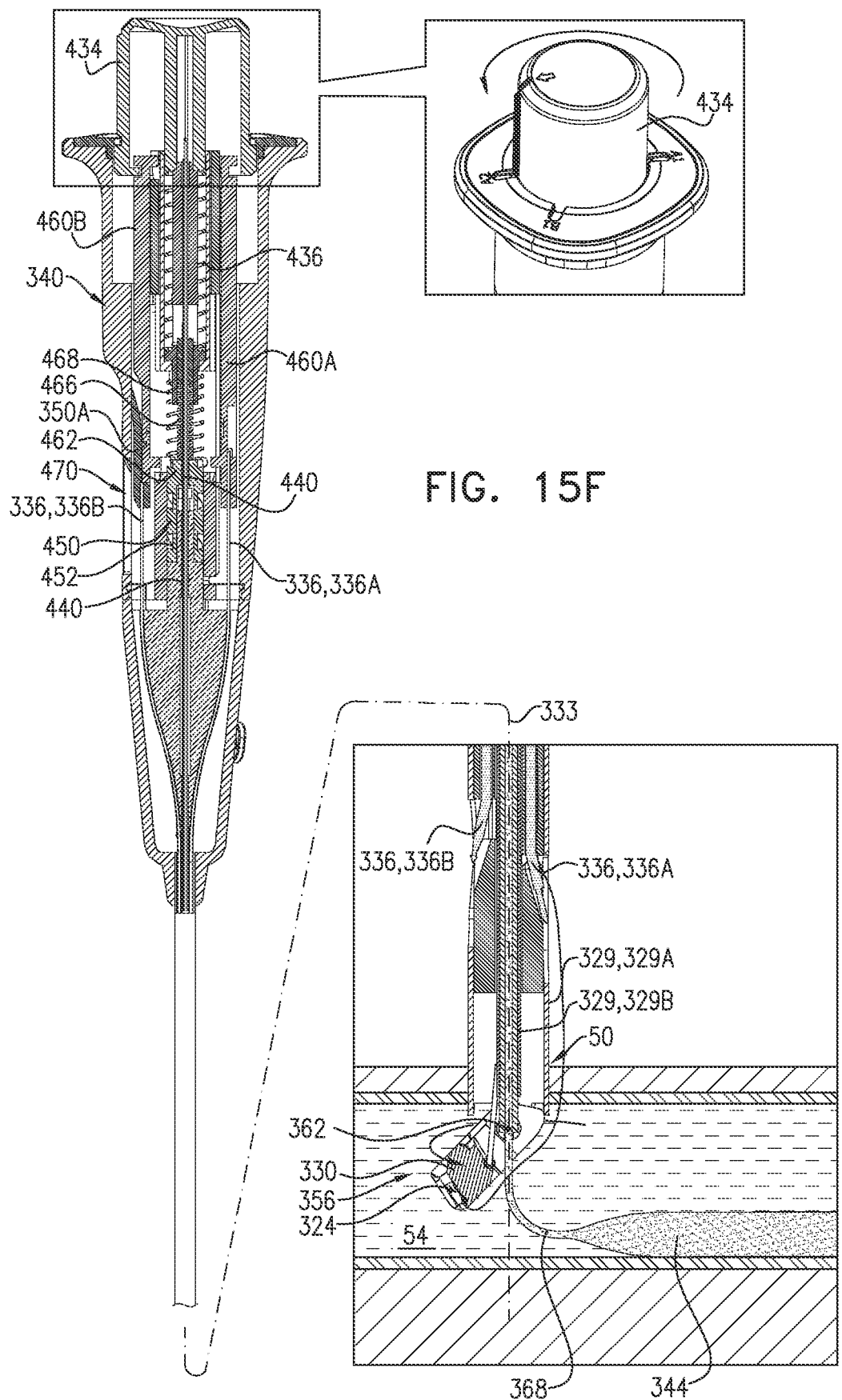

For some applications, as shown in FIG. 15F, actuation of support-and-needle user control 434, such as by rotation of the support-and-needle user control 434 (e.g., comprises a button), rotates suture-positioning support 330 about distal-support central longitudinal axis 333 such as described hereinabove with reference to FIG. 13H. This rotation may be implemented by rotating extension-control-shaft 440 and inner shaft 329B. The rotation may be either clockwise or counterclockwise. FIGS. 15A-E, as well as FIGS. 13E-G, show support-and-needle user control 434 in a first, initial rotational position (by way of example, labeled A1 in the figures). FIG. 15F, as well as FIGS. 15G-H and 13H-K, show support-and-needle user control 434 in a second rotational position (by way of example, labeled A2 in the figures). FIGS. 13L-N show support-and-needle user control 434 in a third rotational position (by way of example, labeled B1 in the figures). FIGS. 13O-P show support-and-needle user control 434 in a fourth rotational position (by way of example, labeled B2 in the figures).

For some of these applications, the rotation is achieved by rotation of one or more of the shafts of elongate support 328, with respect to control handle 340, about distal-support central longitudinal axis 333. For example, elongate support 328 may comprise outer tubular shaft 329A and inner shaft 329B, nested within outer tubular shaft 329A, and closure device 320 may be configured to rotate inner shaft 329B while holding outer tubular shaft 329A fixed with respect to control handle 340, such as shown.

Figure 15G:
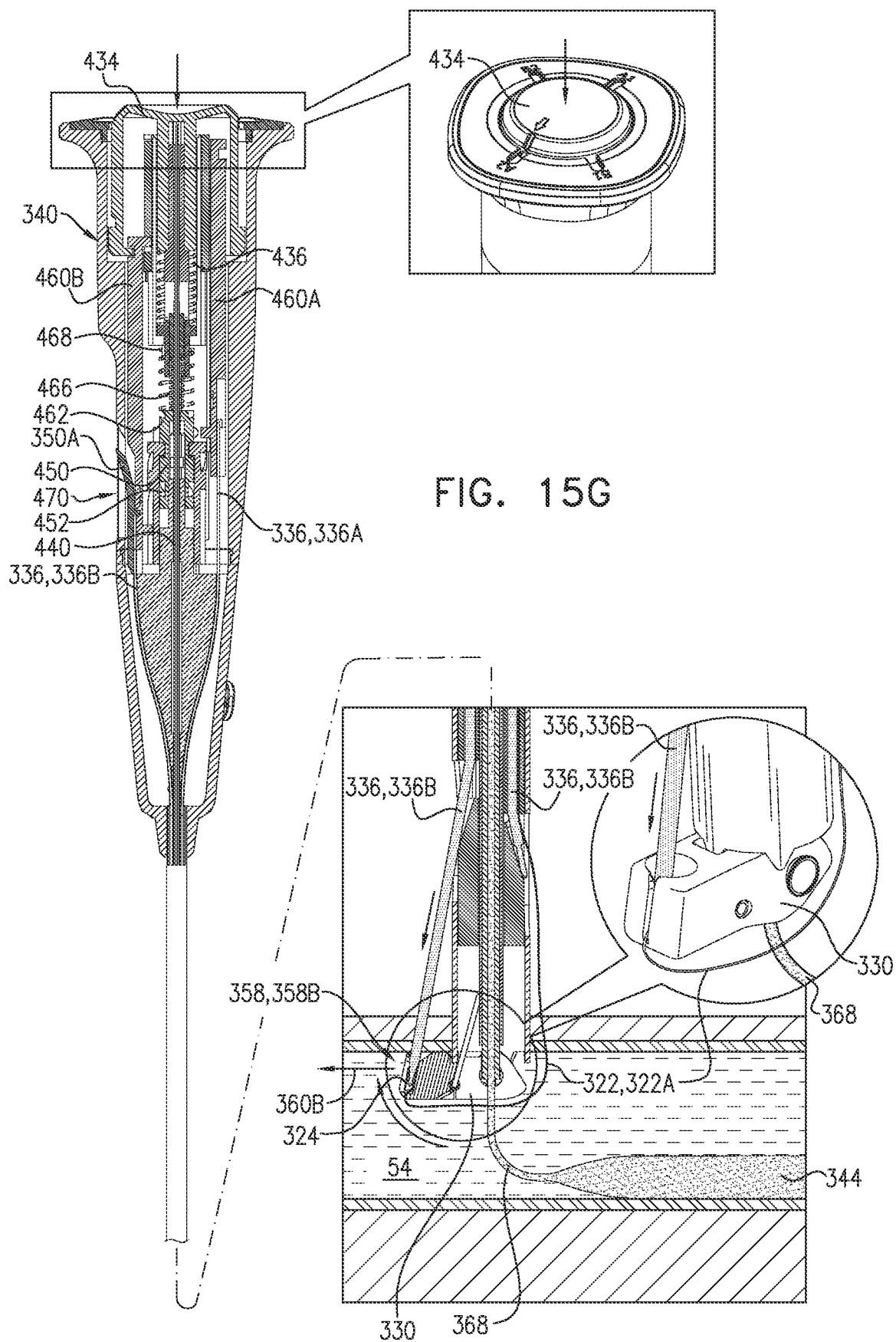

For some applications, such as shown in FIG. 15G, actuation of support-and-needle user control 434 (such as by movement of the user control in a proximal-to-distal direction (such as by depressing the user control, e.g., a button)) causes:

lateral extension of suture-positioning support 330, with respect to distal end portion 332 of elongate support 328, to second deployed position 358, 358B in which suture-positioning support 330 laterally extends in second direction 360B from distal end portion 332 of elongate support 328, second direction 360B different from first direction 360A, such as described hereinabove with reference to the transition between FIG. 13H and FIG. 13I, and distal advancement of first ferrule-withdrawing suturing needle 336, 336B to ferrule 324, which is within ferrule receptacle 334, such as described hereinabove with reference to FIG. 3I.

For some applications, the actuation of support-and-needle user control 434 causes at least a portion of the distal advancement of first ferrule-withdrawing suturing needle 336, 336B to occur as suture-positioning support 330 is extended laterally. For example, the relative timing of the lateral extension of suture-positioning support 330 and the distal advancement of first ferrule-withdrawing suturing needle 336, 336B may be implemented as described hereinabove with reference to FIGS. 15A-C, mutatis mutandis.

Figure 15H:
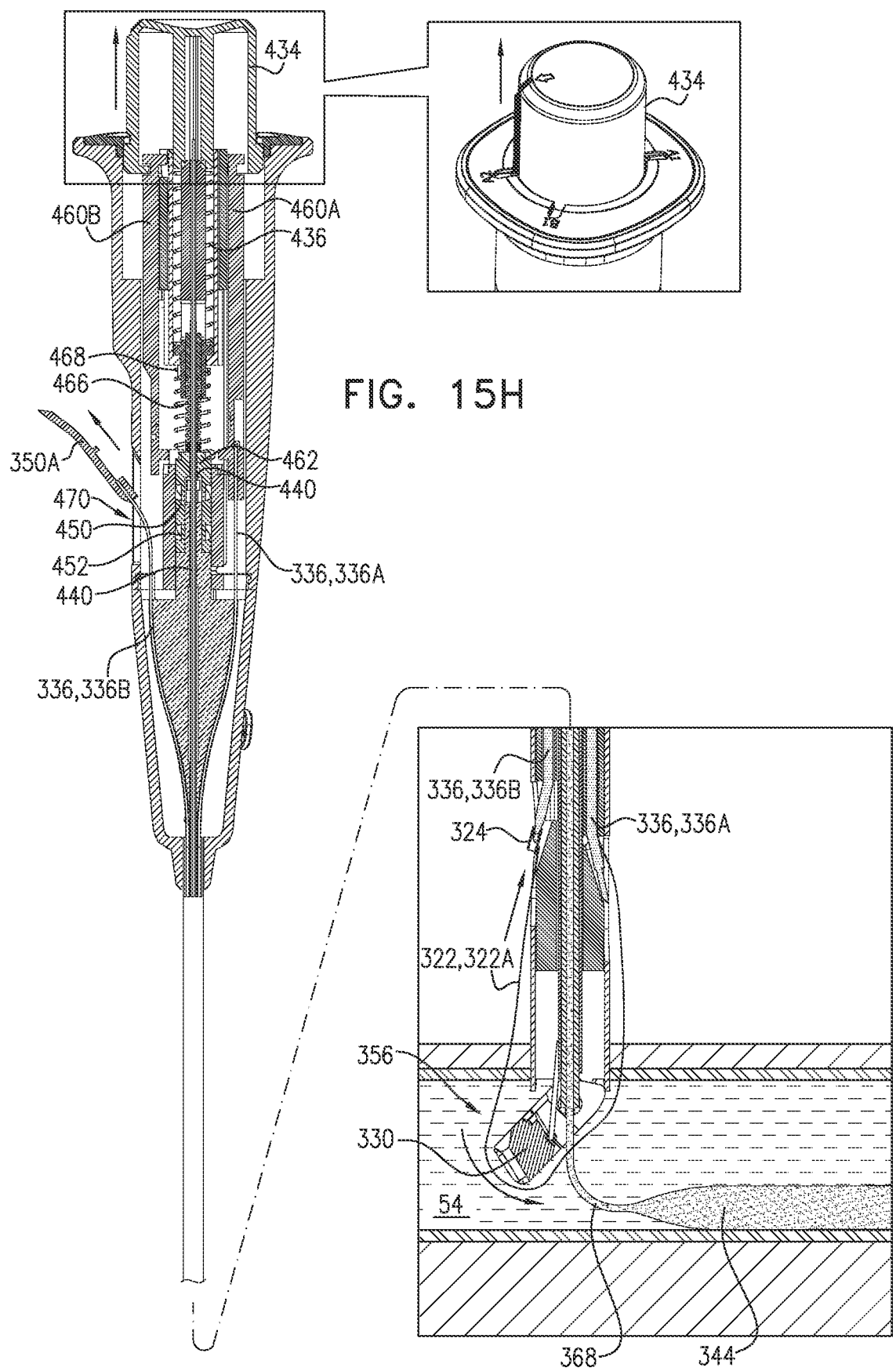

For some applications, such as shown in the transition between FIG. 15G and FIG. 15H, actuation of support-and-needle user control 434 (such as by movement of the user control in a distal-to-proximal direction (such as by releasing the user control, e.g., a button)) causes:

proximal withdrawal of first ferrule-withdrawing suturing needle 336, 336B coupled to ferrule 324, thereby removing ferrule 324 from ferrule receptacle 334, such as described hereinabove with reference to FIG. 13J, and transitioning of suture-positioning support 330 from second deployed position 358, 358B back to delivery position 356, such as described hereinabove with reference to FIG. 13J.

For some applications, the actuation of support-and-needle user control 434 causes at least a portion of the transitioning of suture-positioning support 330 from second deployed position 358, 358B back to delivery position 356 as first ferrule-withdrawing suturing needle 336, 336B is proximally withdrawn. The relative timing of the transitioning of suture-positioning support 330 back to delivery position 356 and the proximal withdrawal of first ferrule-withdrawing suturing needle 336, 336B may be implemented as described hereinabove with reference to FIGS. 15C-E, mutatis mutandis.

Typically, control handle 340 of closure device 320 is configured such that support-and-needle user control 434 performs the above functions, mutatis mutandis, for second ferrule-advancing suturing needle 336, 336C and second ferrule-withdrawing suturing needle 336, 336D, such as described hereinabove with reference to FIGS. 13L-P. These functions typically include the rotation of suture-positioning support 330 about distal-support central longitudinal axis 333 such as described hereinabove with reference to FIG. 13L and the transition between FIG. 13N and FIG. 13O.

Reference is made to FIGS. 15A-D. For some applications, distal end 406 of outer tubular shaft 329A is shaped so as to define one or more protrusions 472, such one or more prongs, and suture-positioning support 330 is shaped so as to define a receptacle 474. Insertion of one of protrusions 472 into receptacle 474 helps assure precise angular lateral extension of suture-positioning support 330 with respect to distal end portion 332 of elongate support 328. Alternatively, for some applications, distal end 406 of outer tubular shaft 329A is shaped so as to define one or more receptacles, and suture-positioning support 330 is shaped so as to define a protrusion, such as a prong (configuration not shown). Insertion of the protrusion into one of the receptacles helps assure precise angular lateral extension of suture-positioning support 330 with respect to distal end portion 332 of elongate support 328.

Reference is again made to FIGS. 15A-H. For some applications, needle handle 350A is coupled to the proximal end of first ferrule-withdrawing suturing needle 336, 336B. As shown in FIG. 15H, after first ferrule-withdrawing suturing needle 336, 336B has been proximally withdrawn within control handle 340, first ferrule-withdrawing suturing needle 336, 336B is removed from control handle 340, such as by using needle handle 350A. As mentioned above, at this stage of the procedure, first ferrule-withdrawing suturing needle 336, 336B is coupled to first suture 322, 322A via first ferrule 324, 324A. Therefore, removal of first ferrule-withdrawing suturing needle 336, 336B from control handle 340 pulls a portion of first suture 322, 322A out of the control handle.

For some applications, needle handle 350A and first ferrule-withdrawing suturing needle 336, 336B are removed from control handle 340 via an opening 470 through a wall of control handle 340. For some applications, such as shown in FIGS. 15A-D, in order to prevent premature passage of needle handle 350A through opening 470, needle handle 350A is initial longitudinally offset from opening 470, such as disposed proximal to opening 470.

Typically, one of the actuations of support-and-needle user control 434 longitudinally aligns needle handle 350A with opening 470. For example, the alignment may be caused by the actuation of support-and-needle user control 434 that inter alia causes distal advancement of first ferrule-withdrawing suturing needle 336, 336B, such as described hereinabove with reference to FIG. 15E. For example, distal movement of second needle-control shaft 460B may distally move needle handle 350A. (The subsequent proximal movement of second needle-control shaft 460B does not proximally return needle handle 350A to its original longitudinal position, because, for example, needle handle 350A may move radially outward slightly during distal movement of second needle-control shaft 460B, thereby preventing needle handle 350A from returning proximally to its original longitudinal position.)

Reference is now made to FIGS. 9B-D. In some applications of the present invention:

first suture 322, 322A is pre-knotted so as to form first pre-tied knot 338A, which is disposed at least partially within closure device 320, such as at least partially within elongate support 328, and/or second suture 322, 322B is pre-knotted so as to form second pre-tied knot 338B, which is disposed at least partially within closure device 320, such as at least partially within elongate support 328.

Proximal withdrawal of first ferrule-withdrawing suturing needle 336, 336B coupled to first ferrule 324, 324A, such as described hereinabove with reference to FIG. 13J, pulls first ferrule-withdrawing suturing needle 336, 336B and distal end portion 326 of first suture 322, 322A (and first ferrule 324, 324A) through first pre-tied knot 338A. Typically, in order to enable this, first ferrule-withdrawing suturing needle 336, 336B is initially disposed passing through first pre-tied knot 338A.

Proximal withdrawal of second ferrule-withdrawing suturing needle 336, 336D coupled to second ferrule 324, 324B, such as described hereinabove with reference to FIG. 13P, pulls second ferrule-withdrawing suturing needle 336, 336D and second suture 322, 322B (and second ferrule 324, 324B) through second pre-tied knot 338B. Typically, in order to enable this, second ferrule-withdrawing suturing needle 336, 336D is initially disposed passing through second pre-tied knot 338B.

Providing two pre-tied knots 338A and 338B may facilitate formation of the X-shaped suturing arrangement described hereinabove with reference to FIG. 13R.

Optionally, during manufacture of closure device 320, pre-tied knots 338A and 338B are heated while on a mandrel, in order to secure the pre-shaping of the knots. For example, the sutures may comprise a polymer, such as polypropylene, or another material described hereinbelow.

Reference is now made to FIGS. 16A and 16B, which are schematic isometric and cross-sectional views of an alternative configuration of a proximal end portion 512 of a dilator 544, in accordance with an application of the present invention. Sheath 410 is shown distally advanced, such as described hereinabove with reference to FIGS. 13C and 14A.

Reference is also made to FIGS. 17A and 17B, which are schematic isometric and cross-sectional views of the alternative configuration of proximal end portion 512 of dilator 544, in accordance with an application of the present invention. Sheath 410 is shown proximally withdrawn, such as described hereinabove with reference to FIGS. 13D and 14B.

Other than as described below, dilator 544 may be identical to dilator 344 described hereinabove, and the features of this configuration may be implemented in combination with any of the features of dilator 344 and/or of closure device 320 described herein, mutatis mutandis.

In this configuration, dilator 544 is shaped so as to define an atraumatic proximal tip 586, which is optionally tapered. Proximal end portion 512 of dilator 544 is shaped so as to define an indentation 588 at least partially around the dilator longitudinally between atraumatic proximal tip 586 and the remaining more distal portion of dilator 544. Indentation 588 may help inhibit (e.g., prevent) distal over-advancement of sheath 410 when sheath 410 is in its distally advanced position, such as shown in FIGS. 17A and 17B and/or during distal advancement of sheath 410, such as described hereinbelow with reference to FIGS. 13Q.

Reference is now made to FIG. 18, which is a schematic cross-sectional illustration of a configuration of sheath 410, elongate support 328, and a portion of control handle 340, in accordance with an application of the present invention. In this configuration, sheath 410, outer tubular shaft 329A of elongate support 328, and the portion of control handle 340 are configured to provide a blood flow path 578 between outside sheath 410 and a side opening 580 of control handle 340. For example, side opening 580 may be disposed at an end of a tube 582 that protrudes laterally from control handle 340. The surgeon visually detects blood emerging from side opening 580 to indicate that sheath 410, and thus suture-positioning support 330, is disposed within the blood vessel.

Blood flow path 578 may be defined, for example, partially by an interior 590 of sheath 410 and/or partially by one or more tubes 594 disposed within sheath 410, outer tubular shaft 329A of elongate support 328, and the portion of control handle 340.

For some applications, sheath 410 is shaped so as to define one or more openings 592 between outside sheath 410 and interior 590 of sheath 410. For example, the one or more openings 592 may be one or more lateral openings through a wall of sheath 410 (such as shown in FIG. 18) and/or one or more distal end openings through the distal end of sheath 410 (configuration not shown).

Figure 19A:
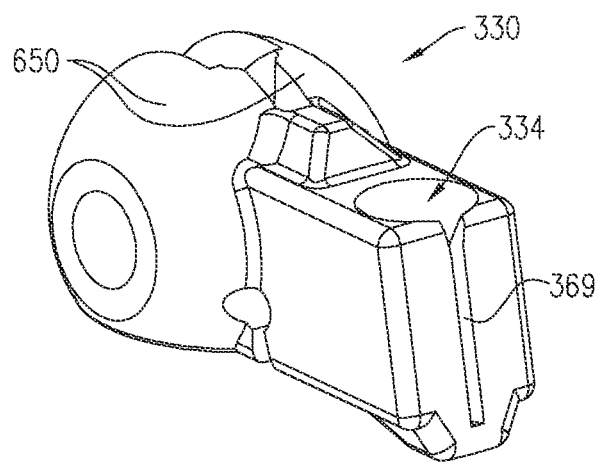
FIGS. 19A-C are schematic illustrations of an alternative configuration of a suture-positioning support of the closure device of FIG. 9A, in accordance with an application of the present invention.
Figure 19B:
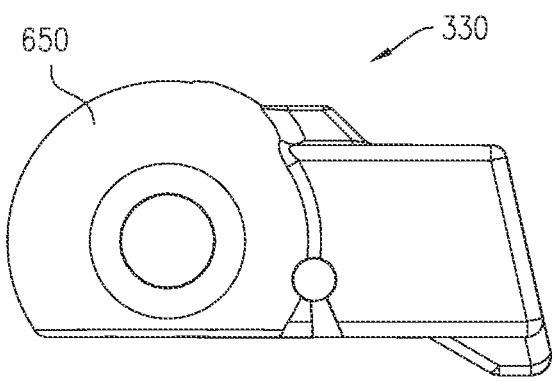
Figure 19C:
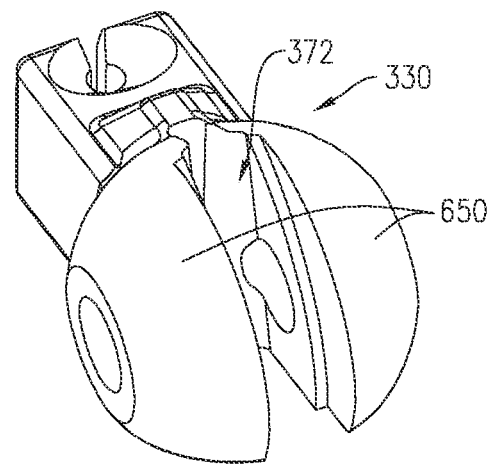

Reference is now made to FIGS. 19A-C, which are schematic illustrations of an alternative configuration of suture-positioning support 330, in accordance with an application of the present invention.

Reference is also made to FIGS. 20A-C, which are schematic illustrations of the alternative configuration of suture-positioning support 330, as well as distal end portion 332 of elongate support 328, elongate flexible dilator connector 368, and a portion of proximal end portion 412 of dilator 344, in accordance with an application of the present invention.

Any of the implementations of suture-positioning support 330 described herein may have the features of the configuration of suture-positioning support 330 shown in FIGS. 19A-C and 20A-C. (By way of example and not limitation, this configuration is also shown in FIGS. 16A-B, 17A-B, and 28A-B.)

In this configuration, an external portion of suture-positioning support 330 that interfaces with distal end portion 332 of elongate support 328 is shaped so as to define one or more partial spherical surfaces 650, such as two partial spherical surfaces 650, as shown in FIGS. 19A-C and 20A-C. These surfaces may help reduce a gap 652 (labeled in FIG. 20B) between the external surface of suture-positioning support 330 and distal end portion 332 of elongate support 328, while still allowing suture-positioning support 330 to pivot between delivery position 356 and the one or more deployed positions 358.

Reference is made to FIG. 20B. For some applications, a length L1 of ferrule 324 is at least 0.8 mm, no more than 2.2 mm, and/or 0.8 mm to 2.2 mm, and/or at least 35%, no more than 100%, and/or 35%-100%, of a length L2 of a cylindrical portion of ferrule receptacle 334 (excluding an optional funnel-shaped portion of ferrule receptacle 334, if provided). These relative lengths may provide a secure fit for the ferrule within the ferrule receptacle.

Reference is now made to FIGS. 21A-C and FIGS. 22A-C, which are schematic isometric and cross-sectional illustrations of pre-tied knots 738A and 738B, respectively, in accordance with respective applications of the present invention. Optionally, the features of pre-tied knots 738A and/or 738B are implemented in first pre-tied knot 338A, second pre-tied knot 338B, or both first pre-tied knot 338A and second pre-tied knot 338B, described hereinabove with reference to FIGS. 9B-D. Each of pre-tied knots 738A and 738B are shown with one of the ferrule-withdrawing suturing needles 336, 336B, 336D disposed passing through the knot, such as shown in FIGS. 9B-D, mutatis mutandis.

Each of pre-tied knots 738A and 738B defines a plurality of turns 740, at least two of which have different respective inner diameters. Typically, each of pre-tied knots 738A and 738B defines 4-7 turns 740.

As shown in FIGS. 21A-C, an inner diameter of a distal-most turn 740A of pre-tied knot 738A is greater than an inner diameter of a second-to-distal-most turn 740B of pre-tied knot 738A. Distal-most turn 740A is the turn 740 of pre-tied knot 738A located closest to a distal pointed end 742 of ferrule-withdrawing suturing needle 336 (distal pointed end 742 is concealed by ferrule 324 in FIGS. 21A-B, but is labeled in FIG. 9C). For some applications, respective inner diameters of all of turns 740 of pre-tied knot 738A decrease in a distal-to-proximal direction, such as shown. The larger inner diameter of the one or more distal turns 740 may facilitate introduction of ferrule 324 into pre-tied knot 738A as ferrule-withdrawing suturing needle 336 is withdrawn proximally, such as described hereinabove with reference to FIGS. 13H and 13P.

Optionally, during fabrication, pre-tied knot 738A is shaped on a conical mandrel.

As shown in FIGS. 22A-C, an inner diameter of a proximal-most turn 740C of pre-tied knot 738B is greater than an inner diameter of a second-to-proximal-most turn 740D of pre-tied knot 738B. Proximal-most turn 740C is the turn 740 of pre-tied knot 738B located farthest from distal pointed end 742 of ferrule-withdrawing suturing needle 336. For some applications, respective inner diameters of all of turns 740 of pre-tied knot 738B of all turns 740 other than proximal-most turn 740C are equal to one another, such as shown; for other applications, respective inner diameters of all of turns 740 of pre-tied knot 738B of all turns 740 other than proximal-most turn 740C decrease in a distal-to-proximal direction, such as shown in FIGS. 21A-C. The larger inner diameter of proximal-most turn 740C may compensate for any decrease in the diameter of this loop that may occur during assembly of closure device 320.

For example, the inner diameter of proximal-most turn 740C of pre-tied knot 738B may equal at least 110%, no more than 200%, and/or 110%-200% of the average inner diameter of the other turns 740 of pre-tied knot 738B. By way of example and not limitation, the inner diameter of proximal-most turn 740C of pre-tied knot 738B may be 0.55-0.65 mm, and the average inner diameter of the other turns 740 of pre-tied knot 738B may be 0.65-0.8 mm.

Reference is now made to FIGS. 23A-C and 24A-C, which are schematic illustrations of respective couplings between distal end portion 326 of suture 322 and a ferrule 324A and a ferrule 324B, in accordance with respective applications of the present invention. As described hereinabove with reference to FIGS. 9A-D, 12, and 13F-O, ferrule 324 is coupled to distal end portion 326 of suture 322 (either first suture 322A and/or second suture 322B), such as by being passed (e.g., looped) through an opening defined by a wall of ferrule 324, and/or by welding, knotting, gluing, or another technique (configurations not shown). These coupling techniques may optionally be implemented in any of the closure devices described herein, including closure devices 20, 120, 220, and 320.

In the configurations of ferrule 324, 324A, 324B shown in FIGS. 23A-C and 24A-C, the ferrule is shaped so as to define a blunt interface 750 with distal end portion 326 of suture 322, in order to avoid inadvertent severing of the suture by the ferrule when force is applied to the suture.

Figures 23A, 23B:
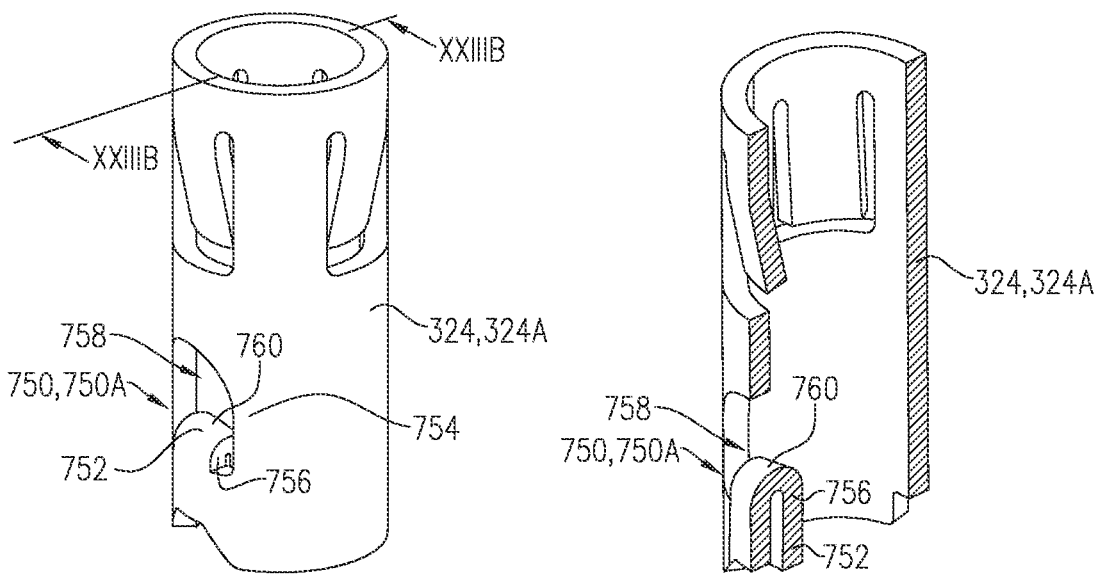
FIGS. 23A-C are schematic illustrations of couplings between a distal end portion of a suture and a ferrule, in accordance with an application of the present invention.
Figure 23C:
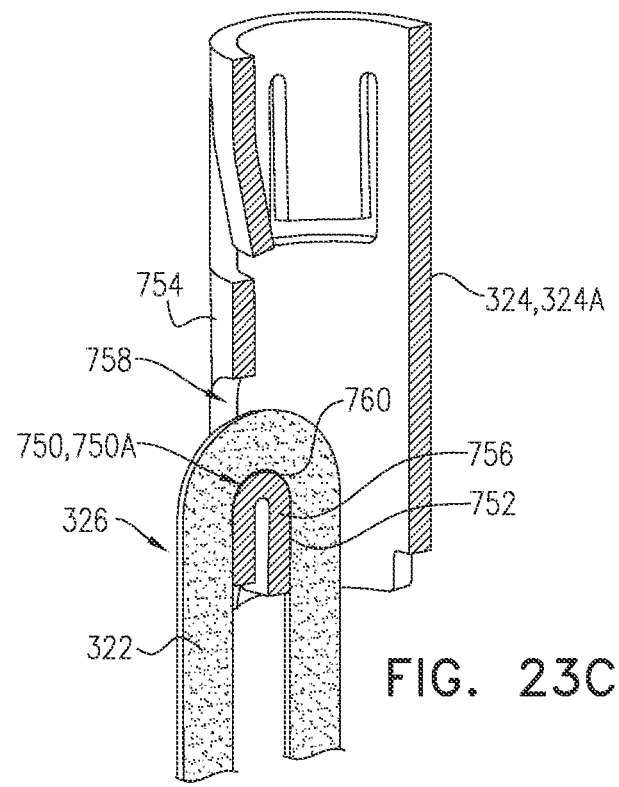

For example, in the configuration of ferrule 324, 324A shown in FIGS. 23A-C, a blunt interface 750, 750A is defined by a flap 752 defined by at least a portion of material 756 cut from a wall 754 of ferrule 324, 324A to define an opening 758 through wall 754. The at least a portion of material 756 is bent so as to define flap 752 having a curved bend 760. The at least a portion of material 756 may be bent inward, such as shown in FIGS. 23A-C, or bent outward (configuration not shown). Distal end portion 326 of suture 322 passes through opening 758 (e.g., is looped through opening 758, as shown). When tension is applied to the suture, the distal end portion of the suture contacts curved bend 760 of flap 752, which provides the blunt interface 750, 750A. Alternatively, distal end portion 326 of suture 322 passes through opening 758, without being looped through opening 758, and is instead secured to ferrule 324, 324A by welding, knotting, gluing, or another technique (configuration not shown).

Figure 24A:
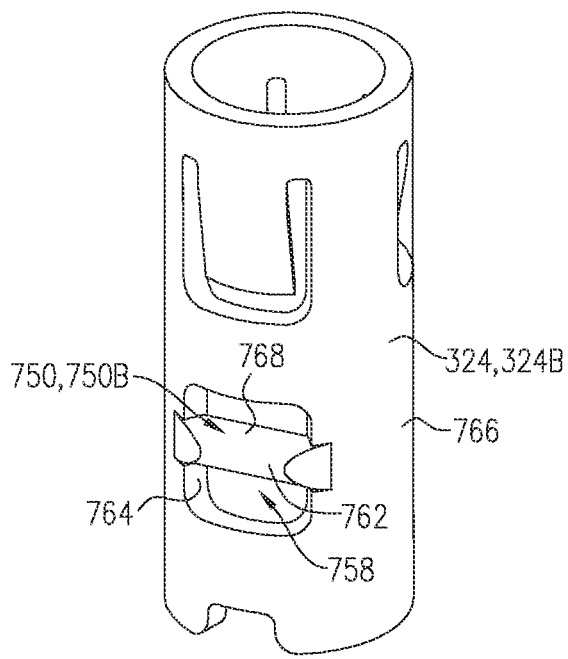
FIGS. 24A-C are schematic illustrations of additional couplings between a distal end portion of a suture and a ferrule, in accordance with an application of the present invention.
Figure 24B:
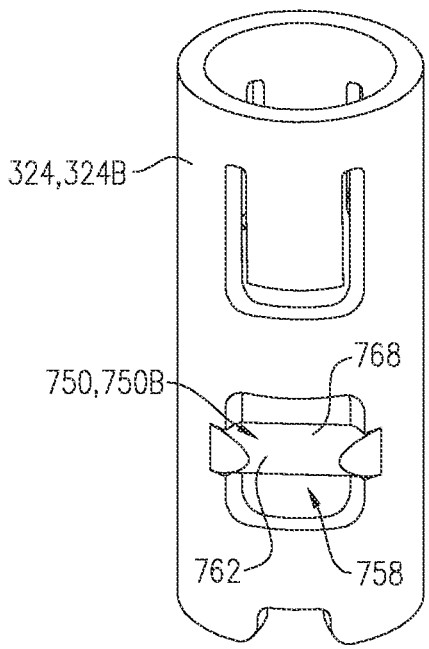
Figure 24C:
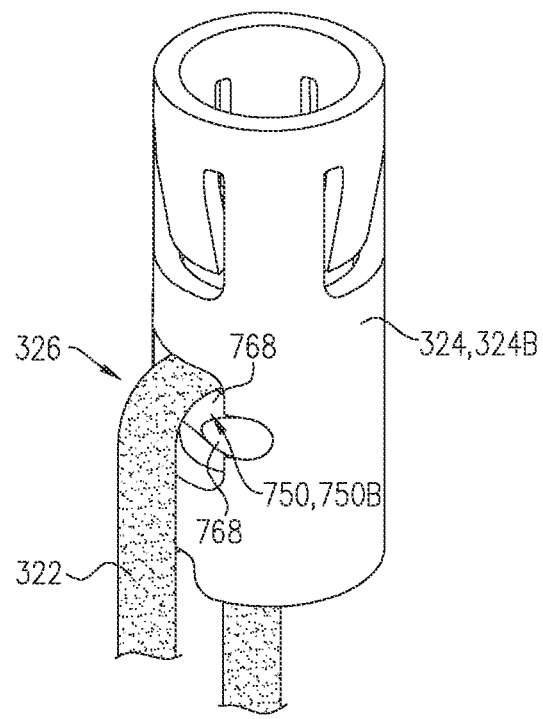

Also for example, in the configuration of ferrule 324, 324B shown in FIGS. 24A-C, a blunt interface 750, 750B is defined by a curved surface 768 of a rod 762 fixed to a perimeter 764 of an opening 758 through a wall 766 of ferrule 324, 324B, such as by welding. Distal end portion 326 of suture 322 passes through opening 758 around rod 762 (e.g., is looped through opening 758 around rod 762, as shown). When tension is applied to the suture, the suture contacts curved surface 768 of rod 762, which provides the blunt interface 750, 750B. Alternatively, distal end portion 326 of suture 322 passes through opening 758 around rod 762, without being looped through opening 758, and is instead secured to ferrule 324, 324B by welding, knotting, gluing, or another technique (configuration not shown).

Figure 25A:
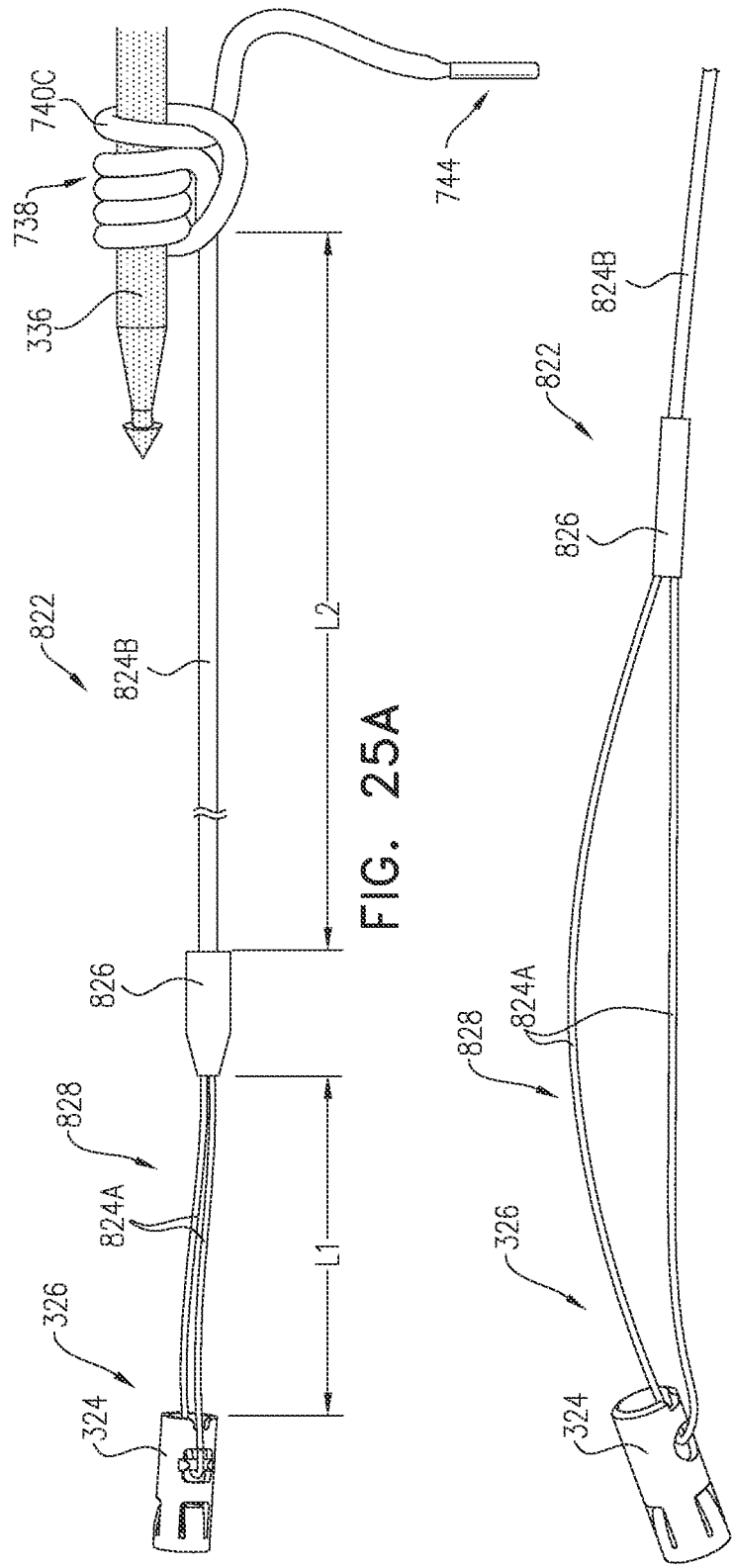
FIGS. 25A-C are schematic illustrations of a suture, in accordance with an application of the present invention.
Figure 25B:
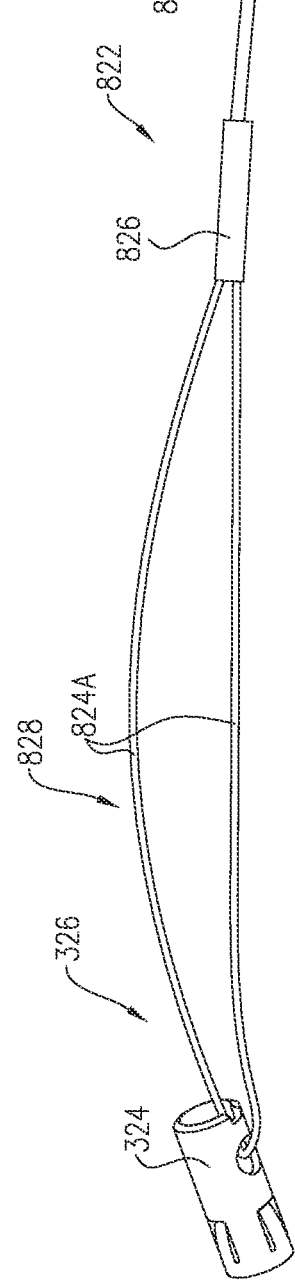
Figure 25C:
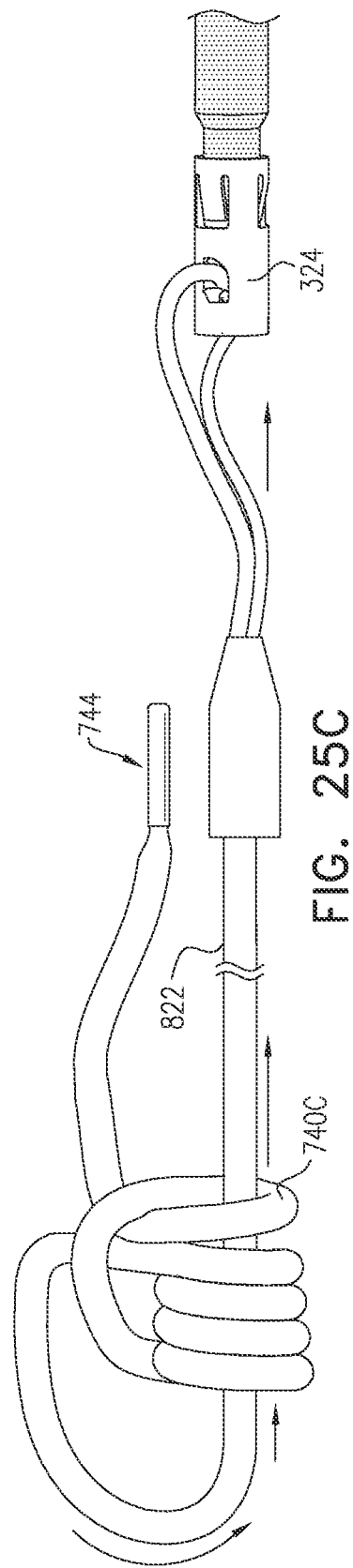

Reference is now made to FIGS. 25A-C, which are schematic illustrations of a suture 822, in accordance with an application of the present invention. Any of the sutures described herein, including sutures 22 and 322, may implement the features of suture 822. FIG. 25C shows suture 822 after ferrule 324 has been pulled through pre-tied knot 738. Pulling on suture 822 in the direction indicated by the arrows in FIG. 25C tightens the knot.

Suture 822 comprises distal and proximal suture segments 824A and 824B, which are non-integral with each other and fixed to each other, for example using a crimp ferrule 826, such as described hereinbelow with reference to FIG. 26A-B, 27A-B, or 27C-D, or by melting, such as described hereinbelow with reference to FIG. 27E. In configurations in which distal and proximal suture segments 824A and 824B are fixed to each other using a crimp ferrule, the distal and the proximal suture segments may or may not touch each other within crimp ferrule 826. For example, ferrule 324 may be coupled to distal end portion 326 of distal suture segment 824A of suture 822, such as by being passed (e.g., looped) through an opening defined by a wall of ferrule 324, and/or by welding, knotting, gluing, or another technique (configurations not shown).

For some applications, distal suture segment 824A is shaped as a loop 828, such as shown, and the two ends of loop 828 of distal suture segment 824A are fixed to proximal suture segment 824B, such as by being fixed within crimp ferrule 826, e.g., within distal portion 850 of crimp ferrule 826.

Optionally, distal and proximal suture segments 824A and 824B have different diameters, such as shown; for example, a diameter of distal suture segment 824A may be less than a diameter of proximal suture segment 824B. Alternatively, distal and proximal suture segments 824A and 824B may have the same diameter (configuration not shown).

Optionally, distal and proximal suture segments 824A and 824B comprise different types of material; by way of example and not limitation, distal suture segment 824A may comprise PTFE, ePTFE, polypropylene, Nylon, or polyester, and/or proximal suture segment 824B may comprise PTFE, ePTFE, Polypropylene, Nylon, or polyester. Alternatively, distal and proximal suture segments 824A and 824B may comprise the same material, such as one of the materials described immediately above. Any of the sutures described herein may optionally comprise any of these materials. Optionally, distal suture segments 824A, proximal suture segment 824B, and/or any of the other sutures described herein may comprise braided sutures, monofilament sutures, absorbable sutures, or non-absorbable sutures.

For example, distal suture segment 824A may have an effective length L1 of at least 0.5 cm, no more than 2 cm, and/or 0.5-2 cm, and/or proximal suture segment 824B may an effective length L2 of at least 25 cm, no more than 40 cm, and/or 25-40 cm. (In configurations in which a suture segment is shaped as loop 828, such as shown for distal suture segment 824A, the effective length is measured along the doubling of the suture segment, as labeled by L1 in FIG.

25A. The effective lengths do not include portions of suture 822 that are not free, e.g., a portion of proximal suture segment 824B that may be shaped so as to define pre-tied knot 738.)

Reference is made to FIGS. 21A-C and 22A-C. For some applications, proximal-most turn 740C of pre-tied knots 738A and 738B functions to secure (i.e., lock) the pre-tied knot when a free proximal end 744 of the suture that defines turn 740C is pulled tightly. For some applications, free proximal end 744 of proximal-most turn 740C is pre-shaped (such as by heating) in order to ensure that the pre-tied knot is disposed in a relaxed position while positioned within control handle 340. In the absence of this pre-shaping, the suture might have a tendency to return to its original, straight shape, which could affect the position and/or inner diameter of the pre-tied knot. Optionally, free proximal end 744 is marked or comprises a marker to enable easy identification of the free end by the surgeon.

Reference is now made FIGS. 26A-B, 27A-B, and 27C-D, which are schematic isometric and cross-sectional views of respective crimping techniques using crimp ferrule 826, in accordance with respective applications of the present invention.

For some applications, distal and proximal suture segments 824A and 824B comprise the above-mentioned materials.

For example, crimp ferrule 826 may have the following dimensions: 0.5 mm×0.39 mm×2.2 mm.

For some applications, a distal end portion of proximal suture segment 824B is disposed within a proximal portion 848 of crimp ferrule 826 and is fixed to crimp ferrule 826 by crimping, i.e., by making radially-inward crimping indentations 838, such as shown. Optionally, a proximal end portion of distal suture segment 824A is also fixed to crimp ferrule 826 by crimping (configuration not shown); alternatively, the proximal end portion of distal suture segment 824A is fixed to crimp ferrule 826 using one of the techniques described hereinbelow.

For some of these applications, crimping indentations 838 are arranged in two or more axial rows 836 along a longitudinal axis of crimp ferrule 826. Each axial row 836 encircles crimp ferrule 826. For example, each axial row 836 may include two (e.g., three) to ten (e.g., eight) crimping indentations 838. For example, crimping indentations 838 may be arranged in two axial rows 836 having four to six crimping indentations 838 per axial row 836, such as shown in FIGS. 26A-B and 27C-D.

For some applications, the crimping indentations 838 of axially-adjacent axial rows 836 are circumferentially offset (angularly shifted) from one another, such as by 30-90 degrees, e.g., by 30-60 degrees, such as by 45 degrees.

Figure 26A:
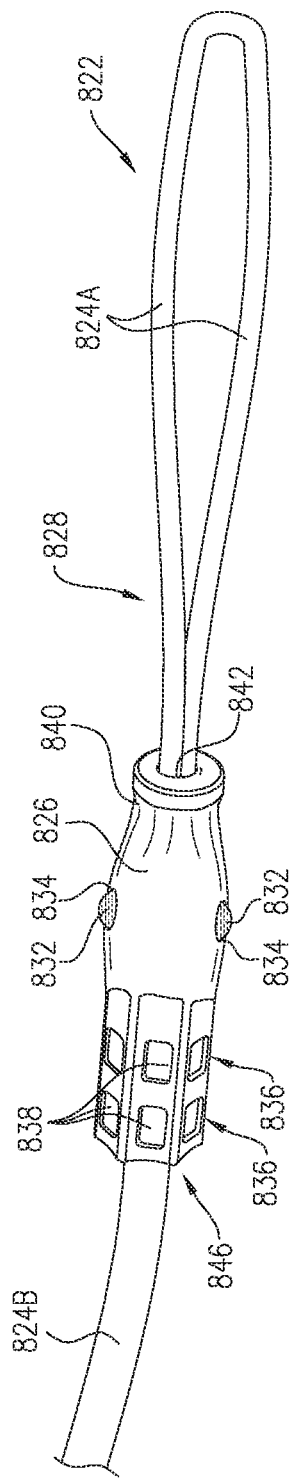
FIGS. 26A-B are schematic isometric and cross-sectional views of a crimping technique using a crimp tube, in accordance with an application of the present invention.
Figure 26B:
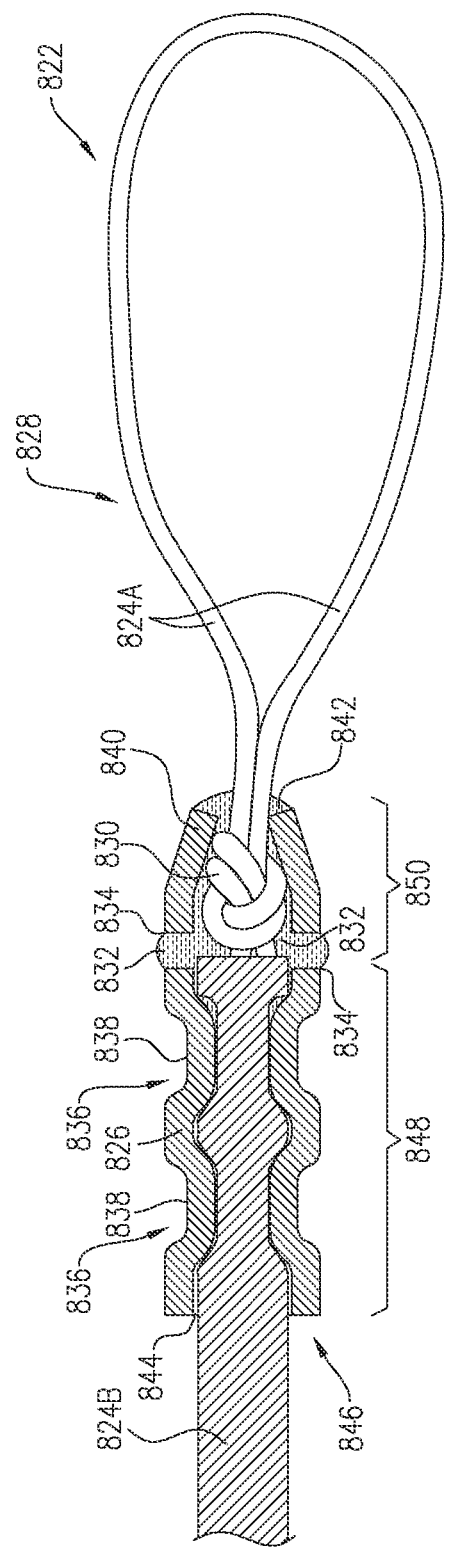

For some applications, the proximal end portion of distal suture segment 824A is disposed within in a distal portion 850 of crimp ferrule 826 (labeled in FIG. 26B).

As labeled in FIGS. 26A-B, distal portion 850 of crimp ferrule 826 may be shaped so as to define a tapered distal tip 840, e.g., a bullet-shaped distal tip, shaped so as to define a distal opening 842 that is smaller than a proximal opening 844 defined by a proximal end 846 of crimp ferrule 826, in order to help hold the proximal end portion of distal suture segment 824A tightly within the crimp ferrule. Typically, during manufacture, distal tip 840 is first tapered and then the proximal end portion of distal suture segment 824A is inserted into distal tip 840.

In the configuration shown in FIGS. 26A-B, the proximal end portion of distal suture segment 824A is knotted into a knot 830 so as to fix the proximal end portion within distal portion 850 of crimp ferrule 826. In configurations in which distal suture segment 824A is shaped as loop 828, the two proximal end portions of loop 828 of distal suture segment 824A are knotted to each other into knot 830, so as to fix the two proximal end portions within distal portion 850 of crimp ferrule 826. Typically, knot 830 is too large to pass through distal opening 842 of crimp ferrule 826. For some applications, an adhesive 832 is disposed at least partially within distal portion 850 of crimp ferrule 826 so as to inhibit unknotting of knot 830. By way of example and not limitation, the knot may comprise a square knot, or a FIG. 8 on a bight knot. Optionally, distal portion 850 of crimp ferrule 826 is shaped so as to define one or more lateral holes 834, and a portion of adhesive 832 protrudes through holes 834 to outside crimp ferrule 826, in order to better secure the distal suture segment with the crimp ferrule. The one or more lateral holes 834 may also be used to introduce adhesive 832 during assembly. For example, each of lateral holes 834 may have a cross-sectional area of 0.007-0.03 mm^2. The configuration shown in FIGS. 26A-B may optionally implement either of the indentation options described above with reference to FIGS. 27A-B and 27C-D, respectively.

In the configurations shown in FIGS. 27A-B and 27C-D, the two proximal end portions of loop 828 of distal suture segment 824A are melted together so as to be fixed within distal portion 850 of crimp ferrule 826. Optionally, distal portion 850 of crimp ferrule 826 is shaped so as to define one or more lateral holes 834, and a portion of the melted material protrudes through holes 834 to outside crimp ferrule 826, in order to better secure the distal suture segment with the crimp ferrule.

Reference is now made to FIG. 27E, which is a schematic illustration of another fixation of distal and proximal suture segments 824A and 824B of suture 822, in accordance with an application of the present invention. In this configuration, distal and proximal suture segments 824A and 824B are fixed to each other by melting. Optionally, the two ends of loop 828 of distal suture segment 824A are fixed to the single end of proximal suture segment 824B.

Reference is now made to FIGS. 28A-B, which are schematic illustrations of another configuration of closure device 320, in accordance with an application of the present invention. For clarity of illustration, suture-positioning support 330 is shown as transparent in FIG. 28B.

In the configuration of closure device 320 shown in FIGS. 28A-B, closure device 320 comprises a dilator-connection shaft 868 and a joint 870 that couples dilator-connection shaft 868 to distal end portion 332 of elongate support 328, so as to allow movement of distal end portion 332 of elongate support 328 with respect to proximal end 348 of dilator 344 with at least one rotational degree of freedom. For some applications, dilator-connection shaft 868 and dilator 344 comprise separate respective elements coupled together. Alternatively, dilator-connection shaft 868 and dilator 344 are integrally formed from a single element.

As described hereinabove with reference to FIGS. 9A-12, for some applications, closure device 320 is configured to allow movement of distal end portion 332 of elongate support 328 with respect to proximal end 348 of dilator 344 with at least two degrees of freedom. For some applications, joint 870 that couples dilator-connection shaft 868 to distal end portion 332 of elongate support 328, so as to allow movement of distal end portion 332 of elongate support 328 with respect to proximal end 348 of dilator 344 with at least two degrees of freedom, typically at least two rotational degrees of freedom. For example, joint 870 may comprise:

a hinge 872, which provides a first rotational degree of freedom, such as about an axis 874 perpendicular to distal-support central longitudinal axis 333; and a twisting joint, which provides a second rotational degree of freedom.

Alternatively, joint 870 may comprise a ball joint, a universal joint, or another joint known in the art.

Joint 870 may be coupled to suture-positioning support 330, such as shown, so as to couple dilator-connection shaft 868 to distal end portion 332 of elongate support 328 via suture-positioning support 330. Alternatively, joint 870 may be directly coupled to distal end portion 332 of elongate support 328.

For example, twisting joint 876 may be coupled to a proximal portion of dilator-connection shaft 868, such as shown, so as to provide the second rotational degree of freedom about distal-support central longitudinal axis 333. Alternatively, twisting joint 876 may couple a distal portion of dilator-connection shaft 868 to proximal end 348 of dilator 344, so as to provide the second rotational degree of freedom about proximal-dilator central longitudinal axis 418 (configuration not shown).

In this configuration, dilator-connection shaft 868 may be flexible or substantially rigid.

Reference is now made to FIGS. 29A-E, which are schematic illustrations of a ferrule-advancing suturing needle 936, in accordance with an application of the present invention. Optionally, first ferrule-advancing suturing needle 336, 336A and/or second ferrule-advancing suturing needle 336, 336C may implement the configuration of ferrule-advancing suturing needle 936. In addition, first suturing needle 36, 36A, described hereinabove with reference to FIGS. 1-8H, may implement the configuration of ferrule-advancing suturing needle 936.

Figure 29A:
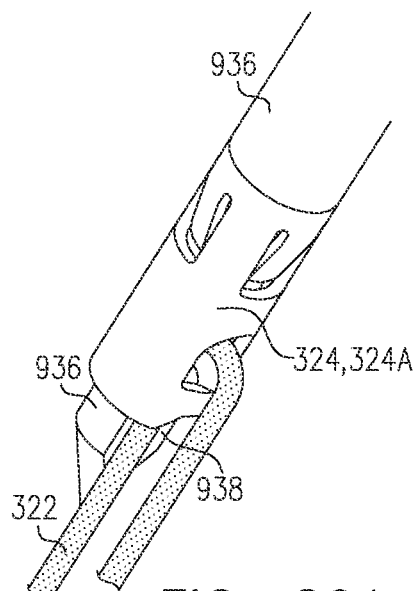
FIGS. 29A-E are schematic illustrations of a ferrule-advancing suturing needle, in accordance with an application of the present invention.
Figure 29B:
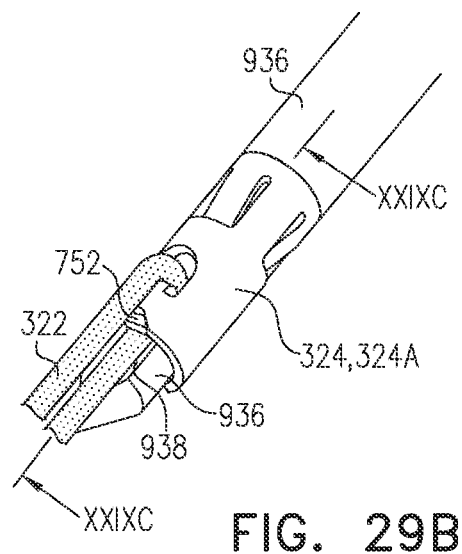
Figure 29C:
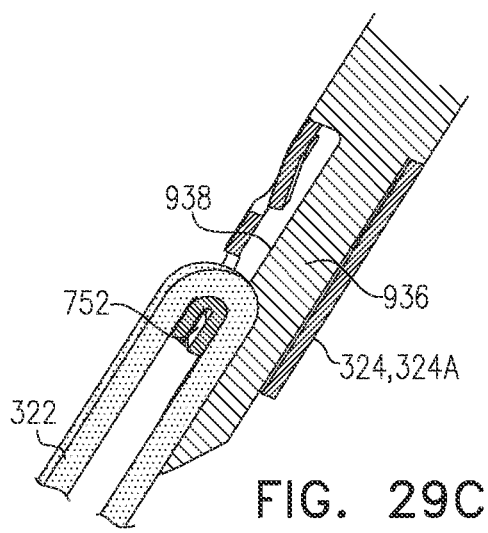
Figure 29D:
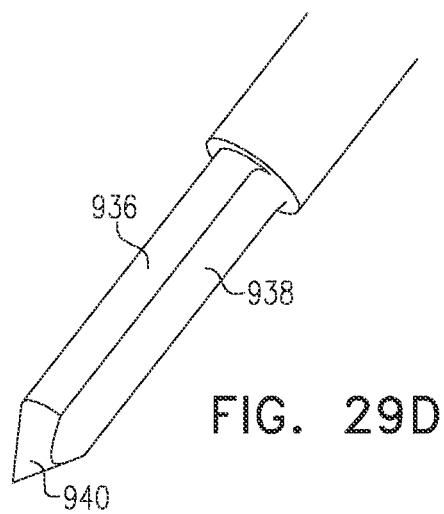
Figure 29E:
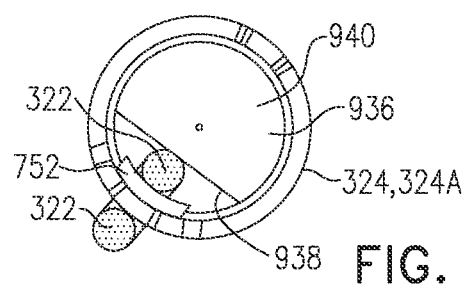
Figure 30A:
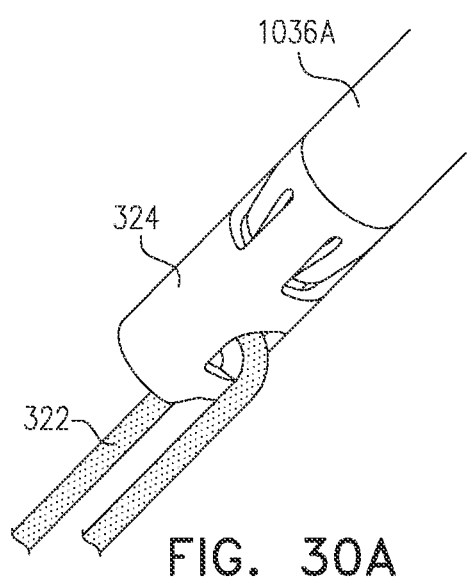
FIGS. 30A-D are schematic illustrations of another ferrule-withdrawing suturing needle, in accordance with an application of the present invention.
Figure 30B:
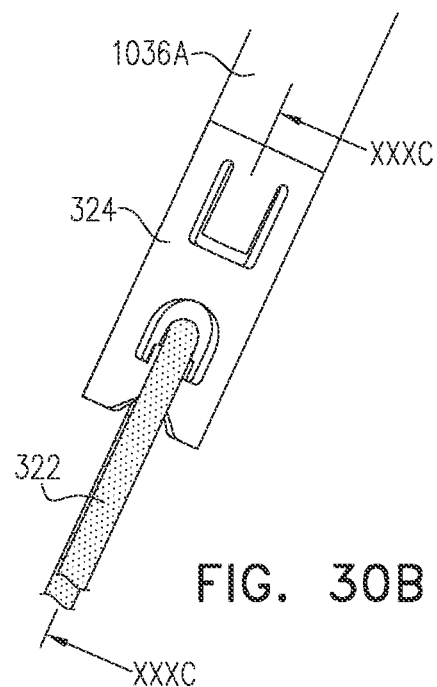
Figure 30C:
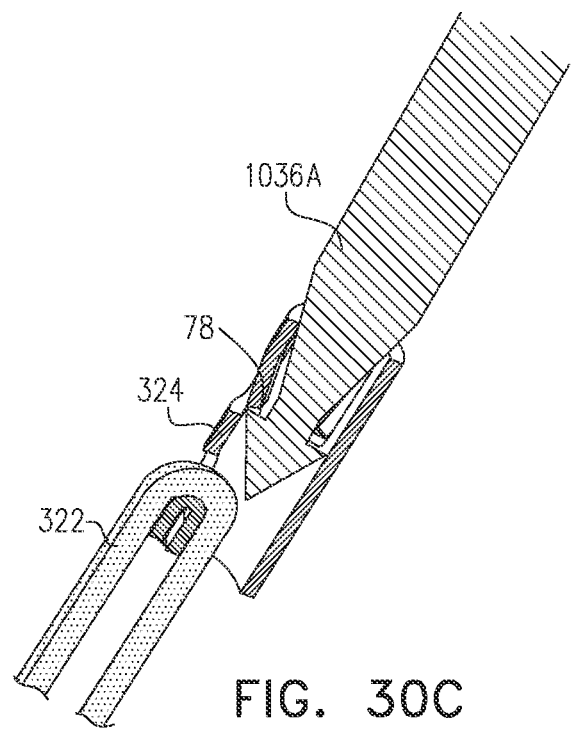
Figure 30D:
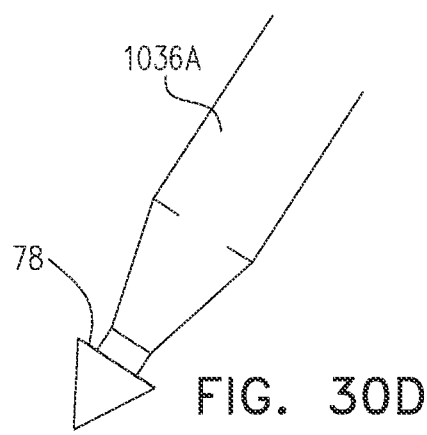
Figure 31A:
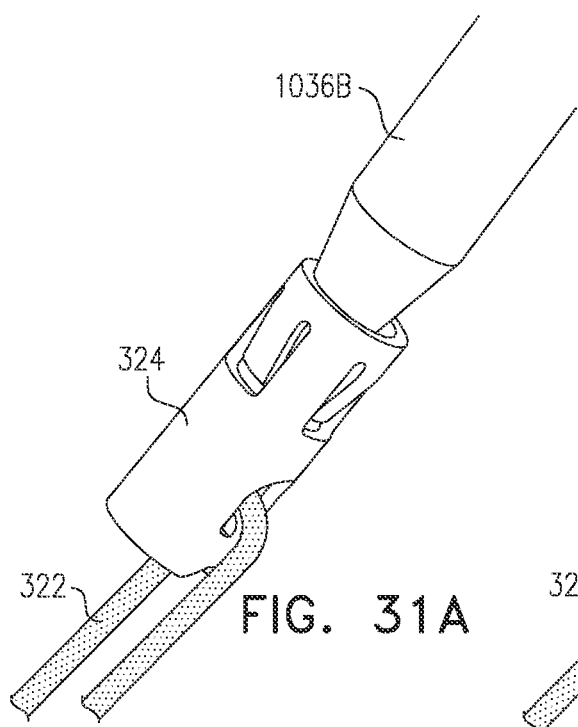
FIGS. 31A-D are schematic illustrations of yet another ferrule-withdrawing suturing needle, in accordance with an application of the present invention.
Figure 31B:
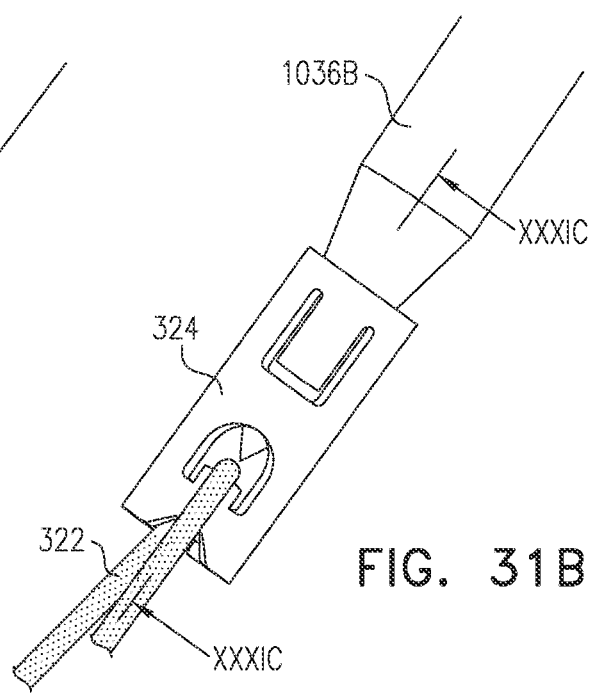
Figure 31C:
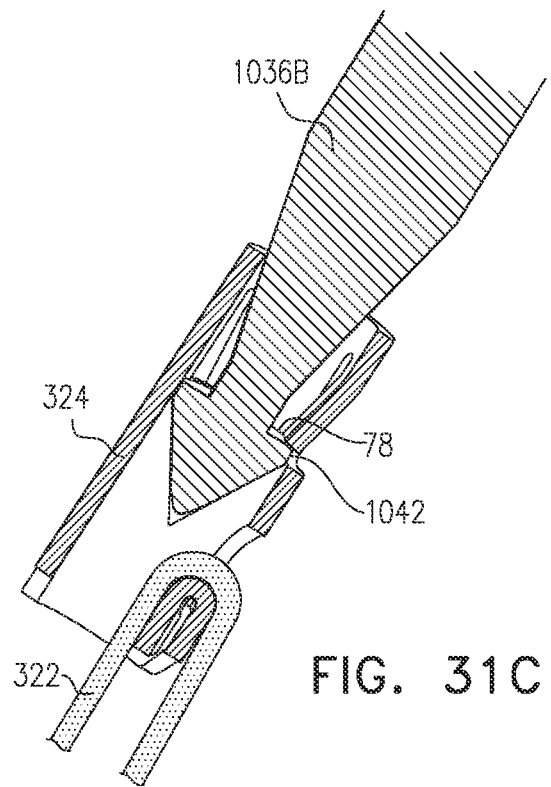
Figure 31D:
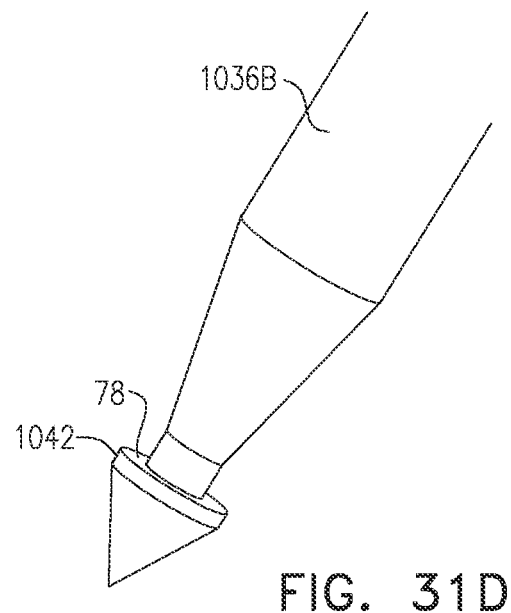

Ferrule-advancing suturing needle 936 is shaped and sized in cross-section so as to be readily insertable into ferrule 324, such as described hereinabove with reference to FIGS. 13F and 13M, while providing space within ferrule 324 for suture 322 alongside a portion of the needle, such as perhaps best seen in FIGS. 23A-C and 24A-C, as well as FIGS. 29C and 29E. For example, at least a longitudinal portion of ferrule-advancing suturing needle 936 may have a flat side 938, such that the needle may have a generally D-shaped cross section taken perpendicular to a longitudinal axis of the needle, such as perhaps best seen in FIG. 29E. Typically, a diameter of a distal end portion of needle 936 is less than a diameter of a main proximal portion of needle 936 in order to allow the ferrule to be centered/concentric with the main proximal portion of the needle, while the perpendicular wall (ridge) between the distal end portion and the main proximal portion allows pushing of the ferrule distally.

For applications in which ferrule-advancing suturing needle 936 is used in combination with ferrule 324, 324A, described hereinabove with reference to FIGS. 23A-C, and as shown by way of example and not limitation in FIGS. 29A-E, the size and shape of ferrule-advancing suturing needle 936 in cross-section may also provide space within ferrule 324, 324A for flap 752 alongside a portion of the needle.

Reference is now made to FIGS. 30A-D, which are schematic illustrations of a ferrule-withdrawing suturing needle 1036A, in accordance with an application of the present invention.

Reference is further made to FIGS. 31A-D, which are schematic illustrations of a ferrule-withdrawing suturing needle 1036B, in accordance with an application of the present invention.

Reference is still further made to FIGS. 32A-D, which are schematic illustrations of a ferrule-withdrawing suturing needle 1036C, in accordance with an application of the present invention.

Optionally, first ferrule-withdrawing suturing needle 336, 336B and/or second ferrule-withdrawing suturing needle 336, 336D may implement the configurations of ferrule-withdrawing suturing needles 1036A, 1036B, and/or 1036C. In addition, second suturing needle 36, 36B may implement the configurations of ferrule-withdrawing suturing needles 1036A, 1036B, and/or 1036C.

Typically, each of ferrule-withdrawing suturing needles 1036A, 1036B, and 1036B is shaped so as to define one or more lateral protrusions 78, which are configured to engage the ferrule upon the insertion of the suturing needle into the ferrule, so as to inhibit withdrawal of the suturing needle from the ferrule, such as described hereinabove with reference to FIG. 5G for second suturing needle 36, 36B and ferrule 24, mutatis mutandis.

As shown in FIGS. 31A-D, ferrule-withdrawing suturing needle 1036B may be shaped so as to define a cylindrical portion 1042 immediately distal (i.e., toward the tip of the needle) to the one or more lateral protrusions 78. For example, cylindrical portion 1042 may have a length of 0.05-1 mm. Cylindrical portion 1042 may facilitate consistent manufacturing of ferrule-withdrawing suturing needle 1036B. Optionally, ferrule-withdrawing suturing needle 1036C also is shaped as to define cylindrical portion 1042, as shown in FIGS. 32A-D; alternatively, suturing needle 1036C does not have this feature (configuration not shown, but as shown for suturing needle 1036A).

As shown in FIGS. 32A-D, ferrule-withdrawing suturing needle 1036C is shaped so as to define a cylindrical portion 1044 having a diameter of 80%-99% of an inner diameter of the ferrule and a length of 0.2-1 mm. This shape may reduce an angular degree of freedom of motion between ferrule-withdrawing suturing needle 1036C and the ferrule when at least a portion of cylindrical portion 1044 is inserted into the ferrule.

Reference is now made to FIGS. 33A-C, which are schematic illustrations of a configuration of control handle 340, in accordance with an application of the present invention. Reference is also again made to FIGS. 14A-B. As described hereinabove with reference to FIGS. 14A-B, for some applications, control handle 340 comprises sheath-control user control 430. As shown in the transition between FIG. 14A and FIG. 14B, actuation of sheath-control user control 430 by a user (e.g., by proximal sliding the user control, such as shown), proximally withdraws sheath 410 along outer tubular shaft 329A so as to expose suture-positioning support 330, dilator connector 368, proximal end portion 412 of dilator 344, and distal lumen opening 367 (all labeled in FIG. 14B).

For some applications, control handle 340 is configured to lock support-and-needle user control 434, thereby preventing actuation thereof, such as shown in FIGS. 33A-B, until actuation of sheath-control user control 430, such as shown in FIG. 33C (i.e., while sheath-control user control 430 is a non-actuated state, such as shown in FIGS. 14A and 33A-B). This feature prevents premature lateral extension of suture-positioning support 330 and distal advancement of ferrule-advancing suturing needles 336, 336A and 336, 336C, while sheath 410 would interfere with these operations. This feature may thus serve as a safety mechanism. Actuation of sheath-control user control 430 unlocks support-and-needle user control 434, so as to allow actuation thereof by the user. (FIG. 33B shows sheath-control user control 430 in an intermediate state of activation.)

As described hereinabove with reference to FIGS. 15A and 15B, rotation of outer cam 450 rotates internal thread 464 thereof, which engages external thread 458 of inner cam 462 and causes proximal motion of inner cam 462 with respect to outer cam 450 and control handle 340. Inner cam 462 is coupled to above-described extension-control-shaft 440, such that the proximal motion of inner cam 462 causes the above-described proximal motion of extension-control-shaft 440, and resulting lateral extension of suture-positioning support 330, such as described above. Each of needle-control shafts 460 comprises a pin 456. As each of needle-control shafts 460 is separately distally advanced, as described above, pin 456 engages one of elongate indentations 452, thereby rotating outer cam 450 about cam axis 454.

For some applications, control handle 340 is configured to lock support-and-needle user control 434 by preventing rotation of outer cam 450. For example, control handle 340 may comprise a key 1110 (which may be considered a pin), and outer cam 450 may be shaped so as to define a keyway 1112 (which may also be considered a groove) shaped to receive key 1110. When sheath-control user control 430 is in a non-actuated state, such as shown in FIGS. 14A and 33A-B, key 1110 is within keyway 1112, thereby preventing rotation of outer cam 450, which in turn prevents lateral extension of suture-positioning support 330 and distal advancement of the currently-engaged needle-control shaft 460, such as described hereinabove with reference to FIGS. 15A-B. This in turn prevents activation of, i.e., locks, support-and-needle user control 434.

For example, control handle 340 may comprise a key-bearing shaft 1108, which comprises key 1110 and is axially moveable with respect to outer cam 450. Actuation of sheath-control user control 430, such as by proximally moving sheath-control user control 430, as shown in FIG. 33C, may move (e.g., push) key-bearing shaft 1108 proximally, thereby removing key 1110 from keyway 1112, and freeing outer cam 450 to rotate upon distal advancement of the currently-engaged needle-control shaft 460. As a result, support-and-needle user control 434 can be activated, i.e., is no longer locked.

For some applications, control handle 340 further comprises a locking interface 1102, which is configured to prevent relocking support-and-needle user control 434 after it has been unlocked. Locking interface 1102 comprises (a) a one-way tab 1104 defined by key-bearing shaft 1108, and (b) a slot 1106. One-way tab 1104 is initially disposed in a slot 1106 when sheath-control user control 430 is the non-actuated state, such as shown in FIGS. 33A-B. The above-described proximal motion of key-bearing shaft 1108 proximally moves one-way tab 1104, thereby removing one-way tab 1104 from slot 1106. Locking interface 1102 is configured to prevent distal movement of one-way tab 1104 after one-way tab 1104 is removed from slot 1106. This prevention of distal movement in turn prevents distal movement of key-bearing shaft 1108, such that key 1110 remains outside keyway 1112, allowing activation of support-and-needle user control 434.

Figure 34A:
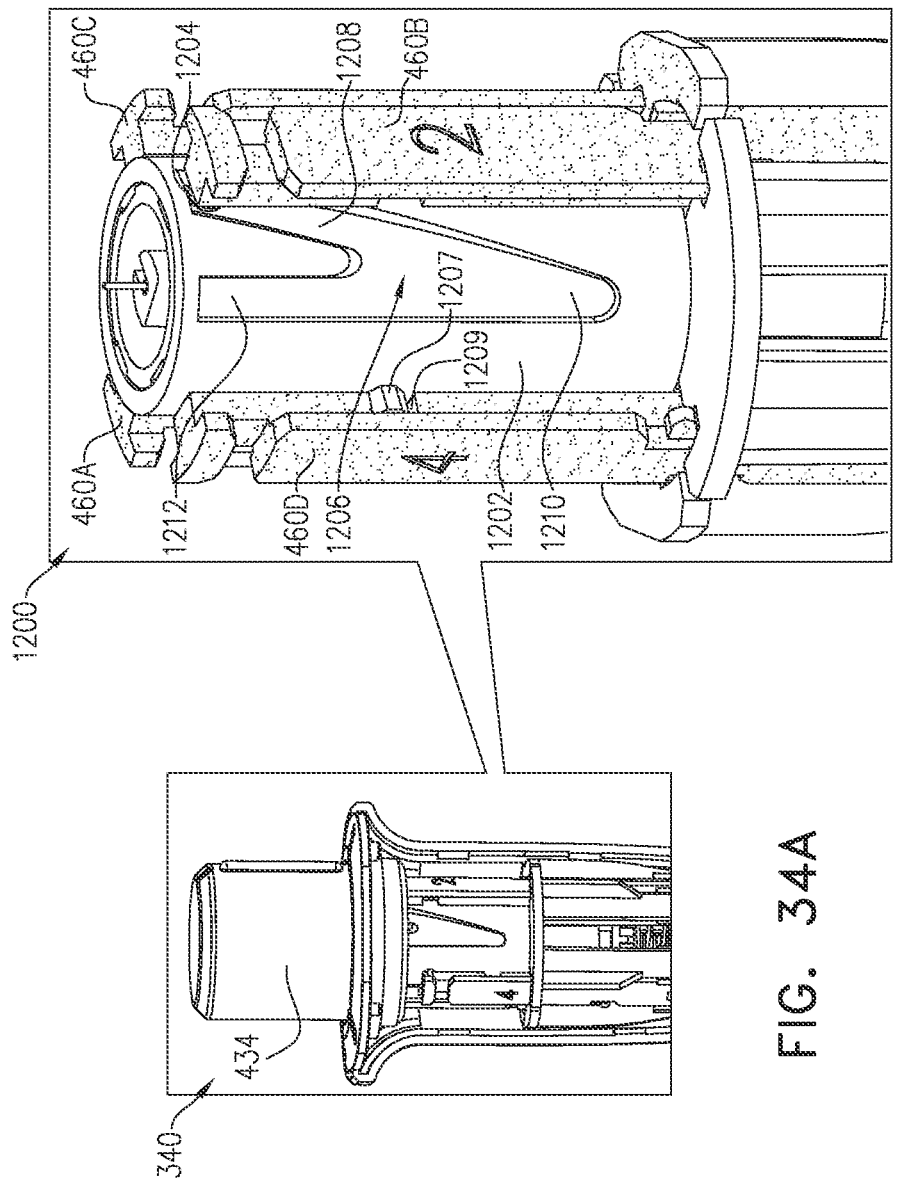
FIGS. 34A-B are schematic illustrations of a needle-advancement safety control assembly, in accordance with an application of the present invention.
Figure 34B:
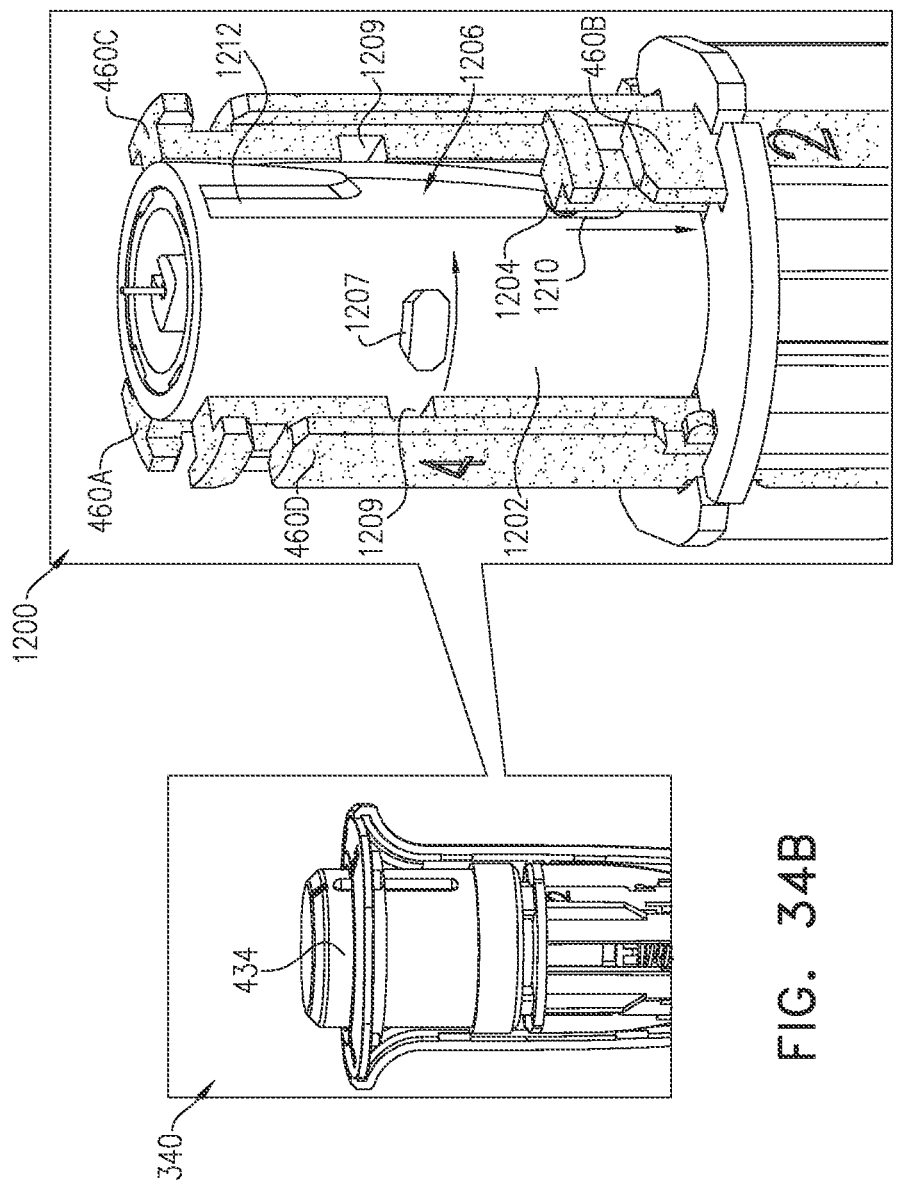

Reference is now made to FIGS. 34A-B, which are schematic illustrations of a needle-advancement safety control assembly 1200, in accordance with an application of the present invention. Control handle 340 may optionally comprise needle-advancement safety control assembly 1200 in combination with any of the other configurations described herein.

Needle-advancement safety control assembly 1200 is configured to prevent distal advancement of second ferrule-advancing suturing needle 336C until first ferrule-withdrawing suturing needle 336B has been distally advanced. This safety feature prevents inadvertent advancement of the suturing needles in the incorrect order.

For some applications, needle-advancement safety control assembly 1200 is configured to prevent distal advancement of second ferrule-advancing suturing needle 336C until first ferrule-withdrawing suturing needle 336B has been distally advanced, by preventing distal advancement of third needle-control shaft 460C (and optionally fourth needle-control shaft 460D), until second needle-control shaft 460B has been distally advanced.

For some of these applications, needle-advancement safety control assembly 1200 comprises a security barrel 1202, an external surface of which is shaped so as to define one or two security pins 1207. Although only one security pin 1207 can be seen in FIGS. 34A-B, a second security pin 1207 is provided on the far side of security barrel 1202.

When needle-advancement safety control assembly 1200 is in a locked state, such as shown in FIG. 34A, security pins 1207 removable engage respective recesses 1209 defined by radially inward surfaces of third needle-control shaft 460C, and optionally fourth needle-control shaft 460D. This engagement prevents axial movement, including distal advancement, of third needle-control shaft 460C, and optionally fourth needle-control shaft 460D.

Rotation of security barrel 1202 transitions needle-advancement safety control assembly 1200 from the locked state shown in FIG. 34A to an unlocked state shown in FIG. 34B. This rotation removes security pins 1207 from the respective recesses 1209, thereby allowing axial movement, including distal advancement, of third needle-control shaft 460C, and optionally fourth needle-control shaft 460D.

Distal advancement of second needle-control shaft 460B causes the above-mentioned rotation of security barrel 1202. For example, the external surface of security barrel 1202 may be shaped so as to define a security track indentation 1206 including a slanted portion 1208 and an axially-aligned portion 1212 that are joined at a distal portion 1210 (e.g., in a quasi-V-like shape). Second needle-control shaft 460B comprises a shaft pin 1204 that extends radially inward and is initially disposed within slanted portion 1208 of security track indentation 1206. The distal advancement of second needle-control shaft 460B distally advances shaft pin 1204 along slanted portion 1208 of security track indentation 1206, which causes the rotation of security barrel 1202. The subsequent proximal movement of second needle-control shaft 460B causes shaft pin 1204 to move proximally within axially-aligned portion 1212 of security track indentation 1206, which does not cause further rotation of security barrel 1202.

Figure 35:
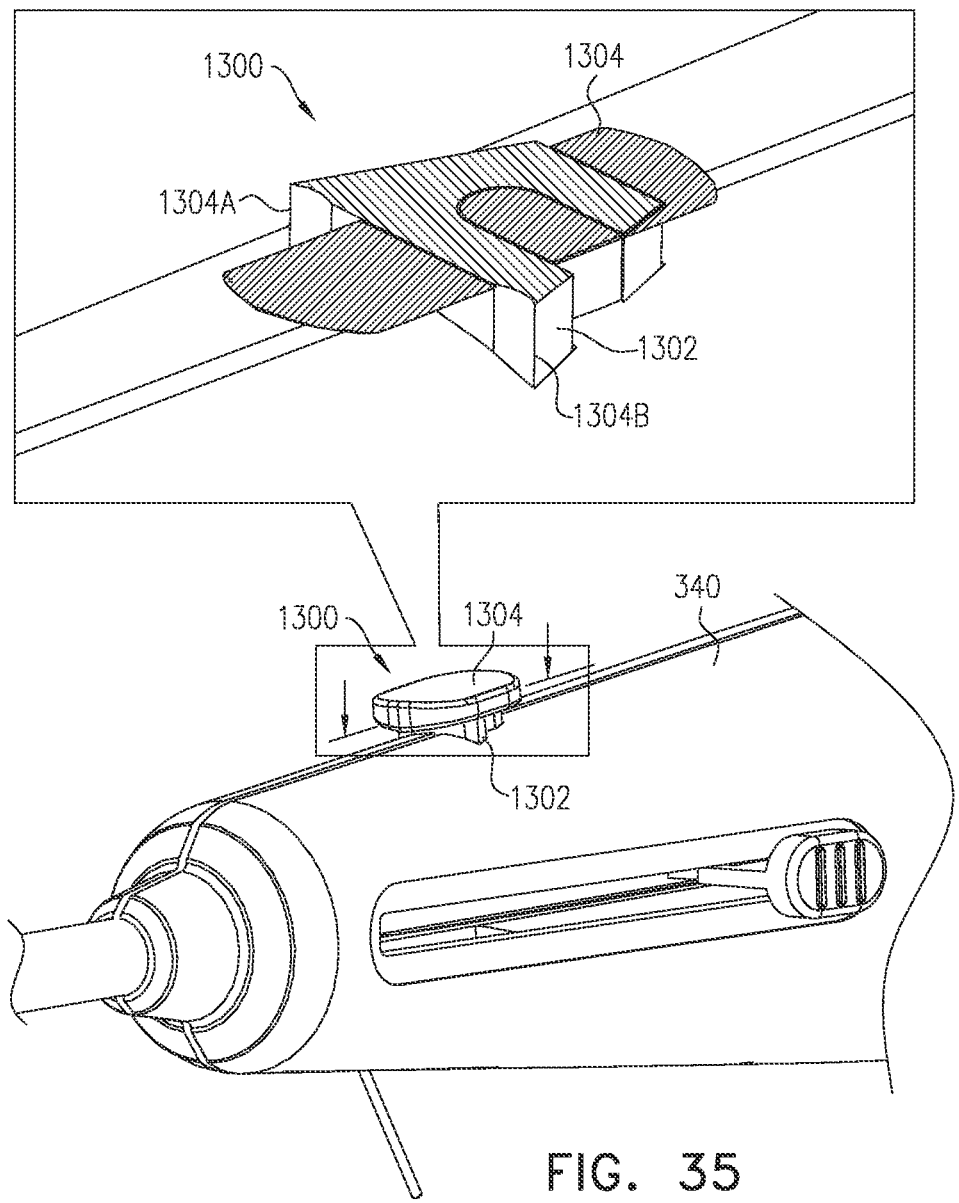
FIG. 35 is a schematic illustration of a cutting blade assembly of a control handle of the closure device of FIG. 9A, in accordance with an application of the present invention.

Reference is now made to FIG. 35, which is a schematic illustration of a cutting blade assembly 1300 of control handle 340, in accordance with an application of the present invention. Cutting blade assembly 1300 is configured to cut the sutures after knotting, as described hereinabove.

Cutting blade assembly 1300 is coupled to an external surface of a housing of control handle 340. Cutting blade assembly 1300 comprises a cutting blade 1302 and a cutting blade cover shield 1304. Cutting blade 1302 is shaped so as to define two sharp edges 1304A and 1304B on opposite sides of cutting blade 1302. Optionally, both sharp edges 1304A and 1304B face at least partially distally. Providing two sharp edges enables the surgeon to cut the suture by pulling it in either direction around control handle 340, such as depending on the handedness of the surgeon or the direction of the knotting.

Although the closure devices have been generally described hereinabove as being used for suturing a puncture through a wall of a blood vessel, the closure devices may alternatively be used to suture internal punctures or wounds or external punctures or wounds, such as an endoscopic puncture through a wall of a body cavity, or for skin closure for orthopedic procedures, such as arthroplasty. The closure devices may also be used for intracorporeal suturing, such as during minimally invasive surgery, such as laparoscopic procedures; for these applications, the closure devices may be implemented as a laparoscopic suturing tool. The closure devices may also be used to secure a lead or catheter to tissue for lead or catheter anchoring.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A closure device for suturing a puncture, the closure device comprising:
 a suture;
 an elongate support, which comprises one or more shafts, including (a) an outer tubular shaft and (b) an inner shaft, nested within the outer tubular shaft;
 a control handle, which is coupled to a proximal end portion of the elongate support, and which comprises one or more user controls, wherein the outer tubular shaft is fixed with respect to the control handle;
 a suture-positioning support, which is (a) coupled to the inner shaft of the elongate support at a distal end portion of the elongate support, (b) laterally extendable with respect to the distal end portion of the elongate support, and (c) configured to removably receive the suture; and
 an elongate dilator, which j is configured to be inserted through the puncture, (b) has a proximal end that is coupled to the distal end portion of the elongate support, and (c) is shaped so as to define a guidewire channel,
 wherein the closure device is configured to:
  allow movement of the distal end portion of the elongate support with respect to the proximal end of the dilator with at least two degrees of freedom, and
  rotate the suture-positioning support about a distal-support central longitudinal axis defined by the distal end portion of the elongate support, by rotating the inner shaft while the closure device holds the outer tubular shaft fixed with respect to the control handle.

2. The closure device according to claim 1, wherein the at least two degrees of freedom include at least one rotational degree of freedom.

3. The closure device according to claim 2, wherein the at least two degrees of freedom include at least two rotational degrees of freedom.

4. The closure device according to claim 3, wherein the at least two degrees of freedom include three rotational degrees of freedom.

5. The closure device according to claim 1, wherein the closure device is configured to allow the movement without requiring the distal end portion of the elongate support to directly or indirectly apply a force to the proximal end of the dilator.

6. The closure device according to claim 1, wherein the closure device is configured to allow the movement without requiring bending of the dilator.

7. The closure device according to claim 1, wherein the closure device is configured to allow the movement without requiring deformation of the dilator.

8. The closure device according to claim 1, further comprising an elongate flexible dilator connector, which couples the proximal end of the dilator to the distal end portion of the elongate support so as to allow the movement.

9. The closure device according to claim 8, wherein an average outer diameter of the dilator connector is less than 20% of a greatest outer diameter of the dilator.

10. The closure device according to claim 8, wherein the dilator connector comprises an element selected from the group of elements consisting of a cable, a cord, a wire, and a string.

11. The closure device according to claim 8, wherein the dilator connector comprises a tube.

12. The closure device according to claim 1, wherein the dilator is shaped so as to define an atraumatic proximal tip that is tapered.

13. The closure device according to claim 1,
 wherein the closure device further comprises:
  a ferrule, which is coupled to a distal end portion of the suture; and
  a suturing needle, which is removably couplable to the ferrule,
 wherein the suture-positioning support is shaped so as to define a ferrule receptacle, which is configured to removably receive the ferrule, such that the suture-positioning support is configured to removably receive the suture, and
 wherein the closure device is configured to direct the ferrule into the ferrule receptacle during distal advancement of the suturing needle removably coupled to the ferrule.

14. The closure device according to claim 1,
 wherein the outer tubular shaft of the elongate support has a distal end,
 wherein the suture-positioning support has proximal and distal end portions at opposite ends of the suture-positioning support,
 wherein the proximal end portion of the suture-positioning support is coupled to the elongate support, and
 wherein the distal end portion of the suture-positioning support is disposed distally to the distal end of the outer tubular shaft.

15. The closure device according to claim 14, wherein the suture-positioning support is coupled to the inner shaft of the elongate support.

16. The closure device according to claim 1, wherein the suture-positioning support is configured to assume:
 a delivery position, in which a suture-positioning support axis of the suture-positioning support (a) forms a first angle of less than 45 degrees with a distal-support central longitudinal axis of the distal end portion of the elongate support, or (b) is parallel with the distal-support central longitudinal axis, and
 one or more deployed positions, in which the suture-positioning support is laterally extended with respect to the distal end portion of the elongate support such that the suture-positioning support axis forms a second angle of at least 60 degrees with the distal-support central longitudinal axis.

17. The closure device according to claim 16, wherein the second angle is at least 75 degrees.

18. The closure device according to claim 1, wherein an external portion of the suture-positioning support that interfaces with the distal end portion of the elongate support is shaped so as to define one or more partial spherical surfaces.

19. A closure device for suturing a puncture, the closure device comprising:
   a suture;
   an elongate support, which comprises one or more shafts, including (a) an outer tubular shaft and (b) an inner shaft, nested within the outer tubular shaft;
   a control handle, which is coupled to a proximal end portion of the elongate support, and which comprises one or more user controls, wherein the outer tubular shaft is fixed with respect to the control handle;
   a suture-positioning support, which is (a) coupled to the inner shaft of the elongate support at a distal end portion of the elongate support, (b) laterally extendable with respect to the distal end portion of the elongate support, and (c) configured to removably receive the suture; and
   an elongate dilator, which O is configured to be inserted through the puncture, (b) has a proximal end that is coupled to the distal end portion of the elongate support, and (c) is shaped so as to define a guidewire channel,
   wherein the closure device is configured to:
      allow movement of the distal end portion of the elongate support with respect to the proximal end of the dilator with at least one translational degree of freedom, and
      rotate the suture-positioning support about a distal-support central longitudinal axis defined by the distal end portion of the elongate support, by rotating the inner shaft while the closure device holds the outer tubular shaft fixed with respect to the control handle.

20. The closure device according to claim 19, wherein the at least one translational degree of freedom includes a translational degree of freedom along a distal-support central longitudinal axis of the distal end portion of the elongate support.

21. The closure device according to claim 19, wherein the at least one translational degree of freedom includes at least two translational degrees of freedom.

22. The closure device according to claim 21, wherein the at least two translational degrees of freedom includes three translational degrees of freedom.

23. The closure device according to claim 19, further comprising an elongate flexible dilator connector, which couples the proximal end of the dilator to the distal end portion of the elongate support so as to allow the movement.

24. The closure device according to claim 23, wherein an average outer diameter of the dilator connector is less than 20% of a greatest outer diameter of the dilator.

25. The closure device according to claim 23, wherein the dilator connector comprises an element selected from the group of elements consisting of a cable, a cord, a wire, and a string.

26. The closure device according to claim 23, wherein the dilator connector comprises a tube.

27. The closure device according to claim 19, wherein the dilator is shaped so as to define an atraumatic proximal tip that is tapered.

28. The closure device according to claim 19, wherein the closure device is configured to allow the movement without requiring bending of the dilator and without requiring deformation of the dilator.

29. The closure device according to claim 19, wherein the suture-positioning support is configured to assume:
   a delivery position, in which a suture-positioning support axis of the suture-positioning support (a) forms a first angle of less than 45 degrees with a distal-support central longitudinal axis of the distal end portion of the elongate support, or (b) is parallel with the distal-support central longitudinal axis, and
   one or more deployed positions, in which the suture-positioning support is laterally extended with respect to the distal end portion of the elongate support such that the suture-positioning support axis forms a second angle of at least 75 degrees with the distal-support central longitudinal axis.

30. A closure device for suturing a puncture, the closure device comprising:
   a suture;
   an elongate support, which comprises one or more shafts;
   a suture-positioning support, which is (a) coupled to a distal end portion of the elongate support, (b) laterally extendable with respect to the distal end portion of the elongate support, and (c) configured to removably receive the suture; and
   an elongate dilator, which is configured to be inserted through the puncture, which has a proximal end that is coupled to the distal end portion of the elongate support, and which is shaped so as to define a guidewire channel,
   wherein the distal end portion of the elongate support defines a distal-support central longitudinal axis, and a proximal end portion of the dilator, which includes the proximal end of the dilator, defines a proximal-dilator central longitudinal axis, and
   wherein the closure device is configured to allow the distal end portion of the elongate support to move with respect to the proximal end of the dilator from defining a first dilator-to-elongate-support angle to defining a second dilator-to-elongate-support angle between the distal-support central longitudinal axis and the proximal-dilator central longitudinal axis while a suture-positioning-support-to-elongate-support angle remains constant,
   wherein the second dilator-to-elongate-support angle is at least 15 degrees greater than the first dilator-to-elongate-support angle, and
   wherein the suture-positioning-support-to-elongate-support angle is defined between (a) a suture-positioning support axis of the suture-positioning support and (b) the distal-support central longitudinal axis.

* * * * *